US011161859B2

(12) United States Patent
Baran et al.

(10) Patent No.: US 11,161,859 B2
(45) Date of Patent: Nov. 2, 2021

(54) CU- AND NI-CATALYZED DECARBOXYLATIVE BORYLATION REACTIONS

(71) Applicant: The Scripps Research Institute, La Jolla, CA (US)

(72) Inventors: Phil Baran, San Diego, CA (US); Chao Li, San Diego, CA (US); Jie Wang, San Diego, CA (US); Arnab Kumar Chatterjee, San Diego, CA (US); Manoj Kumar, San Diego, CA (US); Shan Yu, San Diego, CA (US); Kristen Ann Johnson, Santee, CA (US); Tian Qin, Dallas, TX (US); Ming Shang, San Diego, CA (US)

(73) Assignee: THE SCRIPPS RESEARCH INSTITUTE, La Jolla, CA (US)

( * ) Notice: Subject to any disclaimer, the term of this patent is extended or adjusted under 35 U.S.C. 154(b) by 0 days.

(21) Appl. No.: 16/495,907

(22) PCT Filed: Mar. 14, 2018

(86) PCT No.: PCT/US2018/022394
§ 371 (c)(1),
(2) Date: Sep. 20, 2019

(87) PCT Pub. No.: WO2018/175173
PCT Pub. Date: Sep. 27, 2018

(65) Prior Publication Data
US 2020/0024290 A1    Jan. 23, 2020

Related U.S. Application Data

(60) Provisional application No. 62/474,181, filed on Mar. 21, 2017.

(51) Int. Cl.
*C07F 5/02*     (2006.01)
*B01J 31/02*    (2006.01)
*C07B 47/00*    (2006.01)
*C07K 7/64*     (2006.01)

(52) U.S. Cl.
CPC .......... *C07F 5/027* (2013.01); *B01J 31/0212* (2013.01); *C07B 47/00* (2013.01); *C07K 7/64* (2013.01); *B01J 2231/344* (2013.01); *B01J 2531/16* (2013.01)

(58) Field of Classification Search
None
See application file for complete search history.

(56) References Cited

U.S. PATENT DOCUMENTS

| 5,616,573 | A  | 4/1997 | Zentel et al. |
|-----------|----|--------|---------------|
| 8,969,509 | B2 | 3/2015 | Liu et al. |
| 9,119,868 | B2 | 9/2015 | Walker et al. |
| 2011/0053905 | A1 | 3/2011 | Guo et al. |

FOREIGN PATENT DOCUMENTS

| EP | 0124317 A2     | 11/1984 |
|----|----------------|---------|
| WO | WO-9222309 A1  | 12/1992 |
| WO | WO-2015179441 A2 | 11/2015 |
| WO | WO-2018175173 A1 | 9/2018 |

OTHER PUBLICATIONS

Goldstein et al. Antimicrobial Agents and Chemotherapy (2013), 57(6),2620-2630.*
"International Application Serial No. PCT/US2018/022394, International Preliminary Report on Patentability dated Oct. 3, 2019", 9 pgs.
"International Application Serial No. PCT/US2018/022394, International Search Report dated May 14, 2018", 3 pgs.
"International Application Serial No. PCT/US2018/022394, Written Opinion dated May 14, 2018", 7 pgs.
Ahmed, Farid R., et al., "The crystal structure of N,N'-bismethoxycarbonyi-L-valyi-L-valine, a product of the rearrangement of the symmetrical anhydride of N-methoxycarbonyi-L-valine", Canadian Journal of Chemistry, vol. 64, No. 7, (1986), 1396-1399.
Novozhilov, Y V, et al., "An Improved Kilogram-Scale Preparation of Atorvastatin Calcium", Chemistry Central Journal, vol. 9, No. 7, (Dec. 2015), 1-4.
Simon, T G, et al., "Atorvastatin and Fluvastatin are Associated With Dose-Dependent Reductions in Cirrhosis and Hepatocellular Carcinoma Among Patients With Hepatitis C Virus: Results From ERCHIVES", Hepatology, vol. 64, No. 1, (Feb. 18, 2016), 47-57.
Wang, Jie, et al., "Ni-catalyzed Cross-coupling of Redox-Active Esters with Boronic Acids", Angewandte Chemie International Edition English, vol. 55, No. 33, (Aug. 8, 2016), 9676-9679.
Xie, Jian, et al., "Total Synthesis of [Psi[C(=S)NH]Tpg4]Vancomycin Aglycon,[Psi[C(=NH)NH]Tpg4]Vancomycin Aglycon, and Related Key Compounds: Reengineering Vancomycin for Dual d-Ala-d-Ala and d-Ala-d-Lac Binding", J Am Chem Soc., vol. 134, No. 2, (Jan. 18, 2012), 1284-1297.

* cited by examiner

Primary Examiner — Ana Z Muresan
(74) Attorney, Agent, or Firm — Schwegman Lundberg & Woessner, P.A.

(57) ABSTRACT

The invention is directed to methods of converting a carboxylic acid group in a compound, via a redox active ester, to a corresponding boronic ester by treatment with bis (pinacolato)diboron-alkyllithium complex in the presence of a ligand, a Ni(ll) salt or a copper salt, and an Mg(ll) salt, in the presence of an alkyllithium or a lithium hydroxide or alkoxide salt. The product pinacolato boronate ester can be cleaved to provide a boronic acid. The invention is also directed to methods of preparing various compounds of medical value comprising boronic acid groups, and to novel boronic-acid containing compounds of medicinal value, including an atorvastatin boronic acid analog, a vancomycin aglycone boronic acid analog, and boronic acid containing elastase inhibitors mCBK319, mCBK320, mCBK323, and RPX-7009.

4 Claims, 6 Drawing Sheets

Figure 1 (A and B)
A. Carboxylic to boronic Acids: strategic value.
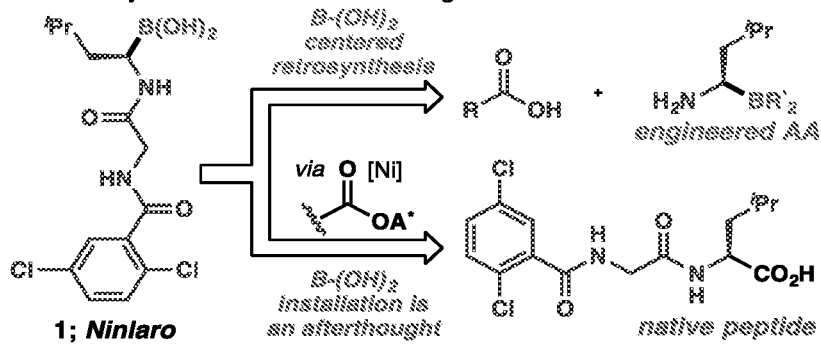
B. Decarboxylative borylation: invention and optimization.
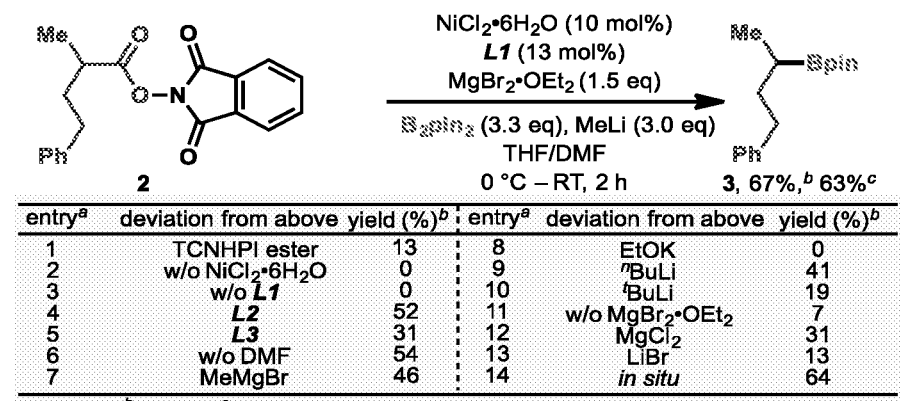
| entry[a] | deviation from above | yield (%)[b] | entry[a] | deviation from above | yield (%)[b] |
|---|---|---|---|---|---|
| 1 | TCNHPI ester | 13 | 8 | EtOK | 0 |
| 2 | w/o NiCl$_2$·6H$_2$O | 0 | 9 | $^n$BuLi | 41 |
| 3 | w/o L1 | 0 | 10 | $^t$BuLi | 19 |
| 4 | L2 | 52 | 11 | w/o MgBr$_2$·OEt$_2$ | 7 |
| 5 | L3 | 31 | 12 | MgCl$_2$ | 31 |
| 6 | w/o DMF | 54 | 13 | LiBr | 13 |
| 7 | MeMgBr | 46 | 14 | in situ | 64 |
[a] 0.1 mmol. [b] GC yield. [c] Isolated yield.
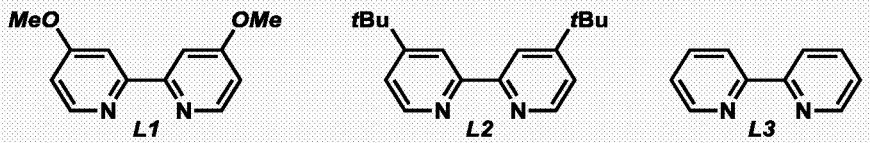

CU- AND NI-CATALYZED DECARBOXYLATIVE BORYLATION REACTIONS

STATEMENT OF GOVERNMENT SUPPORT

This invention was made with government support under GM-118176 awarded by the National Institutes of Health. The government has certain rights in the invention.

BACKGROUND

Boronic acids are of paramount importance to all facets of chemical sciences.

Although their popularization and widespread utilizations can likely be attributed to the incredible utility of the Suzuki coupling, (1) to date, boronic acids have found countless applications in fields far outside of cross-coupling, such as materials science, (2) chemosensors, (3) polymer science, (2) and drug discovery. (4-5) In medicine, two alkyl boronic acids are currently approved by FDA for various oncology indications: ninlaro (1) and velcade (49). Medicinal chemists point to the bioisoteric nature of boronic acids as they can function in certain cases as a carboxylic acid surrogate. (6) Despite their popularity, boronic acids are almost entirely derived through synthesis unlike the carboxylic acids they seek to replace which are ubiquitous and inexpensive. The retrosynthetic analysis employed in such cases can itself be a deterrent to their incorporation into a drug candidate.

As illustrated with 1 (FIG. 1A), the conventional approach focuses all strategic attention on the means with which the boron atom will be incorporated even though this represents <5% of the total molecular weight of 1. (7) The synthesis of an engineered amino acid (AA) is therefore required and each analog must be made individually. In contrast, the direct transformation of the carboxylic acid containing native peptide to the corresponding boronic acid at a late-stage would be far easier and more logical from a strategic perspective. Given the sheer number of alkyl carboxylic acids in feedstock chemicals, natural products, and drug molecules, this transformation could provide the unique opportunity to expediently procure a myriad of previously difficult-to-access boronic acids as versatile building blocks, functional materials, and potent medications.

SUMMARY

This invention provides, in various embodiments, methods for the conversion of a carboxylic acid group to a boronic ester or acid group, when the carboxylic acid group and the boronic ester or acid group is bonded, respectively, to an alkyl, i.e., $sp^3$ hybridized, carbon atom.

An alkyl carboxylic acid compound $RCO_2H$, as the term is used herein, is a compound that has a carboxylic acid, $—CO_2H$, group bonded to an alkyl carbon atom, i.e., an $sp^3$ hybridized carbon atom. Other parts of the molecule can comprise aryl or heteroaryl rings, heteroatoms, unsaturations, and other functional groups, as well as other alkyl carbon atoms.

An alkyl boronic acid compound, $RB(OH)_2$, as the term is used herein, is a compound that has a boronic acid, $—B(OH)_2$, group bonded to an alkyl carbon atom, i.e., an $sp^3$ hybridized carbon atom. Other parts of the molecule can comprise aryl or heteroaryl rings, heteroatoms, unsaturations, and other functional groups, as well as other alkyl carbon atoms.

A pinacolato ester of an alkyl boronic acid is of formula

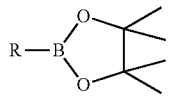

and both the ester and the acid boronate structures can comprise the same R group unchanged from the R group of the carboxylic acid $RCO_2H$. Consequently, the reaction is very chemoselective for a carboxylic acid substrate, tolerating a wide range of chemical functionality elsewhere in the molecule. Because a boronic acid group is a pharmaceutically interesting isosteric replacement for a carboxylic acid group, this chemoselectivity allows a wide range of pharmaceuticals that contain a carboxylic acid group to be converted to the corresponding boronic acid compounds without disruption of functional groups elsewhere in the molecule.

The invention in its various embodiments provides the following advantages in carrying out the transformation described, that replaces a carboxylic acid group with a boronic acid group under conditions that are selective, mild, and cost effective. Some of the advantages of practicing a method of the invention include: Practicality: the invention uses inexpensive reagents with minimal precaution. Therefore, it can be readily adopted in both discovery and process settings. Broad scope: carboxylic acids which are amongst the most ubiquitous functional groups in commercial chemicals and pharmaceuticals are used in this transformation. The reaction also exhibits high chemoselectivity, thereby can be readily used to diversify a broad array of substrates. Urgency: there is increasing awareness of the importance of boronic acids in drug discovery but effective and general methods of boronic acid synthesis are lacking. This invention fills up this gap in methodology.

The invention provides, in various embodiments, a method of converting an alkyl carboxylic acid compound $RCO_2H$ to a corresponding alkyl boronic pinacolato ester compound

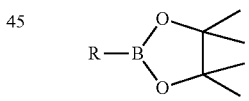

wherein R is a hydrocarbyl group comprising an $sp^3$ hybridized carbon atom bonded to the $CO_2H$ or the boron atom, respectively, R optionally further comprising alkyl or alkyenyl groups, both optionally comprising heteroatoms, or optionally comprising aryl, heterocyclyl, or heteroaryl groups, or any combination thereof;

the method comprising:

a) forming a redox active ester (RAE) of the alkyl carboxylic acid compound; then, b) contacting the redox active ester of the alkyl carboxylic acid compound in an aprotic solvent, and bis(pinacolato) diboron ($B_2pin_2$), in the presence of at least 20 mole % of a Mg(II) salt and of at least one molar equivalent a lithium compound comprising a (C1-C4)alkyllithium, a (C1-C4) alkoxylithium, or lithium hydroxide, and at least 10 mole % of a Cu or Ni salt;

in the presence of a 1,3-dicarbonyl ligand forming with the Cu a compound of formula (M)

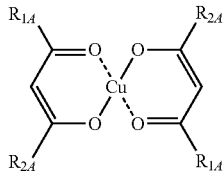

wherein $R_{1A}$ and $R_{2A}$ are each independently selected (C1-C4)alkyl, trifluoromethyl, or phenyl;

or in the presence of a ligand of formula (L) comprising a bipyridyl of formula

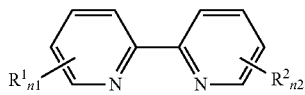

wherein $R_1$ and $R_2$ are each independently selected (C1-C4)alkyl or (C1-C4)alkoxy, n1 and n2 are each independently 0, 1, or 2, or of a 1,10-phenanthroline of formula

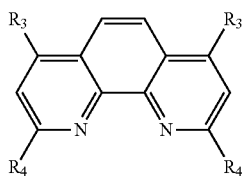

wherein $R_3$ and $R_4$ are each independently (C1-C4)alkyl, (C1-C4)alkoxy or phenyl;

to provide the corresponding alkyl boronic pincolato ester compound.

More specifically, the invention provides, in various embodiments, a method of converting the alkyl carboxylic acid compound to the corresponding alkyl boronic pinacolato ester compound, comprising:

a) forming the redox active ester (RAE) of the alkyl carboxylic acid compound; then, b) either: 1) contacting in aprotic solvent the redox active ester, at least one molar equivalent bis(pinacolato)diboron ($B_2pin_2$), and effective amounts of a Mg(II) salt in the present of lithium hydroxide or a lithium (C1-C4)alkoxide, and in the presence of a Cu(I) or a Cu(II) complex or both of a 1,3-dicarbonyl compound, the complex being of formula (M)

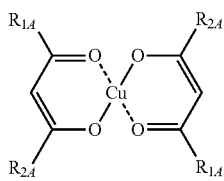

wherein $R_{1A}$ and $R_{2A}$ are each independently selected (C1-C4)alkyl, trifluoromethyl, or phenyl, or in the presence of a Cu(I) or a Cu(II) salt or both and an effective amount of a ligand (L) comprising a bipyridyl of formula

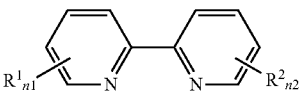

wherein $R_1$ and $R_2$ are each independently selected (C1-C4)alkyl or (C1-C4)alkoxy, n1 and n2 are each independently 0, 1, or 2, or of a 1,10-phenanthroline of formula

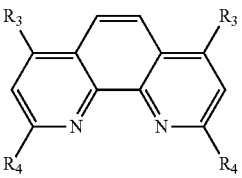

wherein $R_3$ and $R_4$ are each independently (C1-C4)alkyl, (C1-C4)alkoxy or phenyl;

or: 2) contacting in aprotic solution the redox active ester and effective amounts of a Ni(II) salt and a Mg(II) salt, in the presence of an effective amount of a ligand (L) comprising a bipyridyl of formula

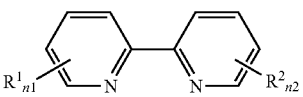

wherein $R_1$ and $R_2$ are each independently selected (C1-C4)alkyl or (C1-C4)alkoxy, n1 and n2 are each independently 0, 1, or 2, or of a 1,10-phenanthroline of formula

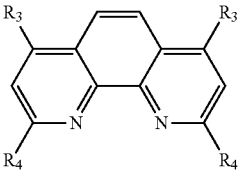

wherein $R_3$ and $R_4$ are each independently (C1-C4)alkyl, (C1-C4)alkoxy or phenyl;

then, adding a premixed solution comprising at least one molar equivalent of an organolithium compound and at least one molar equivalent bis(pinacolato)diboron ($B_2pin_2$);

to provide the pinacolato ester of the corresponding alkyl boronic ester compound.

More specifically, in carrying out a method of the invention, the redox active ester of the alkyl carboxylic acid can be an N-hydroxyphthalimide (NHPI) or can be a tetrachloro-N-hydroxyphthalimide (TCNHPI) ester.

More specifically, in carrying out a method of the invention, for the Cu-catalyzed reaction the Cu(II) salt can be Cu(acac)$_2$, or for the Ni-catalyzed reaction the Ni(II) salt can be NiCl$_2$.

More specifically, in carrying out a method of the invention, the Mg(II) salt can be MgBr$_2$ or Mg Cl$_2$.

More specifically, in carrying out a method of the invention, for the Cu-catalyzed reaction the lithium compound can be LiOH or a lithium (C1-C4)alkoxide, or for the Ni-catalyzed reaction the organolithium compound can be methyllithium.

More specifically, in carrying out a method of the invention, the aprotic solvent can comprise THF or dioxane, and DMF.

The invention further provides, in various embodiments, the method disclosed above, further comprising step c) cleaving under acidic conditions the pinacolato ester of the alkyl boronic acid compound

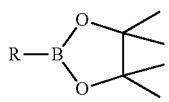

to provide the alkyl boronic acid compound $RB(OH)_2$. For instance, the step of cleaving the pinacolato ester of the alkyl boronic acid compound can comprise contacting the ester with $BCl_3$ followed with methanol, or contacting the ester with trifluoroacetic acid, or contacting the ester with a boronic acid, such as phenylboronic acid or 2-methylpropylboronic acid in aqueous HCl.

In various embodiments of the invention, the ligand (L) can be a bipyridyl of formula L1-L5

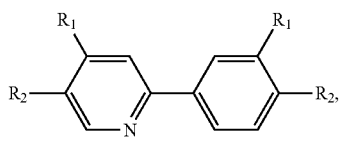

wherein
$R_1$=OMe, $R_2$=H, L1
$R_1$=tBu, $R_2$=H, L2
$R_1$=H, $R_2$=H, L3
$R_1$=Me, $R_2$=H, L4
$R_1$=OMe, $R_2$=OMe, L5;
or the ligand (L) can be a 1,10-phenanthroline of formula L7-L9

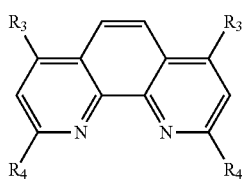

wherein
$R_3$=H, $R_4$=H, L7
$R_3$=Ph, $R_4$=H, L8
$R_3$=OMe, $R_4$=H, L9.

In various embodiments of the reaction, the Cu ligand of formula (M) can be

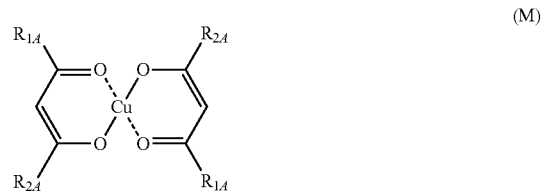

wherein each $R_{1A}$ and $R_{2A}$ is independently selected (C1-C4)alkyl, trifluoromethyl, or phenyl.

For example, the invention provides in various embodiments a method of preparation of alkyl boronic compound ninlaro (1)

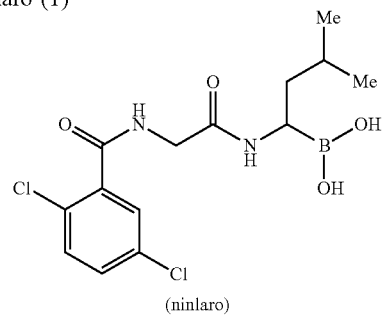

from alkyl carboxylic acid compound:

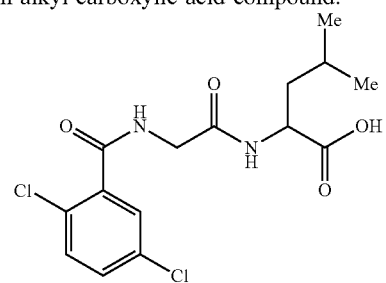

by carrying out the steps a), b), and c) as disclosed above.

For example, the invention provides in various embodiments a method of preparing a boronate ester analog of atorvastatin ketal, comprising, first, a) forming the N-hydroxyphthalimide (NHPI) ester of atorvastatin ketal to provide redox active ester

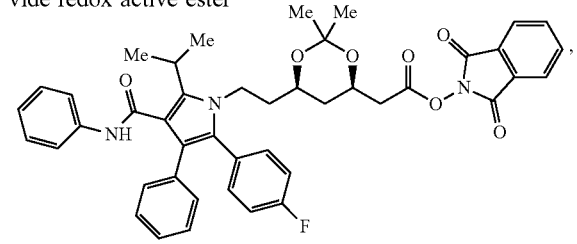

then, carrying out step b) disclosed above, to provide the boronate ester of the analog of atorvastatin ketal

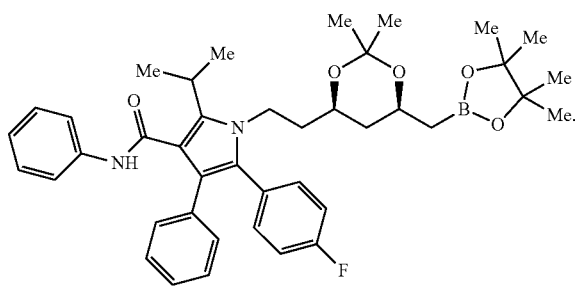 [SMILES: CC(C)c1c(C(=O)Nc2ccccc2)c(-c2ccccc2)c(-c2ccc(F)cc2)n1CC[C@@H]1C[C@H](CB2OC(C)(C)C(C)(C)O2)OC(C)(C)O1]

The invention further provides, as a composition of matter, a boronate ester analog of atorvastatin ketal of formula

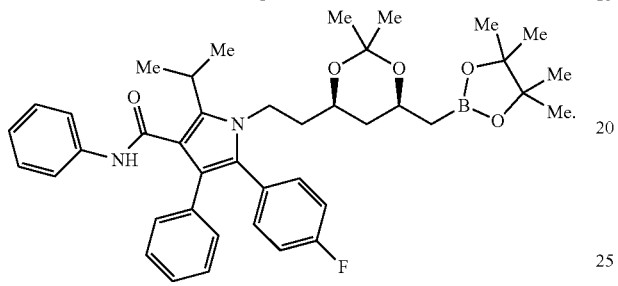

The invention further provides, as a composition of matter, a boronic acid analog, freed of the pinacolato ester group, of atorvastatin ketal of formula

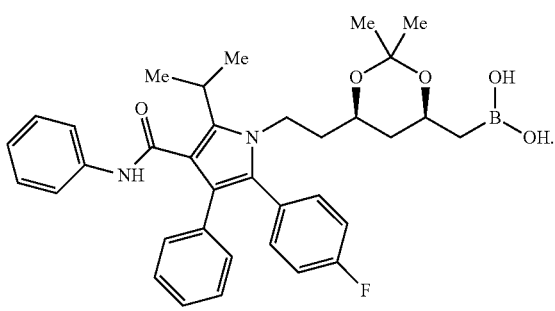 [SMILES: CC(C)c1c(C(=O)Nc2ccccc2)c(-c2ccccc2)c(-c2ccc(F)cc2)n1CC[C@@H]1C[C@H](CB(O)O)OC(C)(C)O1]

For example, the invention provides in various embodiments a method of preparing a dimethyl-t-butylsilyl (TBS) hydroxyl-protected boronic acid analog of a vancomycin aglycone

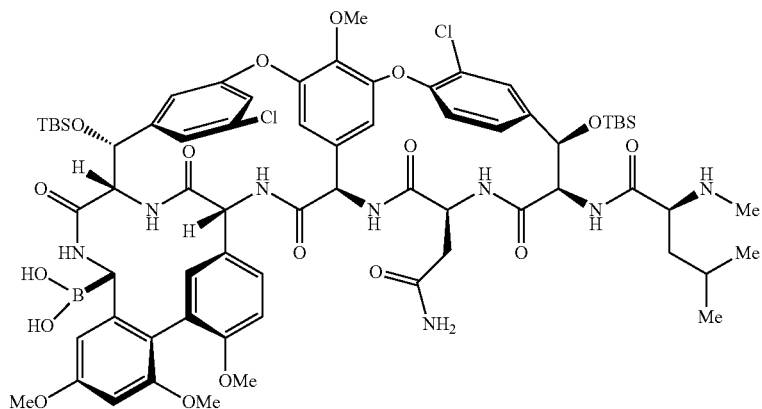

comprising, first, a) converting the carboxylic acid

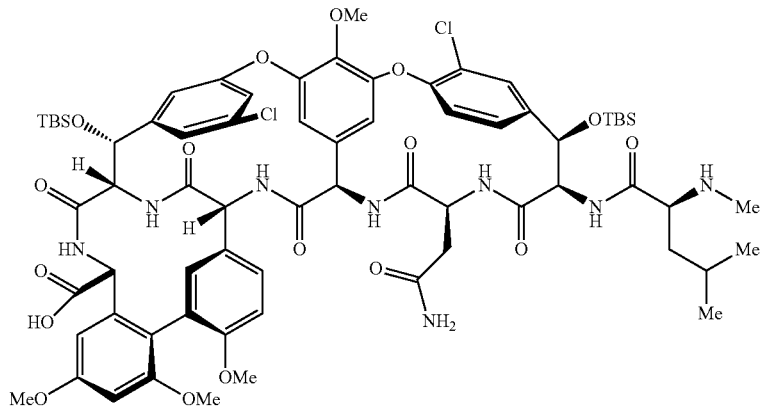

to the corresponding NHPI redox activated ester, then carrying out step b), above, to provide an O-protected boronate pinacolato ester of the boronic acid, then carrying out step c), above, cleaving the boronic ester group to provide the O-protected boronic acid compound of formula

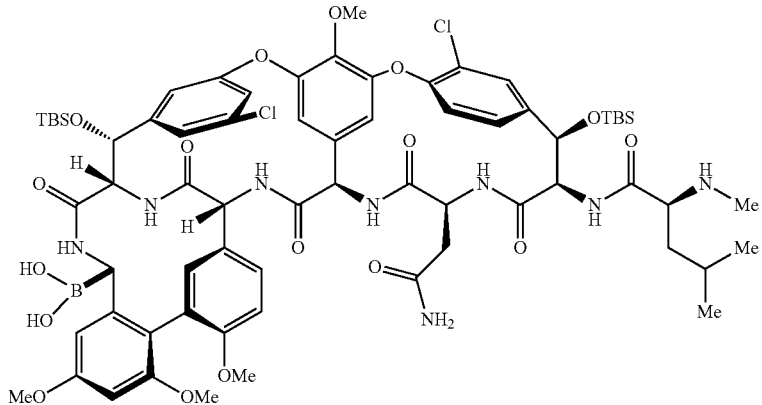

The invention further provides, as a composition of matter, a hydroxyl-protected boronic acid analog of a vancomycin aglycone

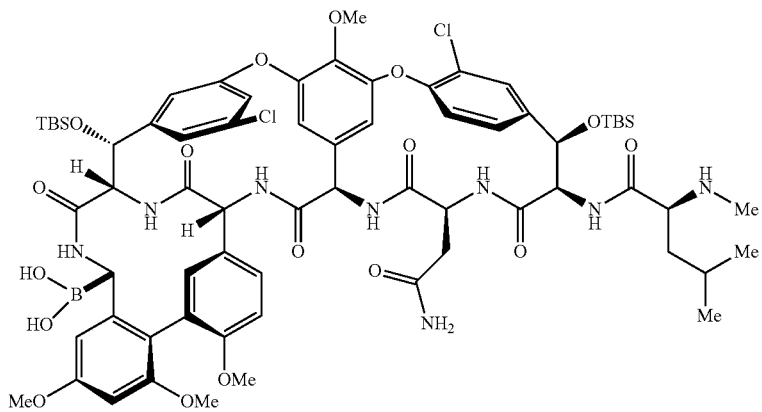

wherein TBS signifies a dimethyl-t-butylsilyl O-protecting group.

The invention also provides, as a method and as a composition of matter, a boronic acid analog of vancomycin aglycone of formula

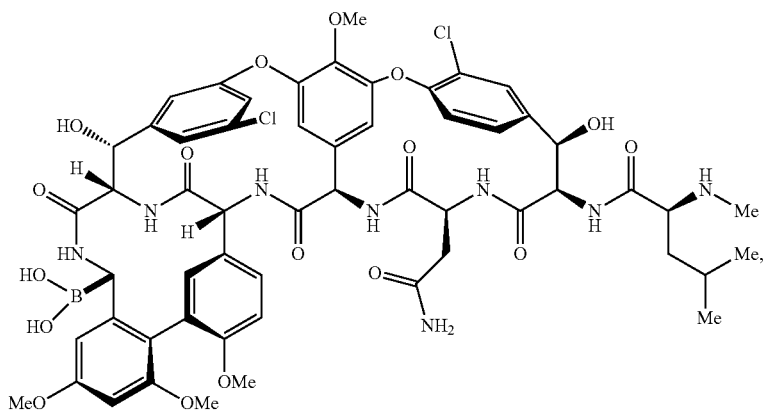

prepared by cleavage of the t-butyldimethylsilyl (TBS) esters of the two protected hydroxyl groups using standard synthetic conditions such as tris(dimethylamino)sulfonium difluorotrimethylsilicate (TASF) in DMF.

For example, the invention provides in various embodiments a method of preparing boronic acid mCBK319 elastase inhibitor compound

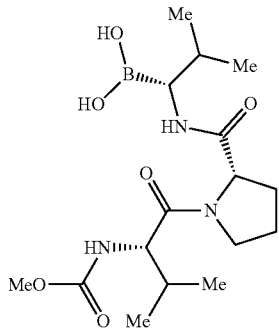 [SMILES: COC(=O)N[C@H](C(=O)N1CCC[C@H]1C(=O)N[C@H](B(O)O)C(C)C)C(C)C]

comprising carrying out steps a), b), and c) as described above starting with carboxylic acid compound

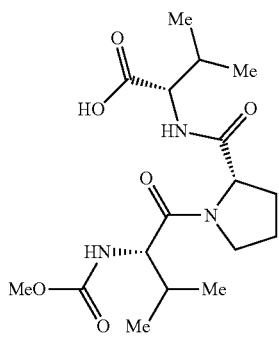 [SMILES: COC(=O)N[C@H](C(=O)N1CCC[C@H]1C(=O)N[C@H](C(=O)O)C(C)C)C(C)C]

The invention further provides, as a composition of matter, a boronic acid mCBK319 (50) elastase inhibitor compound of formula

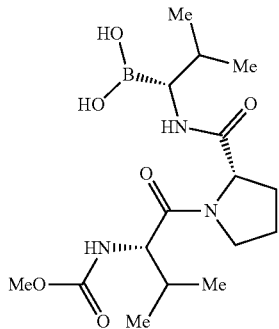 [SMILES: COC(=O)N[C@H](C(=O)N1CCC[C@H]1C(=O)N[C@H](B(O)O)C(C)C)C(C)C]

For example, the invention provides in various embodiments a method of preparing the Boc-protected boronic ester compound of formula

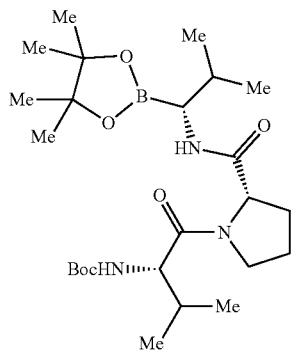 [SMILES: CC(C)[C@H](NC(=O)[C@@H]1CCCN1C(=O)[C@@H](NC(=O)OC(C)(C)C)C(C)C)B1OC(C)(C)C(C)(C)O1]

comprising carrying out step b), above, on compound

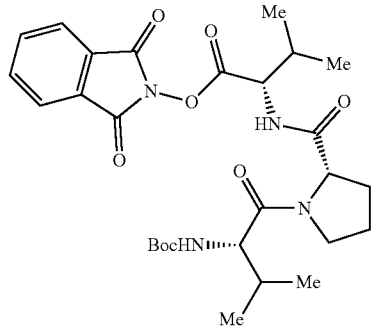 [SMILES: CC(C)[C@H](NC(=O)[C@@H]1CCCN1C(=O)[C@@H](NC(=O)OC(C)(C)C)C(C)C)C(=O)ON1C(=O)c2ccccc2C1=O]

to provide the Boc-protected boronic pinacolato ester compound

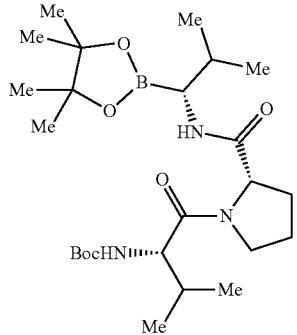 [SMILES: CC(C)[C@H](NC(=O)[C@@H]1CCCN1C(=O)[C@@H](NC(=O)OC(C)(C)C)C(C)C)B1OC(C)(C)C(C)(C)O1]

In additional embodiments, the Boc-protected boronic pinolcolato ester compound

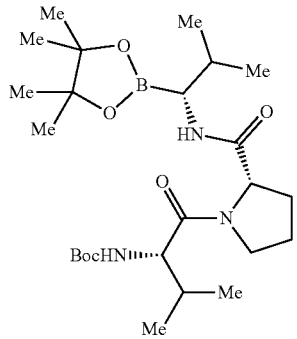 [SMILES: CC(C)[C@H](NC(=O)[C@@H]1CCCN1C(=O)[C@@H](NC(=O)OC(C)(C)C)C(C)C)B1OC(C)(C)C(C)(C)O1]

can further undergo cleaving the Boc group of the compound with trifluoroacetic acid, followed by condensation of the resulting free amino group with compound

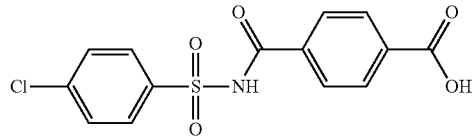 [SMILES: O=C(O)c1ccc(C(=O)NS(=O)(=O)c2ccc(Cl)cc2)cc1]

followed by cleavage of the pinacolato boronate ester group with phenylboronic acid in aqueous HCl to provide the boronic acid mCBK320 (51) elastase inhibitor compound of formula

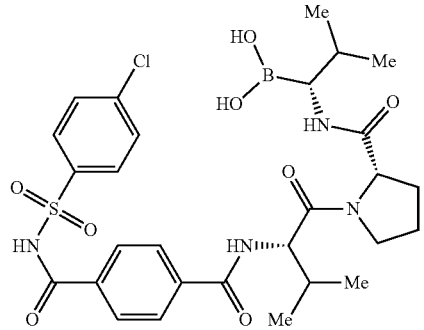

The invention further provides, as a composition of matter, a boronic acid mCBK320 elastase inhibitor compound of formula

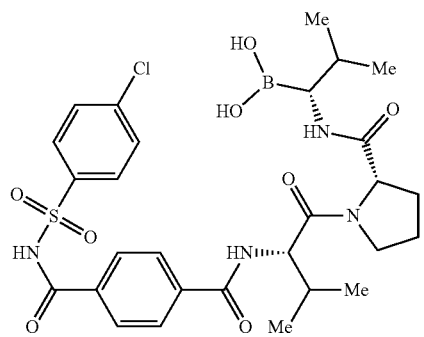 [SMILES: CC(C)[C@H](NC(=O)[C@@H]1CCCN1C(=O)[C@@H](NC(=O)c1ccc(C(=O)NS(=O)(=O)c2ccc(Cl)cc2)cc1)C(C)C)B(O)O]

In further embodiments, the above Boc-protected boronic pinolcolato ester compound can further undergo cleaving the Boc group and of the boronate ester of the compound with trifluoroacetic acid, followed by condensation of the resulting free amino group with a compound of formula

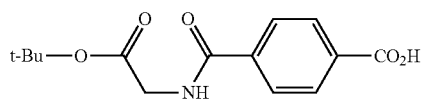 [SMILES: CC(C)(C)OC(=O)CNC(=O)c1ccc(C(=O)O)cc1]

followed by cleavage of the t-Bu ester, to provide a boronic acid compound of formula (mCBK323 elastase inhibitor, 53)

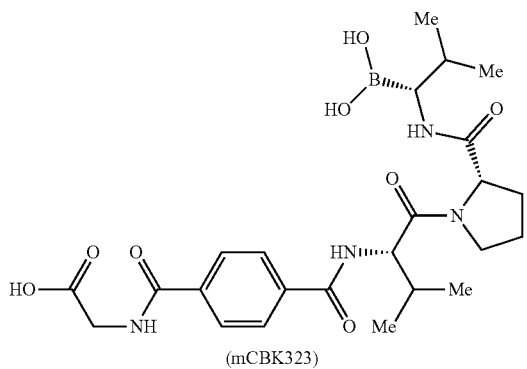

The invention further provides, as a composition of matter, a boronic acid compound of formula (mCBK323, elastase inhibitor)

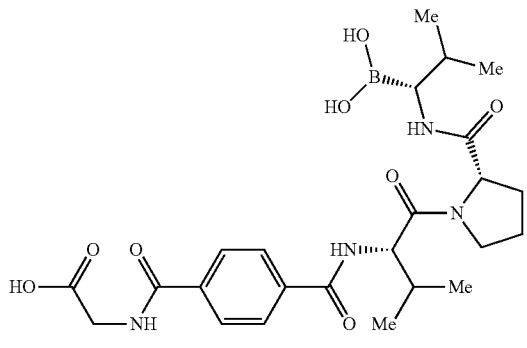

The invention further provides, in various embodiments, a method of preparation of an arylomycin sidechain analog boronic acid

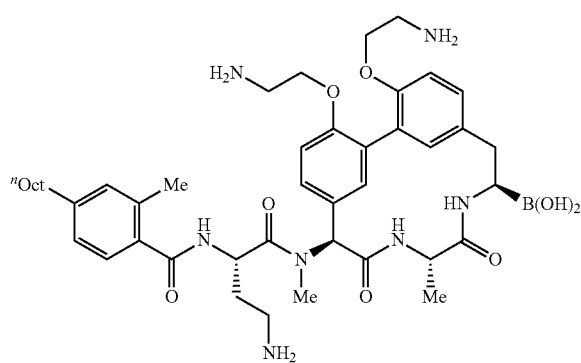

comprising carrying out the conversions comprising steps a), b) and c) as described above, followed by removal of the N-Boc groups with acid, starting with an arylomycin sidechain analog carboxylic acid of formula

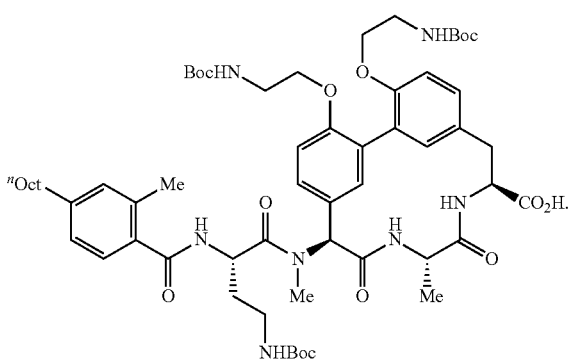

The invention also provides, as a novel composition of matter, an arylomycin sidechain analog boronic acid of formula

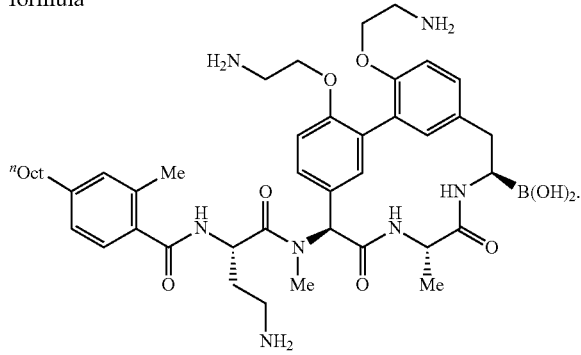

The invention further provides, in various embodiments, a method of synthesis of a Cyclic Boronic Acid β-Lactamase Inhibitor (RPX7009), of formula

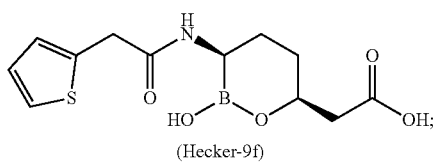 [SMILES: O=C(O)C[C@@H]1CC[C@H](NC(=O)Cc2cccs2)B(O)O1]

(Hecker-9f)

and related boronic acid analogs, see "Discovery of a Cyclic Boronic Acid β-Lactamase Inhibitor (RPX7009) with Utility vs Class A Serine Carbapenemases" by Scott J. Hecker, et al., DOI: 10.1021/acs.jmedchem.5b00127, *J. Med. Chem.* (2015), 58, 3682-3692. A key intermediate in the synthesis of β-Lactamase Inhibitor (RPX7009), Hecker-9f, and analogs as described in the cited article, is compound Hecker-12 therein,

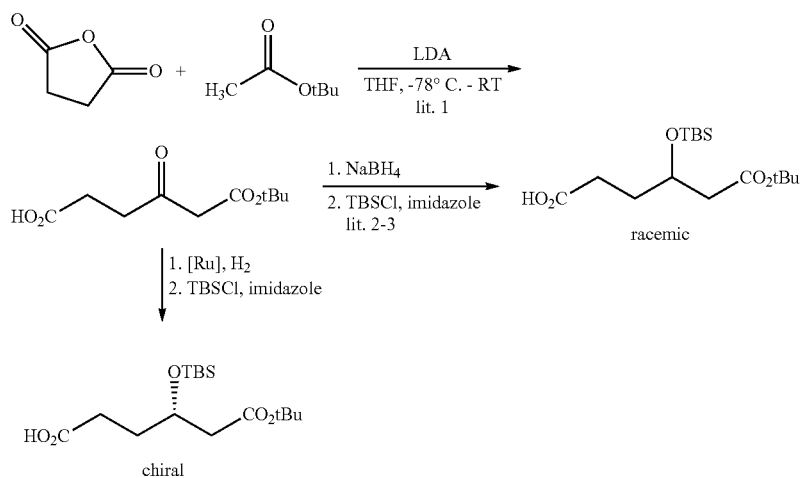

(Hecker-12)

wherein TBDMS signifies a t-butyldimethylsilyl protecting group. This key intermediate can be prepared according to a method of the present invention from a compound of formula the preparation of which is described in racemic form in publication M. Ghosh, M. J. Miller, *Tetrahedron,* 1996, 52, 4225. Use of a borylation method of the invention can yield compound Hecker-12 from this carboxylic acid intermediate. Methods to effect stereoselective reduction of beta-ketoesters to yield a chiral alcohol are well known to those skilled in the art, e.g. chiral borohydride reagents, or a ruthenium catalyzed asymmetric hydrogenation reaction, providing the Ghosh carboxylic acid in chiral form. For instance, the preparation of the carboxylic acid precursor for the borylation reaction of the invention can be prepared according to the following route:

The remainder of the synthesis can be carried out as described in Hecker, where use of a chiral pinanediol in the boronate ester exchange reaction of compound Hecker—12 to yield chiral Hecker—13 (see Scheme 1 of Hecker, et al.) can provide intermediates of good enantiomeric purity. These intermediates can be used in the preparation of all of β-Lactamase Inhibitors such as RPX7009, compounds Hecker-9a through Hecker-9r (see Table 1 of Hecker et al. publication).

See also related documents: "Reaktion von a-Lithioessigsaureestern mit Bernsteinsaureanhydriden" Von Franz-Peter Montforts und Silvio Ofner, *Angew. Chem.* (1979) 91, no. 8, p. 656; "Highly Enantioselective Hydrogenation of β-Keto Esters under Mild Conditions" Mark J. Burk,* T. Gregory P. Harper, and Christopher S. Kalberg, (1995) *J. Am. Chem. Soc.*, 117, 4423-4424; and "Asymmetric Hydrogenation of α-Keto Carboxylic Esters. A Practical, Purely Chemical Access to α-Hydroxy Esters in High Enantiomeric Purity" R. Noyori,* T. Ohkuma, and M. Kitamura (1987), *J. Am. Chem. Soc.*, Vol. 109, No. 19, 5856.

While the invention has been described and exemplified in sufficient detail for those skilled in this art to make and use it, various alternatives, modifications, and improvements will be apparent to those skilled in the art without departing from the spirit and scope of the claims.

Standard abbreviations for chemical groups such as are well known in the art are used; e.g., Me=methyl, Et=ethyl, i-Pr=isopropyl, Bu=butyl, t-Bu=tert-butyl, Ph=phenyl, Bn=benzyl, Ac=acetyl, Bz=benzoyl, and the like.

BRIEF DESCRIPTION OF THE FIGURES

FIGS. 1A and 1B. Development of the decarboxylative borylation reaction. (FIG. 1A) Carboxylic Acids to Boronic Acids: Strategic Value. (FIG. 1B) Decarboxylative Borylation: Invention and Optimization.

FIG. 2A Standard Reaction conditions: Redox active NHPI ester (1.0 equiv), $NiCl_2.6H_2O$ (10 mol %), L1 (13 mol %), $MgBr_2.OEt_2$ (1.5 equiv), $B_2pin_2$ (3.3 equiv), MeLi (3.0 equiv), THF/DMF (2.5:1), 0° C.-RT, 2 h; examples of primary and secondary boronates; FIG. 2B examples of tertiary boronates and natural products.

(FIG. 3A) Decarboxylative borylation enabled late-stage diversification of Lipitor. (FIG. 3B) Synthesis and biological evaluation of a borono-vancomycin analog. (FIG. 3C) Synthesis and biological evaluation of human Elastase inhibitors.

FIG. 4B inhibitory activities of HNE inhibitors 50-58 as a function of concentration.

DETAILED DESCRIPTION

Figure 2A:
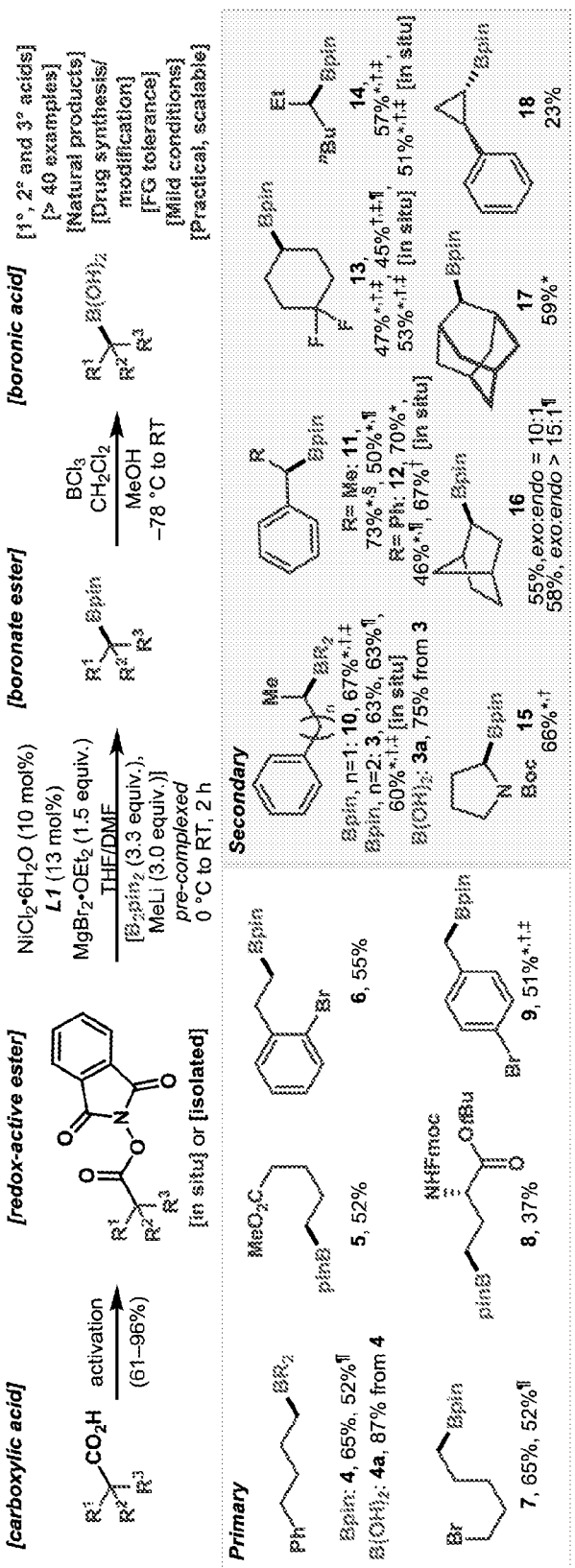
FIGS. 2A and 2B. Scope of the Ni-catalyzed decarboxylative borylation reaction of redox-active esters.

In this report, a simple method for nickel-catalyzed decarboxylative borylation is presented that is mild, scalable, and general across a range of primary, secondary, tertiary, peptidic, and even naturally occurring substrates. A diverse array of boronates which would otherwise require lengthy de novo synthesis were furnished directly from the corresponding carboxylic acids. This method's capacity to directly transform native peptides into α-amino boronic acids has led to the discovery of three potent small molecule elastase inhibitors.

Recent efforts in our laboratory revealed redox active esters (RAEs, e.g., N-hydroxyphthalimide ester 2) derived from alkyl carboxylic acids as convenient surrogates for alkyl halides in nickel or iron catalyzed cross-coupling reactions. These versatile intermediates, most commonly used in amide-bond forming reactions, have enabled practical means of C—C bond formation in various modalities, including decarboxylative Negishi (22-23), Suzuki (24), and Kumada (25) couplings, as well as Giese reactions (26). Although RAEs have yet to be used in carbon-heteroatom cross-coupling reactions, our earlier discoveries, coupled with Fu's (10) pioneering work on nickel catalyzed Miyaura borylation of alkyl halides (11-14), prompted us to investigate the possibility of harnessing them for C—B bond formation, thereby achieving direct conversion of alkyl carboxylic acids into boronic acid derivatives.

Realization of this seemingly straightforward transformation required considerable experimentation. FIG. 1B provides the optimal reaction parameters alongside an abbreviated picture of the optimization process on 2-methyl-4-phenylbutanoic acid. The simple NHPI ester (2) proved to be the optimal substrate for borylation with bis(pinacolato) diboron $(B_2pin_2)$;

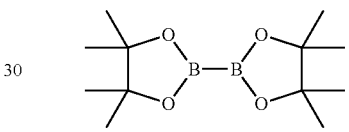

other RAEs such as the tetrachloro-NHPI ester were less effective (entry 1). The inexpensive combination of $NiCl_2.6H_2O$ and bipyridine ligand L1 emerged as the best catalyst system after an exhaustive screening—use of alternative catalysts (see SI) or ligands (entries 3-5) have deleterious effects. Choice of solvent is critical: a binary mixture of THF and DMF gave the optimal result; lower yields were observed in the absence of DMF (entry 6). Pre-mixing methyl lithium with $B_2pin_2$ is necessary to activate the diboron species toward transmetalation; numerous other organometallic reagents surveyed (e.g., entries 8-10) were less effectual, affording borylation products in lower yields if at all. Magnesium salts were also indispensable to the reaction: in the absence of the $MgBr_2.OEt_2$, virtually no products were attained (entries 11-13). Boronoester product 3 can be accessed directly from the carboxylic in comparable yields using a one-pot procedure wherein RAE 2 is formed in situ in a similar vein to amide coupling (entry 14). Overall, the reaction proceeds smoothly at room temperature over the course of 2 hours.

Figure 2B:
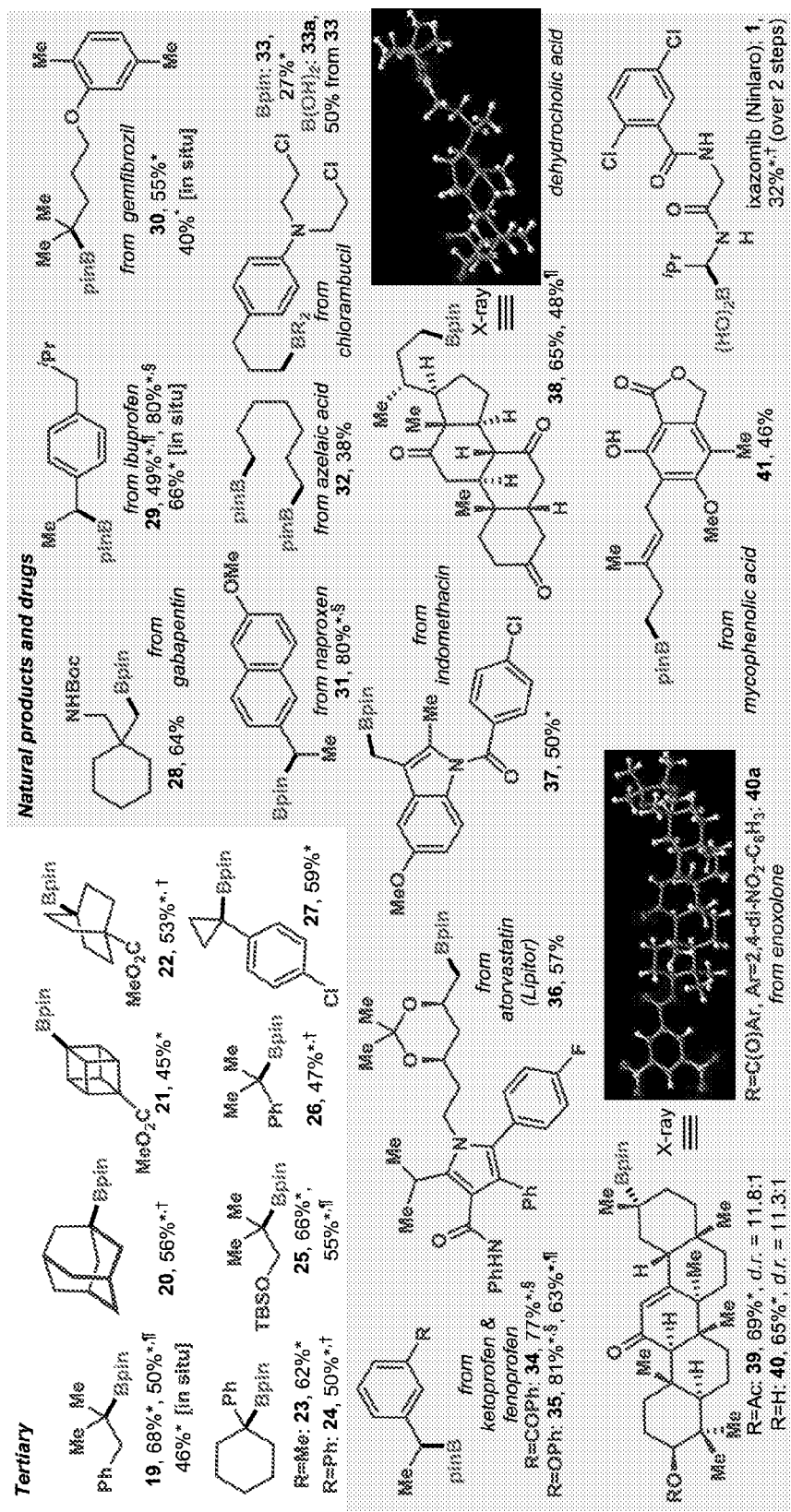

With the optimized conditions in hand, the scope of this methodology was subsequently explored. RAEs derived from a broad selection of primary, secondary, and tertiary carboxylic acids were all found to be viable substrates (FIG. 2). These encompass acyclic, cyclic, caged, bridgehead, fluoroalkyl, and benzylic acids which were transformed to the corresponding Bpin boronate esters smoothly. Scalability of the reaction is evident through the preparation of 29 on a gram scale. Additionally, 12 of the products (3, 4, 7, 11, 12, 13, 16, 19, 25, 29, 35, 38) were obtained in comparable yields when only 2.5 mol % of nickel catalyst (3.3 mol % of ligand) was used, further attesting to the adaptability of this method in a process setting.

As the methyl lithium was pre-mixed with B₂pin₂ to form ate-complexes, strongly nucleophilic/basic organometallic species were sequestered from the substrate: a gamut of functionalities such as ethers (30, 31, 35, 37, 41), esters (5, 8, 21, 22, 39, 41), carbamates/amides (8, 15, 28, 36, 37, 1), ketones (34, 38, 39, 40), olefins (39, 40, 41), and hydroxyl (40, 41) were left unscathed under the mild reaction conditions. Indeed, even the highly base-sensitive Fmoc group was tolerated (see 8). The compatibility with alkyl bromides (7) and chlorides (33) points to the orthogonality of this reaction to halide-based Miyaura borylations. Enoxolone derived boronates 39 and 40 were obtained with similar yields, suggesting that the free hydroxyl group had minimal influence on the reaction. The discrete isolation of RAEs, as alluded to earlier, is not necessary. Tertiary and secondary boronate esters can be prepared directly from carboxylic acids when RAEs are generated in situ. This one-pot procedure also pertains to primary substrates, albeit at lower yields.

Although some of the products presented herein (e.g., 4, 17, 19, 20, 23) can be synthesized from the analogous halides via Miyaura borylation reactions, the starting organohalides are oftentimes not commercially available and require extraneous steps to prepare (usually from the corresponding alcohols). Conversely, the use of readily available carboxylic acids largely circumvents this problem. A great majority of products in FIG. 2 are derived directly from commercially available acids. For instance, 21 was conveniently prepared from a cubane-based carboxylic acid whereas the reported synthesis of the analogous halide enlisted a harsh Hundsdiecker reaction (Br₂ and HgO) on the same acid (29). Furthermore, the scope of this borylation protocol can be extended to amino acid derivatives to furnish α-amino boronate esters such as 15. Synthesis of 15 through halide-based Miyaura borylation is simply not feasible as the corresponding α-amino halide starting material would be unstable. In this regard, the decarboxylative borylation strategy allows explorations of previously elusive chemical space The prevalence of alkyl carboxylic acids is demonstrated by their presence in over 450 approved drug molecules (30). To this end, the impressive chemoselectivity of this reaction offers the unique opportunity to pursue late-stage modifications of bioactive molecules that are densely adorned with reactive functionalities. Over 10 carboxylate containing drug molecule/natural products have been successfully converted into pinacol boronate esters (28-41) which would otherwise only be accessible through multi-step functional group interconversions or de novo syntheses.

Figures 3A, 3B, 3C:
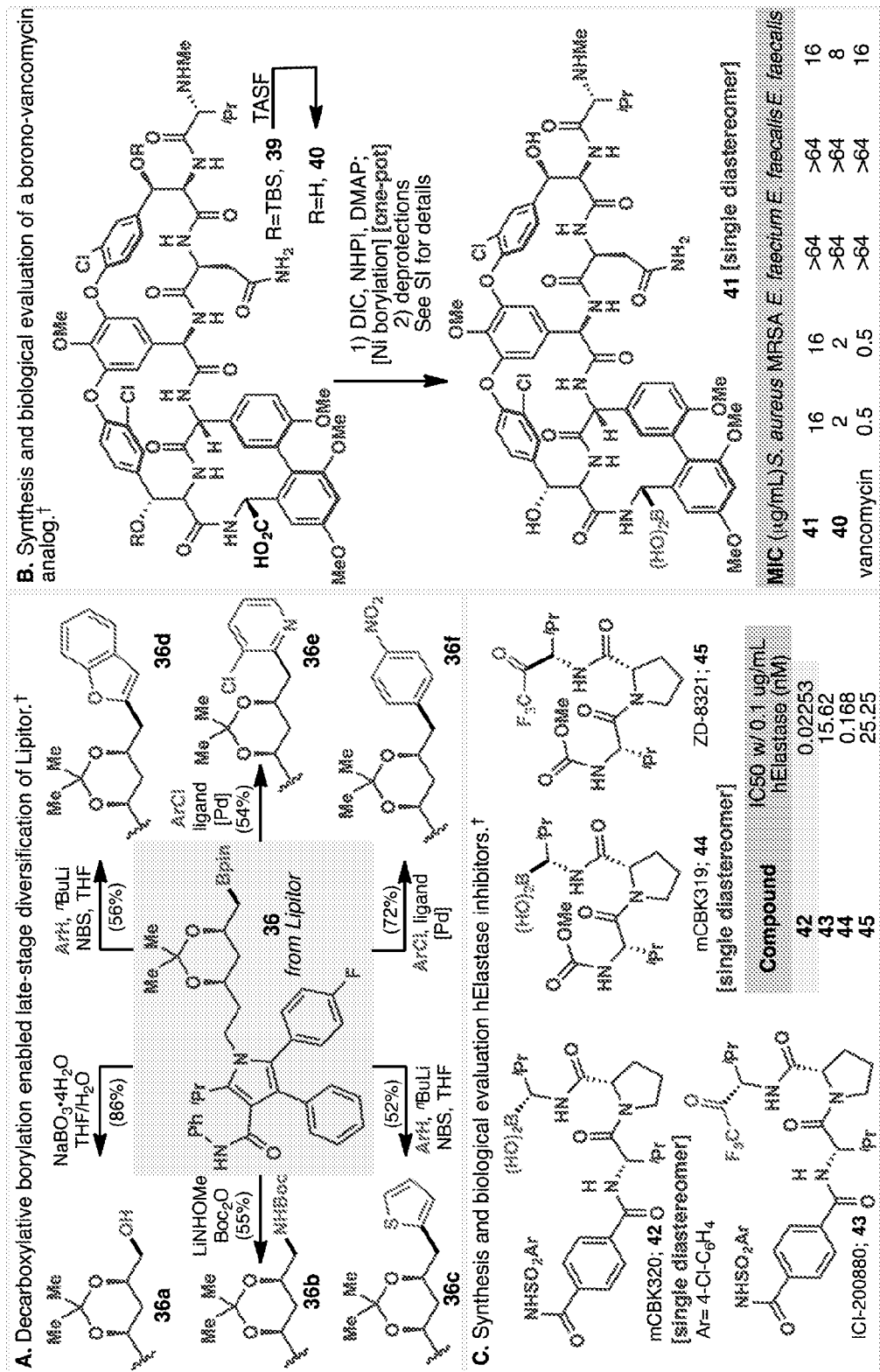
FIGS. 3A, 3B and 3C. Applications of the decarboxylative borylation reaction.

The boronate esters can be conveniently hydrolyzed into the corresponding boronic acids (e.g., 4a, 3a, 33a, 1) (FIG. 2). This allows the transformation of bioactive carboxylic acids into their borono-bioisoteres to identify compounds with superior potency or pharmacokinetic properties. Alternatively, boronate esters could be diversified into a variety of structural motifs (31-33). As an illustrative example, the Lipitor derived Bpin ester (36) can be expediently elaborated into the corresponding alcohol (36a) or carbamate (36b) (34) upon treatment with appropriate oxidants (FIG. 3A). Under conditions reported by Aggarwal, 36c and 36d were directly accessed through reaction with aryllithium species (35). Decarboxylative borylation could also convert RAEs, which are electrophiles in cross-couplings, into Bpin esters that serve as nucleophiles in Suzuki reactions (e.g., 36 to 36e and 36 to 36f) (36). This "umpolung" approach is particularly strategic in the case of 36e whereby the 2-pyridylboronic acid or organozinc species are often not viable Suzuki substrates owing to a lack of stability.

Moreover, selective decarboxylative borylation at the C-terminus of native peptides allowed rapid access to coveted α-amino boronic acids which are privileged medicinal chemistry motifs (18, 37). Ninlaro (1), for example, was obtained in three steps from a simple peptide (FIG. 2). This opens up a distinct dimension to the study of peptide-based therapeutics: in perhaps the most striking example, vancomycin was converted into a boronic acid analogue (44) through the decarboxylative borylation of 42 (FIG. 3B) (38).

This process proceeded smoothly in the presence of four methylated phenoxy groups, two TBS-protected hydroxyls, two aryl chlorides, six secondary amides, one primary amide, one secondary amine, and seven epimerizable stereocenters. Although 44 showed less activity compared to the parent acid 43, such remarkable chemoselectivity still attests to the potential utility of this reaction.

Unpredictable stereoselectivity of radical processes oftentimes presents a hurdle to their broad adoption in late-stage modifications of drug leads or natural products. Complex α-amino boronic acid 44 was obtained as a single diastereomer in this radical-based decarboxylative borylation reaction. This result prompted us to investigate the stereoselectivity of the decarboxylative borylation on several dipeptides (FIG. 3D). We found that increased steric bulk on the N-terminal residue resulted in better diastereoselectivity: though both diastereomers were furnished in almost equal quantities for 45, higher selectivities were observed for 46 and 47. Meanwhile, 46 was obtained in the same diastereomeric ratio from Boc-l-Val-l-Val and Boc-l-Val-d-Val. Lower reaction temperatures could also be used to enhance the stereoselectivity. At −15° C., 48 was furnished in greater than 5 to 1 d.r., enabling a stereoselective synthesis of Velcade (49) in a short sequence.

Figure 4A:
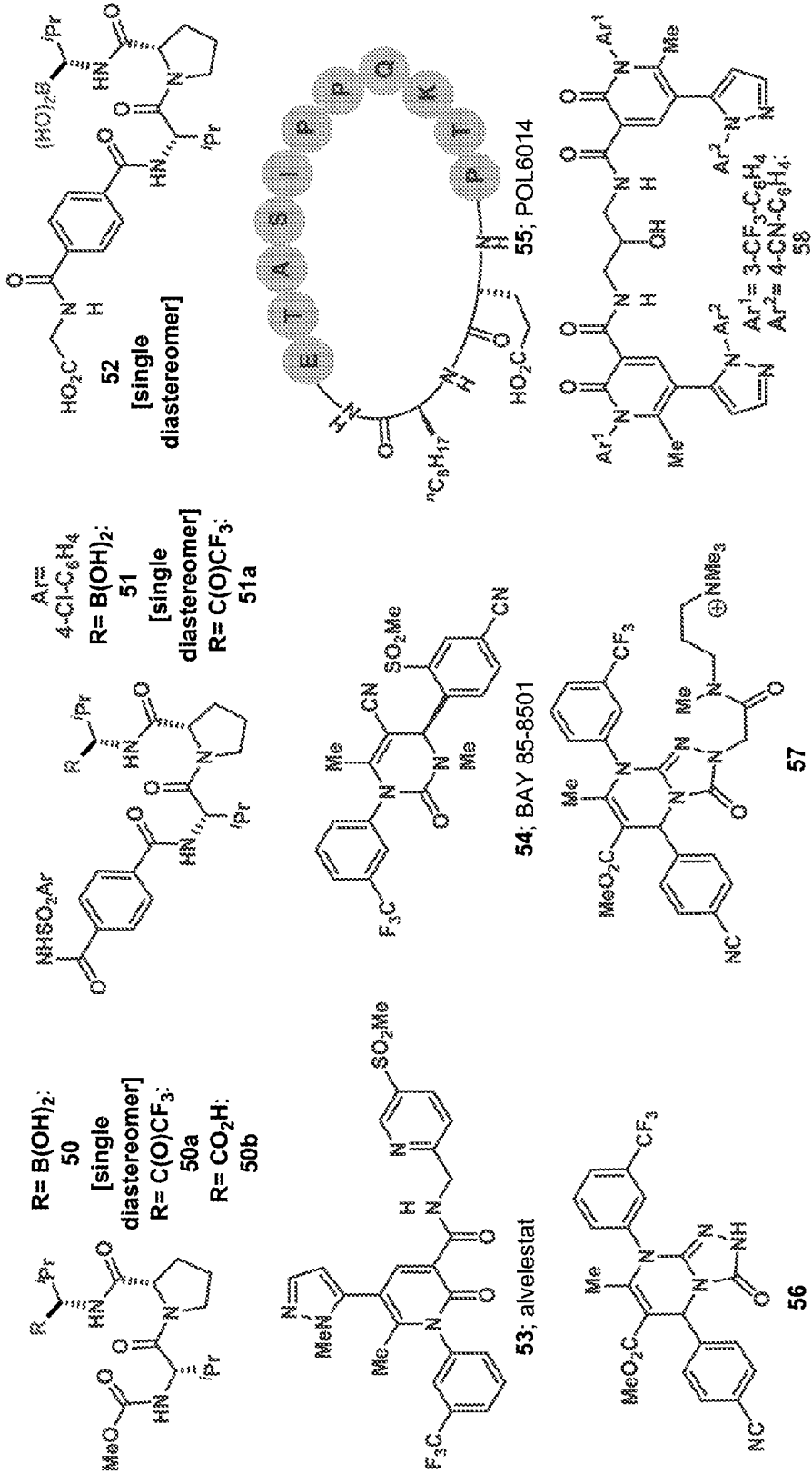
FIGS. 4A and 4B. Discovery of novel human neutrophil elastase (HNE) inhibitors, FIG. 4A compounds tested.

By wedding the rich medicinal potential of boronates to the ubiquity of alkyl carboxylic acids, the decarboxylative borylation reaction has the potential to open up new vistas in drug development. For example, application of the decarboxylative borylation reaction to readily available dipeptides allowed the expedient preparations of 50-52 which were formed as single diastereomers and found to be potent inhibitors of human neutrophil elastase (HNE) (FIGS. 4A and B). Notably, the carboxylic acid precursor to 50 (50b) was found to be devoid of any inhibitory activities while 50 and 51 displayed substantially enhanced potency compared to their trifluoroketones congeners (50a and 51a), which have been examined in phase II clinical trials for lung diseases such cystic fibrosis (39-45). HNE, a highly active serine protease, plays a pivotal role in the immune response, tissue remodelling, and the onset/resolution of inflammation by breaking down mechanically important structures of the body's cellular matrix as well as proteins of foreign origin (46). While five generations of HNE inhibitors have been evaluated clinically in multiple inflammatory lung diseases (e.g., cystic fibrosis, emphysema, and bronchiectasis), none have been overwhelmingly efficacious in humans to make a significant impact in these conditions (46).

Toward this end, 52 exhibited an $IC_{50}$=15 pM (Ki=3.7 pM) while 51 exhibited an $IC_{50}$=30 pM (Ki=34 pM) against purified HNE. The $IC_{50}$ values were determined head-to-head with other pre-clinically and clinically validated HNE inhibitors (53-57), including BAY 85-8501 (54, a leading clinical candidate with reported Ki=80 pM) (47), 55 (POL6014, a phase I peptide-based clinical candidate for cystic fibrosis) (48) as well as 56 and 57 (reported by Chiesi Pharmaceuticals) (49). Additionally, 51 and 52 retained much of their inhibitory activities in sputum samples of cystic fibrosis (CF) and chronic obstructive pulmonary disease (COPD) patients, underscoring their potency in the context of a more patho-physiologically relevant environment than the traditional biochemical assay. Conversely, while dimeric compound 58 from AstraZeneca (IC50=11 pM, Ki=2.7 pM) (50), and BAY 85-8501 (54) showcased low $IC_{50}$ values, their potencies diminished drastically in patient derived sputum. Comparison of the LipE values in COPD sputum revealed that the superior potency of 52 is not driven by increased lipophilicity (10.2 versus 9.45 for 57) (51).

Additionally, the $IC_{50}$ value of 52 was found to remain unchanged with increasing incubation times (between 5-60 minutes) while that of 58, a non-covalent inhibitor exhibited a 55-fold increase in potency under the same conditions. These data retain the profile that is expected: compound 52 is behaving like a partial mechanism-based inhibitor (or a covalent reversible inhibitor) likely due to the potentially slow off-rate of the α-amino boronic acid. This correlates with tighter binding and potentially long residence time seen in other amino boronic acid compounds unlike the many reversible elastase inhibitors (i.e. 58) (52). Clinically, this mechanism has been proven successfully through Velcade (49), which inhibits the catalytic site of the 26S proteasome-covalent reversible bonding between the boronate and the nucleophilic oxygen results in a slow disassociation rate (53-54). As most clinical elastase inhibitors (such as 54, BAY 85-8501, one of the most potent molecules reported to date) are non-reactive, reversible, transition state inhibitors, 52's high potency and the inherent mechanism of the amino boronic acids could help address these limitations. Through this "hybrid" enzymatic inhibitory approach (based upon Fischer's Lock and Key model/Ehrlich's Pharmacophore Model), boronic acids such as 52, which combine a rapid, potent binding with a slow off-rate, may effectively restore the protease versus anti-protease balance in a clinical setting. They could therefore be tuned toward lung-specific clinical applications rapidly.

To further evaluate the therapeutic potential of 51 and 52, the in vitro ADME properties were probed to determine if any deleterious effects of the boronate replacements of the ketone would be revealed (FIG. 4C). These amino boronic acids displayed comparable kinetic solubility to the trifluoromethyl ketone analog (51a). A substantial portion (90% and 79% respectively) of 51 and 52 were found to be intact in CD-1 mouse plasma over 2 hours. 51 and 52 exhibited similar metabolic stability as the trifluoroketone 51a. 51 and 51a also demonstrated similar levels of permeability in Caco-2 cells (See Page 176 of the supplementary information). These data suggest that the novel boronates simply improve potency without changing the drug-like properties of their ketone congeners.

Method Summary:

Procedurally, the conversion of redox active esters into boronate esters is achieved in three stages: namely, the preparation of catalyst mixture, the preparation of [$B_2pin_2Me$]Li complex and the nickel catalyzed decarboxylative borylation reaction. An abbreviated experimental protocol is presented herein with a graphical guide. Comprehensive information on the commercial source and purity of chemicals or variations in experimental details for different substrate classes can be found in the supplementary information.

Preparation of $NiCl_2.6H_2O$/Ligand Stock Solution or Suspension:

A flask charged with $NiCl_2.6H_2O$ (1.0 equiv.) and ligand (L1 or L2, 1.3 equiv.) was evacuated and backfilled with argon for three times. THF (the concentration of $NiCl_2.6H_2O$ was 0.025 M) or DMF (the concentration of $NiCl_2.6H_2O$ was 0.050 M) was added. The resulting mixture was stirred at room temperature overnight (or until no granular $NiCl_2.6H_2O$ was observed) to afford a green solution or suspension. [Note: All the solutions or suspensions kept under argon can be used for several days without appreciable deteriorations in reaction yields.]

Preparation of [$B_2Pin_2Me$]Li Complex:

To a solution of $B_2pin_2$ (1.1 equiv.) in THF (the concentration of $B_2pin_2$ was 1.1 M) was added MeLi (1.6 M in $Et_2O$, 1.0 equiv.) at 0° C. under argon. The reaction mixture was warmed to room temperature and stirred for 1 h to afford a milky white suspension.

Ni-Catalyzed Decarboxylative Borylation:

A flask charged with the redox-active ester (1.0 equiv.) and $MgBr_2.OEt_2$ (1.5 equiv.) was evacuated and backfilled with argon for three times. Catalyst solution or suspension (containing 10 mol % of $NiCl_2.6H_2O$ and 13 mol % of ligand) was added via a syringe. When a catalyst suspension/solution in DMF was used, an additional portion of THF (twice the volume of the DMF suspension/solution needed) was added to the reaction vessel prior to the addition of the catalyst mixture [this process can be exothermic on large scales and cooling (with ice/water bath) may be necessary]. The resulting mixture was stirred vigorously until no visible solid was observed at the bottom of the reaction vessel [this was found to be accelerated by sonication]. This mixture was cooled to 0° C. before a suspension of [$B_2pin_2Me$]Li in THF (3 equiv.) was added in one portion. After stirring for 1 hour at 0° C., the reaction was warmed to room temperature and stirred for another 1 hour. When thin layer chromatography (TLC) analysis indicated the completion of the reaction, the reaction was quenched with aqueous HCl (0.1 M) or saturated aqueous $NH_4Cl$ and extracted with diethyl ether ($Et_2O$) or ethyl acetate (EtOAc). Alternatively, on larger scales, as is the case shown in FIG. 5, the reaction mixture was directly poured onto $Et_2O$ and the resulting suspension was filtered through a pad of silica gel and celite. Purification by column chromatography afforded the desired boronate ester.

Through the exclusive use of N-hydroxy-phthalimide redox active esters, a simple means to interconvert two functional groups of paramount importance in organic chemistry has been enabled. The practicality and chemoselectivity are illustrated through numerous complex substrates including drug molecules. The broad scope, epitomized by the ability to directly transform native peptides into borono-isosteres in good stereoselectivities, is unmatched by halide-based Miyaura-Suzuki protocols. Alkyl boronates can be introduced at any stages of a synthesis, reshaping the strategic paradigm toward their preparations. By wedding the rich medicinal potentials of boronates to the ubiquity of alkyl carboxylic acids, this method will likely open up new vistas in drug development. This is already evident from the discovery of mCBK 320, a highly potent elastase inhibitor with potentials in cancer therapy.

DOCUMENTS CITED

1. A. Suzuki, *Angew. Chem. Int. Ed.* 50, 6722 (2011).
2. W. L. A. Brooks, B. S. Sumerlin, *Chem. Rev.* 116, 1375 (2016).
3. S. D. Bull, et al. *Acc. Chem. Res.* 46, 312 (2013).

4. P. C. Trippier, C. McGuigan *Med. Chem. Commun.* 1, 183 (2010).
5. A. Draganov, D. Wang, B. Wang, *Top. Med. Chem.* 17, 1 (2016).
6. C. Ballatore, D. M. Huryn, A. B. Smith, *ChemMedChem* 8, 385 (2013).
7. R. Smoum, A. Rubinstein, V. M. Dembitsky, M. Srebnik, *Chem. Rev.* 112, 4156 (2012).
8. H. C. Brown, *Hydroboration* (Benjamin/Cummings, 1980).
9. C. M. Vogels, S. A. Westcott, *Curr. Org. Chem.* 9, 687 (2005).
10. A. S. Dudnik, G. C. Fu, *J. Am. Chem. Soc.* 134, 10693 (2012).
11. T. C. Atack, R. M. Lecker, S. P. Cook, *J. Am. Chem. Soc.* 136, 9521 (2014).
12. R. B. Bedford et al., *Organometallics* 33, 5940 (2014).
13. C.-T. Yang et al., *Angew. Chem. Int. Ed.* 51, 528 (2012).
14. H. Ito, K. Kubota, *Org. Lett.* 14, 890 (2012).
15. H. C. Brown, T. E. Cole, *Organometallics* 2, 1316 (1983).
16. K.-s. Lee, A. R. Zhugralin, A. H. Hoveyda, *J. Am. Chem. Soc.* 131, 7253 (2009).
17. J. A. Schniffner, K. Mither, M. Oestreich, *Angew. Chem. Int. Ed.* 49, 1194 (2010).
18. P. Andres, G. Ballano, M. Isabel Calaza, C. Cativiela, *Chem. Soc. Rev.* 45, 2291 (2016).
19. M. A. Beenen, C. An, J. A. Ellman, *J. Am. Chem. Soc.* 130, 6910 (2008).
20. I. A. Mkhalid, J. H. Barnard, T. B. Marder, J. M. Murphy, J. F. Hartwig, *Chem. Rev.* 110, 890 (2010). E. J. Olhava, M. D. Danca, U.S. Pat. No. 7,442,830B1 (2008).
21. T. Qin et al., *Science* 352, 801 (2016).
22. J. Cornella et al., *J. Am. Chem. Soc.* 138, 2174 (2016).
23. J. Wang et al., *Angew. Chem. Int. Ed.* 55, 9676 (2016).
24. F. Toriyama et al., *J. Am. Chem. Soc.* 138, 11132 (2016).
25. T. Qin et al., *Angew. Chem. Int. Ed.* 55, 266 (2016).
26. T. Hatakeyama et al., *J. Am. Chem. Soc.* 132, 10674 (2010).
27. R. B. Bedford et al., *Chem. Eur. J.* 20, 7935 (2014).
28. R. A. Hussainy et al., *J. Med. Chem.* 54, 3480 (2011).
29. P. Lassalas et al., *ACS Med. Chem. Lett.* 59, 3183 (2016).
30. J. Schmidt, J. Choi, A. Liu, M. Slusarczyk, G. C. Fu, *Science* 354, 1265 (2016).
31. Y. Xi, J. Hartwig, *J. Am. Chem. Soc.* 138, 6703 (2016).
32. G. A. Molander, N. Ellis, *Acc. Chem. Res.* 40, 275 (2007).
33. S. N. Mlyanrski, A. S. Karns, J. P. Morken, *J. Am. Chem. Soc.* 134, 16449 (2012).
34. A. Bonet, M. Odachowski, D. Leonori, S. Essafi. V. K. Aggarwal, *Nat. Chem.* 6, 584 (2014).
35. S. Laulhé, J. M. Blackburn, J. L. Roizen, *Org. Lett.* 18, 4440 (2016). V. M. Dembitsky, M. Srebnik, *Tetrahedron* 59, 579 (2003). J. J. McAtee, S. L. Castle, Q. Jin, D. L. Boger, *Bioorg. Med. Chem. Lett.* 12, 1319 (2002).
36. P. R. Bernstein et al., *J. Med. Chem.* 37, 1259 (1994).
37. C. A. Veale et al., *J. Med. Chem.* 40, 3173 (1997).
38. P. R. Bernstein et al., *J. Med. Chem.* 38, 212 (1995).
39. J. P. Burkhart et al., *J. Med. Chem.* 37, 223 (1995).
40. P. D. Edwards et al., *J. Med. Chem.* 40, 1876 (1997).
41. K. Hemmi, I. Shima, K. Imai, H. Tanaka, EP0494071A2 (1992).
42. T. Kinoshita, I. Nakanishi, A. Sato, T. Tada, *Bioorg. Med. Chem. Lett.* 13, 21 (2003).
43. F. von Nussbaum, V. M.-J. Li, *Bioorg. Med. Chem. Lett.* 25, 4370 (2015).
44. F. von Nussbaum, et al., *ChemMedChem* 10, 1163 (2015).
45. F. Otto, et al., WO 2015096873 (2015).
46. T. J. Blench, et al., WO2013037809A1 (2013).
47. L. Bergstrom, M. Lundkvist, H. Lönn, P. Sjö, WO2008030158 A1 (2008).
48. M. D. Schultz, *Bioorg. Med. Chem. Lett.* 23, 5992 (2013).
49. A. Zervosen, et al., *J. Am. Chem. Soc.* 133, 10839 (2011).
50. M. Groll, C. R. Berkers, H. L. Ploegh, H. Ovaa, *Structure* 14, 451 (2006).
51. M. D. Schultz, *Bioorg. Med. Chem. Lett.* 23, 5992 (2013).
52. A. Zervosen, et al., *J. Am. Chem. Soc.* 133, 10839 (2011).
53. M. Groll, C. R. Berkers, H. L. Ploegh, H. Ovaa, *Structure* 14, 451 (2006).
54. 54. A. F. Kisselev, W. A. van der Linden, H. S. Overkleeft, *Chem. Biol.* 19, 99 (2012).
55. 55. S. P. Thomas, M. D. Greenhalgh, *Chem. Commun.* 49, 11230 (2013).
56. Y. Wen, J. Xie, C. Deng, C. Li, *J. Org. Chem.* 80, 4142 (2015).
57. S. Roesner, et al., *Chem. Commun.* 50, 4053 (2014).
58. J. Yi, et al., *Adv. Synth. Catal.* 354, 1685 (2012).
59. J. Hu, et al., *J. Org. Chem.* 81, 14 (2016).
60. A. Chen, L. Ren, C. M. Crudden, *J. Org. Chem.* 64, 9704 (1999).
61. T. Furukawa, et al., *Bioorg. Med. Chem.* 20, 2002 (2012).
62. D. L. Boger, et al., *J. Am. Chem. Soc.* 120, 8920 (1998).
63. CLSI document M07-A9 of *Methods for Dilution Antimicrobial Susceptibility Tests for Bacteria That Grow Aerobically* (Clinical and Laboratory Standards Institute: Wayne, Pa., 9th Ed., 2012).
64. S. Kokinaki, L. Leondiadia, N. Ferderigos, *Org. Lett.* 7, 1723 (2005).
65. T. Miyazawa, S. Hiramatsu, Y. Tsuboi, T. Yamada, S. Kuwata, *Bull. Chem. Soc. Jpn.* 58, 1976 (1985).
66. J. Liu, K. R. West, C. R. Bondy, K. M. Sanders, *Org. Biomol. Chem.* 5, 778 (2007).
67. A. W. Buesking, V. Bacauanu, I. Cai, J. A. Ellman, *J. Org. Chem.* 79, 3671 (2014).
68. R. A. Copeland, *Evaluation of Enzyme Inhibitors in Drug Discovery A Guide for Medicinal Chemists and Pharmacologists* (Wiley, New York, 2005).

EXAMPLES

Boronic Acid Inhibitors of Human Neutrophil Elastase Prepared by Method of the Invention Compounds for Disclosure ($IC_{50}$ on Human Neutrophil Elastase)

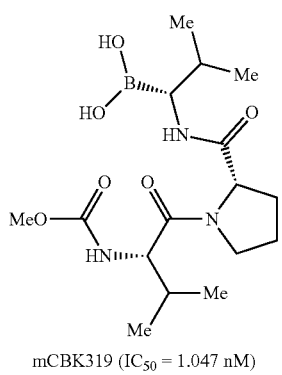

mCBK319 ($IC_{50}$ = 1.047 nM)

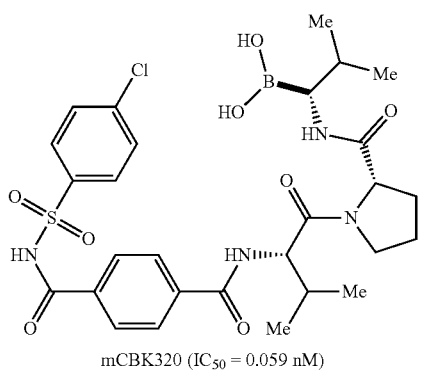
mCBK320 (IC$_{50}$ = 0.059 nM)
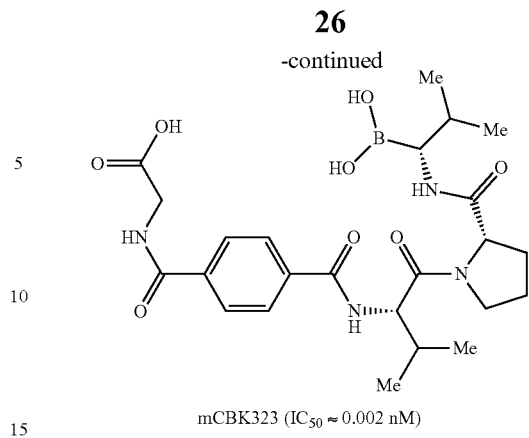
mCBK323 (IC$_{50}$ ≈ 0.002 nM)
Synthetic Routes to Boronic Acid Inhibitors of Human Neutrophil Elastase
Preparation of mCBK319
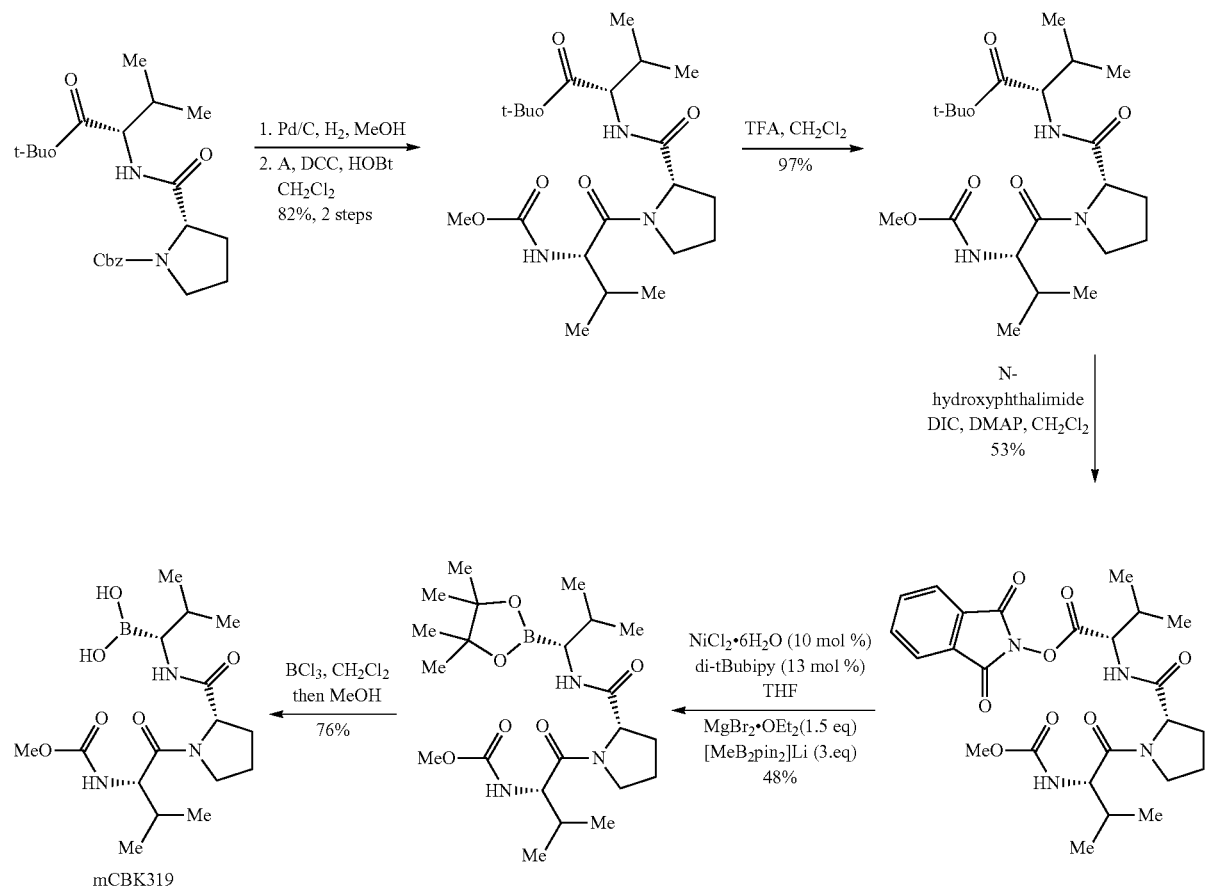
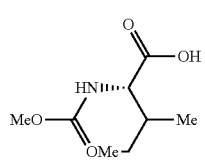

Preparation of mCBK320 and mCBK323
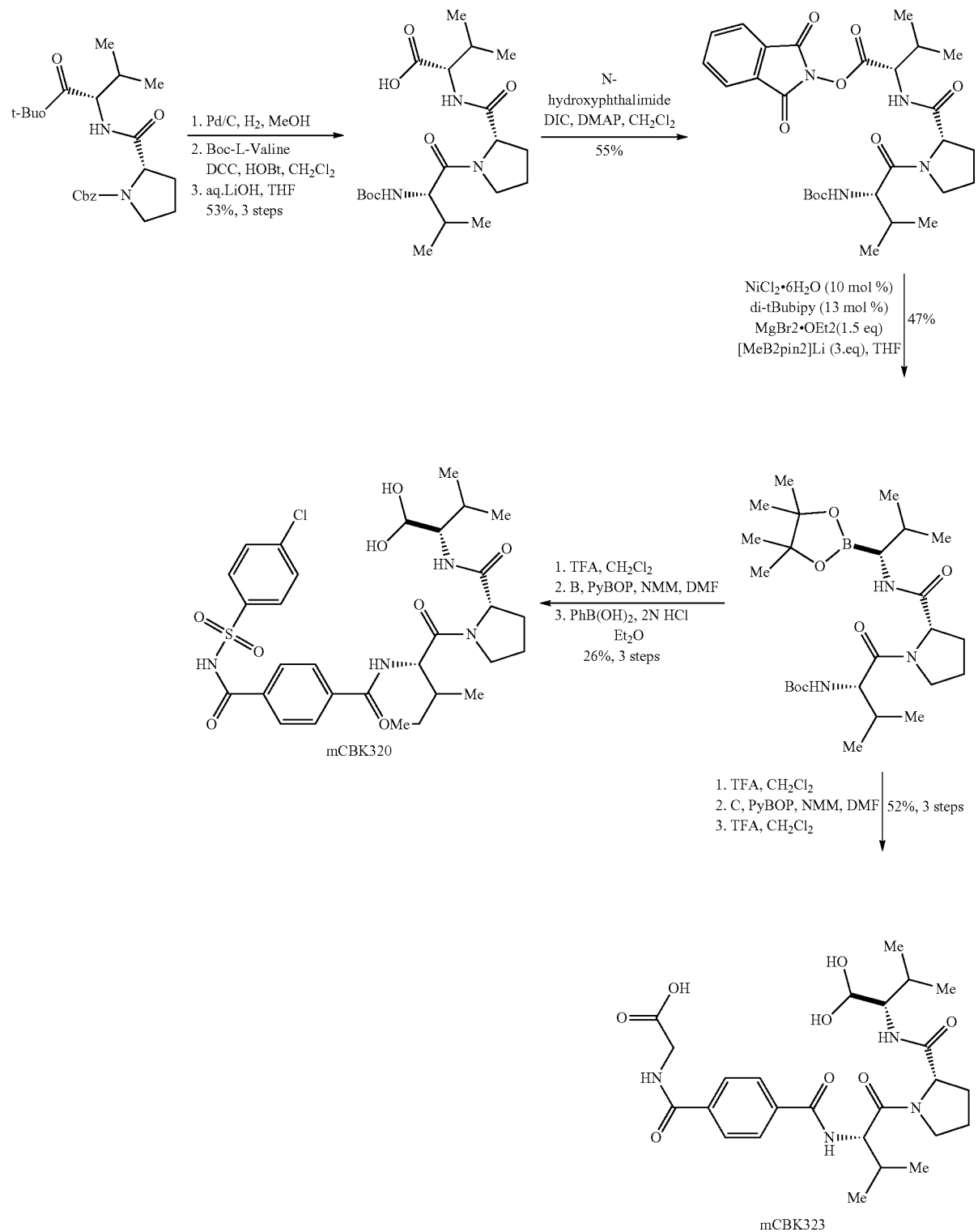

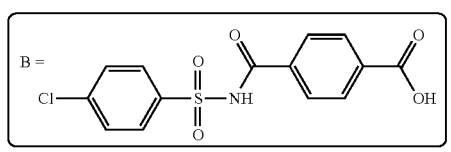

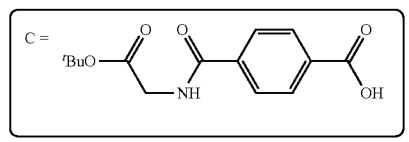

All three compounds (mCBK319, mCBK320, and mCBK323) were found to possess a high propensity toward trimerization at the boronic acid motif. The bioactivities of these trimers may warrant further investigations. These novel elastase inhibitors have potential applications as therapeutics for cancer, cycstic fibrosis, and bronchiectasis.

The compounds have displayed enhanced potency compared to lead compounds screened (100-1000 fold increase compared to the analogous trifluoroketone lead compounds) as elastase inhibitors. The unique physiochemical properties of the boronic acid motif may give rise to favorable pharmacokinetic attributes. The processes for preparation disclosed herein are concise and easily amenable for scale up.

General Information

Tetrahydrofuran (THF), N,N-dimethylformamide (DMF), acetonitrile (CH3CN) dichloromethane (CH2Cl2) were obtained by passing the previously degassed solvents through activated alumina columns. Other solvents and reagents were purchased at the highest commercial quality and used without further purification, unless otherwise stated.

Yields refer to chromatographically and spectroscopically (1H-NMR) homogeneous material, unless otherwise stated. Reactions were monitored by GC/MS, LC/MS, and thin layer chromatography (TLC). TLC was performed using 0.25 mm E. Merck silica plates (60F-254), using short-wave UV light as visualizing agent, as well as potassium permanganate (KMnO$_4$) or ceric ammonium molybdate (CAM) and heat as developing agents. NMR spectra were recorded on Bruker DRX-600, DRX-500 or DPX-400 instruments and are calibrated using residual undeuterated solvent (1H: δ 7.26 for CDCl3, δ 3.31 for MeOH-d4, δ 3.58, 1.73 for THF-d8, δ 2.50 for DMSO-d6, δ 2.05 for acetone-d6; 13C: δ 77.16 for CDCl3, δ 49.0 for MeOH-d4, δ 67.6, 25.5 for THF-d8, δ 39.50 for DMSO-d6, δ 29.84 for acetone-d6). The following abbreviations were used to explain multiplicities: s=singlet, d=doublet, t=triplet, q=quartet, m=multiplet, br=broad. Column chromatography was performed using E. Merck silica gel (60, particle size 0.043-0.063 mm), and preparative TLC was performed on 0.25 mm E. Merck silica plates (60F-254). High resolution mass spectra (HRMS) were recorded on an Agilent LC/MSD TOF mass spectrometer by electrospray ionization time of flight reflectron experiments. Preparative high performance liquid chromatography (HPLC) was performed using an Agilent SD-1 prepstar system equipped with Phenomenex Gemini 10 μm C18 column with dimension 200×50 mm. Melting points were recorded on a Fisher-Johns 12-144 melting point apparatus and are uncorrected. All X-ray diffraction data were collected and analyzed by the UCSD small molecule X-ray facility. The deactivated silica gel (35 wt % H$_2$O) was prepared by mixing silica gel and deionized water, followed by vigorous shaking until a fluffy powder was observed.

B$_2$pin$_2$ is bis(pinacolato)diboron.

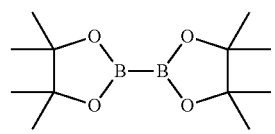

NHPI is N-hydroxyphthalimide. TCNHPI is tetrachloro-N-hydroxyphthalimide. Standard abbreviations for chemical groups such as are well known in the art are used; e.g., Me=methyl, Et=ethyl, i-Pr=isopropyl, Bu=butyl, t-Bu=tert-butyl, Ph=phenyl, Bn=benzyl, Ac=acetyl, Bz=benzoyl, TBS=dimethyl-t-butylsilyl, Boc=t-butoxycarbonyl, and the like.

Preparative HPLC was performed using an Agilent SD-1 prepstar system equipped with Phenomenex Gemini 10 μm C18 column with dimension 200×50 mm. Melting points were recorded on a Fisher-Johns 12-144 melting point apparatus and are uncorrected. All X-ray diffraction data were collected and analyzed by the UCSD small molecule X-ray facility. The deactivated silica gel (35 wt. % H2O) was prepared by mixing silica gel and deionized water, followed by vigorous shaking until a fluffy powder was observed.

General Procedure for the Synthesis of Redox-Active Esters (RAEs) (General Procedure A)

A round bottom flask was charged with the carboxylic acid (1.0 equiv), N-hydroxyphthalimide (NHPI, 1.0 equiv) or tetrachloro-N-hydroxyphthalimide (TCNHPI, 1.0 equiv) and DMAP (0.1 equiv). CH2Cl2 (0.2 M) was added, followed by N,N'-diisopropylcarbodiimide (DIC, 1.1 equiv), both at room temperature. The mixture was allowed to stir at room temperature until all the acid was consumed (as indicated by TLC). The resulting mixture was quickly filtered and the solid residue was rinsed with more CH2Cl2. The filtrate was concentrated in vacuo and purified by flash column chromatography to afford the corresponding redox-active esters, which were used without further purification unless otherwise noted.

Optimization Details

All reactions were screened based on 0.1 mmol scale. The optimization started with S1. TCNHPI esters were used in the initial screening since earlier conditions indicated better performance than NHPI esters (NHPI esters were used in the optimized conditions in the end.

TABLE 1
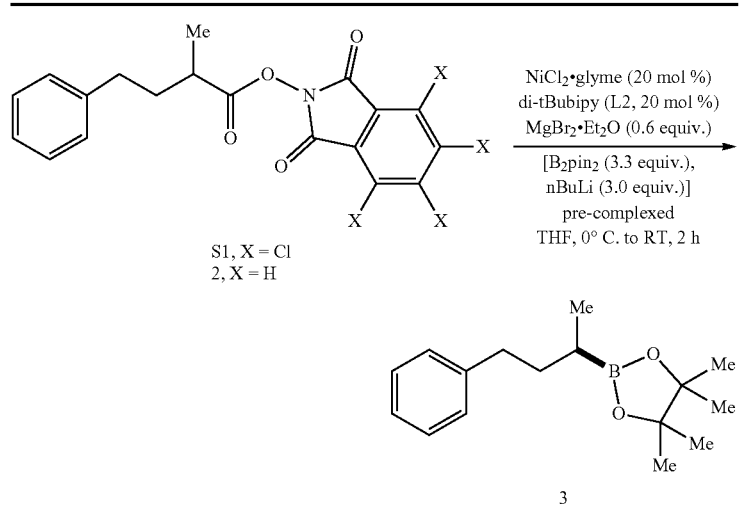
| RAEs | Yield* |
|---|---|
| X = H | 31% |
| X = Cl | 45% |
*Yields determined by GC-FID with dodecane as internal standard.
TABLE 2
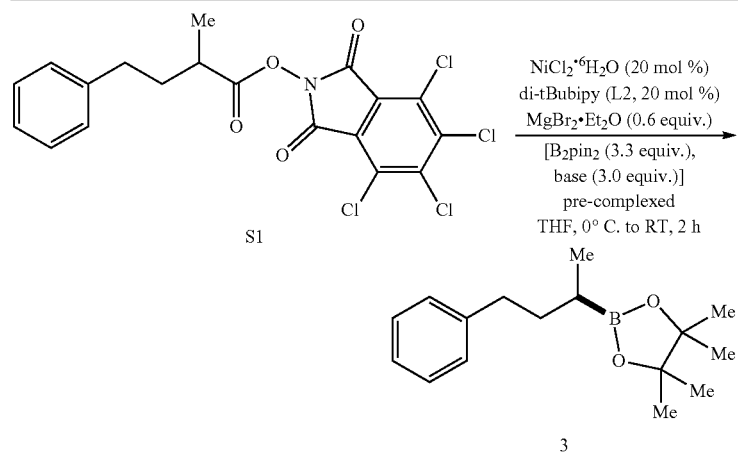
| Base | Yield* |
|---|---|
| w/o base | 0 |
| MeLi | 58% (54%[†]) |
| MeLi·LiBr | 58% |
| nBuLi | 45% |
| tBuLi | 36% |
| MeMgBr | 11% |
| MeMgBr (w/o MgBr$_2$) | 7% |
| EtMgBr | 10% |
| EtOK | 0 |
| tBuOK | 0 |
| MeOLi | 0 |
| NaHMDS | 0 |
| KHMDS | 0 |
| LiHMDS | 0 |
| KF | 0 |
| CsF | 0 |
*Yields determined by GC-FID with dodecane as internal standard. [†]Isolated yield.

TABLE 3

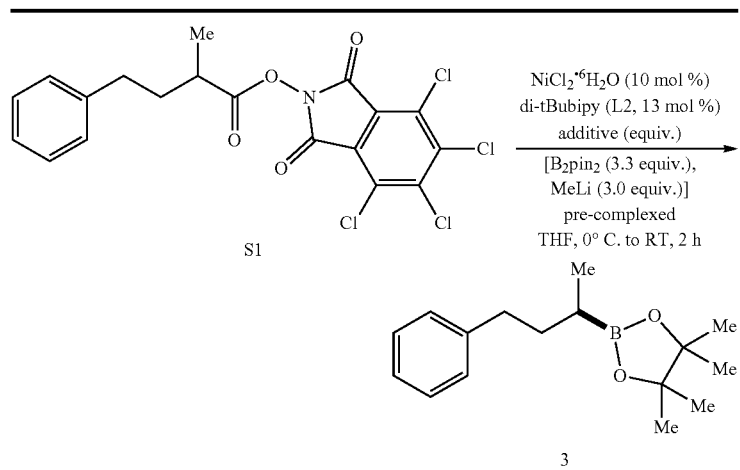

| Additive (equiv.) | Yield* |
| --- | --- |
| w/o | 4% |
| Mg(OAc)₂ (1.5 equiv.) | <1% |
| Mg(acac)₂ (1.5 equiv.) | <1% |
| MgCl2 (1.5 equiv.) | 13% |
| MgSO₄ (1.5 equiv.) | <1% |
| LiBr (3.0 equiv.) | 34% |
| ZnCl₂ (1.5 equiv.) | 14% |
| MgBr₂·OEt₂ (0.2 equiv.) | 23% |
| MgBr₂·OEt₂ (0.6 equiv.) | 53% |
| MgBr₂·OEt₂ (1.0 equiv.) | 64% |
| MgBr₂·OEt₂ (1.5 equiv.) | 67% (63%[†]) |
| MgBr₂·OEt₂ (2.0 equiv.) | 66% |
| MgBr₂·OEt₂ (2.5 equiv.) | 57% |

*Yields determined by GC-FID with dodecane as internal standard. [†]Isolated yield.

TABLE 4

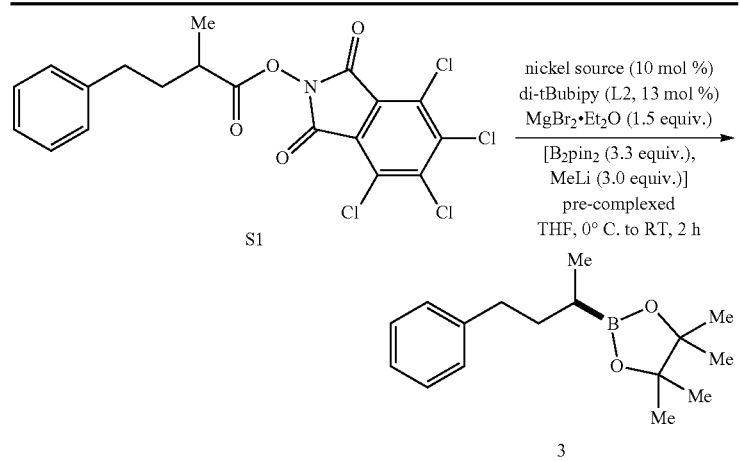

| Nickel source | Yield* |
| --- | --- |
| NiCl₂·6H₂O | 67% (63%[†]) |
| NiCl₂·glyme | 58% |
| NiBr₂·glyme | 63% |
| NiI₂ | 14% |
| Ni(acac)₂·2H₂O | 17% |
| Ni(ClO₄)₂ | 3% |
| Ni(PCy)₃Cl₂ | 4% |
| w/o nickel | 0 |

*Yields determined by GC-FID with dodecane as internal standard. [†]Isolated yield.

TABLE 5
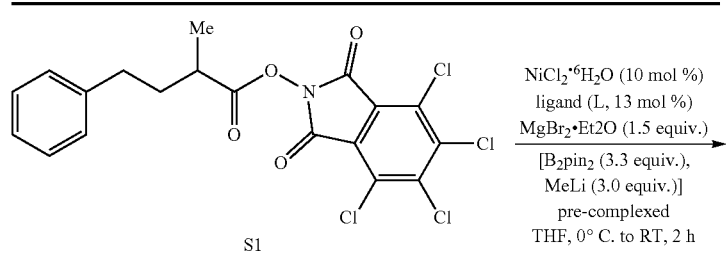
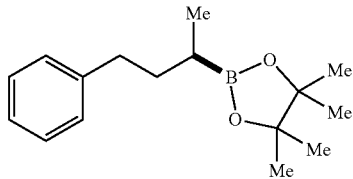
| Ligand | Yield* |
| --- | --- |
| L2 | 67% (63%[†]) |
| L2 (20 mol %) | 57% |
| L1 | 51% |
| L3 | 23% |
| L4 | 26% |
| L5 | 4% |
| L6 | 0 |
| L7 | 13% |
| L8 | 11% |
| L9 | 17% |
| L10 | 0 |
| L11 | 0 |
| L12 | 1% |
| L13 | 1% |
| L14 | 0 |
| L15 | 1% |
| L16 | 1% |
| w/o ligand | 0 |
*Yields determined by GC-FID with dodecane as internal standard. [†]Isolated yield.
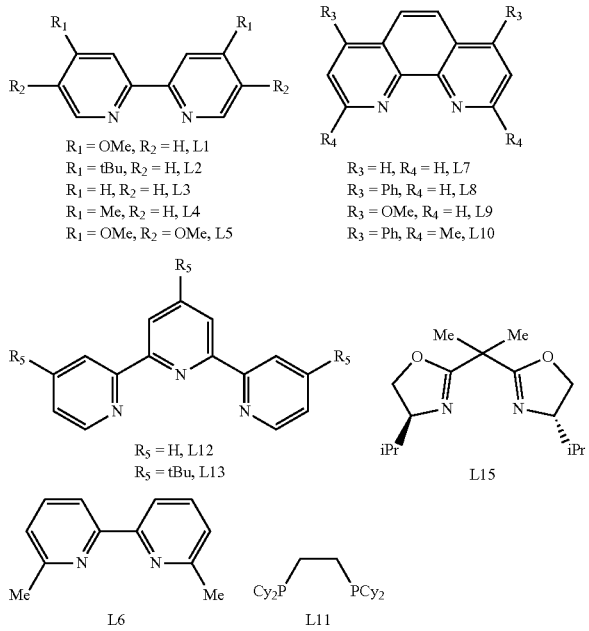

TABLE 5-continued
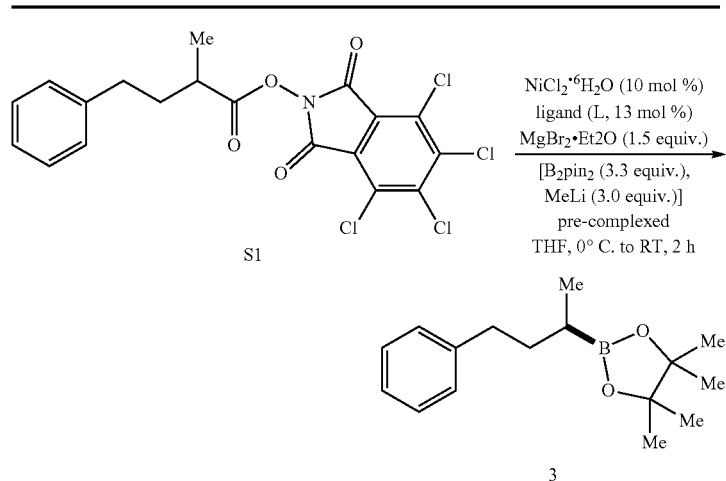
| Ligand | Yield* |
|---|---|
| L14, L16 | |
TABLE 6
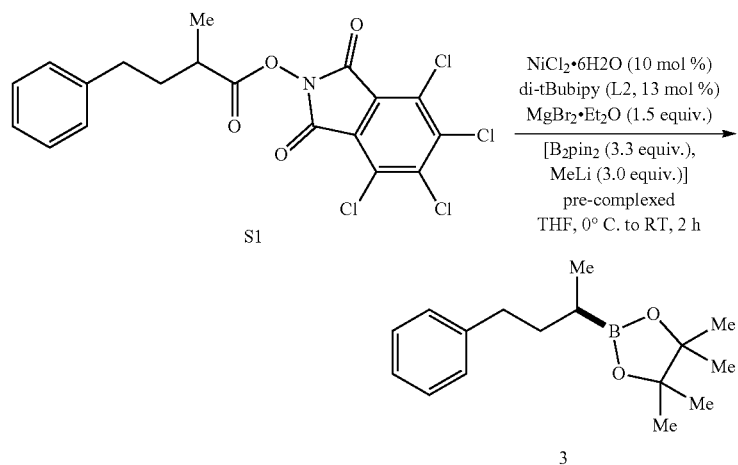
| $B_2pin_2$ (equiv.), MeLi (equiv.) | Yield* |
|---|---|
| $B_2pin_2$ (2.2 equiv.), MeLi (2.0 equiv.) | 51% |
| $B_2pin_2$ (2.75 equiv.), MeLi (2.5 equiv.) | 65% |
| $B_2pin_2$ (3.3 equiv.), MeLi (3.0 equiv.) | 67% (63%†) |
| $B_2pin_2$ (3.85 equiv.), MeLi (3.5 equiv.) | 60% |
| $B_2pin_2$ (4.4 equiv.), MeLi (4.0 equiv.) | 57% |
*Yields determined by GC-FID with dodecane as internal standard. †Isolated yield.

TABLE 7
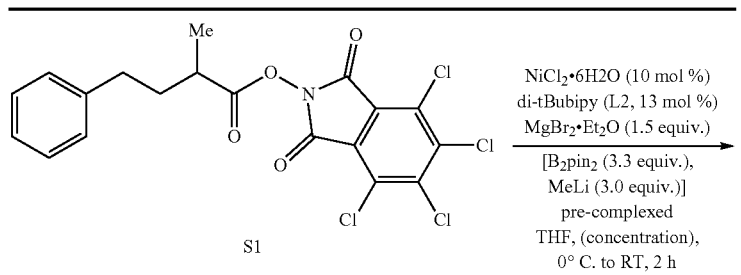
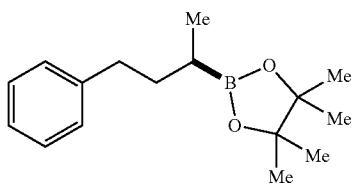
| Concentration | Yield* |
|---|---|
| 0.025 M | 44% |
| 0.033 M | 58% |
| 0.05 M | 67% |
| 0.10 M | 67% (63%†) |
| 0.15 M | 65% |
*Yields determined by GC-FID with dodecane as internal standard. †Isolated yield.
However, under the aforementioned optimized conditions for S1, decarboxylative borylation of S2a proceeded in lower yield than the NHPI ester of S2.
TABLE 8
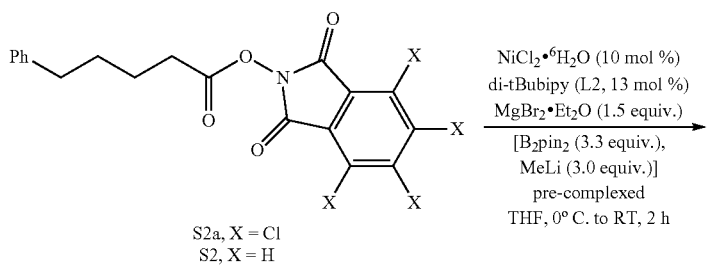
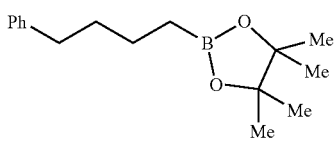
| RAEs | Yield* |
|---|---|
| X = H | 39% |
| X = Cl | 28% |
*Yields determined by GC-FID with dodecane as internal standard.

In order to identify a more general set of conditions, further optimization efforts were undertaken on the NHPI ester S2.

TABLE 9

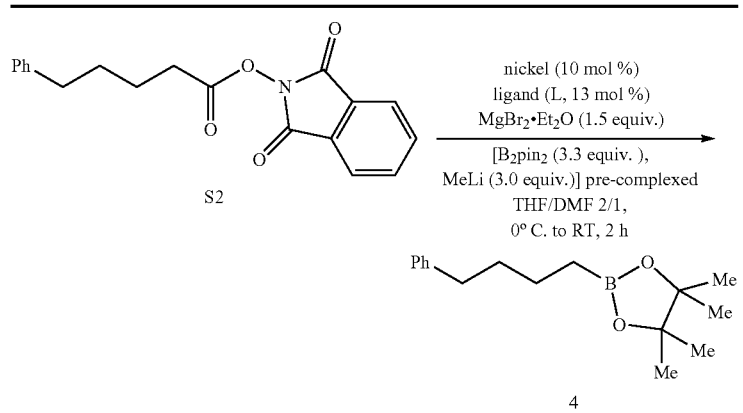

| Nickel/ligand | Yield* |
| --- | --- |
| NiCl$_2$•6H$_2$O/L1 | 67% (65%†) |
| NiCl$_2$•6H$_2$O/L2 | 28% |
| NiCl$_2$•6H$_2$O/L4 | 32% |
| NiCl$_2$•6H$_2$O/L5 | 55% |
| NiCl$_2$•glyme/L1 | 53% |
| NiBr$_2$•glyme/L1 | 64% |
| Ni(OAc)$_2$•4H$_2$O/L1 | 61% |
| Ni(acac)$_2$/L1 | 46% |
| Ni(ONO$_3$)$_2$•6H$_2$O/L1 | 58% |

*Yields determined by GC-FID with dodecane as internal standard.
†Isolated yield.

TABLE 10

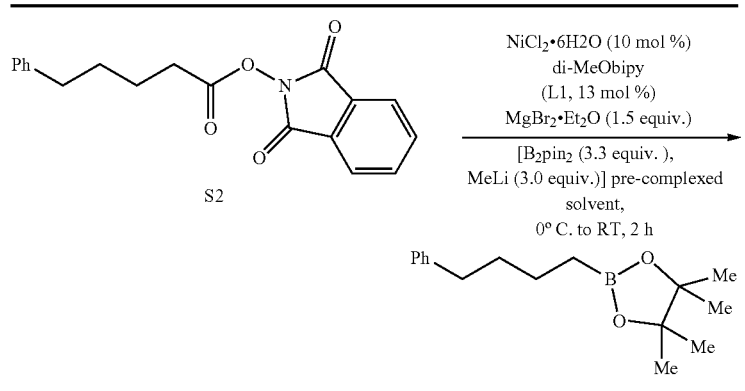

| Solvent | Yield* |
| --- | --- |
| THF (0.4 mL) | 54% |
| DMF (0.4 mL) | 44% |
| THF/DMF (0.2/0.2 mL) | 67% |
| THF/DMF (0.4/0.2 mL) | 67% (65%†) |
| THF/DMF (0.6/0.2 mL) | 67% |
| THF/DMF (1.0/0.2 mL) | 62% |
| THF/DMF (1.4/0.2 mL) | 57% |
| dioxane/DMF (0.4/0.2 mL) | 41% |
| glyme/DMF (0.4/0.2 mL) | 49% |
| diglyme/DMF (0.4/0.2 mL) | 43% |
| Et$_2$O/DMF (0.4/0.2 mL) | 38% |
| THF/DMA (0.4/0.2 mL) | 39% |
| THF/CH$_3$CN (0.4/0.2 mL) | 8% |
| THF/HMPA (0.4/0.2 mL) | 63% |

TABLE 10-continued

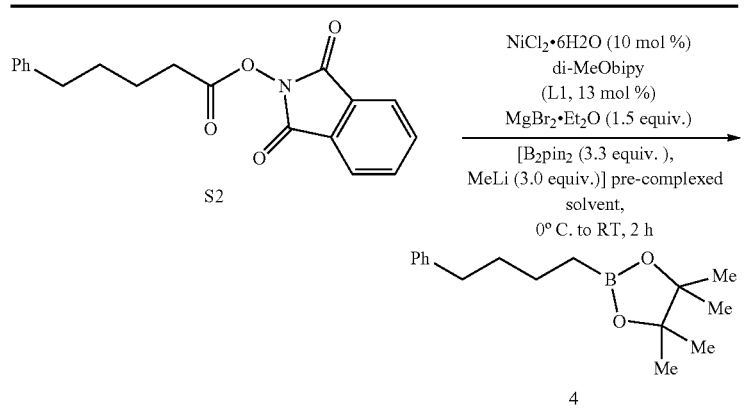

| Solvent | Yield* |
|---|---|
| THF/DMPU (0.4/0.2 mL) | 45% |
| THF/DMSO (0.4/0.2 mL) | 10% |
| THF/NMP (0.4/0.2 mL) | 45% |

*Yields determined by GC-FID with dodecane as internal standard.
†Isolated yield.

This optimized set of condition for the decarboxylative borylation of S2 (1° RAE) was more general, and was also suitable for 2 (2° RAE).

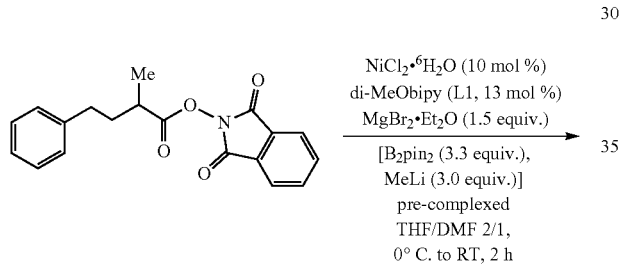

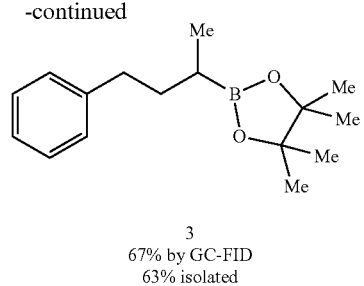

3
67% by GC-FID
63% isolated

Further screening indicated that employing THF as sole solvent gave the best yield for tertiary carboxylic acids (3° RAEs).

TABLE 11

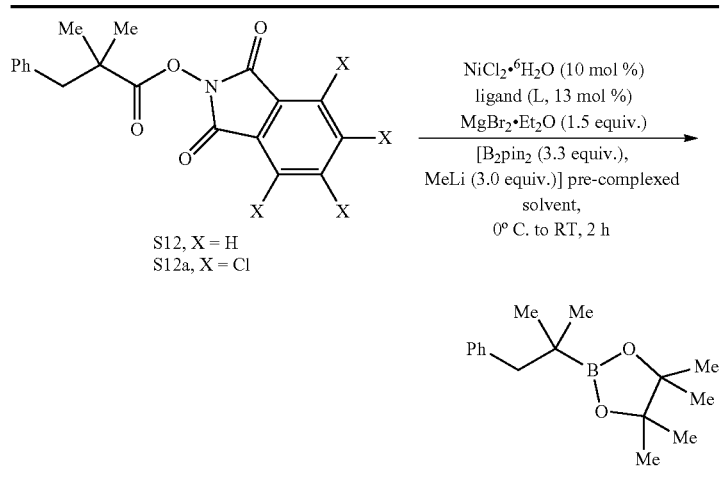

| X | Ligand | Solvent | Yield* |
|---|---|---|---|
| H | L2 | THF (0.4 mL) | 26% |
| H | L1 | THF (0.4 mL) | 74%(68%†) |

TABLE 11-continued

| H | L1 | THF/DMF (0.4/0.2 mL) | 66% |
| H | L5 | THF (0.4 mL) | 62% |
| Cl | L2 | THF (0.4 mL) | 70% |
| Cl | L1 | THF (0.4 mL) | 52% |

*Yields determined by GC-FID with dodecane as internal standard.
†Isolated yield.

General Procedure for Ni-Catalyzed Borylation of Redox-Active Esters
Part I. Preparation of $NiCl_2.6H_2O$/Ligand Stock Solution or Suspension
(1) Suspension A: $NiCl_2.6H_2O$/di-MeObipy (L1) in THF (0.025 M).

A screw-capped culture tube charged with $NiCl_2.6H_2O$ (23.8 mg, 0.1 mmol) and 4,4'-dimethoxy-2,2'-bipyridine (L1, 28.1 mg, 0.13 mmol) was evacuated and backfilled with argon for three times. THF (4.0 mL) was added and the resulting mixture was stirred at room temperature overnight (or until no granular $NiCl_2.6H_2O$ was observed) to afford a pale green suspension.
(2) Suspension B: $NiCl_2.6H_2O$/di-MeObipy (L1) in DMF (0.05 M).

A screw-capped culture tube charged with $NiCl_2.6H_2O$ (23.8 mg, 0.1 mmol) and 4,4'-dimethoxy-2,2'-bipyridine (L1, 28.1 mg, 0.13 mmol) was evacuated and backfilled with argon for three times. DMF (2.0 mL) was added and the resulting mixture was stirred at room temperature overnight to afford a pale green suspension.
(3) Suspension C: $NiCl_2.6H_2O$/di-tBubipy (L2) in THF (0.025 M).

A screw-capped culture tube charged with $NiCl_2.6H_2O$ (23.8 mg, 0.1 mmol) and 4,4'-di-tert-butyl-2,2'-bipyridine (L2, 34.8 mg, 0.13 mmol) was evacuated and backfilled with argon for three times. THF (4.0 mL) was added and the resulting mixture was stirred at room temperature overnight (or until no granular $NiCl_2.6H_2O$ was observed) to afford a pale green suspension.
(4) Solution D: $NiCl_2.6H_2O$/di-tBubipy (L2) in DMF (0.05 M).

A screw-capped culture tube charged with $NiCl_2.6H_2O$ (23.8 mg, 0.1 mmol) and 4,4'-di-tert-butyl-2,2'-bipyridine (L2, 34.8 mg, 0.13 mmol) was evacuated and backfilled with argon for three times. DMF (2.0 mL) was added and the resulting mixture was stirred at room temperature for 2 h to afford a green solution.
Note: All the solutions or suspensions kept under argon can be used for several days without appreciable deteriorations in reaction yields.
Part II. Preparation of $[B_2Pin_2Me]Li$ Suspension To a solution of $B_2pin_2$ (168 mg, 0.66 mmol) in THF (0.6 mL) was added MeLi (0.38 mL, 1.6 M in $Et_2O$, 0.6 mmol) at 0° C. under argon. The reaction mixture was warmed to room temperature and stirred for 1 h to afford a suspension (sometimes we also experienced to obtain this complex as a clear solution).
Note: The resulting mixture can be stored with stirring for several hours without appreciable deterioration.
Part III. Ni-Catalyzed Cross-Coupling Reaction
General Procedure B A screw-capped culture tube charged with the redox-active ester (0.2 mmol, 1.0 equiv) and $MgBr_2.OEt_2$ (77 mg, 0.3 mmol, 1.5 equiv) was evacuated and backfilled with argon for three times. THF (0.8 mL) was added, and the mixture was stirred until no granular $MgBr_2.OEt_2$ was observed (ca. 10 min) before suspension B (0.4 mL, $NiCl_2.6H_2O$ (10 mol %)/di-MeObipy (13 mol %) in DMF), or solution D (0.4 mL, $NiCl_2.6H_2O$ (10 mol %)/di-tBubipy (13 mol %) in DMF) was added via a syringe. The resulting mixture was stirred vigorously until no visible solid was observed on the bottom of the reaction vessel (ca. 10 min). This mixture was cooled to 0° C. before a suspension of $[B_2pin_2Me]Li$ in THF (3 eq, 1.1 mL) was added in one portion (note: do not add it dropwise!). After stirring for 1 h at 0° C., the reaction was warmed to room temperature and stirred for another 1 h before quenched with 0.1 N HCl (10 mL). The resulting mixture was extracted with $Et_2O$ or EtOAc (3 mL×2). The combined organic layers were concentrated in vacuo, and the crude product was purified by flash column chromatography. For acid labile substrate, the reaction was alternatively quenched with saturated aqueous $NH_4Cl$ (10 mL).
General Procedure C A screw-capped culture tube charged with the redox-active ester (0.2 mmol, 1.0 equiv) and $MgBr_2.OEt_2$ (77 mg, 0.3 mmol, 1.5 equiv) was evacuated and backfilled with argon for three times. Suspension A (0.8 mL, $NiCl_2.6H_2O$ (10 mol %)/di-MeObipy (13 mol %) in THF) or C (0.8 mL, $NiCl_2.6H_2O$ (10 mol %)/di-tBubipy (13 mol %) in THF) was added via a syringe. The mixture was stirred vigorously at room temperature until no granular $MgBr_2.OEt_2$ was observed (ca. 15 min). This suspension was cooled to 0° C. before a suspension of $[B_2pin_2Me]Li$ was added in one portion (note: do not add it dropwise!). After stirring for 1 h at 0° C., the reaction was warmed to room temperature and stirred for another 1 h. The reaction mixture was diluted with $Et_2O$ (10 mL), filtered through a short pad of silica gel and celite (top layer: celite, bottom layer: silica gel, v/v celite: silica gel=1:1), washed with $Et_2O$ (50 mL). The filtrate was concentrated, and the crude product was purified by column chromatography.

For polar substrates, such as peptides, the reaction was quenched either with 0.1 N HCl (10 mL) or sat. aqueous $NH_4Cl$ (10 mL) followed by extraction with EtOAc (3 mL×2). The combined organic layers were dried over $Na_2SO_4$, concentrated in vacuo and purified by flash column chromatography.
General Procedure for Gram-Scale Ni-Catalyzed Borylation of Redox-Active Esters (Borylation of Ibuprofen).

The gram-scale procedure was slightly modified from General Procedure C. A flame-dried round bottom flask charged with $B_2pin_2$ (2.57 g, 10.1 mmol, 3.3 equiv) was evacuated and backfilled with argon for three times. THF (9.2 mL) was added, and the clear solution was cooled to 0° C. when MeLi (5.8 mL, 1.6 M in $Et_2O$, 9.3 mmol, 3.0 equiv) was added dropwise. The reaction mixture was then warmed to room temperature and stirred for 1 h.

The NHPI redox-active ester of ibuprofen S18 (1.08 g, 3.07 mmol) and $MgBr_2.OEt_2$ (powder, 792 mg, 3.07 mmol, 1.0 equiv) were sequentially added to another flame-dried round-bottom flask. This flask was evacuated and backfilled with argon for three times and was cooled to 0° C. THF (12 mL) was added, the mixture was sonicated until no granular $MgBr_2.OEt_2$ was observed. A suspension of $NiCl_2.6H_2O$ (73 mg, 0.31 mmol) and di-MeObipy (L2, 86 mg, 0.40 mmol) in THF (12 mL) was added, and the resulting mixture was sonicated again until there was no visible solid on the bottom of the flask. The mixture was then cooled to 0° C. before a suspension of [B₂pin₂Me]Li in THF was added in one portion. After stirring for 1 h at 0° C., the reaction mixture was warmed to room temperature and stirred for another 1 h.

The reaction mixture was then poured into Et₂O (100 mL), and the flask was rinsed with additional Et₂O (100 mL). The resulting mixture was filtered through a plug of silica gel and celite (top layer: celite, bottom layer: silica gel, v/v celite:silica gel=1:1), the solid residue was washed with Et₂O (350 mL), and the filtrate was concentrated in vacuo. Purification by flash column chromatography (silica gel, hexanes to 1:30 Et₂O:hexanes) afforded product (709 mg, 80%) as a colorless oil.

General Procedure for Ni-Catalyzed Decarboxylative Borylation of Alkyl Carboxylic Acids Via In Situ Generated RAEs (General Procedure D)

Examples of Ni-Catalyzed Decarboxylative Borylation of Alkyl Carboxylic Acids Via In Situ Generated RAEs This in situ procedure was demonstrated on six alkyl carboxylic acids following General Procedure D.

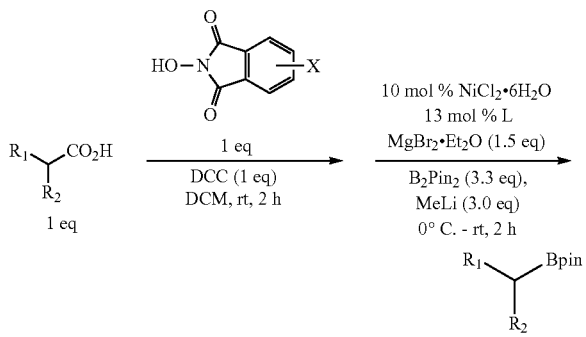

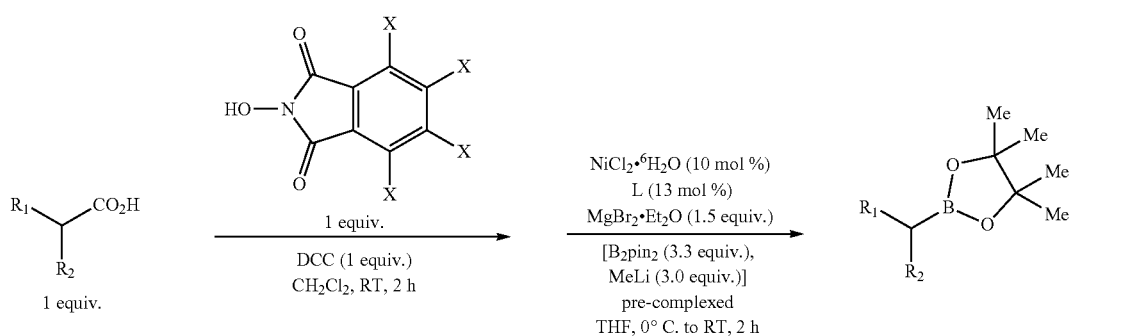

A screw-capped culture tube with a stir bar was charged with alkyl carboxylic acid (0.2 mmol), N-hydroxyphthalimide or tetrachloro-N-hydroxyphthalimide (0.2 mmol, 1.0 equiv) and N,N'-dicyclohexylcarbodiimide (0.2 mmol, 1.0 equiv). The tube was then evacuated and backfilled with argon for three times. CH₂Cl₂ (2.0 mL) was added and the resulting mixture was stirred at room temperature for 2 h before the volatiles were removed in vacuo. MgBr₂.OEt₂ (77 mg, 0.3 mmol, 1.5 equiv) was added. The tube was evacuated and backfilled with argon for three times. Suspension A (0.8 mL, NiCl₂.6H₂O (10 mol %)/L1 (13 mol %) in THF) or suspension C (0.8 mL, NiCl₂.6H₂O (10 mol %)/L2 (13 mol %) was added. The mixture was stirred vigorously at room temperature for 15 min (or until no granular MgBr₂.OEt₂ was observed) and was subsequently cooled to 0° C. before a suspension of [B₂pin₂Me]Li in THF (1.1 mL) was added in one portion (note: do not add it dropwise!). After being stirred for 1 h, the reaction was warmed to room temperature and stirred for another 1 h. The reaction mixture was then quenched with 0.1 N HCl (10 mL) and extracted with Et₂O (5 mL×2). The combined organic layers were dried over Na₂SO₄, concentrated in vacuo and purified by column chromatography to give the desired product.

-continued

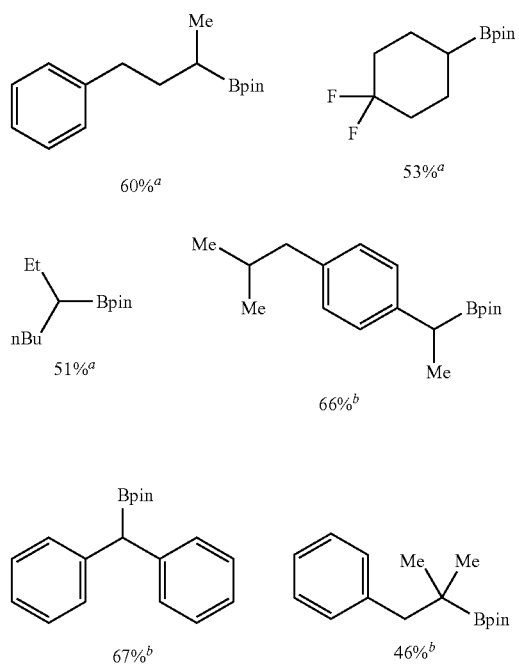

-continued

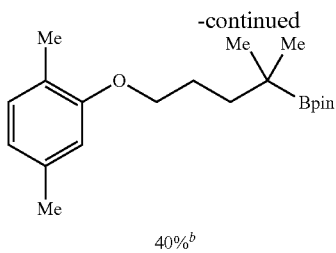

40%[b]

[a]X = Cl, L = di-tBubipy (L2). [b]X = H, L = di-MeObipy (L1)

General Procedure D is Less Effective for Primary Carboxylic Acids (Typically 20% Yield).
General Procedure for Ni-Catalyzed Borylation of Redox-Active Esters with 2.5 Mol % Nickel
Part I. Preparation of NiCl$_2$.6H$_2$O/Ligand Stock Solution or Suspension
(1) Suspension E: NiCl$_2$.6H$_2$O/di-MeObipy (L1) in THF (6.25 mM).
A screw-capped culture tube charged with NiCl$_2$.6H$_2$O (23.8 mg, 0.1 mmol) and 4,4'-dimethoxy-2,2'-bipyridine (L1, 28.1 mg, 0.13 mmol) was evacuated and backfilled with argon for three times. THF (16.0 mL) was added and the resulting mixture was stirred at room temperature overnight (or until no granular NiCl$_2$.6H$_2$O was observed) to afford a pale green suspension.
(2) Solution F: NiCl$_2$.6H$_2$O/di-MeObipy (L1) in DMF (12.5 mM).
A screw-capped culture tube charged with NiCl$_2$.6H$_2$O (23.8 mg, 0.1 mmol) and 4,4'-dimethoxy-2,2'-bipyridine (L1, 28.1 mg, 0.13 mmol) was evacuated and backfilled with argon for three times. DMF (8.0 mL) was added and the resulting mixture was stirred at room temperature overnight to afford a light green solution.
(3) Suspension G: NiCl$_2$.6H$_2$O/di-tBubipy (L2) in THF (6.25 mM).
A screw-capped culture tube charged with NiCl$_2$.6H$_2$O (23.8 mg, 0.1 mmol) and 4,4'-di-tert-butyl-2,2'-bipyridine (L2, 34.8 mg, 0.13 mmol) was evacuated and backfilled with argon for three times. THF (16.0 mL) was added and the resulting mixture was stirred at room temperature overnight (or until no granular NiCl$_2$.6H$_2$O was observed) to afford a pale green suspension.
Note: All the solutions or suspensions kept under argon can be used for two weeks without appreciable deteriorations in reaction yields.
Part II. Ni-Catalyzed Cross-Coupling Reaction
Borylation of redox-active esters with 2.5 mol % nickel loading followed General Procedure B/C with Suspension E/Solution F/Suspension G.
Examples of Ni-Catalyzed Borylation of Redox-Active Esters with 2.5 Mol % Nickel

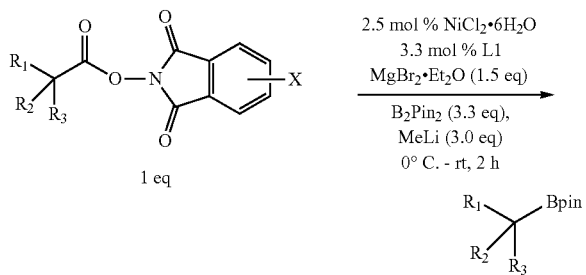

-continued

Primary

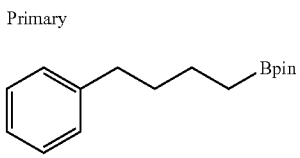

52%

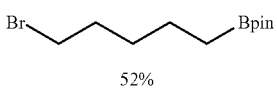

52%

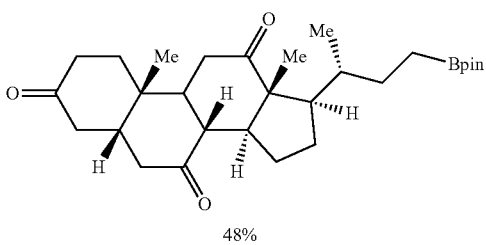

48%

Secondary

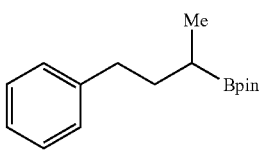

63%

58%
dr > 15:1

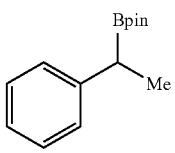

50%[a]

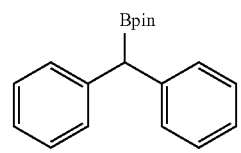

46%[a]

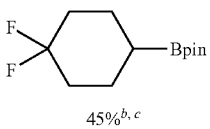

45%[b,c]

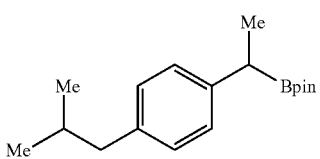

49%[a]

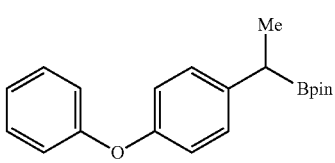

63%[a]

-continued

Tertiary

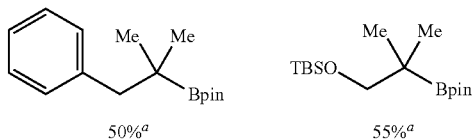

50%[a]   55%[a]

[a]using THF as solvent. [b]using L2 as ligand and THF as solvent. [c]using TCNHPI ester Standard Reaction conditions: Redox active NHPI ester (1.0 equiv), $NiCl_2 \cdot 6H_2O$ (2.5 mol %), L1 (3.3 mol %), $MgBr_2 \cdot OEt_2$ (1.5 equiv), $B_2pin_2$ (3.3 equiv), MeLi (3.0 equiv), THF/DMF (2.5:1), 0° C.-RT, 2 h.

Copper-Catalyzed Borylation of Redox-Active Esters

In further embodiments of the invention, the copper-catalyzed borylation of alkyl carboxylic acids to yield alkyl boronic acids, is disclosed and claimed herein. This invention entails the conversion of carboxylate functionalities into the corresponding boronic derivatives via copper-catalyzed decarboxylative borylation of redox active esters. In various embodiments, this transformation enables late-stage modifications of pharmaceuticals or analogs thereof; it allows the expedient syntheses of boron-containing bioactive molecules, including FDA-approved drugs; it allows for the preparations of boron-containing building blocks which have been broadly used in the syntheses of pharmaceutical ingredients. Compared with other methods, it allows simple procedure and inexpensive reagents which can be readily adopted in process chemistry.

Cu(II) salts were screened for borylation catalytic activity comprising copper complexed with various ligands, including bipyridyl-type ligands of formula L (e.g., 4,4'-di-t-Bu-2,2'-bipyridyl, L2, see above), and 1,3-dicarbonyl-type ligands that form with a copper ion (Cu(I) or Cu(II)) a complex of formula M (e.g., acetonylacetonate, M1).

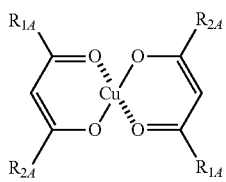

M1-M7
M1 $R_{1A}=R_{2A}=Me$, $Cu(acac)_2$
M2 $R_{1A}=R_{2A}=tBu$
M3 $R_{1A}=R_{2A}=iPr$
M4 $R_{1A}=R_{2A}=Ph$
M5 $R_{1A}$, $R_{2A}=tBu$, Me
M6 $R_{1A}=R_{2A}=CF_3$
M7 $R_{1A}$, $R_{2A}=tBu$, $CF_3$ Table 12, below, shows initial screening results using Cu salts (Cu(I) or Cu(II)) with various bases and ligands in carrying out the borylation reaction of the invention. As can be seen, use of phosphine ligands such as $PPh_3$ and $PCy_3$, even in combination with tBubipy (ligand L2) resulted in zero percent product or low yields, but Cu(I) salts with tBubipy with and without $MgBr_2$ gave a better result.

Table 13 shows a study of results using varying loads of $MgBr_2$, and various Cu salts. As can be seen, $MgBr_2$ appears to inhibit the reaction; best results were obtained with tBubipy as ligand, no $MgBr_2$, and CuCl, CuCl2, $CuCl_2 \cdot 6H_2O$, CuI, and $Cu(OAc)_2$ as copper sources; both Cu(I) and Cu(II) states were catalytically active in this system.

Table 14 shows the effect of solvent on the copper-catalyzed borylation reaction using lithium t-butoxide, $Cu(OAc)_2$ (i.e., a Cu(II) salt) in the presence of the tBubipy ligand L2. the most effective solvent mixtures seem to be DMF plus an ether, such as dioxane, THF, or glyme, diglyme or diethyl ether, although DMF mixtures with other solvents such as $CH_2Cl_2$, EtOAc, or toluene, were also effective. Interestingly, pure DMF gave a lower yield.

Table 15 shows significant increases in yield obtained using LiOH and LiOtBu, even in the presence of $MgBr_2$, with $Cu(OAc)_2$ as the copper source and tBubipy L2 as the ligand.

Table 16 shows the effect on yield of solvent using variants of the preferred dixoane/DMF solvent system, with the $Cu(OAc)_2$/tBubipy catalytic complex, in the presence of $LiOH/MgBr_2-Et_2O$. As a replacement for dioxane, other ethers and esters seem to be most effective. As a replacement for DMF, other dipolar aprotic solvents were effective, as were pyridine and acetone.

Table 17 shows the effect on yield of catalysts and copper sources using $Cu(OAc)_2$ as a copper source in the presence of LiOH and $MgBr_2-Et_2O$ in dioxane-DMF solvent system. The effective ligands were much as seen before, the bipyridyl ligand L2 being more effective than phosphine type ligands, but interestingly it was noted that adding the 1,3-dicarbonyl ligand acetonylacetonate (acac) increased the yield when tBubipy L2 was the primary ligand for the copper complex.

Tables 18 and 19 show the effect on yield using various 1,3-dicarbonyl type ligands, M1-M7, as defined above, in the dioxane-DMF solvent system in the presence of LiOH and $MgBr_2 \cdot Et_2O$. Ligand M1, copper acetonylacetonate itself, along with other 1,3-dicarbonyl ligands M2-M7, were broadly effective, while when $Cu(acac)_2$ was the primary catalyst, the presence of other Cu salts did not bring about large changes in the yields obtained.

Table 20 shows the yields of the copper-catalyzed borylation reactions in the dioxane-DMF solvent system, in the presence of LiOH and in the absence of any bipyridyl ligand L2, with various Mg sources and LiOH loadings. It was found that $MgCl_2$ could be substituted for the more expensive $MgBr_2$ with no loss in yield, while LiOH loadings beyond about 15 equivalents did not produce a significant yield increase.

Table 21 shows a final optimization of the reaction using $Cu(acac)_2$ M1 in the presence of LiOH and $MgCl_2$ in dioxane/DMF, with production cost estimate comparisons.

TABLE 12

Copper-catalyzed Borylation of Redox-Active Esters; Ligand Screening

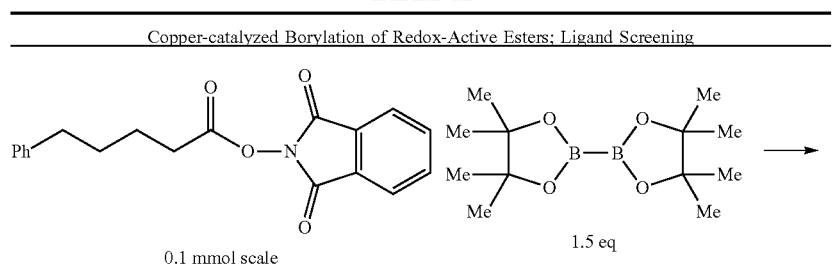

| Entry | Conditions | Result |
|---|---|---|
| | (tBuOLi (1.5 eq) as base) | |
| 1 | CuTc/tBubipy (10/10 mol %), THF/NMP | 0% |
| 2 | CuTc/tBubipy/PPh₃ (10/10/10 mol %), THF/NMP | 0% |
| 3 | CuTc/tBubipy/PCy₃ (10/10/10 mol %), THF/NMP | 0% |
| | tBuOLi (1.5 eq) as base | |
| 1 | CuI/PPh₃, THF | 0% |
| 2 | CuI/PPh₃, THF/DMF | trace |
| 3 | CuI/PPh₃, THF, w/MgBr₂∞Et₂O | 0% |
| 4 | CuI/PPh₃, THF/DMF, w/MgBr₂∞Et₂O | 0% |
| 5 | CuI/tBubipy, THF | 14% |
| 6 | CuI/tBubipy, THF/DMF | 4% |
| 7 | CuI/tBubipy, THF, w/MgBr₂∞Et₂O | 21% |
| 8 | CuI/tBubipy, THF/DMF, w/MgBr₂∞Et₂O | 17% |

TABLE 13

Copper-catalyzed Borylation of Redox-Active Esters; Effect of MrBr₂ Loading and Cu Salt

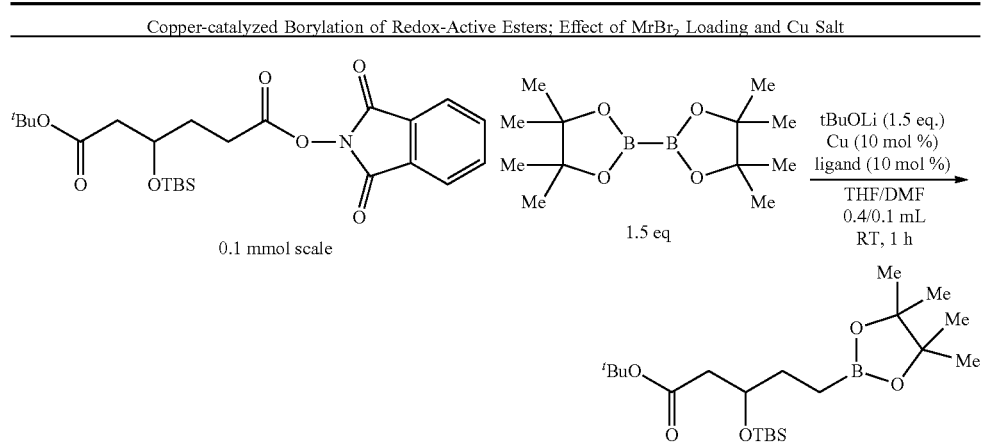

| Entry | Conditions | Result |
|---|---|---|
| | (w/CuI/tBubipy) | |
| 1 | MgBr₂∞Et₂O, 0 eq | 14% |
| 2 | MgBr₂•Et₂O, 0.2 eq | 6% |
| 3 | MgBr₂•Et₂O, 0.5 eq | 3% |
| 4 | MgBr₂•Et₂O, 1.0 eq | 0% |
| 5 | MgBr₂•Et₂O, 1.5 eq | 0% |
| | tBubipy as ligand, no MgBr₂•Et₂O | |
| 1 | CuCl | 12% |
| 2 | CuBr | 9% |
| 3 | CuCN | trace |
| 4 | Cu(MeCN)₄PF₆ | 8% |
| 5 | CuCl₂ | 11% |
| 6 | CuCl₂•2H₂O | 19% |

TABLE 13-continued

Copper-catalyzed Borylation of Redox-Active Esters; Effect of MrBr$_2$ Loading and Cu Salt

*Reaction: tBuO-substrate with OTBS and N-hydroxyphthalimide ester (0.1 mmol scale) + B$_2$pin$_2$ (1.5 eq), tBuOLi (1.5 eq.), Cu (10 mol %), ligand (10 mol %), THF/DMF 0.4/0.1 mL, RT, 1 h → pinacol boronate product*

| Entry | Conditions | Result |
|---|---|---|
| 7 | CuBr$_2$ | 9% |
| 8 | CuF$_2$ | 0% |
| 9 | CuSO$_4$·5H$_2$O | trace |
| 10 | Cu(OAc)$_2$ | 19% |
| 11 | CuI (10 mol %), tBubipy (15 mol %) | 16% |
| 12 | CuI (10 mol %), tBubipy (20 mol %) | 19% |

TABLE 14

Copper-catalyzed Borylation of Redox-Active Esters

Screening with copper

*Reaction: tBuO-substrate with OTBS and N-hydroxyphthalimide ester (0.1 mmol scale) + B$_2$pin$_2$ (1.5 eq), tBuOLi (1.5 eq.), Cu (10 mol %), ligand (10 mol %), THF/DMF 0.4/0.1 mL, RT, 1 h → pinacol boronate product*

| Entry | Conditions | Result |
|---|---|---|
| | (Cu(OAc)$_2$/tBubipy (10/10 mol %)) | |
| 1 | THF only | 11% |
| 2 | THF/DMA 4/1 | 10% |
| 3 | THF/NMP 4/1 | 11% |
| 4 | THF/NMP 9/1 | 18% |
| 5 | THF/CH$_3$CN 4/1 | 11% |
| 6 | dioxane/DMF 4/1 | 24% |
| 7 | glyme/DMF 4/1 | 20% |
| 8 | DMF only | 5% |
| | Cu(OAc)$_2$/tBubipy (10/20 mol %) | |
| 1 | THF/DMF 4/1 | 22% |
| 2 | dioxane/DMF 9/1 | 25% |
| 3 | ether/DMF 9/1 | 19% |
| 4 | glyme/DMF 9/1 | 21% |
| 5 | diglyme/DMF 9/1 | 17% |
| 6 | hexane/DMF 9/1 | 9% |

TABLE 14-continued

Copper-catalyzed Borylation of Redox-Active Esters

Screening with copper

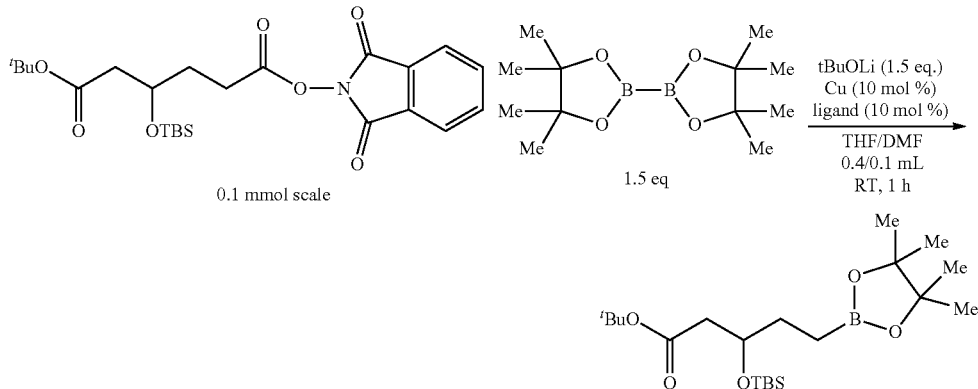

0.1 mmol scale

| Entry | Conditions | Result |
|---|---|---|
| 7 | CH$_2$Cl$_2$/DMF 9/1 | 17% |
| 8 | toluene/DMF 9/1 | 23% |
| 9 | EtOAc/DMF 9/1 | 25% |

TABLE 15

Copper-catalyzed Borylation of Redox-Active Esters; LiOH vs. LiOtBu, Second Ligand Effect Screening with copper

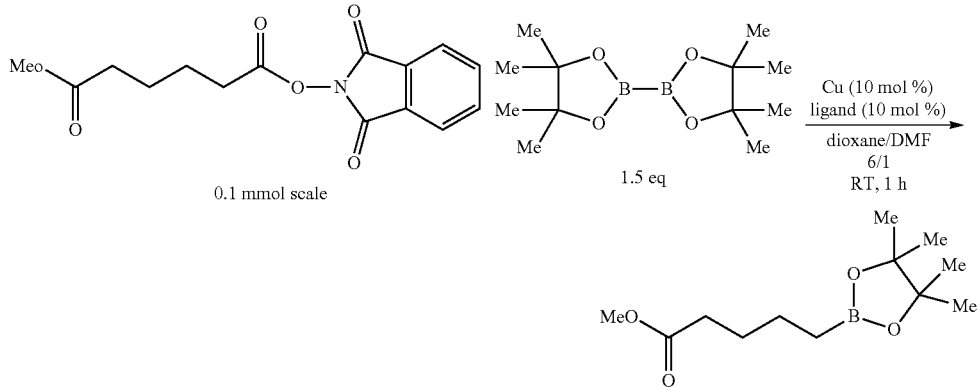

0.1 mmol scale

| Entry | Conditions | Result |
|---|---|---|
| | (Cu(OAc)$_2$/tBubipy (10/10 mol %)) | |
| 1 | tBuOLi (4 eq, batch 1), MgBr$_2$∞Et$_2$O (0.8 eq) | 40% |
| 2 | LiOH (4 eq), MgBr$_2$∞Et$_2$O (0 eq) | 27% |
| 3 | LiOH (4 eq), MgBr$_2$∞Et$_2$O (0.2 eq) | 47% |
| 4 | LiOH (4 eq), MgBr$_2$∞Et$_2$O (0.5 eq) | 26% |
| 5 | LiOH (4 eq), MgBr$_2$∞Et$_2$O (0.8 eq) | 25% |
| 6 | LiOH∞H$_2$O (4 eq), MgBr$_2$∞Et$_2$O (0 eq) | 27% |
| 7 | LiOH∞H$_2$O (4 eq), MgBr$_2$∞Et$_2$O (0.1 eq) | 43% |
| 8 | LiOH∞H$_2$O (4 eq), MgBr$_2$∞Et$_2$O (0.2 eq) | 48% |
| 9 | LiOH∞H$_2$O (4 eq), MgBr$_2$∞Et$_2$O (0.3 eq) | 39% |
| | LiOH∞H$_2$O (4 eq), MgBr$_2$∞Et$_2$O (0.2 eq) | |
| 1 | Cu(OAc)$_2$/tBubipy/PPh$_3$ (10/10/10 mol %) | 35% |
| 2 | Cu(OAc)$_2$/tBubipy/PCy$_3$ (10/10/10 mol %) | 35% |
| 3 | Cu(OAc)$_2$/tBubipy/PCy$_3$∞HBF$_4$ (10/10/10 mol %) | 34% |
| 4 | Cu(OAc)$_2$/tBubipy/dppe (10/10/10 mol %) | 19% |
| 5 | Cu(OAc)$_2$/dppe (10/10 mol %) | 34% |
| 6 | Cu(OAc)$_2$/dppe (10/15 mol %) | 16% |
| 7 | Cu(OAc)$_2$/dppe (10/20 mol %) | trace |

TABLE 16

Copper-catalyzed Borylation of Redox-Active Esters; Solvent Effect

Screening with copper

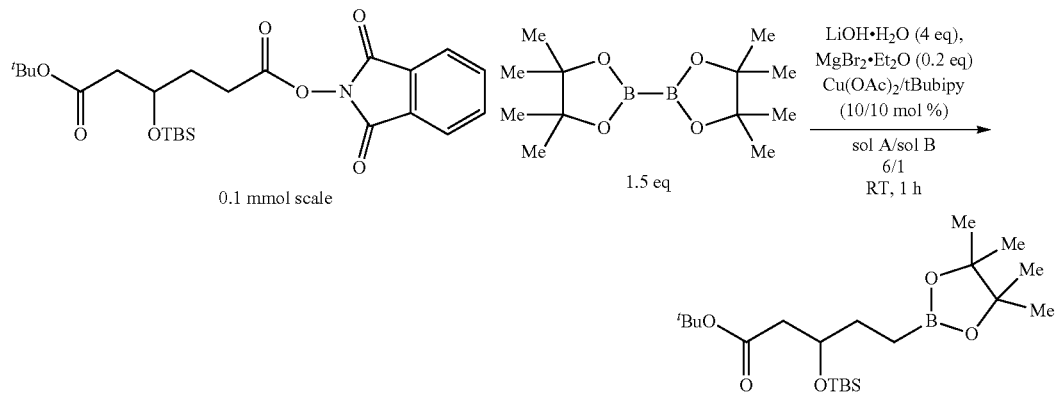

0.1 mmol scale

| Entry | Sol A/DMF (6/1) | Result | Entry | Dioxane/sol B (6/1) | Result |
| --- | --- | --- | --- | --- | --- |
| 1 | THF | 23% | 1 | DMA | 32% |
| 2 | Et$_2$O | 26% | 2 | NMP | 22% |
| 3 | glyme | 12% | 3 | HMPA | 6% |
| 4 | TBME | 35% | 4 | DMSO | 24% |
| 5 | CH$_2$Cl$_2$ | 23% | 5 | CH$_3$CN | 27% |
| 6 | toluene | 18% | 6 | DMPU | 10% |
| 7 | EtOAc | 26% | 7 | pyridine | 29% |
| 8 | acetone | 6% | 8 | TMEDA | 9% |
| 9 | DMF | 9% | 9 | acetone | 31% |
| 10 | CH$_3$CN | 5% | 10 | Et$_3$N | 7% |
| 11 | DMSO | 11% | | | |

TABLE 17

Copper-catalyzed Borylation of Redox-Active Esters; Catalysts and Copper Sources

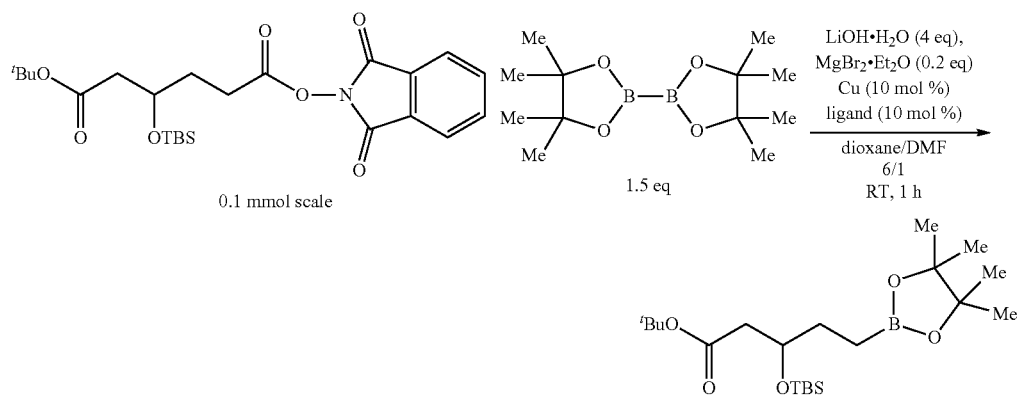

0.1 mmol scale

| Entry | Cu(OAc)$_2$/ligand (10/10 mol %) | Result | Entry | Copper/tBubipy (10/10 mol %) | Result |
| --- | --- | --- | --- | --- | --- |
| 1 | tBubipy | 42% | 1 | CuOAc | 3% |
| 2 | PPh$_3$ | 36% | 2 | CuI | 35% |
| 3 | PCy$_3$ | 22% | 3 | CuCl | 39% |
| 4 | PnBu$_3$ | 10% | 4 | CuCl$_2$·2H$_2$O | 36% |
| 5 | P(Nap)$_3$ | 29% | 5 | Cu(TFA)$_2$ | 29% |
| 6 | SPhos | 23% | 6 | Cu(OTf)$_2$ | 40% |
| 7 | dppe | 45% | 7 | Cu(ClO$_4$)$_2$·6H$_2$O | 40% |
| 8 | dppp | 9% | 8 | Cu(acac)$_2$ | 41% |
| 9 | dppb | trace | | Cu(OAc)$_2$/tBubipy (10/10 mol %) | |
| 10 | dppbz | trace | 1 | additive K$_2$CO$_3$ | 28% |
| 11 | dppf | 0% | 2 | EtOH | 13% |
| 12 | BINAP | 9% | 3 | TBAB | 22% |
| 13 | Xantphos | 10% | 4 | TBAF | 8% |
| 14 | IMes·HCl | 20% | 5 | pyridine (2 eq) | 26% |
| 15 | IPr·HCl | 0% | 6 | DMAP | 12% |

TABLE 17-continued

Copper-catalyzed Borylation of Redox-Active Esters; Catalysts and Copper Sources 0.1 mmol scale; 1.5 eq; LiOH•H$_2$O (4 eq), MgBr$_2$•Et$_2$O (0.2 eq), Cu (10 mol %), ligand (10 mol %), dioxane/DMF 6/1, RT, 1 h

| Entry | Cu(OAc)$_2$/ligand (10/10 mol %) | Result | Entry | Copper/tBubipy (10/10 mol %) | Result |
|---|---|---|---|---|---|
| 16 | IAd•HCl | 8% | 7 | 4-CN pyridine | 14% |
| 17 | bathocuproine | 29% | 8 | FeBr$_2$ | 19% |
|  |  |  | 9 | NiBr•3H$_2$O | <5% |
|  |  |  | 10 | MnBr$_2$•4H$_2$O | 27% |

TABLE 18

Copper-catalyzed Borylation of Redox-Active Esters; 1,3-dicarbonyl ligands

Screening with copper 0.1 mmol scale; 1.5 eq; Cu (10 mol %), ligand (10 mol %), dioxane/DMF 6/1, RT, 1 h

| Entry | Conditions | Result |
|---|---|---|
| (LiOH•H$_2$O (4 eq), MgBr$_2$•Et$_2$O (0.2 eq)) | | |
| 1 | Cu(acac)$_2$ (10 mol %) | 47% |
| 2 | R$_{1A}$ = R$_{2A}$ = tBu (10 mol %) | 45% |
| 3 | R$_{1A}$ = R$_{2A}$ = Pr (10 mol %) | 35% |
| 4 | R$_{1A}$ = R$_{2A}$ = Ph (10 mol %) | 45% |
| 5 | R$_{1A}$, R$_{2A}$ = tBu, Me (10 mol %) | 48% |
| 6 | R$_{1A}$ = R$_{2A}$ = CF$_3$ (10 mol %) | 31% |
| 7 | R$_{1A}$, R$_{2A}$ = tBu, CF$_3$ (10 mol %) | 30% |
| LiOH•H$_2$O (10 eq), MgBr$_2$•Et$_2$O (0.8 eq) | | |
| 1 | Cu(OAc)$_2$/tBubipy (10/10 mol %) | 62% |
| 2 | Cu(acac)$_2$ (10 mol %) | 51% |
| 3 | Cu(acac)$_2$ (20 mol %) | 62% |
| 4 | Cu(acac)$_2$ (30 mol %) | 63% |
| 5 | Cu(acac)$_2$ (20 mol %), additive H$_2$O (50 uL, 28 eq) | 59% |
| 6 | Cu(acac)$_2$ (20 mol %), additive tBuOLi (2 eq) | 60% |
| 7 | Cu(acac)$_2$ (10 mol %), CuI (10 mol %) | 66% |
| 8 | Cu(acac)$_2$ (10 mol %), CuCl (10 mol %) | 59% |

TABLE 18-continued

Copper-catalyzed Borylation of Redox-Active Esters; 1,3-dicarbonyl ligands

Screening with copper

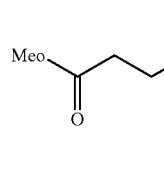

0.1 mmol scale 1.5 eq

Cu (10 mol %)
ligand (10 mol %)
―――――――――→
dioxane/DMF
6/1
RT, 1 h

| Entry | Conditions | Result |
|---|---|---|
| 9 | Cu(acac)$_2$ (10 mol %), Cu(OAc)$_2$ (10 mol %) | 50% |
| 10 | Cu(acac)$_2$/Cu(ClO$_4$)$_2$•6H$_2$O (10/10/10 mol %) | 48% |
| 11 | Cu(acac)$_2$/CuCl/tBubipy (10/10/10 mol %) | 59% |
| 12 | Cu(acac)$_2$/Cu(OAc)$_2$/tBubipy (10/10/10 mol %) | 59% | tBubipy = compound L2;
acac = acetylacetonate

TABLE 19

Copper-catalyzed Borylation of Redox-Active Esters

Screening with copper

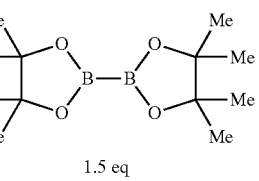

0.1 mmol scale 1.5 eq

Cu (10 mol %)
ligand (10 mol %)
―――――――――→
dioxane/DMF
6/1
RT, 1 h

| Entry | Conditions | Result |
|---|---|---|
| (LiOH•H$_2$O (4 eq), MgBr$_2$•Et$_2$O (0.2 eq)) | | |
| 1 | Cu(acac)$_2$ (10 mol %) | 47% |
| 2 | R$_{1A}$ = R$_{2A}$ = tBu (10 mol %) | 45% |
| 3 | R$_{1A}$ = R$_{2A}$ = iPr (10 mol %) | 35% |
| 4 | R$_{1A}$ = R$_{2A}$ = Ph (10 mol %) | 45% |
| 5 | R$_{1A}$, R$_{2A}$ = tBu, Me (10 mol %) | 48% |
| 6 | R$_{1A}$ = R$_{2A}$ = CF$_3$ (10 mol %) | 31% |
| 7 | R$_{1A}$, R$_{2A}$ = tBu, CF$_3$ (10 mol %) | 30% |
| LiOH•H$_2$O (10 eq), MgBr$_2$•Et$_2$O (0.8 eq) | | |
| 1 | Cu(OAc)$_2$/tBubipy (10/10 mol %) | 62% |
| 2 | Cu(acac)$_2$ (10 mol %) | 51% |
| 3 | Cu(acac)$_2$ (20 mol %) | 62% |
| 4 | Cu(acac)$_2$ (30 mol %) | 63% |

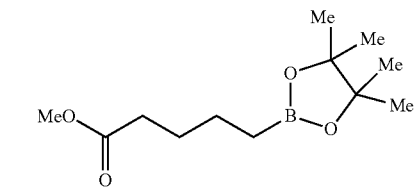 [SMILES: COC(=O)CCCCB1OC(C)(C)C(C)(C)O1]

TABLE 19-continued

Copper-catalyzed Borylation of Redox-Active Esters

Screening with copper

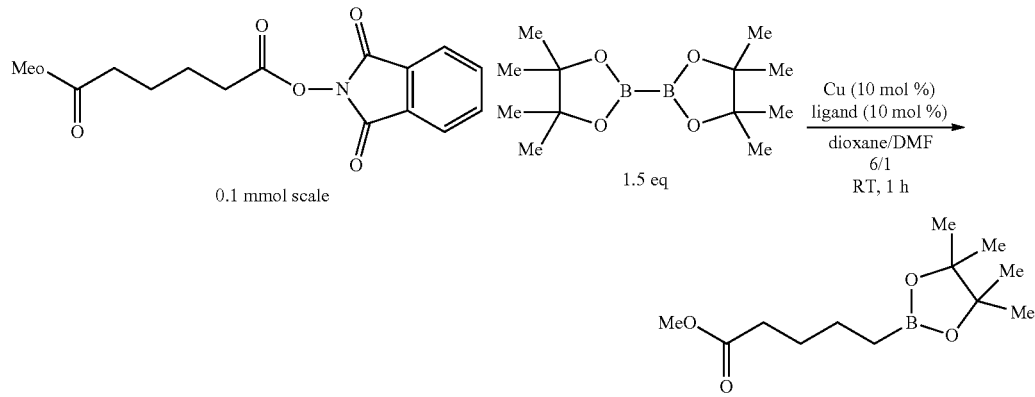

| Entry | Conditions | Result |
|---|---|---|
| 5 | Cu(acac)$_2$ (20 mol %), additive H$_2$O (50 uL, 28 eq) | 59% |
| 6 | Cu(acac)$_2$ (20 mol %), additive tBuOLi (2 eq) | 60% |
| 7 | Cu(acac)$_2$ (10 mol %), CuI (10 mol %) | 66% |
| 8 | Cu(acac)$_2$ (10 mol %), CuCl (10 mol %) | 59% |
| 9 | Cu(acac)$_2$ (10 mol %), Cu(OAc)$_2$ (10 mol %) | 50% |
| 10 | Cu(acac)$_2$/Cu(ClO$_4$)2•6H$_2$O (10/10/10 mol %) | 48% |
| 11 | Cu(acac)$_2$/CuCl/tBubipy (10/10/10 mol %) | 59% |
| 12 | Cu(acac)$_2$/Cu(OAc)$_2$/tBubipy (10/10/10 mol %) | 59% |

TABLE 20

Copper-catalyzed Borylation of Redox-Active Esters; Mg source and LiOH Loading

Screening with copper

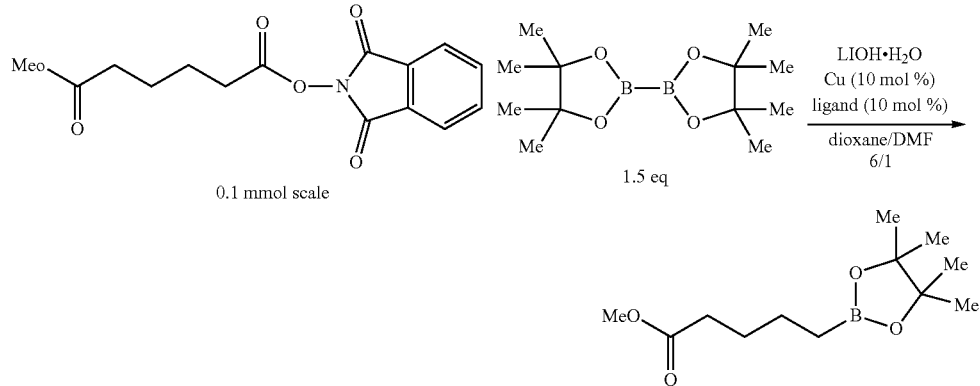

| Entry | Conditions | Result |
|---|---|---|
| | (LiOH•H$_2$O (10 eq), Cu(acac)$_2$ (20 mol %)) | |
| 1 | MgCl$_2$ | 61% |
| 2 | Mg(OTf)$_2$ | 19% |
| 3 | Mg(ClO$_4$)$_2$ | 12% |
| 4 | MgO | trace |
| 5 | Mg(OAc)$_2$•4H$_2$O | 24% |
| | Cu(acac)$_2$ (20 mol %), MgBr$_2$•Et$_2$O (0.8 eq) | |
| 1 | 15 eq LiOH•H$_2$O (63 mg) | 69% |
| 2 | 20 eq LiOH•H$_2$O (84 mg) | 69% |
| 3 | 30 eq LiOH•H$_2$O (126 mg) | 67% |

TABLE 20-continued

Copper-catalyzed Borylation of Redox-Active Esters; Mg source and LiOH Loading

[Reaction scheme: tBuO-substrate with OTBS and N-hydroxyphthalimide ester (0.1 mmol scale) + B₂Pin₂ (1.5 eq) with LiOH·H₂O, Cu(acac)₂ (20 mol %), MgBr₂·Et₂O (0.2 eq) in dioxane/DMF 0.6/0.1 mL, RT, 1 h → tBuO-substrate with OTBS and Bpin]

| Entry | Conditions | Result |
|---|---|---|
| 1 | 10 eq LiOH·H₂O (42 mg) | 55% |
| 2 | 15 eq LiOH·H₂O (63 mg) | 61% |

TABLE 21

Reaction Condition Optimization and Cost Estimate Comparison, Cu-catalyzed versus Ni-catalyzed Borylation

[Reaction scheme: tBuO-substrate with OTBS and N-hydroxyphthalimide ester (0.1 mmol scale) + B₂Pin₂ (1.5 eq) with LiOH·H₂O (15 eq), Cu(acac)₂ (20 mol %), additives in dioxane/DMF 0.6/0.1 mL, RT, 1 h → tBuO-substrate with OTBS and Bpin]

| Entry | Final conditions w/ MgCl₂ | Result |
|---|---|---|
| 1 | MgCl₂ (0.8 eq) | 59% |
| 2 | MgCl₂ (1.5 eq) | 61% |
| 3 | MgCl₂ (1.5 eq), dioxane/DMF 4/1 | 64% |
| 4 | MgCl₂ (1.5 eq), dioxane/DMF 4/1, PPh₃ (20 mol %) | 59% |

| | B₂Pin₂ | LiOH·H2O | Cu(acac)2 | Mg source | Total |
|---|---|---|---|---|---|
| Cost (/mol) | $ 137 | $ 66 | $ 13 | $ 280 (MgBr₂·Et₂O) | $ 496 |
| | | | | $ 8 (MgCl₂) | $ 224 |

[Structure: MeO-(CH₂)₃-Bpin ester]
52%, Scripps (Ni)
41%, Aggarwal
69%, Scripps (Cu)
55% isolated on gram scale (3.5 mmol)

[Structure: tBuO-ester with OTBS and Bpin]
48%, Scripps (Ni)
unknown, Aggarwal
64%, Scripps (Cu)
60% isolated on gram scale (2.5 mmol)

Copper-Catalyzed Borylation Procedure: Optimized

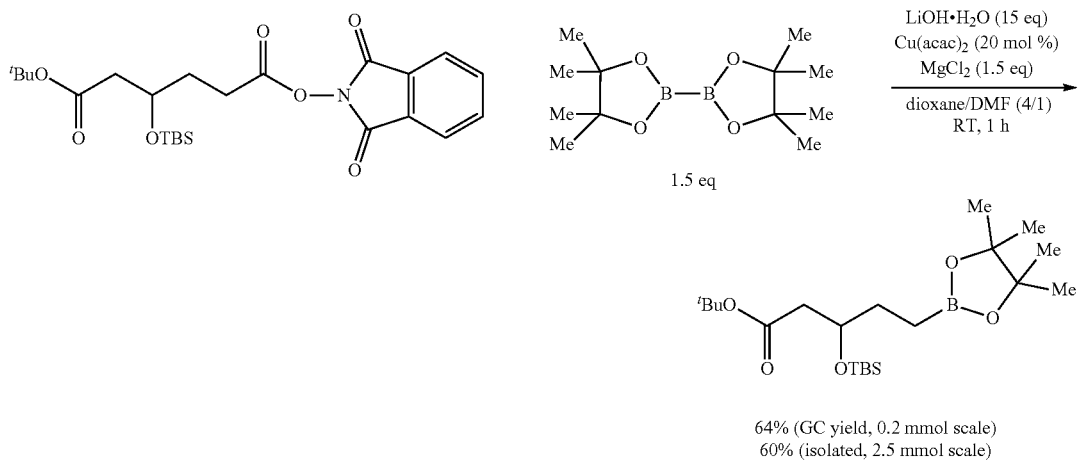

64% (GC yield, 0.2 mmol scale)
60% (isolated, 2.5 mmol scale)

Procedure:

To a 15 mL culture tube equipped with a stir bar were added redox-active ester (0.2 mmol), $B_2Pin_2$ (76 mg, 1.5 eq), LiOH·$H_2O$ (126 mg, 15 eq), Cu(acac)$_2$ (10.4 mg, 20 mol %) and MgCl$_2$ (28.5 mg, 1.5 eq). The tube was evacuated and backfilled with argon for 3 times. Degassed dioxane/DMF (from Acros extra-dry bottles, 4/1, 1.4 mL) was added and the resulting mixture was stirred under 1000 rpm at RT for 30 min before diluted with EtOAc (7 mL) and washed with saturated NH$_4$Cl (7 mL). The organic phase was dried over anhydrous Na$_2$SO$_4$, evaporated and purified by silica gel chromatography to give the desired product.

Gram Scale Procedure:

To a 50 mL flask equipped with a stir bar were added redox-active ester (1.2 g, 2.5 mmol), $B_2Pin_2$ (953 mg, 1.5 eq), LiOH·$H_2O$ (1.58 g, 15 eq), Cu(acac)$_2$ (130 mg, 20 mol %) and MgCl$_2$ (356 mg, 1.5 eq). The flask was evacuated and backfilled with argon for 3 times. The solid in the flask was stirred for 2 min before degassed dioxane/DMF (from Acros extra-dry bottles, 4/1, 17.5 mL) was added and the resulting mixture was stirred under 1000 rpm at RT for 30 min before diluted with Et$_2$O (50 mL) and washed with saturated NH$_4$Cl (30 mL) and brine (30 mL) successively. The organic phase was collected, dried over anhydrous Na$_2$SO$_4$, evaporated and purified by silica gel chromatography to afford the borylation product (625 mg, 60%).

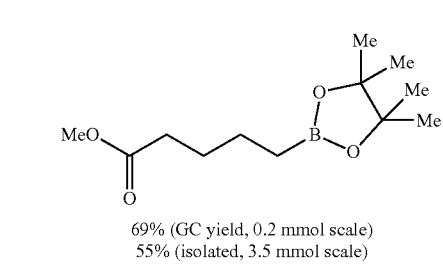 [SMILES: COC(=O)CCCCB1OC(C)(C)C(C)(C)O1]

69% (GC yield, 0.2 mmol scale)
55% (isolated, 3.5 mmol scale)

For the adipic acid substrate, shown above, 69% GC yield was obtained on 0.2 mmol scale while 55% isolated yield on 3.5 mmol scale. The graphic, below, shows additional substrates and yields obtained in this reaction system.

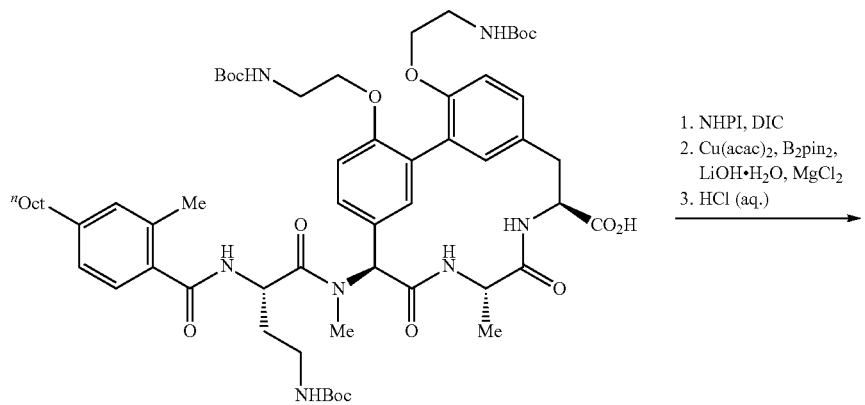

1. NHPI, DIC
2. Cu(acac)$_2$, B$_2$pin$_2$, LiOH·$H_2O$, MgCl$_2$
3. HCl (aq.)

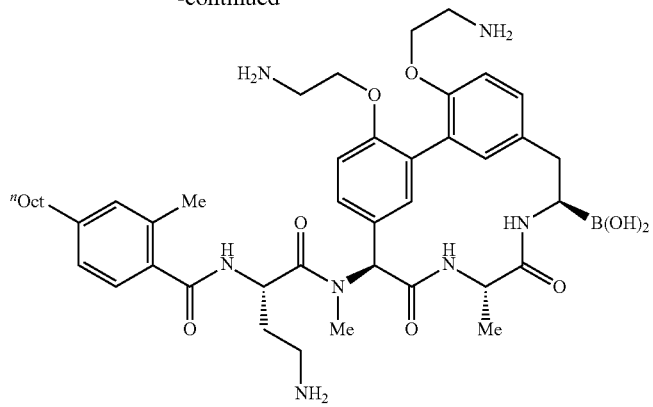

Arylomycin Sidechain Analog Boronic Acid

Experimental:

The starting carboxylic acid (50 mg, 0.044 mmol) and N-hydroxyphalmide (6.0 mg, 0.047 mmol, 1.1 eq) was placed in an oven dried culture tube fixed with a stirbar. This was evacuated and backfilled with argon 3 times. To this was added DCM (0.5 mL) via syringe, creating a suspension. While stirring, N,N'-diisopropylcarbodiimide (9.5 µL, 7.7 mg, 0.047 mmol, 1.1 eq.) was added via syringe. After consumption of starting material as monitored by TLC (~1 h), the solvent was blown off under a stream of nitrogen, and placed on high vacuum for 2 hours. After this, Cu(acac)$_2$ (11.5 mg, 0.044 mmol, 1.0 eq.), B$_2$pin$_2$ (83.8 mg, 0.33 mmol, 7.5 eq.), LiOH.H$_2$O (55.4 mg, 1.32 mmol, 30 eq.), and MgCl$_2$ (31.4 mg, 0.33 mmol, 7.5 eq.) were quickly added to the tube and resealed. It was evacuated and backfilled with argon 3 times. A 6:1 mixture of dioxane/DMF (0.5 mL) was added to the reaction tube. The resulting mixture was then stirred vigorously for 45 minutes at room temperature. It was then quenched with 2 mL of saturated aqueous NH$_4$Cl. This was extracted three times with EtOAc. The combined organic layers were rinsed with brine and dried over MgSO$_4$. The solvent was removed under reduced pressure. The crude material was purified by a swift flash chromatography column (SiO$_2$— 3% DCM in MeOH) to provide 31.2 mg semi-pure product as an off-white solid (~50% yield). This material was dissolved in 0.4 mL of dioxane. To this was added 3 mL of 3M HCl (aq.). The resulting mixture was stirred at room temperature for 24 hours. The reaction was concentrated on a rotary evaporator. The resulting residue was dissolved in 3 mL of 1:1 MeCN/H$_2$O and purified by preparatory HPLC (C$_{18}$; gradient of H$_2$O to MeCN each containing 0.1% formic acid) providing 2.1 mg.

Copper-Catalyzed Borylation Examples

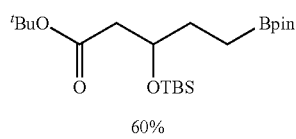

60%

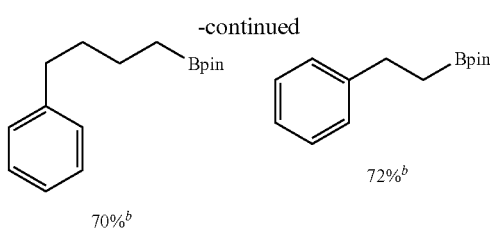

70%[b]

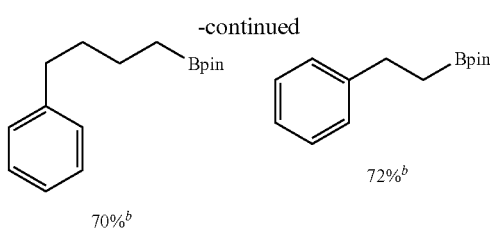

72%[b]

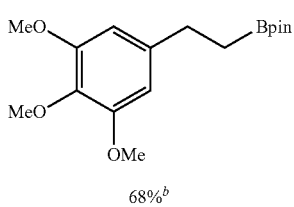

68%[b]

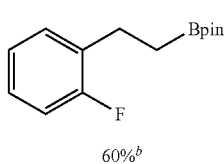

60%[b]

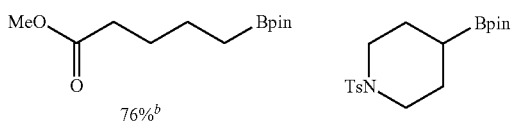

76%[b]       66%[b]

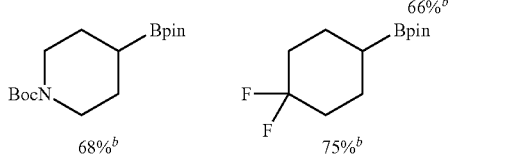

68%[b]       75%[b]

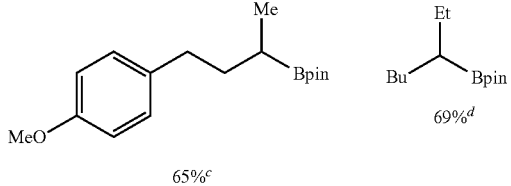

65%[c]       69%[d]

35%[b]

[a]: Cu(acac)₂ (20 mol%), B₂pin₂ (1.5 eq), dioxane/DMF 4/1; [b]: Cu(acac)₂ (30 mol%), B₂pin₂ (3.0 eq), dioxane/DMF 4/1; [c]: Cu(acac)₂ (30 mol%), B₂pin₂ (3.0 eq), dioxane/DMF 2/1; [d]: Cu(acac)₂ (30 mol%), B₂pin₂ (3.0 eq), dioxane/DMF 1/2

Experimental Procedures and Characterization Data for Redox-Active Esters

Compound 2

1,3-dioxoisoindolin-2-yl 2-methyl-4-phenylbutanoate (2)

On 8.75 mmol scale, General Procedure A was followed with 2-methyl-4-phenylbutanoic acid. Purification by flash column chromatography (silica gel, 1:9 EtOAc:hexanes) furnished 2 (2.31 g, 82%).

Physical state: colorless oil;
$R_f$=0.60 (silica gel, 3:7 EtOAc:hexanes);
$^1$H NMR (600 MHz, CDCl₃): δ 7.92-7.88 (m, 2H), 7.81-7.78 (m, 2H), 7.32-7.29 (m, 2H), 7.27-7.25 (m, 2H), 7.22-7.20 (m, 1H), 2.90-2.74 (m, 3H), 2.20-2.14 (m, 1H), 1.96-1.90 (m, 1H), 1.40 (d, J=7.2 Hz, 3H) ppm;
$^{13}$C NMR (151 MHz, CDCl₃): δ 172.7, 162.2, 141.3, 134.9, 129.2, 128.7, 128.6, 126.2, 124.1, 36.7, 35.7, 33.1, 17.2 ppm;
HRMS (ESI-TOF, m/z): Calcd for $C_{19}H_{18}NO_4$ [M+H]⁺ 324.1230; found 324.1230.

Compound S1

4,5,6,7-tetrachloro-1,3-dioxoisoindolin-2-yl 2-methyl-4-phenylbutanoate (S1)

On 13 mmol scale, General Procedure A was followed with 2-methyl-4-phenylbutanoic acid. Purification by flash column chromatography (silica gel, 1:10 EtOAc:hexanes) furnished a yellow product. This compound was then recrystallized from CH₂Cl₂/MeOH to yield S1 (4.12 g, 69%).

Physical state: white solid;
m.p.=80-81° C.;
$R_f$=0.63 (silica gel, 1:4 EtOAc:hexanes);
$^1$H NMR (600 MHz, CDCl₃): δ 7.32-7.28 (m, 2H), 7.26-7.19 (m, 3H), 2.89-2.72 (m, 3H), 2.20-2.13 (m, 1H), 1.95-1.88 (m, 1H), 1.39 (d, J=8.4 Hz, 3H) ppm;
$^{13}$C NMR (151 MHz, CDCl₃): δ 172.3, 157.8, 141.1, 141.0, 130.6, 128.6, 126.3, 124.9, 36.6, 35.5, 33.1, 17.3 ppm;
HRMS (ESI-TOF, m/z): Calcd for $C_{19}H_{14}Cl_4NO_4$ [M+H]⁺ 459.9671; found 459.9659.

Compound S3

1,3-dioxoisoindolin-2-yl 3-(2-bromophenyl)propanoate (S3)

On 5.0 mmol scale, General Procedure A was followed with 3-(2-bromophenyl) propanoic acid. Purification by flash column chromatography (silica gel, 1:9 EtOAc:hexanes) furnished S3 (1.63 g, 87%).

Physical state: white solid;
m.p.=158-160° C.;
$R_f$=0.36 (silica gel, 1:4 EtOAc:hexanes);
$^1$H NMR (600 MHz, CDCl₃): δ 7.90-7.87 (m, 2H), 7.80-7.77 (m, 2H), 7.56 (dd, J=1.2 Hz, 7.8 Hz, 1H), 7.34 (dd, J=7.8 Hz, 1.8 Hz, 1H), 7.28 (dt, J=7.8 Hz, 1.2 Hz, 1H), 7.12 (dt, J=7.8 Hz, 1.8 Hz, 1H), 3.21 (t, J=7.2 Hz, 2H), 3.02 (t, J=7.2 Hz, 2H) ppm;
$^{13}$C NMR (151 MHz, CDCl₃): δ 168.8, 162.0, 138.5, 134.9, 133.1, 130.1, 129.0, 128.7, 127.9, 124.4, 124.1, 31.2, 31.0 ppm;
HRMS (ESI-TOF, m/z): Calcd for $C_{17}H_{13}BrNO_4$ [M+H]⁺ 374.0022; found 374.0022.

Compound S4

1,3-dioxoisoindolin-2-yl 6-bromohexanoate (S4)

On 5.0 mmol scale, General Procedure A was followed with 6-bromohexanoic acid. Purification by flash column chromatography (silica gel, 1:10 EtOAc:hexanes) furnished S4 (1.52 g, 89%).

Physical state: white solid;
m.p.=60-62° C.;
$R_f$=0.45 (silica gel, 1:4 EtOAc:hexanes);

¹H NMR (600 MHz, CDCl₃): δ 7.89-7.86 (m, 2H), 7.79-7.77 (m, 2H), 3.42 (t, J=7.2 Hz, 2H), 2.68 (t, J=7.2 Hz, 2H), 1.94-1.89 (m, 2H), 1.84-1.79 (m, 2H), 1.63-1.57 (m, 2H) ppm;
¹³C NMR (151 MHz, CDCl₃): δ 169.4, 162.0, 134.9, 129.0, 124.1, 33.3, 32.3, 30.9, 27.5, 24.0 ppm;
HRMS (ESI-TOF, m/z): Calcd for $C_{14}H_{15}BrNO_4$ [M+H]⁺ 340.0179; found 340.0178.
Compound S5

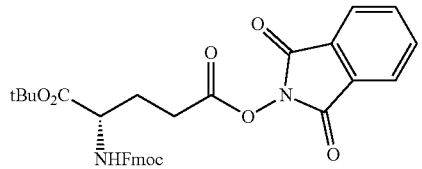

1-(tert-butyl) 5-(1,3-dioxoisoindolin-2-yl) (((9H-fluoren-9-yl)methoxy)carbonyl)-L glutamate (S5)

On 3.0 mmol scale, General Procedure A was followed with Fmoc-Glu-O′Bu. Purification by flash column chromatography (silica gel, 1:3 EtOAc:hexanes) furnished S5 (1.53 g, 89%).
Physical state: white foam;
$R_f$=0.49 (silica gel, 1:4 EtOAc:hexanes);
¹H NMR (600 MHz, CDCl₃): δ 7.90-7.86 (m, 2H), 7.80-7.76 (m, 4H), 7.67-7.61 (m, 2H), 7.42-7.38 (m, 2H), 7.31 (dt, J=7.2 Hz, 1.2 Hz, 2H), 5.52 (br d, J=7.8 Hz, 1H), 4.50 (dd, J=10.8 Hz, 7.2 Hz, 1H), 4.39-4.36 (m, 2H), 4.23 (t, J=7.2 Hz, 1H), 2.82-2.77 (m, 1H), 2.73-2.67 (m, 1H), 2.40-2.34 (m, 1H), 2.15-2.09 (m, 1H), 1.50 (s, 9H) ppm;
¹³C NMR (151 MHz, CDCl₃): δ 170.6, 169.1, 162.0, 156.2, 143.9, 141.5, 134.9, 129.0, 127.9, 127.2, 125.4, 125.2, 124.2, 120.1, 83.1, 67.2, 53.7, 47.4, 28.1, 28.0, 27.6 ppm;
HRMS (ESI-TOF, m/z): Calcd for $C_{32}H_{30}N_2NaO_8$ [M+Na]⁺ 593.1894; found 593.1895;
$[\alpha]_D^{20}$=+5.4 (c 1.0, CHCl₃).
Compound S6

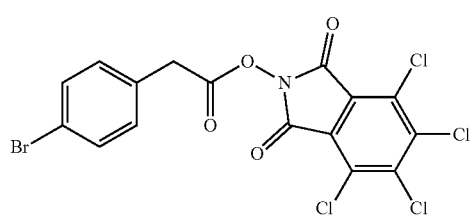

4,5,6,7-tetrachloro-1,3-dioxoisoindolin-2-yl 2-(4-bromophenyl)acetate (S6)

On 5.0 mmol scale, General Procedure A was followed with 2-(4-bromophenyl)acetic acid. After completion of the reaction, reaction mixture was filtered through a short pad of silica gel and washed with EtOAc/hexanes (1:8). The filtrate was concentrated, and S6 was obtained after recrystallization with CH₂Cl₂/MeOH (1.52 g, 61%).

Physical state: pale yellow solid;
m.p.=212-213° C.;
$R_f$=0.57 (silica gel, 1:4 EtOAc:hexanes);
¹H NMR (600 MHz, DMSO-d₆): δ 7.61-7.59 (m, 2H), 7.37-7.35 (m, 2H), 4.25 (s, 2H) ppm;
¹³C NMR (151 MHz, DMSO-d₆): δ 167.7, 157.5, 139.3, 131.7, 131.6, 131.6, 129.0, 125.2, 120.9, 35.8 ppm;
HRMS (ESI-TOF, m/z): Calcd for $C_{16}H_7BrCl_4NO_4$ [M+H]⁺ 495.8307; found 495.8323.
Compound S7

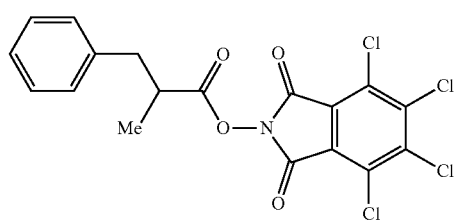

4,5,6,7-tetrachloro-1,3-dioxoisoindolin-2-yl 2-methyl-3-phenylpropanoate (S7)

On 5.0 mmol scale, General Procedure A was followed with 2-methyl-3-phenylpropanoic acid. Purification by flash column chromatography (silica gel, 1:10 EtOAc:hexanes) furnished a yellow product which was recrystallized from CH₂Cl₂/MeOH to yield S7 (1.45 g, 65%).
Physical state: pale yellow solid;
m.p.=127-128° C.
$R_f$=0.63 (silica gel, 1:4 EtOAc:hexanes);
¹H NMR (600 MHz, CDCl₃): δ 7.35-7.32 (m, 2H), 7.28-7.23 (m, 3H), 3.25 (dd, J=13.8 Hz, 6.6 Hz, 1H), 3.14-3.08 (m, 1H), 2.82 (dd, J=13.8 Hz, 7.8 Hz, 1H), 1.34 (d, J=7.2 Hz, 3H) ppm;
¹³C NMR (151 MHz, CDCl₃): δ 171.9, 157.7, 141.2, 137.8, 130.6, 129.2, 128.8, 127.0, 124.9, 39.3, 39.0, 16.6 ppm;
HRMS (ESI-TOF, m/z): Calcd for $C_{18}H_{12}Cl_4NO_4$ [M+H]⁺ 445.9515; found 445.9516.
Compound S8

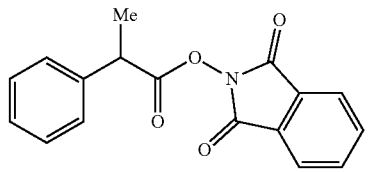

1,3-dioxoisoindolin-2-yl 2-phenylpropanoate (S8)

On 5.0 mmol scale, General Procedure A was followed with 2-phenylpropanoic acid. Purification by flash column chromatography (silica gel, 1:10 EtOAc:hexanes) furnished S8 (1.19 g, 81%).
Physical state: colorless oil;
$R_f$=0.21 (silica gel, 1:4 EtOAc:hexanes);
¹H NMR (600 MHz, CDCl₃): δ 7.87-7.85 (m, 2H), 7.79-7.76 (m, 2H), 7.43-7.39 (m, 4H), 7.34-7.31 (m, 1H), 4.13 (q, J=7.2 Hz, 1H), 1.68 (d, J=7.2 Hz, 3H) pm;

$^{13}$C NMR (151 MHz, CDCl$_3$): δ 170.9, 162.0, 138.5, 134.9, 129.1, 129.1, 127.9, 127.7, 124.1, 43.1, 19.1 ppm;
HRMS (ESI-TOF, m/z): Calcd for C$_{17}$H$_{14}$NO$_4$ [M+H]$^+$ 296.0917; found 296.0920.

Compound S9

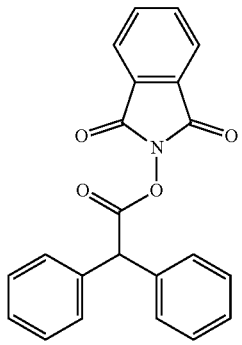

1,3-dioxoisoindolin-2-yl 2,2-diphenylacetate (S9)

On 1.5 mmol scale, General Procedure A was followed with diphenylacetic acid. Purification by flash column chromatography (silica gel, 1:4 EtOAc:hexanes) furnished S9 (0.46 g, 86%).
Physical state: white solid;
m.p.=135-137° C.;
R$_f$=0.33 (silica gel, 1:4 EtOAc:hexanes)
$^1$H NMR (600 MHz, CDCl$_3$): δ 7.89-7.86 (m, 2H), 7.80-7.77 (m, 2H), 7.42-7.37 (m, 8H), 7.34-7.31 (m, 2H), 5.42 (s, 1H) ppm;
$^{13}$C NMR (151 MHz, CDCl$_3$): δ 169.2, 162.0, 136.9, 134.9, 129.1, 129.0, 128.9, 128.0, 124.1, 54.2 ppm;
HRMS (ESI-TOF, m/z): Calcd for C$_{22}$H$_{16}$NO$_4$ [M+H]$^+$ 358.1074; found 358.1078.

Compound S10

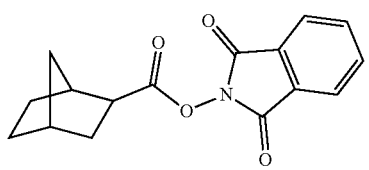

1,3-dioxoisoindolin-2-yl-bicyclo[2.2.1]heptane-2-carboxylate (S10)

On 3.0 mmol scale, General Procedure A was followed with bicyclo[2.2.1]heptane-2-carboxylic acid (mixture of endo and exo). Purification by flash column chromatography (silica gel, 1:19 to 1:9 EtOAc:hexanes) furnished S10 (0.75 g, 88%) as mixture of exo/endo isomers.
Physical state: white solid;
R$_f$=0.41 (silica gel, 1:4 EtOAc:hexanes);
$^1$H NMR (600 MHz, CDCl$_3$): δ 7.90-7.86 (m, 2H), 7.80-7.77 (m, 2H), 3.15-3.11 (m, 0.82H), 2.81 (br s, 0.82H), 2.77 (br d, J=4.2 Hz, 0.18H), 2.70 (dd, J=9.6 Hz, 6.0 Hz, 0.18H), 2.38 (br t, J=4.2 Hz, 0.18H), 2.35-2.33 (br, m, 0.82H), 2.00-1.96 (m, 0.18H), 1.86-1.81 (m, 0.82H), 1.74-1.70 (m, 0.82H), 1.63-1.67 (m, 3.28H), 1.51-1.44 (m, 1.64H), 1.38-1.25 (m, 1.26H) ppm;
$^{13}$C NMR (151 MHz, CDCl$_3$): δ171.5, 162.3, 134.8, 129.2, 124.0, 43.4, 41.0, 40.5, 37.0, 32.7, 29.0, 24.9 ppm (major isomer); 172.3, 162.3, 134.8, 129.2, 124.0, 43.7, 41.7, 36.7, 36.2, 34.6, 29.5, 28.6 ppm (minor isomer).
HRMS (ESI-TOF, m/z): Calcd for C$_{16}$H$_{16}$NO$_4$ [M+H]$^+$ 286.1074; found 286.1071.

Compound S11

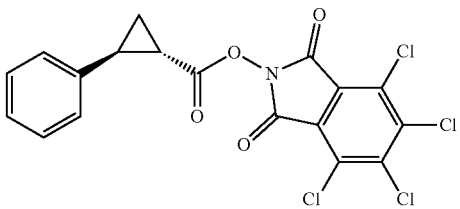

4,5,6,7-tetrachloro-1,3-dioxoisoindolin-2-yl trans-2-phenylcyclopropane-1-carboxylate (S11)

On 3.0 mmol scale, General Procedure A was followed with trans-2-phenylcyclopropane-1-carboxylic acid. Upon complete consumption of starting material (TLC), the reaction mixture was filtered through celite, washed with CH$_2$Cl$_2$ (100 mL), and concentrated under reduced pressure. The crude product was purified by crystallization (CH$_2$Cl$_2$/MeOH) to furnish S11 (949 mg, 71%).
Physical state: pale yellow needle;
m.p.=203-205° C.;
R$_f$=0.48 ((silica gel, 1:9 EtOAc:hexanes);
$^1$H NMR (600 MHz, CDCl$_3$): δ 7.34-7.31 (m, 2H), 7.28-7.25 (m, 1H), 7.18-7.16 (m, 2H), 2.80-2.77 (m, 1H), 2.22-2.19 (m, 1H), 1.84 (dt, J=10.2 Hz, 5.4 Hz, 1H), 1.69-1.66 (m, 1H) ppm;
$^{13}$C NMR (151 MHz, CDCl$_3$): δ 169.4, 157.7, 141.2, 138.3, 130.6, 128.8, 127.4, 126.5, 124.8, 28.8, 21.0, 18.6 ppm;
HRMS (ESI-TOF, m/z): Calcd for C$_{18}$H$_{10}$Cl$_4$NO$_4$ [M+H]$^+$ 443.9358; found 443.9356.

Compound S12

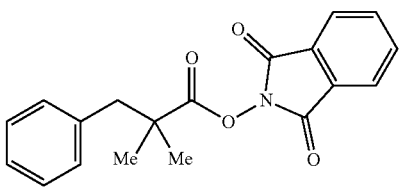

1,3-dioxoisoindolin-2-yl 2,2-dimethyl-3-phenylpropanoate (S12)

On 5.0 mmol scale, General Procedure A was followed with 2,2-dimethyl-3-phenylpropanoic acid. Purification by flash column chromatography (silica gel, 1:10 EtOAc:hexanes) furnished S12 (1.36 g, 84%).
Physical state: white solid;
m.p.=70-72° C.;
R$_f$=0.45 (silica gel, 1:4 EtOAc:hexanes);

¹H NMR (600 MHz, CDCl₃): δ 7.92-7.88 (m, 2H), 7.81-7.78 (m, 2H), 7.36-7.31 (m, 4H), 7.29-7.26 (m, 1H), 3.10 (s, 2H), 1.40 (s, 6H) ppm;
¹³C NMR (151 MHz, CDCl₃): δ 173.7, 162.2, 136.5, 134.8, 130.6, 129.1, 128.3, 127.0, 124.0, 45.8, 43.3, 25.0 ppm;
HRMS (ESI-TOF, m/z): Calcd for C₁₉H₁₈NO₄ [M+H]⁺ 324.1230; found 324.1232.

Compound S13

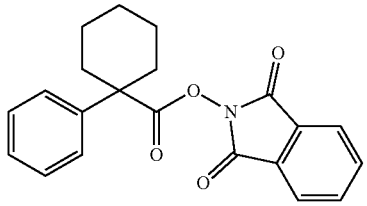

1,3-dioxoisoindolin-2-yl 1-phenylcyclohexane-1-carboxylate (S13)

On 5.0 mmol scale, General Procedure A was followed with 2-phenylpropanoic acid. Purification by flash column chromatography (silica gel, 1:9 EtOAc:hexanes) furnished S13 (1.64 g, 81%).
Physical state: white solid;
m.p.=108-109° C.;
R$_f$=0.39 (silica gel, 1:4 EtOAc:hexanes);
¹H NMR (600 MHz, CDCl₃): δ 7.87-7.84 (m, 2H), 7.78-7.75 (m, 2H), 7.54-7.52 (m, 2H), 7.44-7.41 (m, 2H), 7.34-7.31 (m, 1H), 2.64 (br d, J=13.2 Hz, 2H), 1.89-1.73 (m, 7H), 1.37-1.30 (m, 1H) ppm;
¹³C NMR (151 MHz, CDCl₃): δ 171.8, 162.2, 142.3, 134.8, 129.2, 128.9, 127.7, 126.1, 124.0, 51.3, 35.5, 25.6, 23.6 ppm;
HRMS (ESI-TOF, m/z): Calcd for C₂₁H₂₀NO₄ [M+H]⁺ 350.1387; found 350.1387.

Compound S14

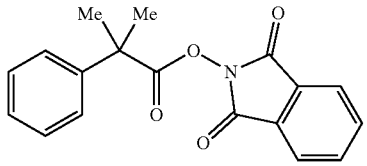

1,3-dioxoisoindolin-2-yl 2-methyl-2-phenylpropanoate (S14)

On 5.0 mmol scale, general procedure A was followed with 2-methyl-2-phenylpropanoic acid. Purification by flash column chromatography (silica gel, 1:8 EtOAc:hexanes) furnished S14 (1.32 g, 85%).
Physical state: white solid;
m.p.=73-74° C.;
R$_f$=0.36 (silica gel, 1:4 EtOAc:hexanes);
¹H NMR (600 MHz, CDCl₃): δ 7.88-7.85 (m, 2H), 7.79-7.75 (m, 2H), 7.51-7.49 (m, 2H), 7.44-7.41 (m, 2H), 7.34-7.31 (m, 1H), 1.79 (s, 6H) ppm;

¹³C NMR (151 MHz, CDCl₃): δ 173.4, 162.1, 142.7, 134.8, 129.1, 128.8, 127.5, 125.9, 124.0 46.5, 27.0 ppm;
HRMS (ESI-TOF, m/z): Calcd for C₁₈H₁₆NO₄ [M+H]⁺ 310.1074; found 310.1082.

Compound S15

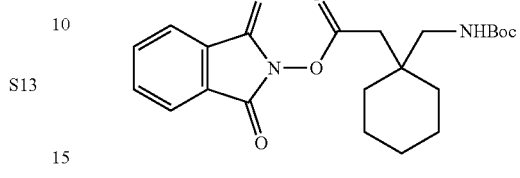

1,3-dioxoisoindolin-2-yl 2-(1-(((tert-butoxycarbonyl)amino)methyl)cyclohexyl) acetate (S15)

On 0.44 mmol scale, General Procedure A was followed with Boc protected gabapentin. Purification by flash column chromatography (silica gel, 1:5 EtOAc:hexanes) furnished S15 (165 mg, 85%).
Physical state: white solid;
m.p.=76-79° C.;
R$_f$=0.32 (silica gel, 1:5 EtOAc:hexanes);
¹H NMR (600 MHz, CDCl₃): δ 7.90-7.87 (m, 2H), 7.82-7.77 (m, 2H), 4.95 (br t, J=7.2 Hz, 1H), 3.38 (d, J=6.6 Hz, 2H), 2.63 (s, 2H), 1.65-1.43 (m, 10H), 1.44 (s, 9H) ppm;
¹³C NMR (151 MHz, CDCl₃): δ 168.3, 162.1, 156.6, 135.0, 129.0, 124.2, 79.3, 46.9, 39.1, 37.8, 33.9, 28.5, 26.0, 21.6 ppm;
HRMS (ESI-TOF, m/z): Calcd for C₂₂H₂₉N₂O₆ [M+H]⁺ 417.2020; found 417.2022.

Compound S16

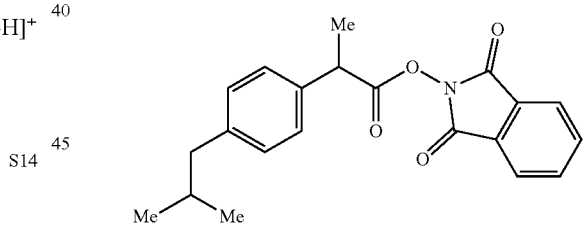

1,3-dioxoisoindolin-2-yl 2-(4-isobutylphenyl)propanoate (S16)

On 5.0 mmol scale, General Procedure A was followed with ibuprofen. Purification by flash column chromatography (silica gel, 1:9 EtOAc:hexanes) furnished S16 (1.48 g, 84%).
Physical state: colorless oil;
R$_f$=0.42 (silica gel, 1:4 EtOAc:hexanes);
¹H NMR (600 MHz, CDCl₃): δ 7.87-7.85 (m, 2H), 7.79-7.76 (m, 2H), 7.31 (d, J=8.4 Hz, 2H), 7.17 (d, J=8.4 Hz, 2H), 4.10 (q, J=7.2 Hz, 1H), 2.48 (d, J=7.2 Hz, 2H), 1.91-1.84 (m, 1H), 1.67 (d, J=7.2 Hz, 3H), 0.91 (d, J=6.6 Hz, 6H) ppm;
¹³C NMR (151 MHz, CDCl₃): δ 171.1, 162.0, 141.4, 135.7, 134.8, 129.8, 129.1, 127.4, 124.0, 45.2, 42.7, 30.3, 22.5, 19.2 ppm;

HRMS (ESI-TOF, m/z): Calcd for $C_{21}H_{22}NO_4$ [M+H]$^+$ 352.1543; found 352.1544.

Compound S17

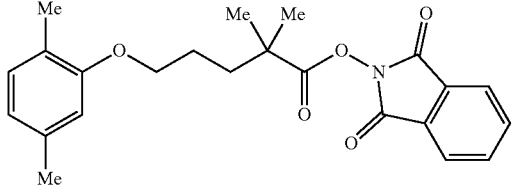

1,3-dioxoisoindolin-2-yl 5-(2,5-dimethylphenoxy)-2,2-dimethylpentanoate (S17)

On 1.0 mmol scale, General Procedure A was followed with gemfibrozil. Purification by flash column chromatography (silica gel, 1:25 EtOAc:hexanes) furnished S17 (0.33 g, 84%).

Physical state: white solid;
m.p.=65-67° C.;
$R_f$=0.50 (silica gel, 1:4 EtOAc:hexanes)
$^1$H NMR (600 MHz, CDCl$_3$): δ 7.90-7.87 (m, 2H), 7.80-7.77 (m, 2H), 7.01 (d, J=7.8 Hz, 1H), 6.67 (d, J=7.8 Hz, 1H), 6.66 (s, 1H), 4.02 (t, J=6.0 Hz, 2H), 2.32 (s, 3H), 2.20 (s, 3H), 1.95-2.00 (m, 4H), 1.46 (s, 6H) ppm;
$^{13}$C NMR (151 MHz, CDCl$_3$): δ 173.9, 162.2, 157.1, 136.6, 134.8, 130.4, 129.2, 124.0, 123.8, 120.8, 112.1, 67.9, 42.1, 37.5, 31.7, 25.3, 25.1, 21.5, 15.9 ppm;
HRMS (ESI-TOF, m/z): Calcd for $C_{23}H_{26}NO_5$ [M+H]$^+$ 396.1805; found 396.1803.

Compound S18

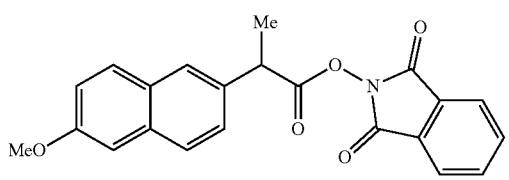

1,3-dioxoisoindolin-2-yl 2-(6-methoxynaphthalen-2-yl)propanoate (S18)

On 5.0 mmol scale, General Procedure A was followed with naproxen. Purification by flash column chromatography (silica gel, 1:7 EtOAc:hexanes) furnished S18 (1.65 g, 88%).

Physical state: white solid;
m.p.=110-111° C.;
$R_f$=0.53 (silica gel, 2:3 EtOAc:hexanes);
$^1$H NMR (600 MHz, CDCl$_3$): δ 7.86 (br s, 2H), 7.80-7.75 (m, 5H), 7.49 (dd, J=8.4 Hz, 1.8 Hz, 1H), 7.17 (dd, J=8.4 Hz, 2.4 Hz, 1H), 7.14 (d, J=2.4 Hz, 1H), 4.26 (q, J=7.2 Hz, 1H), 3.92 (s, 3H), 1.75 (d, J=7.2 Hz, 3H) ppm;
$^{13}$C NMR (151 MHz, CDCl$_3$): δ 171.1, 162.0, 158.0, 134.9, 134.1, 133.6, 129.6, 129.1, 127.7, 126.5, 126.0, 124.1, 119.3, 105.8, 55.5, 43.1, 19.2 ppm;

HRMS (ESI-TOF, m/z): Calcd for $C_{22}H_{18}NO_5$ [M+H]$^+$ 376.1179; found 376.1183.

Compound S19

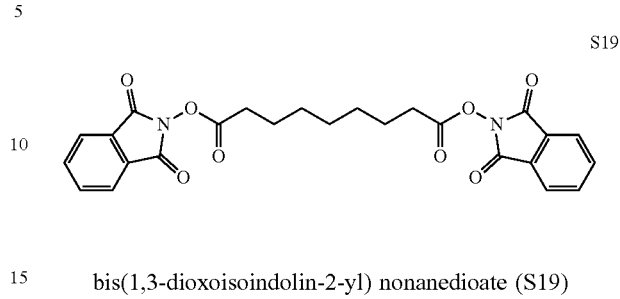

bis(1,3-dioxoisoindolin-2-yl) nonanedioate (S19)

On 5.0 mmol scale, General Procedure A was followed with azelaic acid (5.0 mmol, 1.0 equiv), NHPI (10 mmol, 2.0 equiv), DIC (11 mmol, 2.2 equiv) and DMAP (1 mmol, 0.2 equiv). Purification by flash column chromatography (silica gel, 1:10 EtOAc:CH$_2$Cl$_2$) furnished S19 (1.52 g, 64%).

Physical state: white solid;
m.p.=103-105° C.;
$R_f$=0.55 (silica gel, 1:1 EtOAc:hexanes);
$^1$H NMR (600 MHz, CDCl$_3$): δ 7.90-7.87 (m, 4H), 7.81-7.78 (m, 4H), 2.69 (t, J=4.8 Hz, 4H), 1.85-1.80 (m, 4H), 1.53-1.48 (m, 4H), 1.45-1.42 (m, 2H) ppm;
$^{13}$C NMR (151 MHz, CDCl$_3$): δ 169.1, 161.5, 134.3, 128.5, 123.5, 30.5, 28.1, 28.0, 24.1 ppm;
HRMS (ESI-TOF, m/z): Calcd for $C_{25}H_{23}N_2O_8$ [M+H]$^+$ 479.1449; found 479.1451.

Compound S20

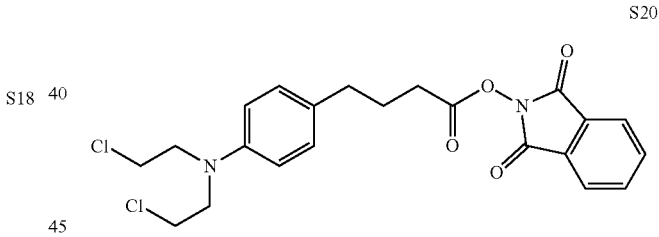

1,3-dioxoisoindolin-2-yl 4-(4-(bis(2-chloroethyl)amino)phenyl)butanoate (S20)

On 1.0 mmol scale, General Procedure A was followed with chlorambucil. Purification by flash column chromatography (silica gel, 1:4 EtOAc:hexanes) furnished S20 (431 mg, 96%).

Physical state: yellow oil;
$R_f$=0.23 (silica gel, 1:4 EtOAc:hexanes);
$^1$H NMR (600 MHz, CDCl$_3$): δ 7.91-7.87 (m, 2H), 7.81-7.77 (m, 2H), 7.12 (d, J=8.5 Hz, 2H), 6.65 (d, J=9.0 Hz, 2H), 3.66 (AB t, J=6.7 Hz, 4H), 3.63 (BA t, J=6.7 Hz, 4H), 2.67 (dt, J=7.5 Hz, 16 Hz, 4H), 2.09-2.02 (m, 2H) ppm;
$^{13}$C NMR (151 MHz, CDCl$_3$): δ 169.6, 162.1, 144.7, 134.9, 130.0, 129.1, 124.1, 112.4, 53.8, 40.7, 33.6, 30.3, 26.6 ppm;
HRMS (ESI-TOF, m/z): Calcd for $C_{22}H_{23}Cl_2N_2O_4$ [M+H]$^+$ 449.1029; found 449.1009.

Compound S21

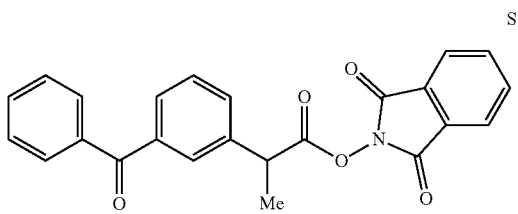

1,3-dioxoisoindolin-2-yl 2-(3-benzoylphenyl)propanoate (S21)

On 5.0 mmol scale, General Procedure A was followed with ketoprofen. Purification by flash column chromatography (silica gel, 1:3 EtOAc:hexanes) furnished S21 (1.91 g, 96%).

Physical state: white solid;
m.p.=118-120° C.;
$R_f$=0.45 (silica gel, 1:2 EtOAc:hexanes);
$^1$H NMR (600 MHz, CDCl$_3$): δ 7.88-7.84 (m, 5H), 7.80-7.76 (m, 3H), 7.67 (dt, J=8.4 Hz, 1.2 Hz, 1H), 7.61-7.58 (m, 3H), 7.55-7.48 (m, 3H), 4.20 (q, J=7.2 Hz, 1H), 1.71 (d, J=7.2 Hz, 3H) ppm;
$^{13}$C NMR (151 MHz, CDCl$_3$): δ 196.4, 170.6, 161.9, 138.7, 138.4, 137.5, 134.9, 132.7, 131.7, 130.3, 129.8, 129.5, 129.1, 129.1, 128.5, 124.1, 43.0, 19.0 ppm;
HRMS (ESI-TOF, m/z): Calcd for $C_{24}H_{18}NO_5$ [M+H]$^+$ 400.1179; found 400.1181.

Compound S22

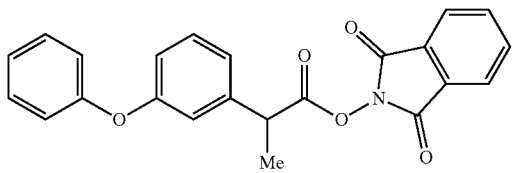

1,3-dioxoisoindolin-2-yl 2-(3-phenoxyphenyl)propanoate (S22)

On 5.0 mmol scale, General Procedure A was followed with fenoprofen. Purification by flash column chromatography (silica gel, 1:8 EtOAc:hexanes) furnished S22 (1.83 g, 94%).

Physical state: colorless oil;
$R_f$=0.50 (silica gel, 1:4 EtOAc:hexanes)
$^1$H NMR (600 MHz, CDCl$_3$): δ 7.89-7.85 (m, 2H), 7.79-7.76 (m, 2H), 7.37-7.33 (m, 3H), 7.16 (dt, J=7.8 Hz, 1.2 Hz, 1H), 7.13-7.10 (m, 1H), 7.09 (t, J=2.4 Hz, 1H), 7.07-7.04 (m, 2H), 6.95 (ddd, J=7.8 Hz, 2.4 Hz, 0.6 Hz, 1H), 4.09 (q, J=7.2 Hz, 1H). 1.67 (d, J=7.2 Hz, 3H) ppm;
$^{13}$C NMR (151 MHz, CDCl$_3$): δ 170.6, 161.9, 157.8, 157.1, 140.3, 134.9, 130.3, 129.9, 129.1, 124.1, 123.5, 122.5, 119.2, 118.4, 118.2, 42.9, 19.0 ppm;
HRMS (ESI-TOF, m/z): Calcd for $C_{23}H_{18}NO_5$[M+H]$^+$ 388.1179; found 388.1178.

Compound S23

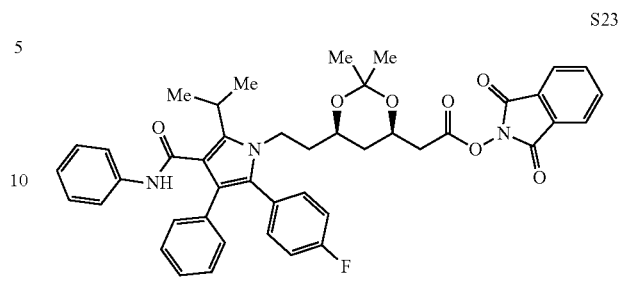

1,3-dioxoisoindolin-2-yl 2-((4R,6R)-6-(2-(2-(4-fluorophenyl)-5-isopropyl-3-phenyl-4-(phenylcarbamoyl)-1H-pyrrol-1-yl)ethyl)-2,2-dimethyl-1,3-dioxan-4-yl)acetate (S23)

On 0.5 mmol scale, General Procedure A was followed with ketal ester of atorvastatin. Purification by flash column chromatography (silica gel, 1:2 EtOAc:hexanes) furnished S23 (0.35 g, 95%).

Physical state: yellow foam;
$R_f$=0.35 (silica gel, 1:2 EtOAc:hexanes);
$^1$H NMR (600 MHz, CDCl$_3$): δ 7.90-7.87 (m, 2H), 7.81-7.77 (m, 2H), 7.21-7.15 (m, 9H), 7.08 (d, J=8.4 Hz, 2H), 7.02-6.97 (m, 3H), 6.88 (br s, 1H), 4.33-4.28 (m, 1H), 4.14-4.07 (m, 1H), 3.89-3.84 (m, 1H), 3.75-3.71 (m, 1H), 3.61-3.56 (m, 1H), 2.85 (dd, J=15.6 Hz, 6.6 Hz, 1H), 2.69 (dd, J=15.0 Hz, 6.6 Hz, 1H), 1.76-1.70 (m, 2H), 1.55-1.53 (m, 7H), 1.40 (s, 3H), 1.35 (s, 3H), 1.18 (dd, J=12.0 Hz, 5.4 Hz, 1H) ppm;
$^{13}$C NMR (151 MHz, CDCl$_3$): δ 166.9, 164.9, 162.4 (d, J=247.8 Hz), 161.9, 141.6, 138.5, 134.9, 134.8, 133.3 (d, J=8.0 Hz), 130.6, 129.0, 128.9, 128.8, 128.4, 128.3 (d, J=3.6 Hz), 126.7, 124.1, 123.6, 121.9, 119.7, 115.5 (d, J=21.3 Hz), 99.2, 66.4, 65.6, 40.9, 38.4, 38.1, 35.8, 29.9, 26.2, 21.9, 21.7, 19.7 ppm;
$^{19}$F NMR (376 MHz, CDCl$_3$): δ −113.91 ppm;
HRMS (ESI-TOF, m/z): Calcd for $C_{44}H_{43}FN_3O_7$[M+H]$^+$ 744.3080; found 744.3061.
$[α]_D^{20}$=+25.1 (c 1.0, CHCl$_3$).

Compound S24

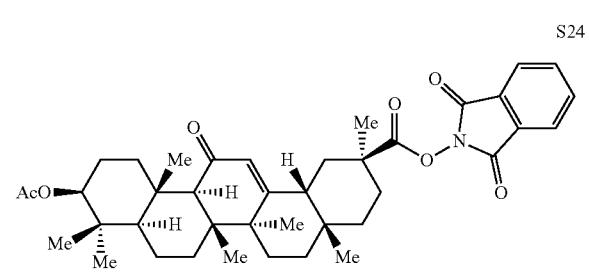

1,3-dioxoisoindolin-2-yl (2S,4aS,6aS,6bR,8aR,10S,12aS,12bR,14bR)-10-acetoxy-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxylate (S24)

On 1.0 mmol scale, General Procedure A was followed with acetyl enoxolone. Purification by flash column chromatography (silica gel, 1:5 EtOAc:hexanes) afforded S24 (0.49 g, 75%).

Physical State: white solid;
m.p.=264° C.;
$R_f$=0.57 (silica gel, 2:3 EtOAc:hexanes);
$^1$H NMR (600 MHz, CDCl$_3$): δ 7.89-7.86 (m, 2H), 7.80-7.77 (m, 2H), 5.76 (s, 1H), 4.51 (dd, J=11.8, 4.6 Hz, 1H), 2.79 (dt, J=13.7, 3.7 Hz, 1H), 2.45 (ddd, J=13.7, 4.3, 1.7 Hz, 1H), 2.35 (s, 1H), 2.15-2.11 (m, 1H), 2.11-2.00 (m, 2H), 2.04 (s, 3H), 1.86 (td, J=13.7, 4.7 Hz, 1H), 1.79 (t, J=13.7 Hz, 1H), 1.74-1.55 (m, 4H), 1.51-1.40 (m, 4H), 1.43 (s, 3H), 1.37 (s, 3H), 1.20 (ddd, J=13.8, 4.6, 2.4 Hz, 1H), 1.15 (s, 3H), 1.14 (s, 3H), 1.10-1.01 (m, 3H), 0.90 (s, 3H), 0.87 (s, 6H), 0.80 (dd, J=11.9, 1.8 Hz, 1H) ppm;
$^{13}$C NMR (151 MHz, CDCl$_3$): δ 200.0, 172.7, 171.1, 168.5, 162.2, 134.8, 129.2, 129.0, 124.0, 80.8, 61.9, 55.2, 47.9, 45.5, 44.0, 43.3, 41.3, 38.9, 38.2, 37.4, 37.1, 32.9, 32.0, 31.6, 28.5, 28.2, 28.1, 26.6, 26.6, 23.7, 23.4, 21.5, 18.8, 17.5, 16.8, 16.6 ppm;
HRMS (ESI-TOF, m/z): Calcd for C$_{40}$H$_{52}$NO$_7$ [M+H]$^+$ 658.3738; found 658.3736;
$[α]_D^{20}$=+191.0 (c 1.0, CHCl$_3$).

Compound S25

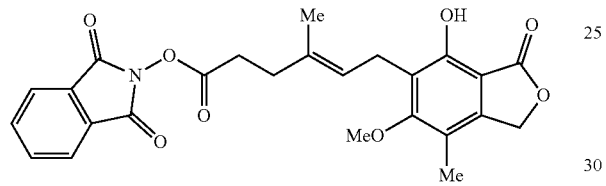

1,3-dioxoisoindolin-2-yl (E)-6-(4-hydroxy-6-methoxy-7-methyl-3-oxo-1,3-dihydroisobenzofuran-5-yl)-4-methylhex-4-enoate (S25)

On 1.0 mmol scale, General Procedure A was followed with mycophenolic acid. Purification by flash column chromatography (silica gel, 1:4 EtOAc:hexanes) furnished S25 (0.36 g, 78%).

Physical state: white solid;
m.p.=126-128° C.;
$R_f$=0.40 (silica gel, 1:3 EtOAc:hexanes);
$^1$H NMR (600 MHz, CDCl$_3$): δ 7.88-7.85 (m, 2H), 7.79-7.77 (m, 2H), 7.68 (s, 1H), 5.34 (t, J=7.2 Hz, 1H), 5.19 (s, 2H), 3.77 (s, 3H), 3.42 (d, J=6.6 Hz, 2H), 2.76 (t, J=7.8 Hz, 2H), 2.45 (t, J=7.8 Hz, 2H), 2.15 (s, 3H), 1.85 (s, 3H) ppm;
$^{13}$C NMR (151 MHz, CDCl$_3$): δ 173.0, 169.3, 163.8, 162.0, 153.8, 144.2, 134.9, 133.1, 129.0, 124.1, 123.9, 122.0, 116.8, 106.5, 70.2, 61.2, 34.1, 29.9, 22.8, 16.2, 11.7 ppm;
HRMS (ESI-TOF, m/z): Calcd for C$_{25}$H$_{24}$NO$_8$ [M+H]$^+$ 466.1496; found 466.1499.

The preparation and spectral data of the following RAEs have been reported.[i, 22-26]

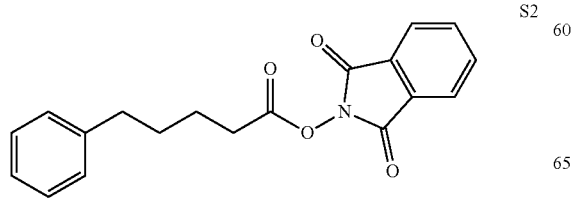

S2

-continued

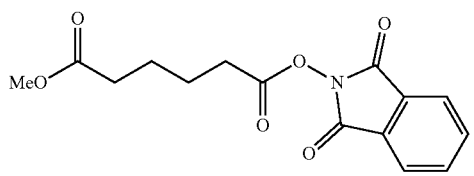

S26

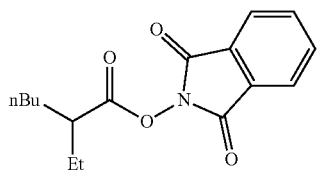

S27

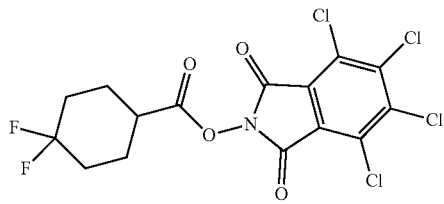

S28

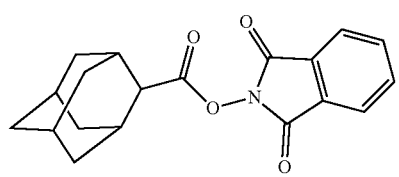

S29

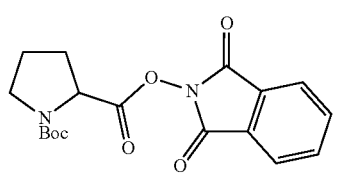

S30

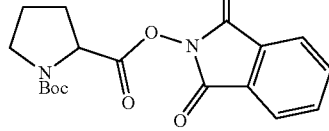

S31

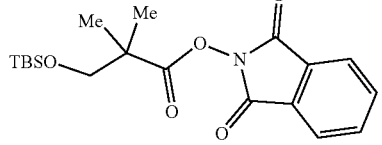

S32

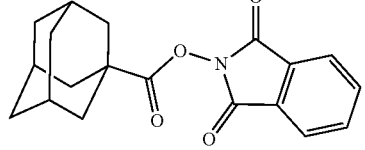

S33

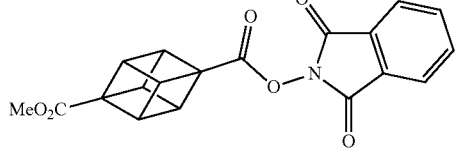

S34

-continued

S35
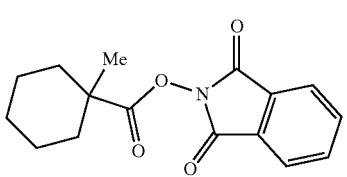

S36
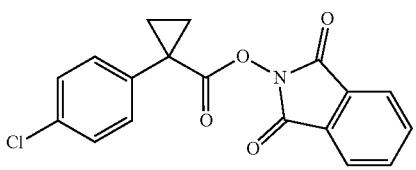

S37
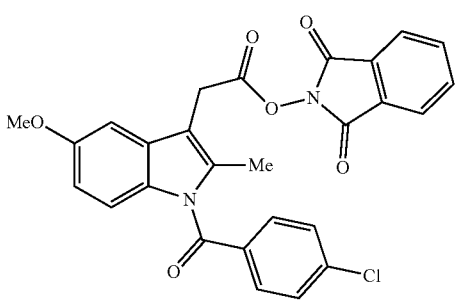

S38
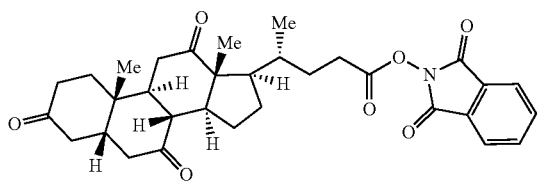

S39
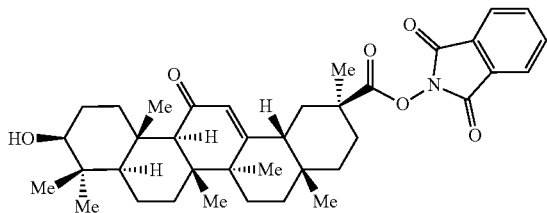

Experimental Procedure and Characterization Data for Borylation Products

Compound 3

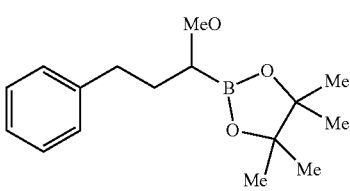

4,4,5,5-tetramethyl-2-(4-phenylbutan-2-yl)-1,3,2-dioxaborolane (3)

On 0.2 mmol scale, General Procedure B was followed with NHPI ester (2) and suspension B (NiCl$_2$.6H$_2$O/di-MeObipy in DMF). Purification by flash column chromatography (silica gel, hexanes to 1:35 Et$_2$O:hexanes) afforded 3 (32.7 mg, 63%).

Physical state: colorless oil;

R$_f$=0.49 (silica gel, 1:12 EtOAc:hexanes);

$^1$H NMR (600 MHz, CDCl$_3$): δ 7.28-7.25 (m, 2H), 7.20-7.14 (m, 3H), 2.66-2.58 (m, 2H), 1.82-1.76 (m, 1H), 1.62-1.57 (m, 1H), 1.25 (s, 12H), 1.10-1.05 (m, 1H), 1.02 (d, J=7.2 Hz, 3H) ppm;

$^{13}$C NMR (151 MHz, CDCl$_3$): δ 143.2, 128.6, 128.3, 125.6, 83.0, 35.5, 35.4, 25.0, 24.9, 15.7 ppm;

Spectroscopic data matches that reported in the literature.[2]

Compound 4

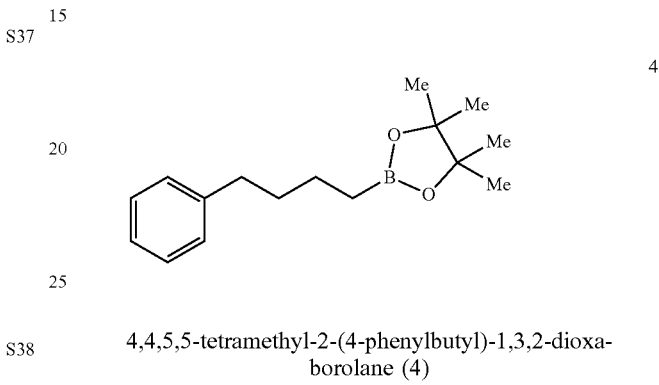

4,4,5,5-tetramethyl-2-(4-phenylbutyl)-1,3,2-dioxaborolane (4)

On 0.2 mmol scale, General Procedure B was followed with NHPI ester (S2) and solution B (NiCl$_2$.6H$_2$O/di-MeObipy in DMF). Purification by flash column chromatography (silica gel, hexanes to 1:30 Et$_2$O:hexanes) afforded 4 (34.0 mg, 65%).

Physical state: colorless oil;

R$_f$=0.50 (silica gel, 1:12 EtOAc:Hexane);

$^1$H NMR (600 MHz, CDCl$_3$): δ 7.28-7.25 (m, 2H), 7.18-7.15 (m, 3H), 2.61 (t, J=7.8 Hz, 2H), 1.66-1.61 (m, 2H), 1.50-1.45 (m, 2H), 1.24 (s, 12H), 0.82 (t, J=7.8 Hz, 2H) ppm;

$^{13}$C NMR (151 MHz, CDCl$_3$): δ 143.1, 128.5, 128.3, 125.6, 83.0, 35.9, 34.3, 25.0, 23.9 ppm;

Spectroscopic data matches that reported in the literature.[3]

Compound 5

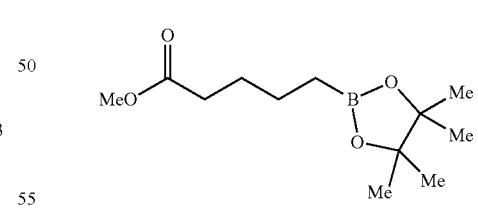

Methyl 5-(4,4,5,5-tetramethyl-1,3,2-dioxaborolan-2-yl)pentanoate (5)

On 0.2 mmol scale, General Procedure B was followed with NHPI ester (S26) and solution B (NiCl$_2$.6H$_2$O/di-MeObipy in DMF). Purification by flash column chromatography (silica gel, hexanes to 1:100 CH$_2$Cl$_2$:hexanes) afforded 5 (25.2 mg, 52%).

Physical state: colorless oil;

R$_f$=0.55 (silica gel, 1:6 EtOAc:hexanes);

¹H NMR (600 MHz, CDCl₃): δ 3.64 (s, 3H), 2.29 (t, J=7.2 Hz, 2H), 1.64-1.59 (m, 2H), 1.45-1.40 (m, 2H), 1.23 (s, 12H), 0.78 (t, J=7.8 Hz, 2H) ppm;
¹³C NMR (151 MHz, CDCl₃): δ 174.4, 83.1, 51.6, 34.1, 27.7, 25.0, 23.8 ppm;
HRMS (ESI-TOF, m/z): Calcd for $C_{12}H_{24}BO_4$ [M+H]⁺ 243.1762; found 243.1765.

Compound 6

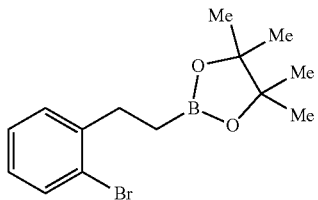

2-(2-bromophenethyl)-4,4,5,5-tetramethyl-1,3,2-dioxaborolane (6)

On 0.2 mmol scale, General Procedure B was followed with NHPI ester (S3) and solution B (NiCl₂·6H₂O/di-MeO-bipy in DMF). Purification by flash column chromatography (silica gel, hexanes to 1:30 Et₂O:hexanes) afforded 6 (34.3 mg, 55%).

Physical state: colorless oil;
$R_f$=0.55 (silica gel, 1:12 EtOAc:hexanes);
¹H NMR (600 MHz, CDCl₃): δ 7.50 (d, J=7.8 Hz, 1H), 7.27 (d, J=7.8 Hz, 1H), 7.21 (t, J=7.8 Hz, 1H), 7.02 (t, J=7.8 Hz, 1H), 2.84 (t, J=7.8 Hz, 2H), 1.24 (s, 12H), 1.15 (t, J=7.8 Hz, 2H) ppm;
¹³C NMR (151 MHz, CDCl₃): δ 143.7, 132.8, 129.9, 127.4, 127.4, 124.5, 83.32, 30.6, 25.0 ppm;
HRMS (ESI-TOF, m/z): Calcd for $C_{14}H_{21}BBrO_2$ [M+H]⁺ 313.0798; found 313.0799.

Compound 7

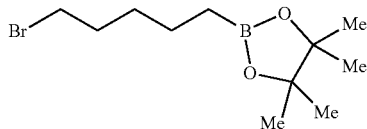

2-(5-bromopentyl)-4,4,5,5-tetramethyl-1,3,2-dioxaborolane (7)

On 0.2 mmol scale, General Procedure B was followed with NHPI ester (S4) and solution B (NiCl₂·6H₂O/di-MeO-bipy in DMF). Purification by flash column chromatography (silica gel, hexanes to 1:30 Et₂O:hexanes) afforded 7 (36.0 mg, 65%).

Physical state: colorless oil;
$R_f$=0.55 (silica gel, 1:12 EtOAc:hexanes)
¹H NMR (600 MHz, CDCl₃): δ 3.40 (t, J=7.2 Hz, 2H), 1.88-1.83 (m, 2H), 1.45-1.42 (m, 4H), 1.24 (s, 12H), 0.80-0.77 (m, 2H) ppm;
¹³C NMR (151 MHz, CDCl₃): δ 83.1, 34.2, 32.8, 31.0, 25.0, 23.4 ppm;
HRMS (ESI-TOF, m/z): Calcd for $C_{11}H_{23}BBrO_2$ [M+H]⁺ 277.0969; found 277.0968.

Compound 8

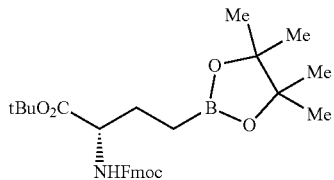

tert-butyl 2-((((9H-fluoren-9-yl)methoxy)carbonyl)amino)-4-(4,4,5,5-tetramethyl-1,3,2-dioxaborolan-2-yl)butanoate (8)

On 0.2 mmol scale, General Procedure B was followed with NHPI ester (S5) and solution B (NiCl₂·6H₂O/di-MeO-bipy in DMF). Purification by flash column chromatography (silica gel, 1:12 EtOAc:hexanes to 1:6 EtOAc:hexanes to 1:4 EtOAc:hexanes) afforded 8 (37.6 mg, 37%).

Physical state: colorless oil;
$R_f$=0.40 (silica gel, 1:4 EtOAc:hexanes)
¹H NMR (600 MHz, CDCl₃): δ 7.76 (d, J=7.2 Hz, 2H), 7.61 (d, J=7.2 Hz, 2H), 7.41-7.38 (m, 2H), 7.33-7.30 (m, 2H), 5.53 (d, J=8.4 Hz, 1H), 4.34-4.24 (m, 2H), 4.23-4.19 (m, 2H), 1.97-1.91 (m, 1H), 1.84-1.78 (m, 1H), 1.47 (s, 9H), 1.23 (s, 12H), 0.89-0.78 (m, 2H) ppm;
¹³C NMR (151 MHz, CDCl₃): δ 171.8, 156.2, 144.2, 144.1, 141.4, 127.8, 127.2, 125.3, 120.1, 83.5, 81.9, 67.0, 56.1, 47.4, 28.2, 27.0, 25.0, 24.9 ppm;
HRMS (ESI-TOF, m/z): Calcd for $C_{29}H_{38}BNNaO_6$ [M+Na]⁺ 530.2684; found 530.2685;
$[\alpha]_D^{20}$=+2.3 (c 0.35, CHCl₃).

Compound 9

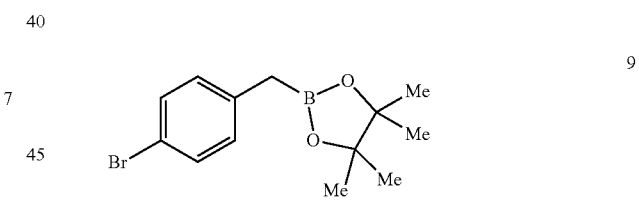

2-(4-bromobenzyl)-4,4,5,5-tetramethyl-1,3,2-dioxaborolane (9)

On 0.2 mmol scale, General Procedure C was followed with TCNHPI ester (S6) and suspension C (NiCl₂·6H₂O/di-tBubipy in THF). Purification by flash column chromatography (silica gel, 1:40 to 1:20 Et₂O:hexanes) afforded 9 (30.5 mg, 51%).

Physical State: colorless oil;
$R_f$=0.30 (silica gel, 1:19 EtOAc:hexanes);
¹H NMR (600 MHz, CDCl₃): δ 7.35-7.33 (m, 2H), 7.06-7.04 (m, 2H), 2.23 (s, 2H), 1.23 (s, 12H) ppm;
¹³C NMR (151 MHz, CDCl₃): δ 137.8, 131.4, 130.9, 118.7, 83.7, 24.9 ppm;
Spectroscopic data matches that reported in the literature.[4]

Compound 10

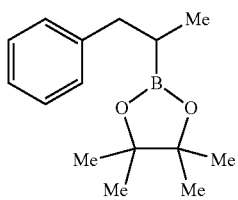

4,4,5,5-tetramethyl-2-(1-phenylpropan-2-yl)-1,3,2-dioxaborolane (10)

On 0.2 mmol scale, General Procedure C was followed with TCNHPI ester (S7) and suspension C (NiCl$_2$.6H$_2$O/di-tBubipy in THF). Purification by flash column chromatography (silica gel, hexanes to 1:35 Et$_2$O:hexanes) afforded 10 (33.1 mg, 67%).

Physical state: colorless oil;

R$_f$=0.53 (silica gel, 1:12 EtOAc:hexanes);

$^1$H NMR (600 MHz, CDCl$_3$): δ 7.26-7.13 (m, 5H), 2.81 (dd, J=13.8 Hz, 7.8 Hz, 1H), 2.54 (dd, J=13.8 Hz, 7.8 Hz, 1H), 1.41-1.34 (m, 1H), 1.19 (s, 6H), 1.18 (s, 6H), 0.97 (d, J=7.8 Hz, 3H) ppm;

$^{13}$C NMR (151 MHz, CDCl$_3$): δ 142.5, 129.0, 128.1, 125.7, 83.1, 39.1, 24.9, 15.3 ppm;

Spectroscopic data matches that reported in the literature.[5]

Compound 11

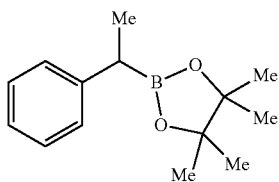

4,4,5,5-tetramethyl-2-(1-phenylethyl)-1,3,2-dioxaborolane (11)

On 0.2 mmol scale, General Procedure C was followed with NHPI ester (S8), MgBr$_2$.OEt$_2$ (52 mg, 0.2 mmol, 1 equiv) and suspension A (NiCl$_2$.6H$_2$O/di-MeObipy in THF). Purification by flash column chromatography (silica gel, hexanes to 1:30 Et$_2$O:hexanes) afforded 11 (33.8 mg, 73%).

Physical State: colorless oil;

R$_f$=0.33 (silica gel, 1:19 EtOAc:hexanes);

$^1$H NMR (600 MHz, CDCl$_3$): δ 7.27-7.21 (m, 4H), 7.15-7.12 (m, 1H), 2.44 (q, J=7.8 Hz, 1H), 1.33 (d, J=7.8 Hz, 3H), 1.21 (s, 6H), 1.20 (s, 6H) ppm;

$^{13}$C NMR (151 MHz, CDCl$_3$): δ 145.1, 128.4, 127.9, 125.2, 83.4, 24.8, 24.7, 17.2 ppm;

Spectroscopic data matches that reported in the literature.[2]

Compound 12

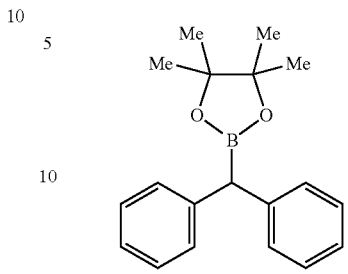

2-benzhydryl-4,4,5,5-tetramethyl-1,3,2-dioxaborolane (12)

On 0.2 mmol scale, General Procedure C was followed with NHPI ester (S9) and suspension A (NiCl$_2$.6H$_2$O/di-MeObipy in THF). Purification by flash column chromatography (silica gel, hexanes to 1:30 Et$_2$O:hexanes) afforded 12 (41.0 mg, 69%).

Physical State: colorless oil;

R$_f$=0.41 (silica gel, 1:9 EtOAc:hexanes);

$^1$H NMR (600 MHz, CDCl$_3$): δ 7.30-7.25 (m, 8H), 7.19-7.15 (m, 2H), 3.88 (s, 1H), 1.24 (s, 12H) ppm;

$^{13}$C NMR (151 MHz, CDCl$_3$): δ 142.2, 129.2, 128.5, 125.7, 83.9, 24.7 ppm;

Spectroscopic data matches that reported in the literature.[6]

Compound 13

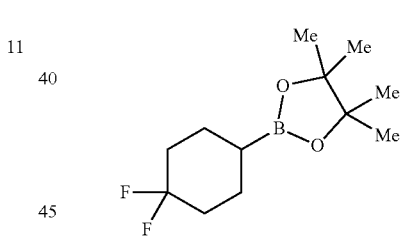

2-(4,4-difluorocyclohexyl)-4,4,5,5-tetramethyl-1,3,2-dioxaborolane (13)

On 0.2 mmol scale, General Procedure C was followed with TCNHPI ester (S27) and suspension C (NiCl$_2$.6H$_2$O/di-tBubipy in THF). Purification by flash column chromatography (silica gel, hexanes to 1:45 Et$_2$O:hexanes) afforded 13 (23.0 mg, 47%).

Physical state: colorless oil;

R$_f$=0.45 (silica gel, 1:9 EtOAc:hexanes);

$^1$H NMR (600 MHz, CDCl$_3$): δ 2.02-1.95 (m, 2H), 1.82-1.78 (m, 2H), 1.75-1.58 (m, 4H), 1.23 (s, 12H), 1.00-0.96 (m, 1H) ppm;

$^{13}$C NMR (151 MHz, CDCl$_3$): δ 123.9 (t, J=239.9 Hz), 83.4, 34.5 (t, J=23.3 Hz), 24.9, 24.4 (t, J=4.6 Hz) ppm;

HRMS (ESI-TOF, m/z): High-resolution mass spec data could not be obtained for this compound.

Compound 14

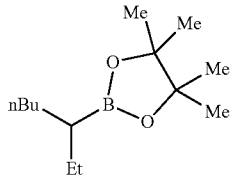

2-(heptan-3-yl)-4,4,5,5-tetramethyl-1,3,2-dioxaborolane (14)

On 0.2 mmol scale, General Procedure C was followed with TCNHPI ester (S26) and suspension C (NiCl$_2$.6H$_2$O/di-tBubipy in THF). Purification by flash column chromatography (silica gel, hexanes to 1:40 Et$_2$O:hexanes) afforded 14 (25.6 mg, 57%).

Physical state: colorless oil;

R$_f$=0.42 (silica gel, 1:19 EtOAc:hexanes);

$^1$H NMR (600 MHz, CDCl$_3$): δ 1.45-1.22 (m, 20H), 0.90-0.86 (m, 7H) ppm;

$^{13}$C NMR (151 MHz, CDCl$_3$): δ 82.9, 31.7, 30.8, 25.0, 24.4, 23.1, 14.3, 13.9 ppm;

Spectroscopic data matches that reported in the literature.

Compound 15

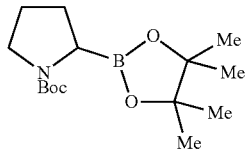

tert-butyl-2-(4,4,5,5-tetramethyl-1,3,2-dioxaborolan-2-yl)pyrrolidine-1-carboxylate (15)

On 0.2 mmol scale, General Procedure C was followed with NHPI ester (S29) and suspension C (NiCl$_2$.6H$_2$O/di-tBubipy in THF). Purification by flash column chromatography (first flash column chromatography: deactivate silica gel, hexanes to 1:9 EtOAc:hexanes; second flash column chromatography (deactivated silica gel, CH$_2$Cl$_2$) afforded 15 (39.2 mg, 66%).

Physical State: colorless oil;

R$_f$=0.45 (silica gel, 1:4 EtOAc:hexanes);

$^1$H NMR (600 MHz, CDCl$_3$): δ 3.42-2.99 (m, 3H), 2.09-1.65 (m, 4H), 1.43 (s, 9H), 1.26-1.22 (m, 12H) ppm;

$^{13}$C NMR (151 MHz, CDCl$_3$): δ 155.1, 83.6, 79.1, 46.1, 28.7, 27.9, 27.3 25.2, 25.0, 24.6 ppm;

HRMS (ESI-TOF, m/z): Calcd for C$_{15}$H$_{29}$BNO$_4$ [M+H]$^+$ 298.2184; found 298.2179;

[α]$_D^{20}$=0 (c 0.3, CHCl$_3$).

Compound 16

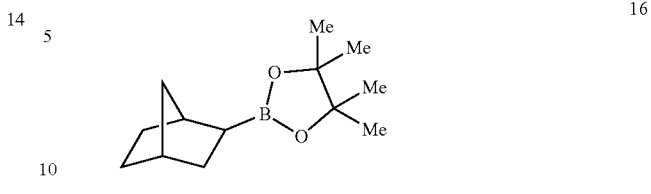

2-(bicyclo[2.2.1]heptan-2-yl)-4,4,5,5-tetramethyl-1,3,2-dioxaborolane (16)

On 0.2 mmol scale, General Procedure B was followed with NHPI ester (S10) and solution B (NiCl$_2$.6H$_2$O/di-MeObipy in DMF). Purification by flash column chromatography (silica gel, hexanes to 1:40 Et$_2$O:hexanes to 1:20 Et$_2$O:hexanes) afforded 16 (24.4 mg, 55%) as mixture of exo/endo isomers.

Physical state: colorless oil;

R$_f$=0.38 (silica gel, 1:19 EtOAc:hexanes);

$^1$H NMR (600 MHz, CDCl$_3$): δ 2.28-2.27 (m, 1H), 2.22-2.21 (m, 1H), 1.56-1.44 (m, 3H), 1.37-1.33 (m, 1H), 1.26-1.21 (m, 14H), 1.20-1.14 (m, 2H), 0.89-0.86 (m, 1H) ppm;

$^{13}$C NMR (151 MHz, CDCl$_3$): δ 82.9, 38.9, 38.3, 36.8, 32.4, 32.3, 29.4, 24.9 ppm (exo); 83.0, 41.1, 39.1, 37.2, 32.3, 30.0, 28.0, 25.1, 25.0 ppm (endo);

Spectroscopic data matches that reported in the literature.[8]

Compound 17

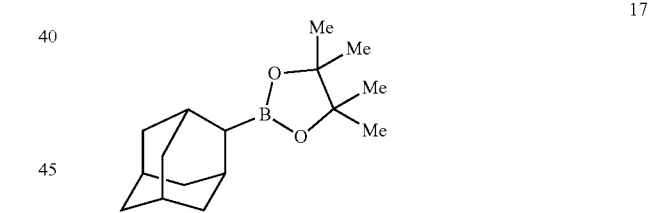

2-adamantan-2-yl-4,4,5,5-tetramethyl-1,3,2-dioxaborolane (17)

On 0.2 mmol scale, General Procedure C was followed with NHPI ester (S28) and suspension A (NiCl$_2$.6H$_2$O/di-MeObipy in THF). Purification by flash column chromatography (silica gel, hexanes to 1:30 Et$_2$O:hexanes) afforded 17 (30.9 mg, 59%).

Physical state: colorless oil;

R$_f$=0.55 (silica gel, 1:9 EtOAc:hexanes);

$^1$H NMR (600 MHz, CDCl$_3$): δ 2.06-2.04 (m, 2H), 1.90-1.67 (m, 12H), 1.37-1.35 (m, 1H), 1.25 (s, 12H) ppm;

$^{13}$C NMR (151 MHz, CDCl$_3$): δ 82.9, 39.5, 37.9, 36.4, 29.5, 28.4, 28.3, 25.0 ppm;

Spectroscopic data matches that reported in the literature.[2]

Compound 18

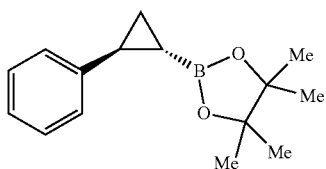

trans-4,4,5,5-tetramethyl-2-(2-phenylcyclopropyl)-1,3,2-dioxaborolane (18)

On 0.2 mmol scale, General Procedure B was followed with TCNHPI ester (S11) and solution D (NiCl$_2$.6H$_2$O/di-tBubipy in DMF). Purification by flash column chromatography (silica gel, hexanes to 1:30 Et$_2$O:hexanes) afforded 18 (11.3 mg, 23%, dr>20:1).

Physical State: colorless oil;

R$_f$=0.48 (silica gel, 1:9 EtOAc:hexanes);

$^1$H NMR (600 MHz, CDCl$_3$): δ 7.25-7.22 (m, 2H), 7.15-7.11 (m, 1H), 7.09-7.06 (m, 2H), 2.10 (dt, J=7.8 Hz, 5.4 Hz, 1H), 1.25 (s, 6H), 1.24 (s, 6H), 1.17-1.14 (m, 1H), 1.02-0.99 (m, 1H), 0.32-0.29 (m, 1H) ppm;

$^{13}$C NMR (151 MHz, CDCl$_3$): δ 143.5, 128.4, 125.8, 125.7, 83.3, 24.9, 24.8, 22.0, 15.2 ppm;

HRMS (ESI-TOF, m/z): Calcd for C$_{15}$H$_{22}$BO$_2$ [M+H]$^+$ 245.1707; found 245.1714.

Compound 19

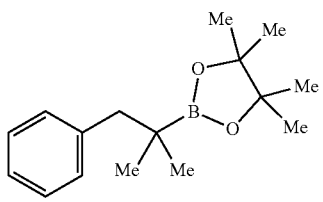

4,4,5,5-tetramethyl-2-(2-methyl-1-phenylpropan-2-yl)-1,3,2-dioxaborolane (19)

On 0.2 mmol scale, General Procedure C was followed with NHPI ester (S12) and suspension A (NiCl$_2$.6H$_2$O/di-MeObipy in THF). Purification by flash column chromatography (silica gel, hexanes to 1:30 Et$_2$O:hexanes) afforded 19 (35.3 mg, 68%).

Physical State: colorless solid;

m.p.=36-37° C.;

R$_f$=0.50 (silica gel, 1:12 EtOAc:hexanes);

$^1$H NMR (600 MHz, CDCl$_3$): δ 7.24-7.19 (m, 4H), 7.17-7.14 (m, 1H), 2.61 (s, 2H), 1.21 (s, 12H), 0.94 (s, 6H) ppm;

$^{13}$C NMR (151 MHz, CDCl$_3$): δ 140.6, 130.3, 127.8, 125.8, 83.24, 46.5, 24.9 ppm.

Spectroscopic data matches that reported in the literature.[2]

Compound 20

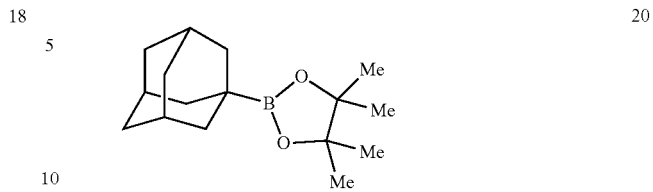

2-adamantan-1-yl-4,4,5,5-tetramethyl-1,3,2-dioxaborolane (20)

On 0.2 mmol scale, General Procedure C was followed with NHPI ester (S31) and suspension C (NiCl$_2$.6H$_2$O/di-tBubipy in THF). Purification by flash column chromatography (silica gel, 1:60 Et$_2$O:hexanes to 1:40 Et$_2$O:hexanes) afforded 20 (29.2 mg, 56%).

Physical State: white amorphous solid;

R$_f$=0.60 (silica gel, 1:9 EtOAc:hexanes);

$^1$H NMR (600 MHz, CDCl$_3$): δ 1.84 (br s, 3H), 1.75 (br t, J=3.6 Hz, 12H), 1.20 (s, 12H) ppm;

$^{13}$C NMR (151 MHz, CDCl$_3$): δ 82.7, 38.1, 37.6, 27.7, 24.8 ppm;

Spectroscopic data matches that reported in the literature.[2]

Compound 21

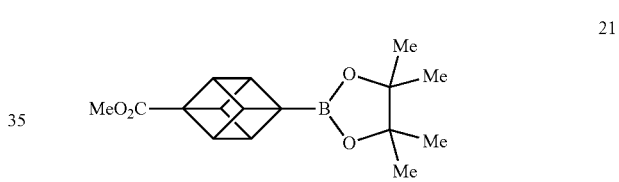

methyl 4-(4,4,5,5-tetramethyl-1,3,2-dioxaborolan-2-yl)cubane-1-carboxylate (21)

On 0.2 mmol scale, General Procedure C was followed with NHPI ester (S32) and suspension A (NiCl$_2$.6H$_2$O/di-MeObipy in THF). Purification by flash column chromatography (silica gel, hexanes to 1:15:15 Et$_2$O:CH$_2$Cl$_2$:hexanes) afforded 21 (26.2 mg, 46%).

Physical State: white solid;

m.p.=152-155° C.;

R$_f$=0.45 (silica gel, 1:6 EtOAc:hexanes);

$^1$H NMR (600 MHz, CDCl$_3$): δ 4.30-4.28 (m, 3H), 4.03-4.01 (m, 3H), 3.70 (s, 3H), 1.26 (s, 12H);

$^{13}$C NMR (151 MHz, CDCl$_3$): δ 172.8, 83.4, 55.4, 51.6, 47.0, 45.2, 24.9 ppm;

HRMS (ESI-TOF, m/z): Calcd for C$_{16}$H$_{22}$BO$_4$ [M+H]$^+$ 289.1606; found 289.1607.

Compound 22

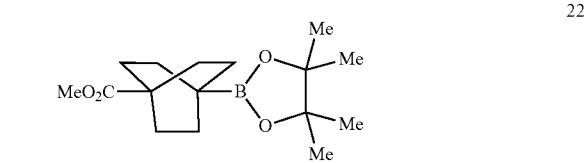 [SMILES: COC(=O)C12CCC(B3OC(C)(C)C(C)(C)O3)(CC1)CC2]

Methyl 4-(4,4,5,5-tetramethyl-1,3,2-dioxaborolan-2-yl)bicyclo[2.2.2]octane-1-carboxylate (22)

On 0.2 mmol scale, General Procedure C was followed with NHPI ester (S34) and suspension C (NiCl$_2$·6H$_2$O/di-tBubipy in THF). Purification by flash column chromatography (silica gel, hexanes to 1:9 Et$_2$O:hexanes) afforded 22 (31.1 mg, 53%).

Physical State: colorless solid; Sublimation at 100° C.;
R$_f$=0.39 (silica gel, 1:5 EtOAc:hexanes);
$^1$H NMR (600 MHz, CDCl$_3$): δ 3.62 (s, 3H), 1.72-1.65 (m, 6H), 1.62-1.54 (m, 6H), 1.19 (s, 12H) ppm;
$^{13}$C NMR (151 MHz, CDCl$_3$): δ 179.0, 83.0, 51.7, 38.6, 27.9, 26.7, 24.8 ppm;
HRMS (ESI-TOF, m/z): Calcd for C$_{16}$H$_{28}$BO$_4$ [M+H]$^+$ 295.2075; found 295.2077.

Compound 23

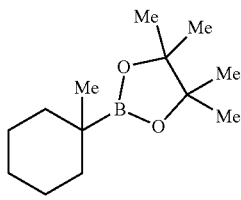

4,4,5,5-tetramethyl-2-(1-methylcyclohexyl)-1,3,2-dioxaborolane (23)

On 0.2 mmol scale, General Procedure C was followed with NHPI ester (S33) and suspension A (NiCl$_2$·6H$_2$O/di-MeObipy in THF). Purification by flash column chromatography (silica gel, hexanes to 1:30 Et$_2$O:hexanes) afforded 23 (27.8 mg, 62%).

Physical State: colorless oil;
R$_f$=0.50 (silica gel, 1:12 EtOAc:hexanes);
$^1$H NMR (600 MHz, CDCl$_3$): δ 1.84-1.80 (m, 2H), 1.64-1.57 (m, 3H), 1.29-1.21 (m, 14H), 1.16-1.08 (m, 1H), 0.92-0.87 (m, 5H) ppm;
$^{13}$C NMR (151 MHz, CDCl$_3$): δ 82.9, 37.2, 26.6, 26.0, 25.7, 24.8 ppm;
Spectroscopic data matches that reported in the literature.[2]

Compound 24

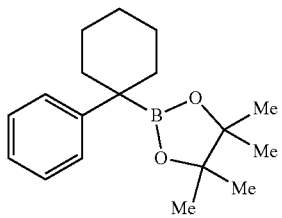

4,4,5,5-tetramethyl-2-(1-phenylcyclohexyl)-1,3,2-dioxaborolane (24)

On 0.2 mmol scale, General Procedure C was followed with NHPI ester (S13) and suspension C (NiCl$_2$·6H$_2$O/di-tBubipy in THF). Purification by flash column chromatography (silica gel, hexanes to 1:30 Et$_2$O:hexanes) afforded 24 (28.5 mg, 50%).

Physical State: white solid;
m.p.=87-88° C.;
R$_f$=0.60 (silica gel, 1:9 EtOAc:hexanes);
$^1$H NMR (600 MHz, CDCl$_3$): δ 7.36-7.34 (m, 2H), 7.29-7.26 (m, 2H), 7.13-7.11 (m, 1H), 2.36-2.32 (m, 2H), 1.82-1.78 (m, 2H), 1.70-1.66 (m, 1H), 1.49-1.38 (m, 4H), 1.21-1.14 (m, 1H), 1.17 (s, 12H) ppm;
$^{13}$C NMR (151 MHz, CDCl$_3$): δ 147.6, 128.2, 126.3, 125.1, 83.4, 35.0, 26.4, 25.9, 25.7 ppm;
HRMS (ESI-TOF, m/z): Calcd for C$_{18}$H$_{28}$BO$_2$ [M+H]$^+$ 287.2177; found 287.2184.

Compound 25

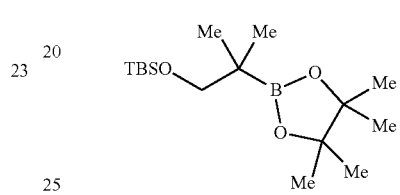

tert-butyldimethyl(2-methyl-2-(4,4,5,5-tetramethyl-1,3,2-dioxaborolan-2-yl)propoxy)silane (25)

On 0.2 mmol scale, General Procedure C was followed with NHPI ester (S30) and suspension A (NiCl$_2$·6H$_2$O/di-MeObipy in THF). Purification by flash column chromatography (silica gel, hexanes to 1:30 Et$_2$O:hexanes) afforded 25 (41.2 mg, 66%).

Physical State: colorless oil;
R$_f$=0.40 (silica gel, 1:12 EtOAc:hexanes);
$^1$H NMR (600 MHz, CDCl$_3$): δ 3.39 (s, 2H), 1.22 (s, 12H), 0.90 (s, 6H), 0.88 (s, 9H), 0.01 (s, 6H) ppm;
$^{13}$C NMR (151 MHz, CDCl$_3$): δ 83.0, 72.0, 26.1, 24.9, 21.4, 18.5, −5.34 ppm;
HRMS (ESI-TOF, m/z): Calcd for C$_{16}$H$_{36}$BO$_3$Si[M+H]$^+$ 315.2521; found 315.2523.

Compound 26

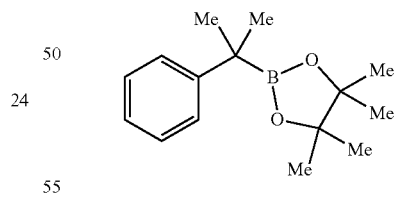

4,4,5,5-tetramethyl-2-(2-phenylpropan-2-yl)-1,3,2-dioxaborolane (26)

On 0.2 mmol scale, General Procedure C was followed with NHPI ester (S14) and suspension C (NiCl$_2$·6H$_2$O/di-tBubipy in THF). Purification by flash column chromatography (silica gel, hexanes to 1:30 Et$_2$O:hexanes) afforded 26 (23.3 mg, 47%).

Physical State: colorless oil;
R$_f$=0.51 (silica gel, 1:9 EtOAc:hexanes);

$^1$H NMR (600 MHz, CDCl$_3$): δ 7.33-7.27 (m, 4H), 7.15-7.12 (m, 1H), 1.35 (s, 6H), 1.20 (s, 12H) ppm;

$^{13}$C NMR (151 MHz, CDCl$_3$): δ 148.8, 128.2, 126.4, 125.1, 83.4, 25.7, 24.7 ppm;

Spectroscopic data matches that reported in the literature.[9]

Compound 27

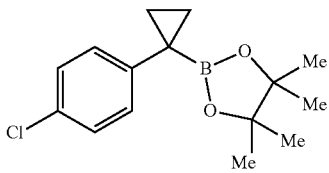

2-(1-(4-chlorophenyl)cyclopropyl)-4,4,5,5-tetramethyl-1,3,2-dioxaborolane (27)

On 0.2 mmol scale, General Procedure C was followed with NHPI ester (S34) and suspension A (NiCl$_2$.6H$_2$O/di-MeObipy in THF). Purification by flash column chromatography (silica gel, hexanes to 1:30 Et$_2$O:hexanes) afforded 27 (32.9 mg, 59%).

Physical State: White solid;
m.p.=83-85° C.;
R$_f$=0.37 (silica gel, 1:19 EtOAc:hexanes);
$^1$H NMR (600 MHz, CDCl$_3$): δ 7.19 (s, 4H), 1.21 (s, 12H), 1.11 (dd, J=6.0 Hz, 3.6 Hz, 2H), 0.87 (dd, J=6.0 Hz, 3.6 Hz, 2H) ppm;
$^{13}$C NMR (151 MHz, CDCl$_3$): δ 143.5, 131.0, 130.5, 128.2, 83.6, 24.7, 13.6 ppm;
HRMS (ESI-TOF, m/z): Calcd for C$_{15}$H$_{21}$BClO$_2$ [M+H]$^+$ 279.1318; found 279.1319.

Compound 28

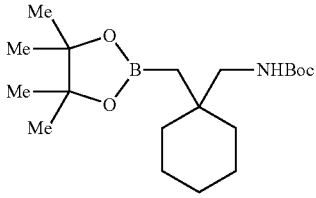

tert-butyl ((1-((4,4,5,5-tetramethyl-1,3,2-dioxaborolan-2-yl)methyl)cyclohexyl) methyl)carbamate (28)

On 0.1 mmol scale, General Procedure B was followed with NHPI ester (S15) and solution B (NiCl$_2$.6H$_2$O/di-MeObipy in DMF). Purification by flash column chromatography (silica gel, 1:20 EtOAc:hexanes) afforded 28 (22.5 mg, 64%).

Physical State: white solid;
m.p.=92-96° C.;
R$_f$=0.28 (silica gel, 1:20 EtOAc:hexanes);
$^1$H NMR (600 MHz, CDCl$_3$): δ 5.32 (br s, 1H), 3.08 (d, J=6.0 Hz, 2H), 1.52-1.41 (m, 4H), 1.43 (s, 9H), 1.38-1.31 (m, 6H), 1.25 (s, 12H), 0.81 (s, 2H) ppm;
$^{13}$C NMR (151 MHz, CDCl$_3$): δ 156.5, 83.4, 78.7, 50.0, 36.7, 36.3, 28.6, 26.4, 25.0, 21.9 ppm;

HRMS (ESI-TOF, m/z): Calcd for C$_{19}$H$_{37}$BNO$_4$ [M+H]$^+$ 354.2810; found 354.2809.

Compound 29

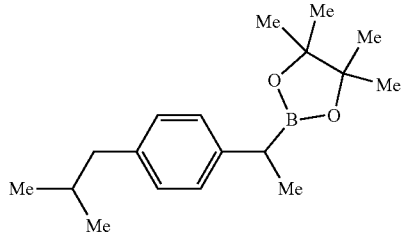

2-(1-(4-isobutylphenyl)ethyl)-4,4,5,5-tetramethyl-1,3,2-dioxaborolane (29)

On 0.2 mmol scale, General Procedure C was followed with NHPI ester (S16), MgBr$_2$.OEt$_2$ (52 mg, 0.2 mmol, 1 equiv) and suspension A (NiCl$_2$.6H$_2$O/di-MeObipy in THF). Purification by flash column chromatography (silica gel, hexanes to 1:30 Et$_2$O:hexanes) afforded 29 (43.0 mg, 75%).

Physical State: colorless oil;
R$_f$=0.59 (silica gel, 1:9 EtOAc:hexanes);
$^1$H NMR (600 MHz, CDCl$_3$): δ 7.12-7.10 (m, 2H), 7.04-7.02 (m, 2H), 2.42 (d, J=7.2 Hz, 2H), 2.40 (q, J=7.2 Hz, 1H), 1.79-1.88 (m, 1H), 1.31 (d, J=7.2 Hz, 3H), 1.21 (s, 6H), 1.20 (s, 6H), 0.89 (d, J=6.6 Hz, 6H) ppm;
$^{13}$C NMR (151 MHz, CDCl$_3$): δ 142.1, 138.4, 129.2, 127.6, 83.4, 45.2, 30.4, 24.8, 24.7, 22.6, 17.2 ppm;

Spectroscopic data matches that reported in the literature.[10]

Compound 30

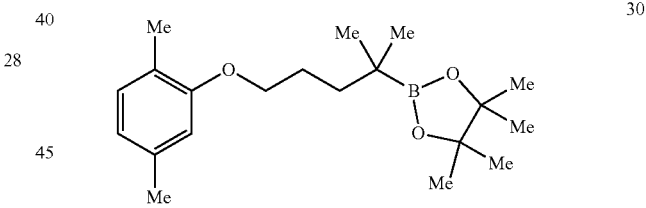

2-(5-(2,5-dimethylphenoxy)-2-methylpentan-2-yl)-4,4,5,5-tetramethyl-1,3,2-dioxaborolane (30)

On 0.2 mmol scale, General Procedure C was followed with NHPI ester (S17) and suspension A (NiCl$_2$.6H$_2$O/di-MeObipy in THF). Purification by flash column chromatography (silica gel, hexanes to 1:30 Et$_2$O:hexanes) afforded 30 (36.3 mg, 55%).

Physical State: colorless solid;
m.p.=59-61° C.;
R$_f$=0.60 (silica gel, 1:12 EtOAc:hexanes);
$^1$H NMR (600 MHz, CDCl$_3$): δ 6.99 (d, J=7.8 Hz, 1H), 6.64 (d, J=7.2 Hz, 1H), 6.62 (s, 1H), 3.92 (t, J=6.6 Hz, 2H), 2.30 (s, 3H), 2.18 (s, 3H), 1.78-1.73 (m, 2H), 1.41-1.44 (m, 2H), 1.23 (s, 12H), 0.96 (s, 6H) ppm;
$^{13}$C NMR (151 MHz, CDCl$_3$): δ 157.3, 136.5, 130.4, 123.8, 120.6, 112.2, 83.1, 68.8, 37.4, 26.6, 25.0, 24.9, 21.6, 16.0 ppm;

HRMS (ESI-TOF, m/z): Calcd for C$_{20}$H$_{34}$BO$_3$ [M+H]$^+$ 333.2595; found 333.2598.

Compound 31

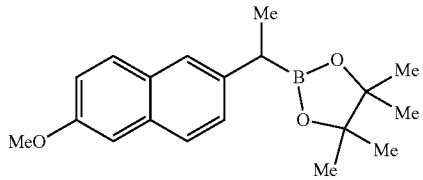

2-(1-(6-methoxynaphthalen-2-yl)ethyl)-4,4,5,5-tetramethyl-1,3,2-dioxaborolane

On 0.2 mmol scale, General Procedure C was followed with NHPI ester (S18), MgBr$_2$.OEt$_2$ (52 mg, 0.2 mmol, 1 equiv) and suspension A (NiCl$_2$.6H$_2$O/di-MeObipy in THF). Purification by flash column chromatography (silica gel, hexanes to 1:25 Et$_2$O:hexanes) afforded 31 (50.0 mg, 80%).

Physical State: white solid;
m.p.=82-84° C.;
R$_f$=0.62 (silica gel, 1:4 EtOAc:hexanes);
$^1$H NMR (600 MHz, CDCl$_3$): δ 7.64-7.67 (m, 2H), 7.57 (s, 1H), 7.35 (dd, J=8.4, 1.8 Hz, 1H), 7.09-7.11 (m, 2H), 3.90 (s, 3H), 2.57 (q, J=7.2 Hz, 1H), 1.41 (d, J=7.2 Hz, 3H), 1.21 (s, 6H), 1.20 (s, 6H) ppm;
$^{13}$C NMR (151 MHz, CDCl$_3$): δ 157.1, 140.3, 132.8, 129.5, 129.1, 127.8, 126.7, 125.3, 118.5, 105.8, 83.5, 55.4, 24.8, 24.8, 17.1 ppm;
HRMS (ESI-TOF, m/z): Calcd for C$_{19}$H$_{26}$BO$_3$ [M+H]$^+$ 313.1969; found 313.1970.

Compound 32

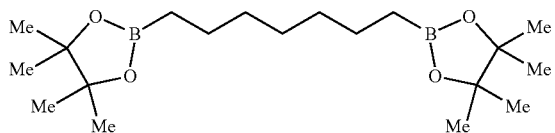

1,7-bis(4,4,5,5-tetramethyl-1,3,2-dioxaborolan-2-yl) heptane (32)

On 0.2 mmol scale, General Procedure B was followed with NHPI ester (S19) and solution B (NiCl$_2$.6H$_2$O (20 mol %)/di-MeObipy (26% mol %) in DMF (0.8 mL)). Purification by flash column chromatography (silica gel, hexanes to 1:20 Et$_2$O:hexanes) afforded 32 (26.5 mg, 38%).

Physical State: colorless oil;
R$_f$=0.45 (silica gel, 1:8 EtOAc:hexanes);
$^1$H NMR (600 MHz, CDCl$_3$): δ 1.41-1.36 (m, 4H), 1.29-1.24 (m, 6H), 1.24 (s, 24H), 0.75 (t, J=7.8 Hz, 4H) ppm;
$^{13}$C NMR (151 MHz, CDCl$_3$): δ 83.0, 32.5, 29.4, 25.0, 24.2 ppm;
HRMS (ESI-TOF, m/z): Calcd for C$_{19}$H$_{39}$B$_2$O$_4$ [M+H]$^+$ 353.3029; found 353.3030.

Compound 33

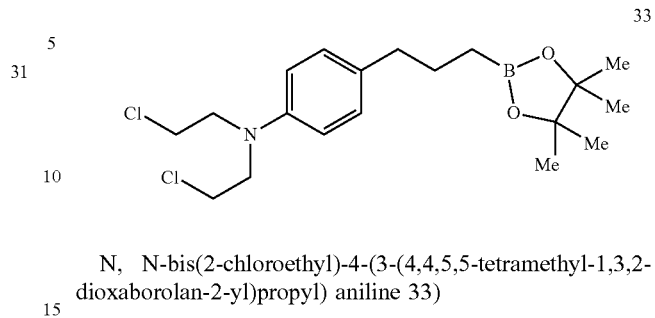

N, N-bis(2-chloroethyl)-4-(3-(4,4,5,5-tetramethyl-1,3,2-dioxaborolan-2-yl)propyl) aniline 33)

On 0.2 mmol scale, General Procedure C was followed with NHPI ester (S20) and suspension A (NiCl$_2$.6H$_2$O/di-MeObipy in THF). Purification by flash column chromatography (silica gel, hexanes to 1:19 EtOAc:hexanes) afforded 33 (20.7 mg, 26%).

Physical State: yellow oil;
R$_f$=0.36 (silica gel, 1:9 EtOAc:hexanes);
$^1$H NMR (600 MHz, CDCl$_3$): δ 7.09-7.04 (m, 2H), 6.63-6.59 (m, 2H), 3.69 (t, J=7.1 Hz, 4H), 3.61 (t, J=7.1 Hz, 4H), 2.54-2.48 (t, J=7.8 Hz, 2H), 1.68 (p, J=7.8 Hz, 2H), 1.24 (s, 12H), 0.81 (t, J=7.8 Hz, 2H) ppm;
$^{13}$C NMR (151 MHz, CDCl$_3$): δ 144.2, 132.2, 129.9, 112.2, 83.1, 53.8, 40.7, 37.6, 26.5, 25.0 ppm;
HRMS (ESI-TOF, m/z): Calcd for C$_{19}$H$_{31}$BCl$_2$NO$_2$ [M+H]$^+$ 386.1819; found 386.1815.

Compound 34

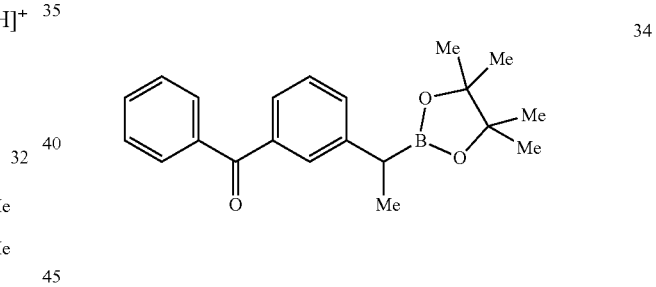

phenyl(3-(1-(4,4,5,5-tetramethyl-1,3,2-dioxaborolan-2-yl)ethyl)phenyl) methanone (34)

On 0.2 mmol scale, General Procedure C was followed with NHPI ester (S21), MgBr$_2$.OEt$_2$ (52 mg, 0.2 mmol, 1 equiv) and suspension A (NiCl$_2$.6H$_2$O/di-MeObipy in THF). Purification by flash column chromatography (silica gel, hexanes to 1:15 EtOAc:hexanes) afforded 34 (51.9 mg, 77%).

Physical State: colorless oil;
R$_f$=0.45 (silica gel, 1:6 EtOAc:hexanes);
$^1$H NMR (600 MHz, CDCl$_3$): δ 7.83-7.81 (m, 2H), 7.66 (t, J=1.8 Hz, 1H), 7.59-7.56 (m, 2H), 7.49-7.44 (m, 3H), 7.38 (t, J=7.8 Hz, 1H), 2.51 (q, J=7.8 Hz, 1H), 1.35 (d, J=7.8 Hz, 3H), 1.21 (s, 6H), 1.21 (s, 6H) ppm;
$^{13}$C NMR (151 MHz, CDCl$_3$): δ 197.2, 145.4, 138.0, 137.7, 132.4, 132.2, 130.3, 129.7, 128.4, 128.3, 127.2, 83.6, 24.8, 24.8, 17.1 ppm;
HRMS (ESI-TOF, m/z): Calcd for C$_{21}$H$_{26}$BO$_3$ [M+H]$^+$ 337.1969; found 337.1971.

Compound 35

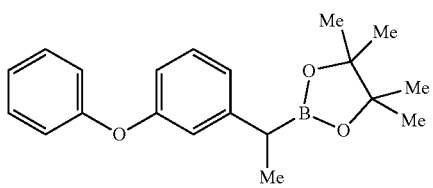

4,4,5,5-tetramethyl-2-(1-(3-phenoxyphenyl)ethyl)-1,3,2-dioxaborolane (35)

On 0.2 mmol scale, General Procedure C was followed with NHPI ester (S22), MgBr$_2$·OEt$_2$ (52 mg, 0.2 mmol, 1 equiv) and suspension A (NiCl$_2$·6H$_2$O/di-MeObipy in THF). Purification by flash column chromatography (silica gel, hexanes to 1:30 Et$_2$O:hexanes) afforded 35 (52.6 mg, 81%).
Physical State: colorless oil;
R$_f$=0.50 (silica gel, 1:12 EtOAc:hexanes);
$^1$H NMR (600 MHz, CDCl$_3$): δ 7.32 (t, J=7.8 Hz, 2H), 7.22 (t, J=7.8 Hz, 1H), 7.07 (t, J=7.8 Hz, 1H), 7.01 (d, J=7.2 Hz, 2H), 6.97 (d, J=7.2 Hz, 1H), 6.91 (t, J=1.8 Hz, 1H), 6.79 (dd, J=7.8 Hz, 2.4 Hz, 1H), 2.42 (q, J=7.8 Hz, 1H), 1.31 (d, J=7.8 Hz, 3H), 1.20 (s, 6H), 1.19 (s, 6H) ppm;
$^{13}$C NMR (151 MHz, CDCl$_3$): δ 157.7, 157.2, 147.3, 129.7, 129.6, 123.0, 123.0, 118.8, 118.7, 115.9, 83.5, 24.8, 24.7, 17.0 ppm;
HRMS (ESI-TOF, m/z): Calcd for C$_{20}$H$_{26}$BO$_3$ [M+H]$^+$ 325.1969; found 325.1970.

Compound 36

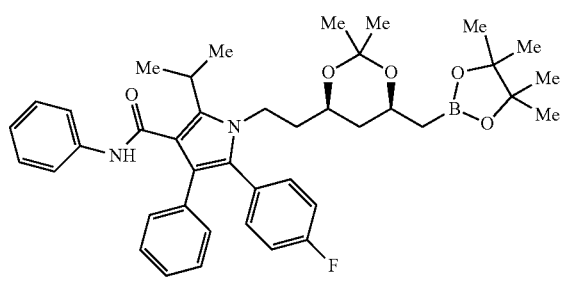

1-(2-((4R,6S)-2,2-dimethyl-6-((4,4,5,5-tetramethyl-1,3,2-dioxaborolan-2-yl)methyl)-1,3-dioxan-4-yl)ethyl)-5-(4-fluorophenyl)-2-isopropyl-N,4-diphenyl-1H-pyrrole-3-carboxamide (36)

On 0.2 mmol scale, General Procedure B was followed with NHPI ester (S23) and solution B (NiCl$_2$·6H$_2$O/di-MeObipy in DMF). Purification by flash column chromatography (silica gel, hexanes to 1:9 EtOAc:hexanes) afforded 36 (77.4 mg, 57%).
Physical State: white foam;
R$_f$=0.52 (silica gel, 1:4 EtOAc:hexanes);
$^1$H NMR (600 MHz, CDCl$_3$): δ 7.21-7.14 (m, 9H), 7.07 (br d, J=8.4 Hz, 2H), 7.00-6.97 (m, 3H), 6.85 (br s, 1H), 4.08-4.03 (m, 1H), 4.00-3.96 (m, 1H), 3.85-3.80 (m, 1H), 3.69-3.65 (m, 1H), 3.60-3.55 (m, 1H), 1.68-1.64 (m, 2H), 1.55 (d, J=1.8 Hz, 3H), 1.53 (d, J=1.8 Hz, 3H), 1.34 (dt, J=13.2 Hz, 1.2 Hz, 1H), 1.34 (s, 3H), 1.30 (s, 3H), 1.23 (s, 12H), 1.08-1.03 (m, 2H), 0.98-0.94 (m, 1H) ppm;
$^{13}$C NMR (151 MHz, CDCl$_3$): δ 165.0, 162.4 (d, J=247.6 Hz), 141.7, 138.6, 134.8, 134.5, 133.3 (d, J=8.2 Hz), 130.7, 128.9, 128.8, 128.5, 128.4 (d, J=3.8 Hz), 126.7, 123.8, 123.6, 121.8, 119.7, 115.4 (d, J=21.3 Hz), 98.6, 83.3, 66.7, 66.7, 41.0, 38.4, 38.3, 30.3, 26.2, 24.9, 24.9, 21.9, 21.7, 20.0 ppm;
HRMS (ESI-TOF, m/z): Calcd for C$_{41}$H$_{51}$BFN$_2$O$_5$ [M+H]$^+$ 681.3870; found 681.3870;
[α]$_D^{20}$=+4.0 (c 0.68, CHCl$_3$).

Compound 37

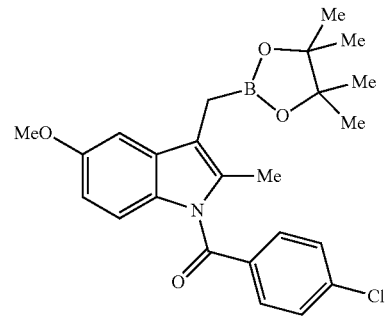

(4-chlorophenyl)(5-methoxy-2-methyl-3-((4,4,5,5-tetramethyl-1,3,2-dioxaborolan-2-yl)methyl)-1H-indol-1-yl)methanone (37)

On 0.1 mmol scale, General Procedure C was followed with NHPI ester (S37) and suspension A (NiCl$_2$·6H$_2$O/di-MeObipy in THF). Purification by flash column chromatography (silica gel, hexanes to 1:17 EtOAc:hexanes) afforded 37 (22.1 mg, 50%).
Physical State: yellow oil;
R$_f$=0.5 (silica gel, 1:4 EtOAc:hexanes);
$^1$H NMR (600 MHz, CDCl$_3$): δ 7.64 (dt, J=9.0 Hz, 1.8 Hz, 2H), 7.45 (m, dt, J=8.4 Hz, 1.8 Hz, 2H), 6.96-6.93 (m, 2H), 6.64 (dd, J=9.0 Hz, 2.6 Hz, 1H), 3.84 (s, 3H), 2.29 (s, 3H), 2.18 (s, 2H), 1.23 (s, 12H) ppm;
$^{13}$C NMR (151 MHz, CDCl$_3$): δ 168.3, 156.0, 138.8, 134.7, 133.2, 132.0, 131.2, 131.1, 129.1, 116.7, 115.0, 111.3, 101.7, 83.7, 55.8, 29.9, 25.0, 13.9 ppm;
HRMS (ESI-TOF, m/z): Calcd for C$_{24}$H$_{28}$BClNO$_4$ [M+H]$^+$ 440.1794; found 440.1794.

Compound 38

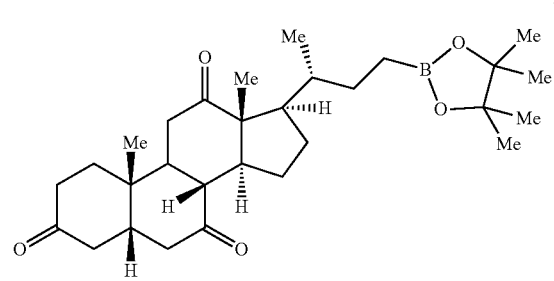

(5S,8R,9S,10S,13R,14S,17R)-10,13-dimethyl-17-((R)-4-(4,4,5,5-tetramethyl-1,3,2-dioxaborolan-2-yl)butan-2-yl)dodecahydro-3H-cyclopenta[a]phenanthrene-3,7,12(2H,4H)-trione (38)

On 0.2 mmol scale, General Procedure B was followed with NHPI ester (S38) and solution B (NiCl$_2$.6H$_2$O/di-MeObipy in DMF). Purification by flash column chromatography (silica gel, hexanes to 1:5 EtOAc:hexanes) afforded 38 (63.0 mg, 65%).

Physical State: white solid;
R$_f$=0.40 (silica gel, 1:3 EtOAc:hexanes);
m.p.=230-232° C.;
$^1$H NMR (600 MHz, CDCl$_3$): δ 2.92-2.82 (m, 3H), 2.35-2.19 (m, 6H), 2.14-2.09 (m, 2H), 2.05-1.94 (m, 4H), 1.80-1.85 (m, 1H), 1.56-1.63 (m, 2H), 1.39 (s, 3H), 1.35-1.12 (m, 16H), 1.06 (s, 3H), 0.87-0.81 (m, 4H), 0.68-0.62 (m, 1H) ppm;
$^{13}$C NMR (151 MHz, CDCl$_3$): δ 212.1, 209.2, 208.9, 83.0, 57.1, 51.9, 49.2, 47.0, 45.8, 45.7, 45.1, 42.9, 38.8, 38.2, 36.6, 36.1, 35.4, 29.4, 27.8, 25.4, 25.0, 24.9, 22.1, 18.6, 12.0 ppm;
HRMS (ESI-TOF, m/z): Calcd for C$_{29}$H$_{45}$BO$_5$ [M+H]$^+$ 485.3433; found 485.3435.
[α]$_D^{20}$=+16.9 (c 0.62, CHCl$_3$).

Compound 39

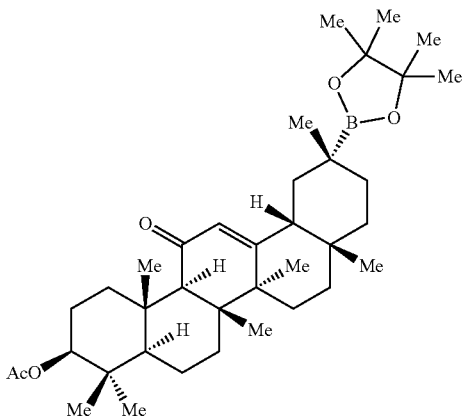

(3S,4aR,6aR,6bS,8aR,11S,12aR,14aR,14bS)-4,4,6a,6b,8a,11,14b-heptamethyl-14-oxo-11-(4,4,5,5-tetramethyl-1,3,2-dioxaborolan-2-yl)-1,2,3,4,4a,5,6,6a,6b,7,8,8a,9,10,11,12,12a,14,14a,14b-icosahydropicen-3-yl acetate (39)

On 0.2 mmol scale, General Procedure C was followed with NHPI ester (S24) and suspension A (NiCl$_2$.6H$_2$O/di-MeObipy in THF). Purification by flash column chromatography (silica gel, 1:12:3 EtOAc:hexanes:CH$_2$Cl$_2$) afforded 39 (82.0 mg, 69%, d.r.=11.8:1).

Physical State: colorless film;
R$_f$=0.34 (silica gel, 1:5 EtOAc:hexanes);
$^1$H NMR (600 MHz, CDCl$_3$): Major isomer δ 5.57 (s, 1H), 4.51 (dd, J=11.8, 4.7 Hz, 1H), 2.79 (dt, J=13.7, 3.6 Hz, 1H), 2.35 (s, 1H), 2.20 (ddd, J=13.3, 4.4, 1.7 Hz, 1H), 2.12 (td, J=13.7, 4.6 Hz, 1H), 2.04 (s, 3H), 1.96 (t, J=13.6 Hz, 1H), 1.80 (td, J=13.7, 4.6 Hz, 1H), 1.75-1.38 (m, 7H), 1.37 (s, 3H), 1.27-1.13 (m, 5H), 1.20 (d, J=1.8 Hz, 12H), 1.15 (s, 3H), 1.12 (s, 3H), 1.02 (td, J=13.5, 3.6 Hz, 1H), 0.99 (s, 3H), 0.94 (ddt, J=13.7, 4.5, 2.2 Hz, 1H), 0.87 (s, 6H), 0.84 (s, 3H), 0.81-0.76 (m, 1H) ppm;
$^{13}$C NMR (151 MHz, CDCl$_3$): Major isomer δ 200.1, 171.1, 171.1, 128.3, 83.0, 80.8, 61.8, 55.2, 45.5, 45.3, 43.6, 38.9, 38.5, 38.2, 37.1, 34.2, 32.9, 32.7, 29.1, 28.2, 27.8, 26.7, 26.6, 24.8, 24.7, 23.7, 23.4, 21.5, 18.9, 17.7, 17.6, 16.8, 16.6 ppm;
HRMS (ESI-TOF, m/z): Calcd for C$_{37}$H$_{60}$BO$_5$ [M+H]$^+$ 595.4528; found 595.4520;
[α]$_D^{20}$=+65.8 (c 1.0, CHCl$_3$).

Compound 40

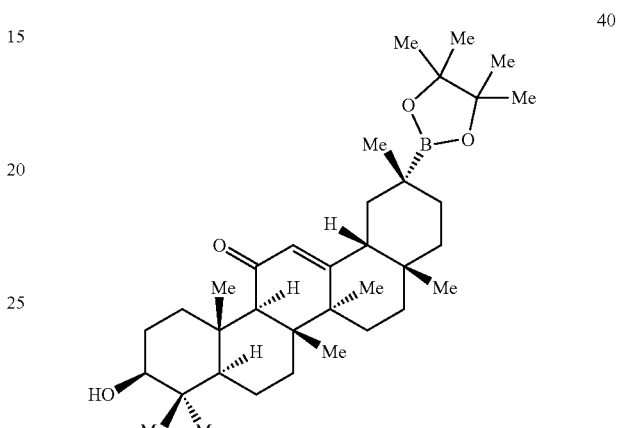

(2S,4aR,6aS,6bR,8aR,10S,12aS,12bR,14bR)-10-hydroxy-2,4a,6a,6b,9,9,12a-heptamethyl-2-(4,4,5,5-tetramethyl-1,3,2-dioxaborolan-2-yl)-1,3,4,4a,5,6,6a,6b,7,8,8a,9,10,11,12,12a,12b,14b-octadecahydropicen-13(2H)-one (40)

On 0.2 mmol scale, General Procedure C was followed with NHPI ester (S39) and suspension A (NiCl$_2$.6H$_2$O/di-MeObipy in THF). Purification by flash column chromatography (silica gel, first flash column chromatography: 1:5.7 to 1:4 EtOAc:hexanes; second flash column chromatography, 1:6:3 to 2:6:3 EtOAc:hexanes:CH$_2$Cl$_2$) afforded 40 (72.1 mg, 65%, d.r.=11.3:1).

Physical State: colorless film;
R$_f$=0.46 (silica gel, 3:7 EtOAc:hexanes);
$^1$H NMR (600 MHz, CDCl$_3$): Major isomer δ 5.59 (s, 1H), 3.27-3.18 (m, 1H), 2.81 (dt, J=13.5, 3.6 Hz, 1H), 2.36 (s, 1H), 2.22 (ddd, J=13.5, 4.5, 1.7 Hz, 1H), 2.14 (td, J=13.7, 4.6 Hz, 1H), 1.99 (t, J=13.6 Hz, 1H), 1.83 (td, J=13.7, 4.7 Hz, 1H), 1.74-1.58 (m, 4H), 1.55 (td, J=13.8, 4.0 Hz, 1H), 1.51-1.35 (m, 2H), 1.41 (s, 3H), 1.33-1.15 (m, 7H), 1.22 (s, 6H), 1.22 (s, 6H), 1.15 (s, 3H), 1.15 (s, 3H), 1.02 (s, 3H), 1.01 (s, 3H), 1.00-0.94 (m, 1H), 0.86 (s, 3H), 0.82 (s, 3H), 0.71 (dd, J=11.8, 1.9 Hz, 1H) ppm;
$^{13}$C NMR (151 MHz, CDCl$_3$): Major isomer δ 200.3, 171.1, 128.3, 83.0, 79.0, 61.9, 55.2, 45.5, 45.3, 43.6, 39.3, 39.3, 38.5, 37.2, 34.2, 33.0, 32.7, 29.1, 28.3, 27.8, 27.5, 26.7, 26.6, 24.8, 24.7, 23.5, 18.9, 17.7, 16.5, 15.7 ppm;
HRMS (ESI-TOF, m/z): Calcd for C$_{35}$H$_{58}$BO$_4$ [M+H]$^+$ 553.4422; found 553.4423;
[α]$_D^{20}$=+73.4 (c 1.0, CHCl$_3$).

Compound 40a

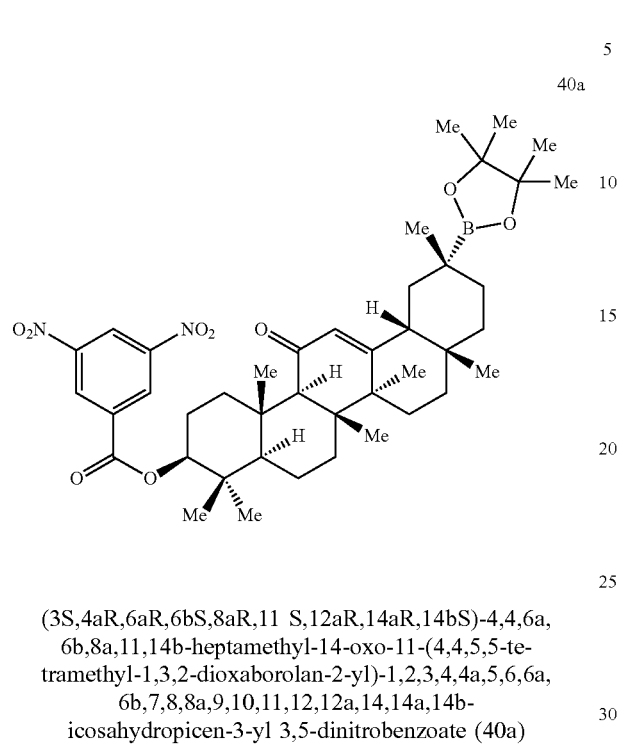

(3S,4aR,6aR,6bS,8aR,11S,12aR,14aR,14bS)-4,4,6a,
6b,8a,11,14b-heptamethyl-14-oxo-11-(4,4,5,5-te-
tramethyl-1,3,2-dioxaborolan-2-yl)-1,2,3,4,4a,5,6,6a,
6b,7,8,8a,9,10,11,12,12a,14,14a,14b-
icosahydropicen-3-yl 3,5-dinitrobenzoate (40a)

A culture tube charged with 40 (30 mg, 0.054 mmol, 1.0 equiv.), 3,5-dinitrobenzoyl chloride (50 mg, 0.22 mmol, 4.1 equiv.), and DMAP (1.3 mg, 0.011 mmol, 0.2 equiv.). $CH_2Cl_2$ (0.3 mL) and $Et_3N$ (30 μL, 0.22 mmol, 4.1 mmol) were added, and the resulting mixture was stirred for 1 h at room temperature. The mixture was loaded directly onto a silica gel column for purification by flash column chromatography (1:11 EtOAc:hexanes) to afford 40a (39.0 mg, 96%, d.r.=11.3:1). The pure product was crystallized from hexanes/$CH_2Cl_2$.

Physical State: pale yellow solid (major isomer is a white solid);

m.p. decompose at 295° C.;

$R_f$=0.45 (silica gel, 1:5.7 EtOAc:hexanes);

$^1$H NMR (600 MHz, $CDCl_3$): Major isomer δ 9.22 (t, J=2.2 Hz, 1H), 9.13 (d, J=2.2 Hz, 2H), 5.60 (s, 1H), 4.88 (dd, J=11.9, 4.7 Hz, 1H), 2.92 (dt, J=13.7, 3.6 Hz, 1H), 2.40 (s, 1H), 2.26-2.19 (m, 1H), 2.13 (td, J=13.7, 4.5 Hz, 1H), 1.98 (t, J=13.6 Hz, 1H), 1.95-1.87 (m, 1H), 1.87-1.75 (m, 2H), 1.74-1.59 (m, 3H), 1.56-1.48 (m, 2H), 1.45 (dt, J=12.8, 3.1 Hz, 1H), 1.40 (s, 3H), 1.30-1.09 (m, 5H), 1.23 (s, 3H), 1.21 (s, 6H), 1.21 (s, 6H), 1.16 (s, 3H), 1.08 (s, 3H), 1.00 (s, 3H), 0.97 (s, 3H), 0.97-0.94 (m, 1H), 0.89 (dd, J=11.8, 1.9 Hz, 1H), 0.86 (s, 3H) ppm;

$^{13}$C NMR (151 MHz, $CDCl_3$): Major isomer δ 199.9, 171.4, 162.3, 148.8, 134.8, 129.5, 128.3, 122.4, 84.3, 83.1, 61.7, 55.3, 45.6, 45.3, 43.6, 38.9, 38.6, 38.5, 37.1, 34.2, 32.8, 32.7, 29.2, 28.5, 27.8, 26.7, 26.6, 24.8, 24.7, 23.8, 23.4, 18.9, 17.7, 17.6, 17.2, 16.6 ppm;

HRMS (ESI-TOF, m/z): Calcd for $C_{42}H_{60}BN_2O_9[M+H]^+$ 747.4386; found 747.4385;

$[\alpha]_D^{20}$=+60.5 (c 1.0, $CHCl_3$).

Compound 41

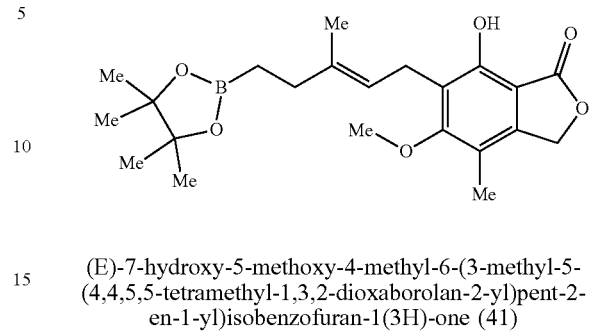

(E)-7-hydroxy-5-methoxy-4-methyl-6-(3-methyl-5-
(4,4,5,5-tetramethyl-1,3,2-dioxaborolan-2-yl)pent-2-
en-1-yl)isobenzofuran-1(3H)-one (41)

On 0.2 mmol scale, General Procedure B was followed with NHPI ester (S25) and solution B ($NiCl_2 \cdot 6H_2O$/di-MeObipy in DMF). Purification by flash column chromatography (silica gel, hexanes to 1:6:6 EtOAc:hexanes: $CH_2Cl_2$) afforded 41 (37.0 mg, 46%).

Physical State: white solid;

m.p.=122-124° C.;

$R_f$=0.40 (silica gel, 1:2 EtOAc:hexanes);

$^1$H NMR (600 MHz, $CDCl_3$): δ 7.64 (s, 1H), 5.21-5.18 (m, 3H), 3.75 (s, 3H), 3.37 (d, J=6.6 Hz, 2H), 2.13 (s, 3H), 2.08 (t, J=7.8 Hz, 2H), 1.77 (s, 3H), 1.17 (s, 12H), 0.86 (t, J=7.8 Hz, 2H) ppm;

$^{13}$C NMR (151 MHz, $CDCl_3$): δ 173.1, 163.9, 153.8, 143.9, 137.8, 122.8, 120.6, 116.8, 106.4, 83.0, 70.1, 61.1, 33.6, 24.9, 22.7, 16.3, 11.7 ppm;

HRMS (ESI-TOF, m/z): Calcd for $C_{22}H_{32}BO_6 [M+H]^+$ 403.2286; found 403.2289.

Experimental Procedure and Characterization Data for Boronic Acids

Compound 4a

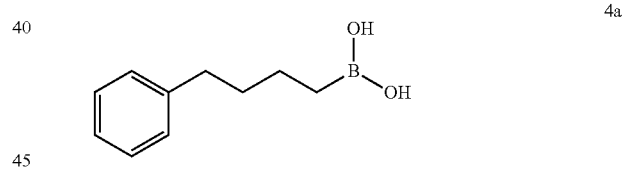

(4-phenylbutyl)boronic Acid (4a)

Pinacol boronate ester 4 (70 mg, 0.27 mmol) was dissolved in $CH_2Cl_2$ (5 mL) under argon and the solution was cooled to −78° C. in a dry ice/acetone bath. $BCl_3$ (0.81 mL, 1.0 M in $CH_2Cl_2$, 3.0 equiv) was added dropwise, after which the mixture was stirred for 1 h at −78° C. The mixture was then allowed to warm up to room temperature, and the volatiles were removed in vacuo. Anhydrous methanol (5 mL) was added and the resulting mixture was stirred for 10 minutes when methanol was removed in vacuo. An additional portion of methanol (5 mL) was added; the mixture was stirred for 10 minutes before it is concentrated in vacuo. This process was repeated for additional three times. The resulting crude product was then purified with preparative thin layer chromatography to afford 4a as a white solid (41.8 mg, 87%).

$^1$H NMR (600 MHz, DMSO-$d_6$/$D_2O$ 100/1): δ 7.28-7.22 (m, 2H), 7.15 (ddt, J=13.9 Hz, 6.9 Hz, 1.5 Hz, 3H), 2.56-2.51 (m, 2H), 1.51 (tt, J=7.8, 6.7 Hz, 2H), 1.38-1.28 (m, 2H), 0.60 (t, J=7.9 Hz, 2H).

$^{13}$C NMR (151 MHz, DMSO-d$_6$/D$_2$O 100/1): δ 142.60, 128.32, 128.27, 125.58, 35.26, 34.21, 23.98, 15.27 (br);
HRMS (ESI-TOF) Calcd for C$_{10}$H$_{16}$BO$_2$ [M+H]$^+$ 179.1238; found 179.1236.
Compound 3a

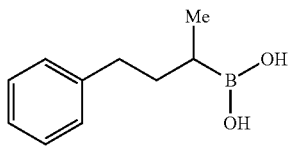

(4-phenylbutan-2-yl)boronic Acid (3a)

Pinacol boronate ester 3 (30 mg, 0.12 mmol) was dissolved in CH$_2$Cl$_2$ (2 mL) under argon and the solution was cooled to −78° C. in a dry ice/acetone bath. BCl$_3$ (0.36 mL, 1.0 M in CH$_2$Cl$_2$, 3.0 equiv) was added dropwise, after which the mixture was stirred for 1 h at −78° C. The mixture was then allowed to warm up to room temperature, and the volatiles were removed in vacuo. Anhydrous methanol (5 mL) was added and the resulting mixture was stirred for 10 minutes before methanol was removed in vacuo. An additional portion of methanol (5 mL) was added; the mixture was stirred for 10 minutes before it was concentrated in vacuo. This process was repeated for additional three times. The resulting crude product was then purified with preparative thin layer chromatography to afford 4a as a white solid (15.4 mg, 75%).

$^1$H NMR (600 MHz, DMSO-d$_6$/D$_2$O 100/1): δ 7.24 (t, J=7.6 Hz, 2H), 7.18-7.10 (m, 3H), 2.53-2.48 (m, 2H), 1.74-1.63 (m, 1H), 1.42 (ddt, J=13.0 Hz, 9.9 Hz, 6.5 Hz, 1H), 0.90 (d, J=7.2 Hz, 3H), 0.89-0.81 (m, 1H) ppm;
$^{13}$C NMR (151 MHz, DMSO-d$_6$/D$_2$O 100/1): δ 143.03, 128.34, 125.61, 35.65, 35.05, 20.33 (br), 16.35 ppm;

HRMS (ESI-TOF) Calcd for C$_{10}$H$_{16}$BO$_2$ [M+H]$^+$ 179.1238; found 179.1232.
Compound 33a

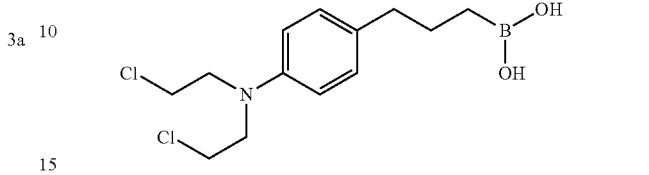

(3-(4-(bis(2-chloroethyl)amino)phenyl)propyl)boronic Acid (33a)

To a solution of pinacol boronate ester 34 (76.2 mg, 0.2 mmol) in CH$_2$Cl$_2$ (1 mL) was added BCl$_3$ (0.79 mL, 1.0 M in CH$_2$Cl$_2$) dropwise at −78° C. The reaction mixture was stirred at −78° C. for 30 minutes followed by another 30 minutes at room temperature. The reaction was quenched with methanol (2 mL) and was concentrated in vacuo. To the residue was added MeOH (2 mL) which was subsequently removed in vacuo; this process was repeated for additional three times. Purification of the resulting residue by preparative reverse-phase HPLC (20-80% CH$_3$CN/H$_2$O over 30 min, both CH$_3$CN and H$_2$O containing 0.1% TFA) afforded 33a (27 mg, 50%) as a colorless oil.

$^1$H NMR (600 MHz, DMSO-d$_6$/D$_2$O 10/1): δ 7.00 (d, J=12.6 Hz, 2H), 6.65 (d, J=12.6 Hz, 2H), 3.71-3.65 (m, 8H), 2.39 (t, J=7.8 Hz, 2H), 1.58-1.53 (m, 2H), 0.59 (t, J=8.4 Hz, 2H) ppm;
$^{13}$C NMR (151 MHz, DMSO-d$_6$/D$_2$O 10/1): δ 144.2, 130.9, 129.3, 111.8, 52.3, 41.2, 37.2, 26.6 ppm;
HRMS (ESI-TOF) Calcd for C$_{13}$H$_{21}$BCl$_2$NO$_2$ [M+H]$^+$ 304.1037; found 304.1030.

Scheme S1. Synthesis of Ninlaro (ixazomib) Synthesis of Ninlaro (ixazomib)

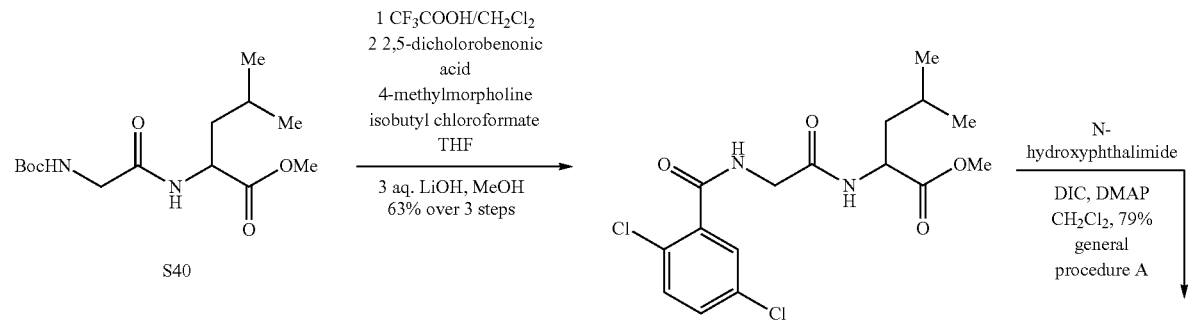

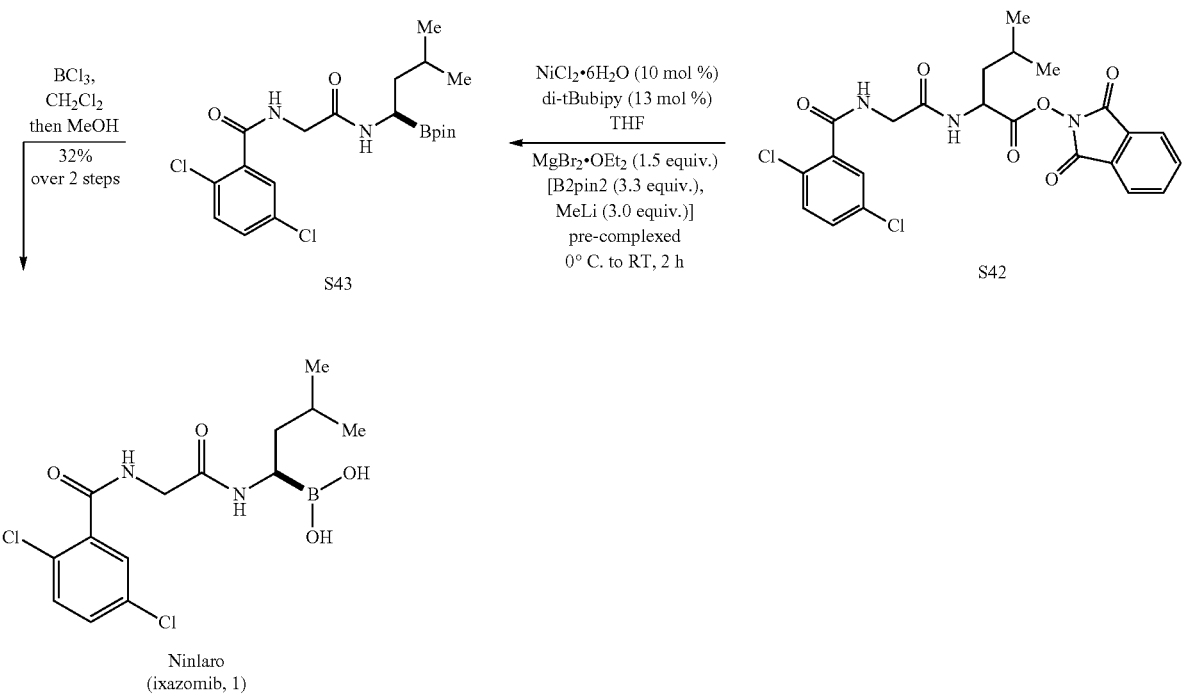

Compound S41

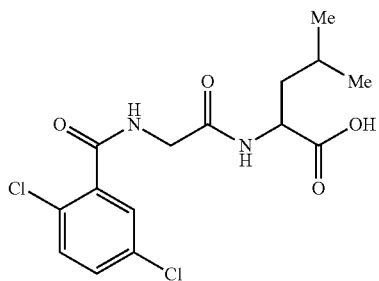

(2,5-dichlorobenzoyl)glycylleucine (S41)

Deprotection of Boc:

To a solution of Boc-Gly-Leu-OMe[11] (3.1 g, 10.26 mmol) in CH$_2$Cl$_2$ (30 mL) was added TFA (15 mL) at room temperature, the reaction mixture was stirred for 1 h before concentrated in vacuo. The residue was used directly in the next step.

Amide Bond Formation:

To a solution 2,5-dichlorobenonic acid (2.94 g, 15.4 mmol) in THF (70 mL) was added 4-methylmorpholine (4.0 mL, 35.9 mmol) at −15° C., the reaction mixture was stirred for 10 min at that temperature. To the resulting white suspension was added isobutyl chloroformate (2.0 mL, 15.4 mmol) dropwise and the mixture was stirred for another 30 min at −15° C. The crude TFA salt (from the deprotection step) in THF (35 mL) was added slowly at the same temperature. The reaction mixture was warmed up to room temperature and stirred for 6 h. The resulting mixture was diluted with EtOAc (100 mL), washed with water (100 mL), sat. aqueous NaHCO$_3$ (100 mL), and brine (100 mL). The combined organic layer was dried over anhydrous Na$_2$SO$_4$, filtered, and concentrated. Purification by a flash column chromatography (silica, 3:2 Hexane/EtOAc) afforded the desired ester which is not very pure but can be used in next step without further purification.

Hydrolysis of Methyl Ester:

To a solution of the aforementioned ester in THF (50 mL) was added aqueous LiOH (1M, 50 mL). The reaction mixture was stirred at room temperature for 2 h and was then washed with EtOAc (60 mL). The aqueous layer was acidified with 1N HCl (65 mL) and extracted with EtOAc (100 mL). The organic layer was washed with brine (100 mL) whereby the aqueous layers were back-extracted with EtOAc (100 mL). The combined organic phase was concentrated in vacuo. To the residue was added CH$_2$Cl$_2$ (30 ml) when the desired product S41 precipitated out and was collected by filtration (2.31 g, 63% over 3 steps).

m.p.=137-138° C.;

$^1$H NMR (600 MHz, MeOH-d4): δ 7.63 (dd, J=1.8 Hz, 0.6 Hz, 1H), 7.45-7.48 (m, 2H), 4.50 (dd, J=9.6 Hz, 5.4 Hz, 1H), 4.08 (dd, J=37.8 Hz, 16.8 Hz, 2H), 1.79-1.72 (m, 1H), 1.70-1.62 (m, 2H), 0.98 (d, J=6.6 Hz, 3H), 0.95 (d, J=6.6 Hz, 3H) ppm;

$^{13}$C NMR (151 MHz, MeOH-d4): δ 175.8, 170.9, 168.7, 138.4, 134.0, 132.6, 132.3, 130.6, 130.2, 52.1, 43.6, 41.9, 26.0, 23.4, 21.9 ppm;

HRMS (ESI-TOF) Calcd for C$_{15}$H$_{19}$Cl$_2$N$_2$O$_4$ [M+H]$^+$ 361.0716; found 361.0706;

$[α]_D^{20}$=−14.0 (c 1.0, MeOH).

Compound S42

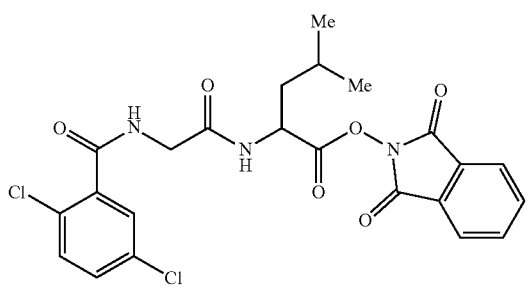

1,3-dioxoisoindolin-2-yl
(2,5-dichlorobenzoyl)glycylleucinate (S42)

On 2.0 mmol scale, general procedure A was followed with S41. Purification by flash column chromatography (deactivated silica gel, 3:7 EtOAc:hexanes) furnished S42 (940 mg, 79%).

Physical state: white solid;
m.p.=164° C.;
$R_f$=0.55 (silica gel, 3:2 EtOAc:hexanes);
$^1$H NMR (600 MHz, THF-d8): δ 8.05 (br s, 1H), 7.99-7.97 (m, 1H), 7.91-7.89 (m, 2H), 7.87-7.85 (m, 2H), 7.58 (dd, J=2.4 Hz, 0.5 Hz, 1H), 7.42-7.38 (m, 2H), 5.10-5.06 (m, 1H), 4.14 (dd, J=16.8 Hz, 6.0 Hz, 1H), 3.99 (dd, J=16.8 Hz, 6.0 Hz, 1H), 1.92-1.83 (m, 2H), 1.80-1.75 (m, 1H), 1.02 (d, J=6.0 Hz, 3H), 1.00 (d, J=6.0 Hz, 3H) ppm;
$^{13}$C NMR (151 MHz, THF-d8): δ 170.5, 169.4, 166.0, 162.4, 139.2, 135.9, 133.5, 132.3, 131.5, 130.7, 130.5, 130.2, 124.7, 49.7, 43.6, 42.3, 25.8, 23.4, 22.1 ppm;
HRMS (ESI-TOF) Calcd for $C_{23}H_{22}Cl_2N_3O_6$ [M+H]$^+$ 506.0880; found 506.0875;
$[α]_D^{20}$=−1.0 (c 1.0, THF).

Compound 1

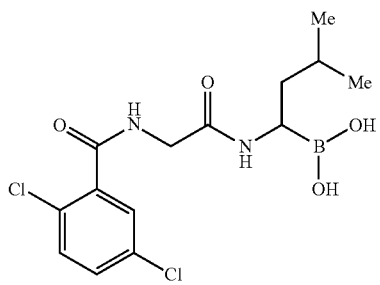

On 0.2 mmol scale, general procedure C was followed using suspension C (NiCl$_2$.6H$_2$O/di-tBubipy in THF) with S42. Flash column chromatography (silica gel, hexanes to 2:3 EtOAc:hexanes to 4:1 EtOAc:hexanes) afforded pinacol aminoboronate ester S43 which was used in the next step without further purification.

The pinacol aminoboronate ester S43 was dissolved in CH$_2$Cl$_2$ (5 mL) under argon and the solution was cooled to −78° C. in a dry ice/acetone bath. BCl$_3$ (0.6 mL, 1.0 M in CH$_2$Cl$_2$, 3.0 equiv.) was added dropwise, after which the mixture was stirred for 1 h at −78° C. The mixture was then allowed to warm up to room temperature, and the volatiles were removed in vacuo. Anhydrous methanol (5 mL) was added and the mixture was stirred for 10 minutes when the methanol was removed in vacuo. An additional portion of methanol (5 mL) was added; the mixture was stirred for 10 minutes before it is concentrated in vacuo. This process was repeated for three times. The resulting residue was then purified by preparative reverse-phase HPLC (10-60% CH$_3$CN/H$_2$O over 35 min, both CH$_3$CN and H$_2$O containing 0.1% TFA) to afford Ninlaro (1, 23.0 mg, 32% over 2 steps).
$^1$H NMR (600 MHz, MeOH-d$_4$): δ 7.60 (t, J=1.5 Hz, 1H), 7.49-7.47 (m, 2H), 4.24 (s, 2H), 2.79 (t, J=7.6 Hz, 1H), 1.68 (ddt, J=14.7 Hz, 13.0 Hz, 6.4 Hz, 1H), 1.38 (tdd, J=13.8 Hz, 10.4 Hz, 5.9 Hz, 2H), 0.94 (dd, J=6.6 Hz, 1.5 Hz, 6H);
$^{13}$C NMR (151 MHz, MeOH-d$_4$): δ 175.6, 168.8, 138.0, 134.0, 132.7, 132.5, 130.7, 130.2, 44.7 (br, a to boron), 40.9, 40.2, 27.1, 23.7, 22.4.
HRMS (ESI-TOF, m/z): calc'd for $C_{14}H_{18}BCl_2N_2O_3$ [M−H$_2$O+H]$^+$ 343.0782; found 343.0779;
$[α]_D^{20}$=−0.6 (c 1.0, MeOH).

Decarboxylative Borylation Enabled Late-Stage Diversification of Lipitor

Compound 36a

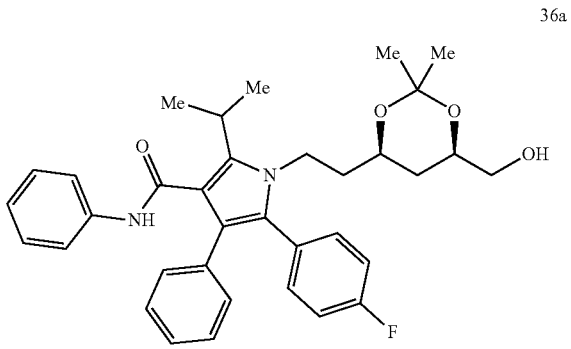 [SMILES: CC(C)c1c(C(=O)Nc2ccccc2)c(-c2ccccc2)c(-c2ccc(F)cc2)n1CC[C@@H]1C[C@H](CO)OC(C)(C)O1]

5-(4-fluorophenyl)-1-(2-((4R,6R)-6-(hydroxymethyl)-2,2-dimethyl-1,3-dioxan-4-yl)ethyl)-2-isopropyl-N,4-diphenyl-1H-pyrrole-3-carboxamide (36a)

To a solution of 36 (50 mg, 0.073 mmol) in THF/H$_2$O (1:1, 0.73 mL) at room temperature open to air was added NaBO$_3$.4H$_2$O (56 mg, 0.37 mmol). The mixture was stirred vigorously for 3 h before H$_2$O (10 mL) was added. The resulting mixture was extracted with EtOAc (10 mL×3). The combined organic extracts were dried over Na$_2$SO$_4$, filtered, and concentrated. Purification by flash column chromatography (silica gel, 2:3 EtOAc:hexanes) afforded 36a (40 mg, 86%).

m.p.=166-170° C.;
$R_f$=0.27 (silica gel, 2:3 EtOAc:hexanes);
$^1$H NMR (600 MHz, CDCl$_3$): δ 7.21-7.15 (m, 9H), 7.07 (d, J=8.0 Hz, 2H), 7.02-6.96 (m, 3H), 6.86 (s, 1H), 4.13-4.05 (m, 1H), 3.92-3.81 (m, 2H), 3.73-3.66 (m, 1H), 3.61-3.52 (m, 2H), 3.45 (dd, J=11.4 Hz, 6.1 Hz, 1H), 1.74-1.61 (m, 2H), 1.54 (s, 3H), 1.53 (s, 3H), 1.37 (s, 3H), 1.34 (s, 3H), 1.74-1.61 (m, 2H);
$^{13}$C NMR (151 MHz, CDCl$_3$): δ 164.9, 162.4 (d, J=247.6 Hz), 141.7, 138.5, 134.8, 133.3 (d, J=8.0 Hz), 130.6, 128.9, 128.8, 128.5, 128.4 (d, J=3.5 Hz), 126.7, 123.6, 121.9, 119.7, 115.5 (d, J=21.4 Hz), 98.9, 69.4, 66.2, 66.0, 41.0, 38.3, 31.9, 30.0, 26.2, 21.9, 21.7, 20.0;
$^{19}$F NMR (376 MHz, acetone-d6): δ −114.00 ppm;
HRMS (ESI-TOF, m/z): Calcd for $C_{35}H_{40}FN_2O_4$[M+H]$^+$ 571.2966; found 571.2963;
$[α]_D^{20}$=−4.6 (c 1.0, CHCl$_3$).

Compound 36b

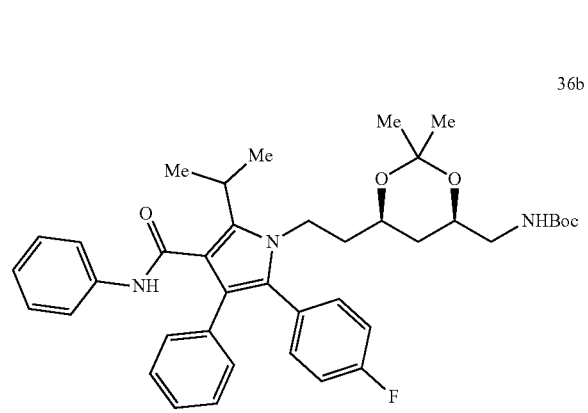 [SMILES: CC(C)c1c(C(=O)Nc2ccccc2)c(-c2ccccc2)c(-c2ccc(F)cc2)n1CC[C@@H]1C[C@H](CNC(=O)OC(C)(C)C)OC(C)(C)O1]

tert-butyl (((4R,6R)-6-(2-(2-(4-fluorophenyl)-5-isopropyl-3-phenyl-4-(phenylcarbamoyl)-1H-pyrrol-1-yl)ethyl)-2,2-dimethyl-1,3-dioxan-4-yl)methyl)carbamate (36b)

The amination was performed following the literature procedure[12] with slight modifications. A solution of O-methylhydroxylamine (63 μL, 2.8 M in THF, 6.0 equiv) was diluted with THF (1 mL). n-BuLi (72 μL, 2.45 M in hexanes, 6.0 equiv) was added at −78° C., and the resulting mixture was stirred for 1 h at that temperature. A solution of pinacol boronate 36 (20 mg, 0.03 mmol) in THF (1 mL) was added dropwise at −78° C. After warming up to room temperature, the reaction mixture was heated to 65° C. and stirred for 36 h. Upon cooling to room temperature, Boc$_2$O (66 mg, 10.0 equiv) was added. The resulting mixture was stirred at room temperature for 1 h before the volatiles were removed in vacuo. Purification of the resulting residue by preparative thin layer chromatography (silica gel, 15:1 DCM:Et$_2$O) afforded 36b (10.7 mg, 54%) as colorless oil.

Physical state: colorless oil;

R$_f$=0.4 (silica gel, 1:3 hexane: EtOAc);

$^1$H NMR (600 MHz, CDCl$_3$): δ 7.24-7.09 (m, 9H), 7.07 (d, J=8.0 Hz, 2H), 7.04-6.94 (m, 3H), 6.86 (s, 1H), 4.84 (s, 1H), 4.07 (ddd, J=15.3 Hz, 10.7 Hz, 5.1 Hz, 1H), 3.82 (ddt, J=15.1 Hz, 10.3 Hz, 6.5 Hz, 2H), 3.66 (tt, J=8.2 Hz, 3.6 Hz, 1H), 3.57 (p, J=7.2 Hz, 1H), 3.24 (d, J=8.7 Hz, 1H), 2.98 (ddd, J=13.8 Hz, 6.8 Hz, 5.1 Hz, 1H), 1.70-1.63 (m, 2H), 1.53 (d, J=7.1 Hz, 6H), 1.44 (s, 9H), 1.34 (s, 3H), 1.31 (s, 3H), 1.27-1.20 (m, 1H), 1.07 (q, J=12.0 Hz, 1H);

$^{13}$C NMR (151 MHz, CDCl$_3$): δ 164.9, 162.4 (d, J=247.9 Hz), 156.2, 141.6, 138.5, 134.8, 133.3 (d, J=8.1 Hz), 130.6, 128.9, 128.8, 128.5, 128.4 (d, J=3.5 Hz), 126.7, 123.6, 121.9, 119.7, 115.5 (d, J=21.3 Hz), 98.8, 79.6, 68.2, 66.3, 45.4, 41.0, 38.3, 33.4, 30.5, 30.0, 28.5, 26.2, 21.9, 21.7, 20.0;

$^{19}$F NMR (376 MHz, CDCl$_3$): δ −113.93 ppm;

HRMS (ESI-TOF, m/z): Calcd for C$_{40}$H$_{49}$FN$_3$O$_5$[M+H]$^+$ 670.3651; found 670.3646;

[α]$_D^{20}$=−2.0 (c 0.74, CHCl$_3$).

Compound 36c

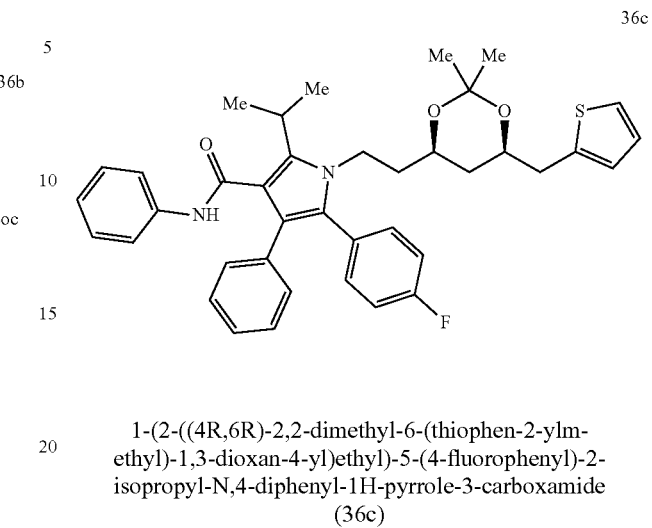

1-(2-((4R,6R)-2,2-dimethyl-6-(thiophen-2-ylmethyl)-1,3-dioxan-4-yl)ethyl)-5-(4-fluorophenyl)-2-isopropyl-N,4-diphenyl-1H-pyrrole-3-carboxamide (36c)

To a solution of thiophene (23 μL, 0.28 mmol) in THF (1.0 mL) was added n-BuLi (0.1 mL, 2.5 M in hexanes, 0.25 mmol) at −78° C. The resulting mixture was warmed to room temperature and stirred for 1 h when some of the resulting yellow solution (0.33 mL) was transferred to a reaction tube. A solution of 36 (12.4 mg, 0.018 mmol) in THF (0.3 mL) was added dropwise at −78° C. The resulting mixture was stirred at the same temperature for 1.5 h when a solution of NBS (14.4 mg, 0.081 mmol) in THF (0.3 mL) was added. After stirring for 1 h at the same temperature, the reaction was quenched with sat. aqueous Na$_2$S$_2$O$_3$ (1 mL) before warming up to room temperature. The resulting mixture was extracted with EtOAc (1 mL×3). The combined organic layers were dried over anhydrous Na$_2$SO$_4$ and concentrated in vacuo. Purification by flash column chromatography (silica gel, 1:9 EtOAc:hexanes) and PTLC (silica gel, 1:6 EtOAc:hexanes) afforded 36c (6.5 mg, 56%).

Physical state: white foam;

R$_f$=0.61 (silica gel, 2:3 EtOAc:hexanes);

$^1$H NMR (600 MHz, acetone-d6): δ 8.29 (br s, 1H), 7.45 (d, J=7.8 Hz, 2H), 7.30-7.27 (m, 2H), 7.24 (dd, J=5.4 Hz, 1.2 Hz, 1H), 7.20 (t, J=7.8 Hz, 2H), 7.13-7.09 (m, 6H), 7.08-7.05 (m, 1H), 6.99-6.96 (m, 1H), 6.92 (dd, J=5.4 Hz, 3.6 Hz, 1H), 6.85-6.84 (m, 1H), 4.11-4.06 (m, 1H), 4.05-4.00 (m, 1H), 3.91-3.86 (m, 1H), 3.85-3.81 (m, 1H), 3.43-3.39 (m, 1H), 2.93-2.90 (m, 1H), 2.87-2.83 (m, 1H), 1.75-1.63 (m, 2H), 1.47 (d, J=1.2 Hz, 3H), 1.45 (d, J=1.2 Hz, 3H), 1.36 (dt, J=12.6 Hz, 3.0 Hz, 1H), 1.36 (s, 3H), 1.28 (s, 3H) 1.05-0.99 (m, 1H) ppm;

$^{13}$C NMR (151 MHz, acetone-d6): δ 166.4, 163.1 (d, J=245.6 Hz), 140.9, 140.6, 139.4, 136.1, 134.5 (d, J=8.2 Hz), 130.8, 129.9 (d, J=3.3 Hz), 129.3, 128.9, 128.6, 127.3, 126.7, 126.7, 124.9, 123.8, 122.4, 120.2, 118.0, 116.0 (d, J=21.6 Hz), 99.2, 70.2, 67.3, 41.3, 39.1, 37.3, 36.5, 30.5, 26.9 22.4, 22.3, 20.1 ppm;

$^{19}$F NMR (376 MHz, acetone-d6): δ −114.91 ppm;

HRMS (ESI-TOF) Calcd for C$_{39}$H$_{42}$FN$_2$O$_3$S [M+H]$^+$ 637.2895; found 637.2892;

[α]$_D^{20}$=+19.2 (c 0.5, CHCl$_3$).

Compound 36d

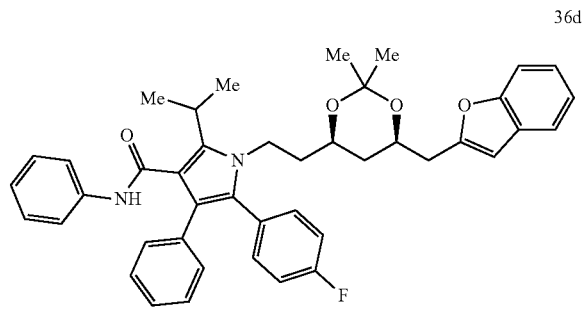 [SMILES: CC(C)c1c(C(=O)Nc2ccccc2)c(-c2ccccc2)c(-c2ccc(F)cc2)n1CC[C@@H]1C[C@H](Cc2cc3ccccc3o2)OC(C)(C)O1]

1-(2-((4R,6R)-6-(benzofuran-2-ylmethyl)-2,2-dimethyl-1,3-dioxan-4-yl)ethyl)-5-(4-fluorophenyl)-2-isopropyl-N,4-diphenyl-1H-pyrrole-3-carboxamide (36d)

To a solution of 2,3-benzofuran (30 µL, 0.27 mmol) in THF (1.0 mL) was added n-BuLi (0.1 mL, 2.5 M in hexanes, 0.25 mmol) at −78° C. The resulting solution was warmed up to room temperature. The resulting mixture was warmed to room temperature and stirred for 1 h when some of the resulting yellow solution (0.33 mL) was transferred to a reaction tube. A solution of 36 (12.0 mg, 0.018 mmol) in THF (0.3 mL) was added dropwise at −78° C. The resulting mixture was stirred at the same temperature for 1 h when a solution of NBS (14.4 mg, 0.081 mmol) in THF (0.3 mL) was added. After stirring for 1 h at the same temperature, the reaction was quenched with sat. aqueous $Na_2S_2O_3$ (1 mL) before warming up to room temperature. The resulting mixture was extracted with EtOAc (1 mL×3). The combined organic layers were dried over anhydrous $Na_2SO_4$ and concentrated in vacuo. Purification by flash column chromatography (silica gel, 1:9 EtOAc:hexanes) and preparative thin layer chromatography (silica gel, 1:9 EtOAc:hexanes) afforded 36d (6.1 mg, 52%).

Physical state: colorless oil;

$R_f$=0.64 (silica gel, 2:3 EtOAc:hexanes);

$^1$H NMR (600 MHz, acetone-d6): δ 8.29 (br s, 1H), 7.54-7.52 (m, 1H), 7.44 (d, J=7.8 Hz, 2H), 7.45-7.42 (m, 1H), 7.31-7.27 (m, 2H), 7.24-7.17 (m, 4H), 7.13-7.05 (m, 7H), 6.99-6.96 (m, 1H), 6.58 (dd, J=1.2 Hz, 0.6 Hz, 1H), 4.29-4.24 (m, 1H), 4.11-4.06 (m, 1H), 3.91-3.85 (m, 2H), 3.44-3.37 (m, 1H), 2.93 (dd, J=15.6 Hz, 6.6 Hz, 1H), 2.79 (dd, J=15.6 Hz, 6.6 Hz, 1H), 1.76-1.65 (m, 2H), 1.46 (s, 3H), 1.45 (s, 3H), 1.46-1.51 (m, 1H), 1.39 (d, J=0.6 Hz, 3H), 1.27 (d, J=0.6 Hz, 3H), 1.14-1.08 (m, 1H) ppm;

$^{13}$C NMR (151 MHz, acetone-d6): δ 166.4, 163.1 (d, J=245.7 Hz), 156.5, 155.5, 140.6, 139.4, 136.1, 134.5 (d, J=8.3 Hz), 130.8, 129.9 (d, J=3.3 Hz), 129.9, 129.3, 128.9, 128.6, 126.7, 124.2, 123.8, 123.4, 122.4, 121.3, 120.2, 120.1, 118.0, 116.0 (d, J=21.6 Hz), 111.4, 104.6, 99.3, 68.1, 67.3, 41.3, 39.1, 37.0, 36.2, 30.4, 26.9, 22.4, 22.3, 20.1 ppm;

$^{19}$F NMR (376 MHz, acetone-d6): δ −114.95 ppm;

HRMS (ESI-TOF) Calcd for $C_{43}H_{44}FN_2O_4[M+H]^+$ 671.3280; found 671.3274;

$[\alpha]_D^{20}$=+28.5 (c 0.5, $CHCl_3$).

Compound 36e

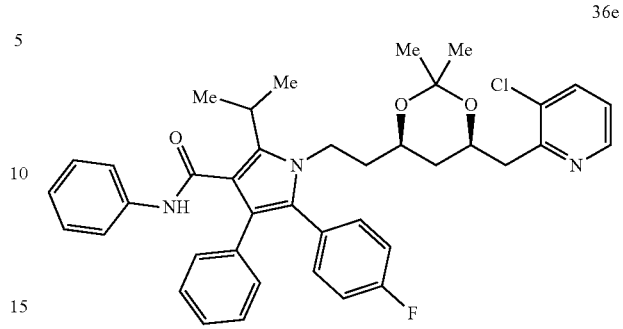

1-(2-((4R,6S)-6-((3-chloropyridin-2-yl)methyl)-2,2-dimethyl-1,3-dioxan-4-yl)ethyl)-5-(4-fluorophenyl)-2-isopropyl-N,4-diphenyl-1H-pyrrole-3-carboxamide (36e)

To a screw-capped culture tube was added $Pd_2(dba)_3$ (1.9 mg, 0.0022 mmol, 0.1 equiv), p-anisyldiphenylphosphine (3.7 mg, 0.0132 mmol, 0.6 equiv), 1-chloro-4-nitrobenzene (35 mg, 0.22 mmol, 10 equiv), and $K_3PO_4$ (47 mg, 0.22 mmol, 10 equiv). This tube was then evacuated and back-filled with argon for three times. 1,4-dioxane (0.4 mL) was then added via a syringe and the resulting mixture was stirred at room temperature for 5 minutes. A solution of 36 (15.0 mg, 0.022 mmol) in dioxane (0.6 mL) and degassed DI water (0.5 mL) were added sequentially. The reaction mixture was heated at 100° C. for 15 h, after which it was cooled to room temperature and treated with brine (4 mL). The resulting mixture was extracted with EtOAc (2 mL×3). The combined organic layers were dried over anhydrous $Na_2SO_4$ and concentrated in vacuo. Purification by flash column chromatography (silica gel, 1:6 to 3:7 EtOAc:hexanes) and PTLC (silica gel, 1:3 EtOAc:hexanes) afforded 36e (7.9 mg, 54%).

Physical state: colorless oil;

$R_f$=0.38 (silica gel, 3:7 EtOAc:hexanes);

$^1$H NMR (600 MHz, acetone-d6): δ 8.45 (dd, J=4.8 Hz, 1.8 Hz, 1H), 8.30 (br s, 1H), 7.79 (dd, J=8.4 Hz, 1.8 Hz, 1H), 7.45 (d, J=7.8 Hz, 2H), 7.30-7.25 (m, 3H), 7.20 (t, J=7.8 Hz, 2H), 7.12-7.05 (m, 7H), 6.99-6.96 (m, 1H), 4.46-4.41 (m, 1H), 4.11-4.06 (m, 1H), 3.91-3.86 (m, 1H), 3.85-3.81 (m, 1H), 3.44-3.39 (m, 1H), 3.13 (dd, J=14.4 Hz, 6.6 Hz, 1H), 2.88 (dd, J=14.4 Hz, 7.2 Hz, 1H), 1.76-1.64 (m, 2H), 1.47 (d, J=0.6 Hz, 3H), 1.45 (d, J=0.6 Hz, 3H), 1.38 (dt, J=12.6 Hz, 2.4 Hz, 1H), 1.34 (s, 3H), 1.24 (s, 3H), 1.16-1.10 (m, 1H) ppm;

$^{13}$C NMR (151 MHz, acetone-d6): δ 166.4, 163.1 (d, J=245.5 Hz), 156.2, 148.3, 140.6, 139.3, 137.6, 136.2, 134.5 (d, J=8.3 Hz), 132.2, 130.8, 129.9 (d, J=3.3 Hz), 129.3, 128.9, 128.6, 126.7, 123.8, 123.8, 122.4, 120.2, 118.0, 116.0 (d, J=21.6 Hz), 99.2, 68.7, 67.3, 42.3, 41.3, 39.2, 37.0, 30.5, 26.9, 22.4, 22.3, 20.1 ppm;

$^{19}$F NMR (376 MHz, acetone-d6): δ −114.92 ppm;

HRMS (ESI-TOF) Calcd for $C_{40}H_{42}ClFN_3O_3[M+H]^+$ 666.2893; found 666.2884;

$[\alpha]_D^{20}$=+26.2 (c 0.5, $CHCl_3$).

Compound 36f

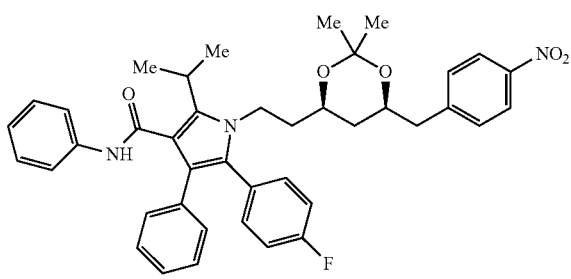

1-(2-((4R,6S)-2,2-dimethyl-6-(4-nitrobenzyl)-1,3-dioxan-4-yl)ethyl)-5-(4-fluorophenyl)-2-isopropyl-N,4-diphenyl-1H-pyrrole-3-carboxamide (36f)

To a screw-capped culture tube was added Pd$_2$(dba)$_3$ (1.9 mg, 0.0022 mmol, 0.1 equiv), p-anisyldiphenylphosphine (3.7 mg, 0.0132 mmol, 0.6 equiv), 1-chloro-4-nitrobenzene (35 mg, 0.22 mmol, 10 equiv), and K$_3$PO$_4$ (47 mg, 0.22 mmol, 10 equiv). This tube was evacuated and backfilled with argon for three times. 1,4-dioxane (0.4 mL) was added via a syringe and the resulting mixture was stirred at room temperature for 5 minutes. A solution of 36 (15.0 mg, 0.022 mmol) in dioxane (0.6 mL) and degassed DI water (0.5 mL) were added sequentially. The reaction mixture was heated to 100° C. for 15 h after which it was cooled to room temperature and treated with brine (4 mL). The resulting mixture was extracted with EtOAc (2 mL×3). The combined organic layers were dried over anhydrous Na$_2$SO$_4$ and concentrated in vacuo. Purification by flash column chromatography (silica gel, 1:9 to 1:3 EtOAc:hexanes) and PTLC (silica gel, 1:4 EtOAc:hexanes) afforded 36f (10.5 mg, 72%).

Physical state: yellow oil;
R$_f$=0.45 (silica gel, 3:7 EtOAc:hexanes);
$^1$H NMR (600 MHz, acetone-d6): δ 8.28 (br s, 1H), 8.15 (dt, J=9.0 Hz, 1.8 Hz, 2H), 7.51 (dt, J=9.0 Hz, 1.8 Hz, 2H), 7.45 (d, J=8.4 Hz, 2H), 7.30-7.27 (m, 2H), 7.20 (t, J=7.8 Hz, 2H), 7.14-7.10 (m, 6H), 7.09-7.05 (m, 1H), 6.99-6.96 (m, 1H), 4.17-4.13 (m, 1H), 4.11-4.06 (m, 1H), 3.92-3.87 (m, 1H), 3.85-3.81 (m, 1H), 3.44-3.37 (m, 1H), 2.87 (dd, J=13.8 Hz, 7.2 Hz, 1H), 2.81 (dd, J=13.8 Hz, 7.2 Hz, 1H), 1.73-1.65 (m, 2H), 1.46 (d, J=0.6 Hz, 3H), 1.45 (d, J=0.6 Hz, 3H), 1.36 (dt, J=12.6 Hz, 2.4 Hz, 1H), 1.32 (s, 3H), 1.25 (s, 3H), 1.09-1.03 (m, 1H) ppm;
$^{13}$C NMR (151 MHz, acetone-d6): δ 166.4, 163.1 (d, J=245.5 Hz), 147.6, 147.5, 140.5, 139.4, 136.1, 134.5 (d, J=8.3 Hz), 131.4, 130.8, 129.9 (d, J=3.8 Hz), 129.3, 128.9, 128.7, 126.7, 123.9, 123.8, 122.4, 120.2, 118.0, 116.0 (d, J=21.4 Hz), 99.2, 69.8, 67.3, 42.9, 41.2, 39.1, 36.7, 30.4, 26.9, 22.4, 22.3, 20.1 ppm;
$^{19}$F NMR (376 MHz, acetone-d6): δ −114.92 ppm;
HRMS (ESI-TOF) Calcd for C$_{41}$H$_{43}$FN$_3$O$_5$ [M+H]$^+$ 676.3181; found 676.3182;
[α]$_D^{20}$=+10.8 (c 0.5, CHCl$_3$).

Synthesis of Borono-Vancomycin Analog

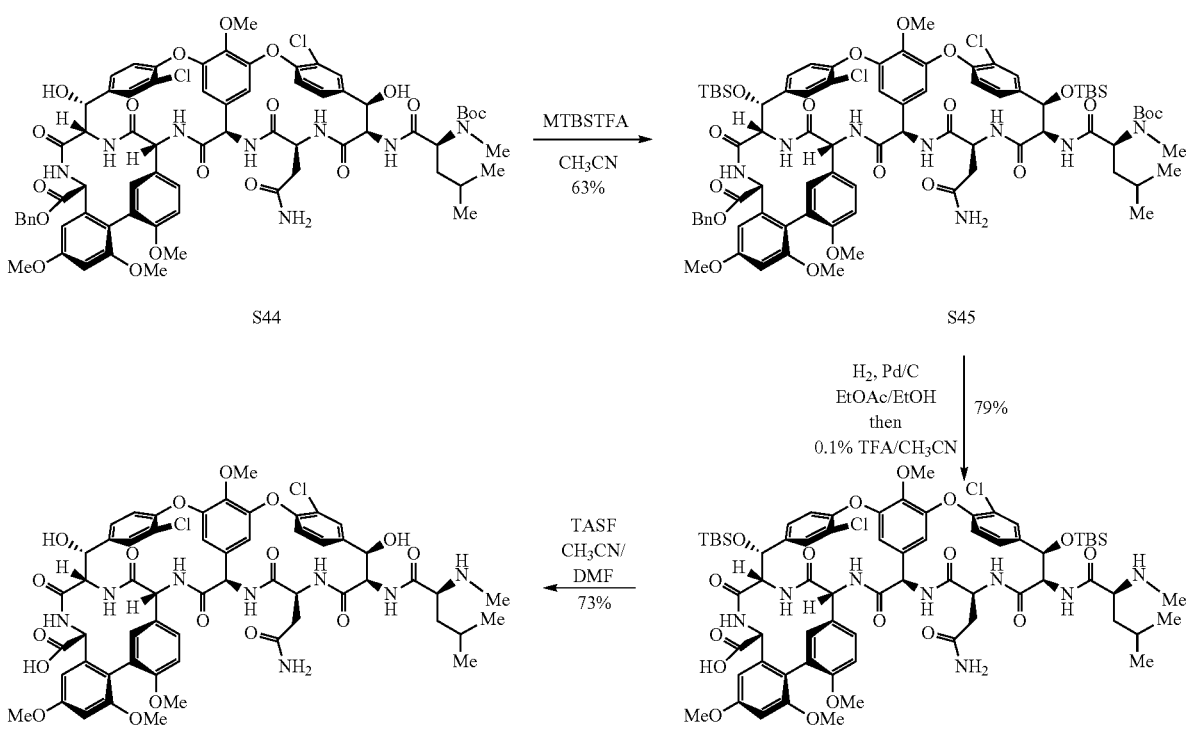

121

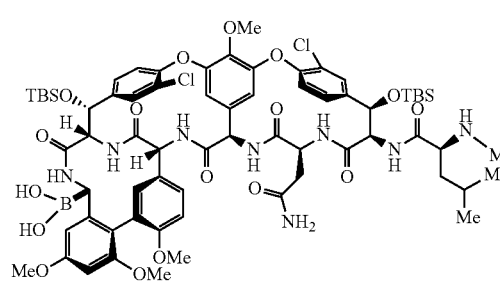

S47

122

-continued

NiCl₂·6H₂O
di-tBubipy
THF
⟵
MgBr₂·OEt₂
B₂pin₂,
MeLi
then
silica gel

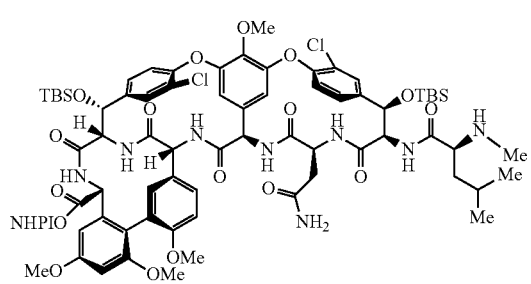

S46

TASF
CH₃CN/DMF | 11% over 3 steps

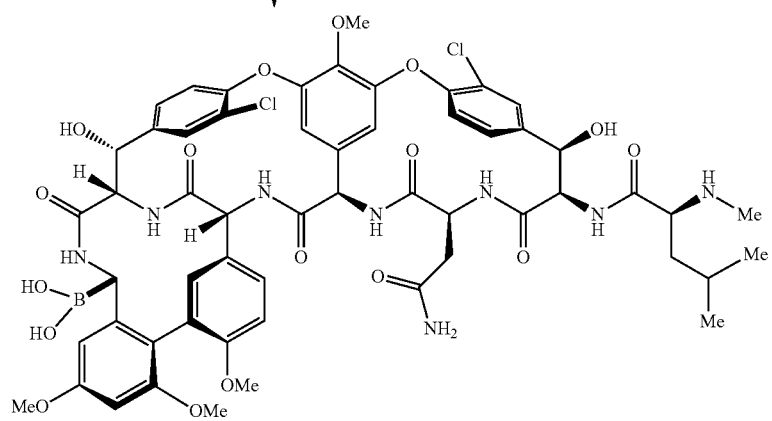

44

Compound S45

S45

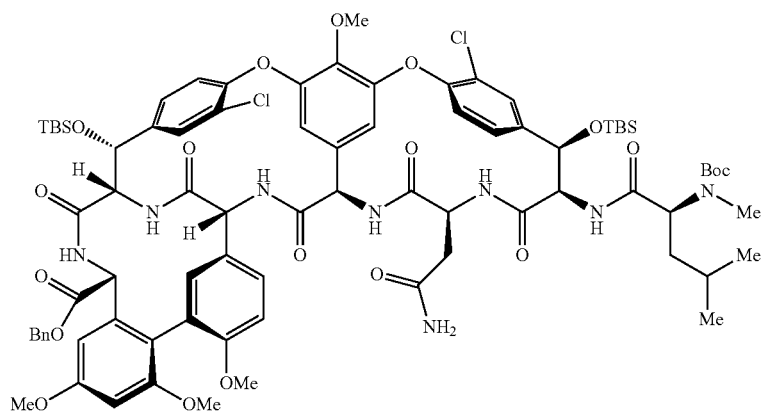

60

To S44 [synthesized according to literature report (38, 62)] (600 mg, 0.43 mmol, 1.0 equiv.) in CH₃CN (5.1 mL) was added N-tert-butyldimethylsilyl-N-methyltrifluoroacetamide (MTBSTFA, 2.4 mL, 10.2 mmol, 23.7 equiv.), the resulting mixture was heated to 50° C. After 30 h, the reaction mixture was poured onto a mixture of sat. aqueous citric acid (50 mL)/EtOAc (20 mL) and stirred vigorously at room temperature for 12 h. The organic layer was separated and washed with sat. aqueous NaHCO₃ (50 mL) and brine (50 mL). The aqueous layers were then back-extracted with EtOAc (20 mL×2). The combined organic layers were dried over anhydrous Na₂SO₄ and concentrated in vacuo. Purification by flash column chromatography (silica gel, 1:1 to 4:1 EtOAc:hexanes) and preparative TLC (7:93 MeOH/CH$_2$Cl$_2$) afforded the desired product S45 (440 mg, 63%).

Physical state: white film;

$R_f$=0.31 (silica gel, 7:93 MeOH/CH$_2$Cl$_2$);

$^1$H NMR (600 MHz, acetone-d$_6$): δ 9.43 (br s, 1H), 7.94 (d, J=6.5 Hz, 1H), 7.57 (dd, J=8.3, 1.9 Hz, 1H), 7.53 (br s, 3H), 7.49 (s, 1H), 7.46 (s, 1H), 7.45 (s, 1H), 7.43-7.33 (m, 4H), 7.26 (d, J=8.3 Hz, 1H), 7.19 (d, J=8.3 Hz, 1H), 7.08 (s, 1H), 7.03 (d, J=8.7 Hz, 1H), 6.77 (d, J=9.9 Hz, 1H), 6.73 (s, 1H), 6.67 (d, J=2.3 Hz, 1H), 6.45 (br s, 1H), 6.31 (d, J=2.3 Hz, 1H), 5.94 (br s, 1H), 5.85 (s, 1H), 5.58 (d, J=4.9 Hz, 1H), 5.54 (s, 1H), 5.51 (s, 1H), 5.39 (d, J=12.3 Hz, 1H), 5.23 (d, J=12.3 Hz, 1H), 5.20 (br s, 1H), 5.10 (br s, 1H), 4.96 (d, J=6.5 Hz, 1H), 4.67 (d, J=5.2 Hz, 1H), 4.63 (t, J=7.2 Hz, 1H), 4.42 (d, J=11.7 Hz, 1H), 4.18 (s, 3H), 3.68 (s, 3H), 3.67 (s, 3H), 3.59 (s, 3H), 2.83 (s, 3H), 2.59 (d, J=16.5 Hz, 1H), 2.42 (d, J=16.3 Hz, 1H), 2.09 (s, 1H), 1.66-1.57 (m, 2H), 1.53 (s, 9H), 1.54-1.48 (m, 2H), 1.00 (s, 9H), 0.92 (s, 9H), 0.92 (d, J=6.5 Hz, 3H) 0.86 (d, J=6.5 Hz, 3H), 0.17 (s, 6H), 0.13 (s, 3H), 0.12 (s, 3H) ppm;

$^{13}$C NMR (151 MHz, acetone-d$_6$): δ 172.3, 171.7, 171.3, 171.3, 171.1, 170.8, 168.9, 168.0, 161.1, 159.9, 158.1, 156.9, 154.5, 153.0, 151.5, 151.5, 141.5, 140.0, 138.4, 137.0, 136.9, 136.2, 135.7, 130.0, 129.3, 129.3, 129.0, 128.3, 127.9, 127.6, 126.1, 125.4, 124.7, 124.1, 122.1, 113.8, 106.5, 106.1, 105.4, 99.6, 80.3, 74.6, 74.0, 67.2, 64.3, 61.5, 60.0, 57.5, 56.5, 56.2, 56.1, 55.7, 55.4, 55.2, 52.0, 38.1, 37.2, 28.9, 28.6, 26.5, 26.3, 26.3, 25.7, 23.7, 23.3, 22.8, 19.1, 19.1, −4.4, −4.6, −4.8, −4.8.

HRMS (ESI-TOF, m/z): Calcd for C$_{81}$H$_{103}$Cl$_2$N$_8$O$_{19}$Si$_2$ [M+H]$^+$ 1617.6249; found 1617.6248.

Compound 42

To a solution of S45 (600 mg, 0.37 mmol) in EtOH/EtOAc (4/1, 50 mL) was added Pd/C (240 mg, 5% Pd/C, 50% wetted powder); the resulting black suspension was stirred under a hydrogen atmosphere at room temperature for 12 h. The reaction mixture was then filtered through celite and washed with EtOH/EtOAc (4:1, 150 mL). The filtrate was concentrated under reduced pressure. The resulting residue was purified by preparative reverse-phase HPLC (85%-100% CH$_3$CN/H$_2$O over 30 min, 100% CH$_3$CN for 30 min, both CH$_3$CN and H$_2$O containing 0.1% TFA) to afford 42 (450 mg, 79%) as a TFA salt.

Note: The Boc group was found to cleaved during the purification process.

Physical state: pale yellow film;

$^1$H NMR (600 MHz, MeOH-d$_4$): δ 8.68 (d, J=5.4 Hz, 1H), 7.60 (dd, J=8.4 Hz, 2.4 Hz, 1H), 7.48 (br s, 1H), 7.42 (br s, 1H), 7.37 (d, J=8.4 Hz, 1H) 7.40-7.35 (br m, 1H), 7.10 (d, J=9.0 Hz, 1H), 7.04-7.02 (m, 2H), 6.68 (d, J=2.4 Hz, 1H), 6.58 (d, J=2.4 Hz, 1H), 6.39 (br s, 2H), 5.77 (d, J=1.2 Hz, 1H), 5.65 (br s, 1H), 5.46 (s, 1H), 5.37 (s, 1H), 5.30 (br s, 1H), 4.80 (s, 1H), 4.60 (d, J=5.4 Hz, 1H), 4.23 (s, 3H), 4.10 (br s, 1H), 3.93-3.90 (m, 1H), 3.87 (s, 3H), 3.73 (s, 3H), 3.67 (s, 3H), 2.83 (s, 3H), 2.83-2.78 (m, 1H), 2.42 (dd, J=16.8, 5.4 Hz, 1H), 1.89-1.82 (m, 1H), 1.79-1.74 (m, 2H), 0.98-0.93 (m, 24H), 0.15 (s, 3H), 0.15 (s, 3H), 0.13 (s, 3H), 0.12 (s, 3H) ppm;

$^{13}$C NMR (600 MHz, MeOH-d$_4$): δ 175.3, 174.0, 172.3, 171.9, 171.8, 171.4, 170.4, 169.4, 169.2, 162.0, 160.4, 159.0, 155.2, 154.2, 153.3, 152.1, 142.2, 140.0, 139.4, 137.3, 136.8, 135.4, 130.6, 129.2, 128.5, 128.5, 128.0, 127.2, 126.1, 125.2, 124.9, 122.5, 114.1, 107.3, 106.7, 106.4, 99.4, 74.9, 65.0, 62.5, 62.4, 61.1, 58.2, 56.6, 56.1, 56.0, 55.6, 52.4, 40.8, 37.0, 33.2, 26.8, 26.5, 25.3, 23.7, 22.0, 19.7, 19.5, −4.3, −4.5, −4.7, −4.7 ppm;

$^{19}$F NMR (376 MHz, MeOH-d$_4$): δ −77.2 ppm;

HRMS (ESI-TOF, m/z): Calcd for C$_{69}$H$_{89}$Cl$_2$N$_8$O$_{17}$Si$_2$ [M+H]$^+$ 1427.5256; found 1427.5258.

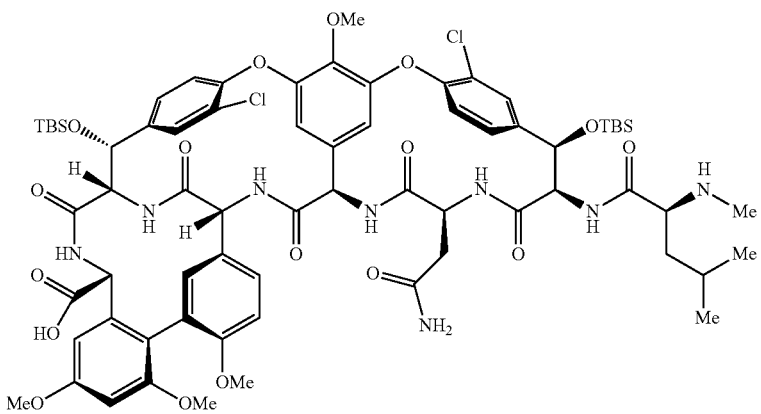

42

Compound 43

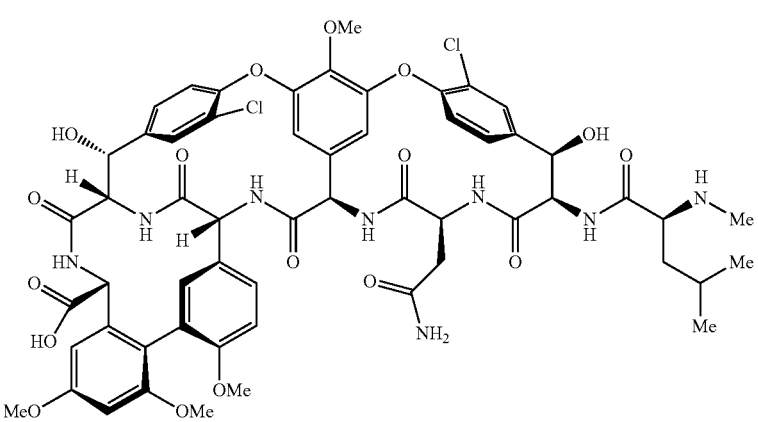

To a solution of 42 (15.0 mg, 0.0097 mmol, 1.0 equiv.) in CH$_3$CN (1.5 mL) was added a solution of tris(dimethylamino)sulfonium difluorotrimethylsilicate (TASF) in DMF (120 µL, 1.0 M, 12.4 equiv.). The resulting mixture was stirred at room temperature for 1.5 h before it was concentrated to a final volume of ca. 0.1 mL under reduced pressure. This residue was purified by preparative reverse-phase HPLC (30%-45% CH$_3$CN/H$_2$O over 40 min, both CH$_3$CN and H$_2$O containing 0.1% TFA) to afford 43 (9.3 mg, 73%) as a TFA salt.

Physical state: white film;
$^1$H NMR (600 MHz, MeOH-d$_4$) δ 9.01 (d, J=6.4 Hz, 0.6H), 8.73 (d, J=5.8 Hz, 0.4H), 7.86 (d, J=8.8 Hz, 1H), 7.75 (d, J=2.1 Hz, 1H), 7.65 (d, J=8.5 Hz, 1H), 7.64 (d, J=2.1 Hz, 1H) 7.61 (ddd, J=8.5, 2.2, 0.9 Hz, 1H), 7.21 (d, J=8.5 Hz, 1H), 7.09 (d, J=2.3 Hz, 1H), 6.85 (d, J=8.8 Hz, 1H), 6.78 (d, J=8.2 Hz, 1H), 6.68 (d, J=2.3 Hz, 1H), 6.51 (d, J=2.2 Hz, 1H), 6.13 (br s, 1H), 6.06 (s, 1H), 5.87 (s, 1H), 5.40 (dd, J=2.2, 1.0 Hz, 1H), 5.37 (s, 1H), 5.27 (d, J=3.5 Hz, 1H), 4.78 (s, 1H), 4.65 (s, 1H), 4.27 (dd, J=9.6, 1.9 Hz, 1H), 4.18 (s, 1H), 4.11 (s, 3H), 4.02 (t, J=7.2 Hz, 1H), 3.86 (s, 3H), 3.66 (s, 3H), 3.63 (s, 3H), 3.03 (d, J=15.7 Hz, 1H), 2.76 (s, 3H), 2.03 (dd, J=15.7, 10.4 Hz, 1H), 1.90 (dt, J=14.0, 7.2 Hz, 1H), 1.69-1.57 (m, 2H), 0.88 (d, J=6.4 Hz, 3H), 0.85 (d, J=6.4 Hz, 3H).

$^{13}$C NMR (600 MHz, MeOH-d$_4$): δ 175.8, 174.6, 172.8, 171.7, 170.0, 169.9, 169.4, 169.0, 161.9, 160.4, 158.7, 154.2, 153.0, 152.3, 151.1, 142.7, 141.7, 138.1, 136.8, 136.7, 136.6, 130.2, 129.0, 129.0, 128.9, 128.5, 127.6, 127.3, 125.3, 125.3, 124.8, 122.4, 113.8, 109.8, 106.7, 106.3, 99.2, 74.3, 73.4, 63.9, 62.1, 61.9, 59.5, 58.5, 56.6, 56.3, 56.2, 56.0, 55.2, 53.0, 52.9, 40.2, 38.7, 36.4, 33.0, 25.5, 23.2, 22.8 ppm;
$^{19}$F NMR (376 MHz, MeOH-d$_4$): δ −76.9 ppm;
HRMS (ESI-TOF, m/z): Calcd for C$_{57}$H$_{61}$Cl$_2$N$_8$O$_{17}$ [M+H]$^+$ 1199.3526; found 1199.3521.

Compound S46

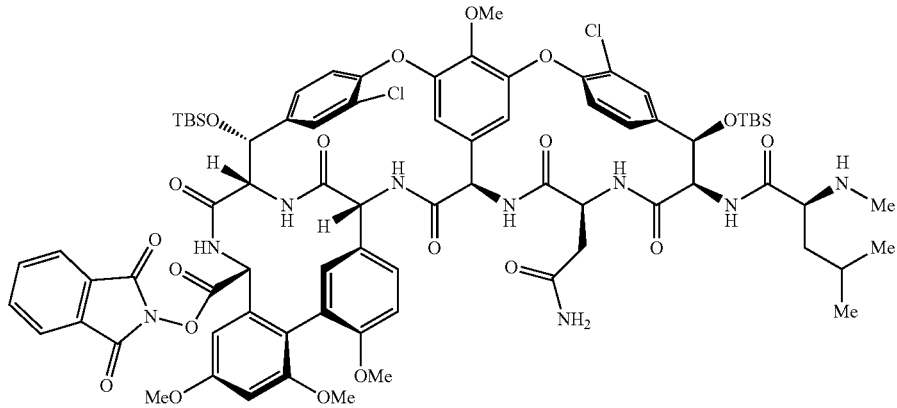

To a suspension of 42 (45 mg, 0.029 mmol, 1.0 equiv.), N-hydroxyphthalimide (26 mg, 0.16 mmol, 5.5 equiv.), and N,N-dimethylpyridin-4-amine (0.4 mg, 0.0033 mmol, 0.11 equiv.) in CH$_2$Cl$_2$ (0.5 mL) was added N,N'-diisopropylcarbodiimide (25 µL, 0.16 mmol, 5.5 equiv.). The reaction mixture was stirred at room temperature for 1 h before AcOH (10 µL) was added. The resulting mixture was stirred for another 2 h and was subjected to flash column chromatography directly (silica gel, column: d 1.6 cm×/7.5 cm, 3:2 EtOAc:hexanes (200 mL) to 1:19 MeOH:CH$_2$Cl$_2$ (120 mL)). The combined fractions eluted with MeOH—CH$_2$Cl$_2$ were concentrated under reduced pressure, and the S46 residue (31 mg) was used in next step without further purification.

Note:
(1) LC/MS indicated that the desired redox-active ester (S46) only eluted with MeOH/$CH_2Cl_2$. Nonpolar impurities, such as 1,3-diisopropylurea, were found to elute with EtOAc:hexanes.
(2) Additional amounts of DMAP or longer reaction time have deleterious effects on the reaction yield.
(3) This redox-active ester (S46) was rather unstable and should be used in next step within 3 h after purification. Alternatively, it can be stored at −20° C.

Compound S47

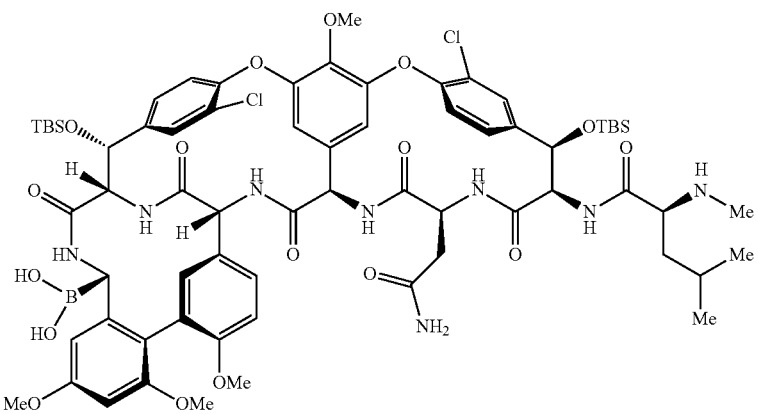

S47

A screw-capped culture tube containing S46 (31 mg), $MgBr_2.OEt_2$ powder (38 mg, 0.15 mmol) was evacuated and backfilled with argon for three times. Suspension C (0.4 mL, $NiCl_2.6H_2O$/di-tBubipy in THF) was added next and the mixture was stirred vigorously at room temperature for 15 min (or sonicated until no granular $MgBr_2.OEt_2$ was observed). The resulting suspension was cooled to 0° C., and the suspension of [$B_2pin_2Me$]Li in THF (0.55 mL) was added in one portion. After stirring for 1 h, the reaction mixture was diluted with $CH_2Cl_2$ (5 mL), filtered through a short pad of silica gel and celite, washed with 5% MeOH/$CH_2Cl_2$ (50 mL). The filtrate was concentrated under reduced pressure, and the residue was subjected to flash column chromatography directly (silica gel, column: d 1.6 cm×17.5 cm, 1:1 EtOAc:hexanes (200 mL) to 1:19 MeOH:$CH_2Cl_2$ (120 mL)). The MeOH—$CH_2Cl_2$ elution was concentrated under reduced pressure, and the S47 residue (16 mg) was used in next step without further purification.

Note:
(1) The pinacol ester was found to hydrolyze during the reaction based on LC/MS analysis.
(2) LC/MS indicated that S47 only elutes with MeOH/$CH_2Cl_2$ based on LC/MS analysis. Nonpolar impurities, such as $B_2pin_2$, were found to elute with EtOAc:hexanes.
(3) Not all impurities can be removed through flash chromatography in this step; instead the unpure materials were carried forward to the next step.

Compound 44

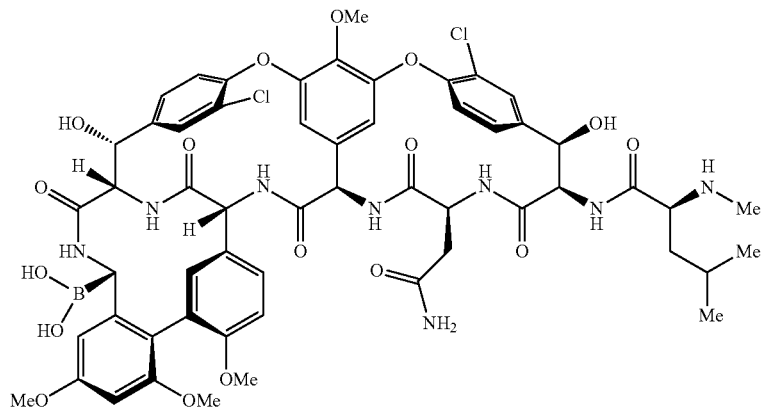

44

To a solution of S47 (16 mg) in $CH_3CN$ (1.3 mL) was added a solution of tris(dimethylamino)sulfonium difluorotrimethylsilicate (TASF) in DMF (120 µL, 1.0 M). The mixture was stirred at room temperature for 1.5 h and was concentrated to a final volume of ca. 0.3 mL under reduced pressure. The residue was purified by preparative reverse-phase HPLC (20%-50% $CH_3CN/H_2O$ over 30 min, both $CH_3CN$ and $H_2O$ containing 0.1% TFA) to afford 44 (4.1 mg, 11% over 3 steps) as a TFA salt.

Note: This compound was not stable in neat condition due to its propensity toward polymerization. Therefore, the purified compound was dissolved immediately. Solutions in MeOH were used for HRMS; solutions in MeOH-$d_4$ were used for NMR study; solutions in DMSO were used for biological studies.

Physical state: white film;

$^1$H NMR (600 MHz, MeOH-$d_4$): δ 9.05 (d, J=6.6 Hz, 1H), 7.65-7.58 (m, 4H), 7.31 (d, J=9.0 Hz, 1H), 7.30 (d, J=9.6 Hz, 1H), 7.15 (dd, J=9.0 Hz, 1.8 Hz, 1H), 6.97-6.91 (m, 2H), 6.81 (s, 1H), 6.52 (d, J=2.4 Hz, 1H), 5.81 (d, J=5.4 Hz, 1H), 5.69 (s, 1H), 5.65 (s, 1H), 5.54 (s, 1H), 5.35 (d, J=3.6 Hz, 1H), 5.07 (br s, 1H), 5.04 (d, J=6.6 Hz, 1H), 4.43 (s, 1H), 4.32 (d, J=5.4 Hz, 1H), 4.14 (s, 3H), 4.03 (t, J=7.2 Hz, 1H), 3.87 (s, 3H), 3.68 (s, 3H), 3.65 (s, 3H), 2.96 (d, J=15.6 Hz, 1H), 2.77 (s, 3H), 2.34 (dd, J=16.2 Hz, 9.0 Hz, 1H), 1.86-1.82 (m, 1H), 1.79-1.73 (m, 1H), 1.71-1.86 (m, 1H), 1.01 (d, J=6.0 Hz, 3H), 0.98 (d, J=6.0 Hz, 3H) ppm;

$^{11}$B NMR (500 MHz, MeOH-$d_4$): δ −0.87 (s) ppm;

HRMS (ESI-TOF, m/z): Calcd for $C_{56}H_{62}BCl_2N_8O_{17}$ [M+H]$^+$ 1199.3698; found 1199.3698.

Experimental Procedure for Antibiotic Evaluation of 43, 44, Vancomycin and Vancomycin Aglycon.

Antibiotic susceptibilities were determined using the Clinical and Laboratory Standards Institute broth microdilution method (63). Briefly, antibiotics were prepared as 2-fold dilutions in 96-well plates containing cation-adjusted Mueller-Hinton broth (*S. aureus* strains) or brain-heart infusion broth (*Enterococcus* strains). Stock solutions of antibiotics were made in dimethyl sulfoxide (DMSO). Wells were inoculated from a fresh plate scrape diluted to a final concentration of 5×10$^5$ CFU/mL and incubated at 37° C. Growth observed visually at 20 h. All MICs are an average of at least three independent determinations.

added into a solution of Boc-L-Ala-L-Val-OH (2.0 mmol, 1.0 equiv.) and NHPI (359 mg, 2.2 mmol, 1.1 equiv.) in $CH_2Cl_2$ (30 mL) at −10° C. After stirring for 1 h at room temperature, the mixture was washed with water and the aqueous phase was extracted with $CH_2Cl_2$ for three times. The combined organic phases were dried over anhydrous $Na_2SO_4$ and concentrated in vacuo. Purification by flash column chromatography (silica gel, 3:7 EtOAc:hexanes to EtOAc) afforded S48 (591 mg, 62%).

Physical state: white foam;

$R_f$=0.36 (silica gel, 2:3 EtOAc:hexanes);

$^1$H NMR (600 MHz, CDCl$_3$): δ 7.88 (dd, J=5.5, 3.1 Hz, 2H), 7.79 (dd, J=5.5, 3.1 Hz, 2H), 6.93-6.79 (br, 1H), 5.02-4.88 (m, 2H), 4.28-4.14 (br, s, 1H), 2.48-2.32 (m, 1H), 1.44 (s, 9H), 1.38 (d, J=7.0 Hz, 3H), 1.10 (d, J=6.9 Hz, 3H), 1.08 (d, J=6.9 Hz, 3H) ppm;

$^{13}$C NMR (151 MHz, CDCl$_3$): δ 172.6, 168.4, 161.6, 155.9, 135.0, 129.0, 124.2, 80.5, 55.6, 50.0, 31.8, 28.4, 18.9, 17.5 ppm;

HRMS (ESI-TOF, m/z): Calcd for $C_{21}H_{28}N_3O_7$ [M+H]$^+$ 434.1922; found 434.1930.

Compound 45

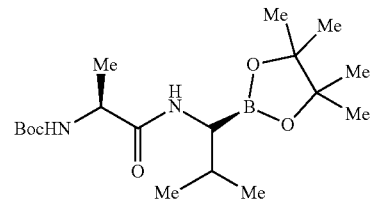

45

| Compd. | *S. aureus*[a] | MRSA[b] | *E. faecium*[c] | *E. faecalis*[d] | *E. faecalis*[e] |
|---|---|---|---|---|---|
| vancomycin | 0.5 | 0.5 | >64 | >64 | 16 |
| vancomycin aglycon | 1 | 1 | >64 | >64 | 32 |
| 43 | 2 | 2 | >64 | >64 | 8 |
| 44 | 16 | 16 | >64 | >64 | 16 |

[a]*Staphylococcus aureus* (ATCC 25923)
[b]*Staphylococcus aureus* (methicillin resistant, ATCC 43300)
[c]*Enterococcus faecium* (Van A, ATCC BAA-2317)
[d]*Enterococcus faecalis* (VanA, BM4166)
[e]*Enterococcus faecalis* (VanB, ATCC 51299)
Note:
compound 44 was not very stable in H$_2$O at 37° C. under air. Under such conditions, ca. 20% of 44 was found to have decomposed after 24 h as indicated by LC/MS analysis (254 nM UV detector).

Probing the Stereoselectivity on Peptide Substrates
Compound S48

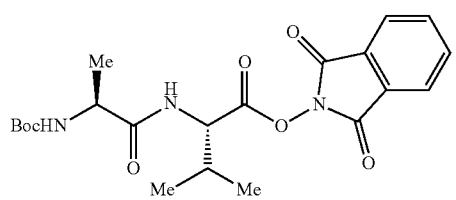

1,3-dioxoisoindolin-2-yl (tert-butoxycarbonyl)-L-alanyl-L-valinate (S48)

N-(3-Dimethylaminopropyl)-N'-ethylcarbodiimide hydrochloride (EDC, 422 mg, 2.2 mmol, 1.1 equiv.) was tert-butyl ((2S)-1-((2-methyl-1-(4,4,5,5-tetramethyl-1,3,2-dioxaborolan-2-yl)prop-yl)amino)-1-oxopropan-2-yl)carbamate (45)

On 0.2 mmol scale, General Procedure C was followed with suspension C (NiCl$_2$.6H$_2$O/di-tBubipy in THF). Flash column chromatography (silica gel, 3:7 EtOAc:hexanes) afforded 45 as a mixture of inseparable diastereomers (50 mg, dr=1:1, 67%)

Physical state: colorless oil;

$R_f$=0.22 (silica gel, 3:7 EtOAc:hexanes);

$^1$H NMR (600 MHz, C$_6$D$_6$): δ 6.77 (s, 1H), 6.73 (s, 1H), 5.56 (s, 1H), 5.37 (s, 1H), 4.23 (s, 1H), 4.11 (s, 1H), 3.05 (s, 2H), 2.10-2.04 (m, 2H), 1.41 (s, 9H), 1.40 (s, 9H), 1.25-0.92 (m, 42H) ppm;

$^{13}$C NMR (151 MHz, C$_6$D$_6$): δ 174.7, 174.2, 156.0, 155.9, 82.8, 82.6, 79.4, 74.7, 49.1, 49.0, 37.0, 30.3, 28.4, 25.3, 25.3, 25.2, 25.0, 20.7, 20.7, 20.0, 19.9, 17.9, 17.7 ppm;

HRMS (ESI-TOF, m/z): Calcd for C$_{18}$H$_{36}$BN$_2$O$_5$[M+H]$^+$ 371.2712; found 371.2710.

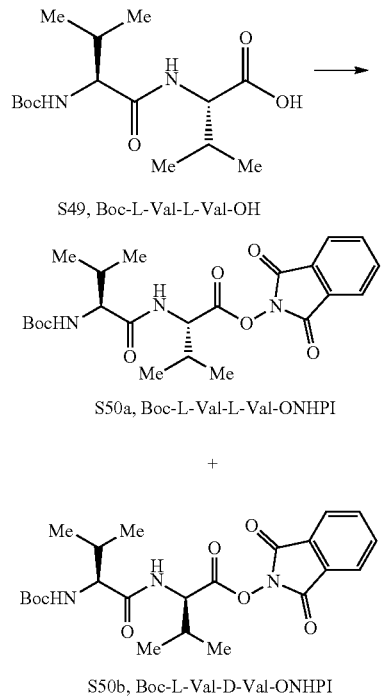

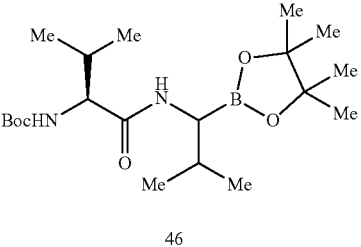

On a 2.0 mmol scale, General Procedure A was followed with Boc-L-Val-L-Val-OH (S49). Purification by flash column chromatography (silica gel, 1:3 EtOAc:hexanes) afforded S50a (187 mg, 20%) and S50b (395 mg, 43%).

Compound S50a

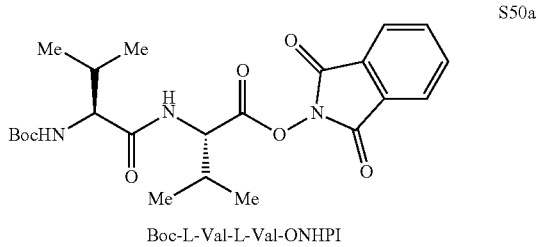 [SMILES: CC(C)[C@H](NC(=O)OC(C)(C)C)C(=O)N[C@H](C(=O)ON1C(=O)c2ccccc2C1=O)C(C)C]

1,3-dioxoisoindolin-2-yl (tert-butoxycarbonyl)-L-valyl-L-valinate (S50a)

Physical state: white foam;

R$_f$=0.40 (silica gel, 1:2 EtOAc:hexanes);

$^1$H NMR (600 MHz, CDCl$_3$): δ 7.90-7.88 (m, 2H), 7.81-7.79 (m, 2H), 6.48 (br d, J=8.8 Hz, 1H), 5.09 (br d, J=8.4 Hz, 1H), 4.98 (dd, J=8.8, 5.1 Hz, 1H), 3.91 (dd, J=8.7, 6.8 Hz, 1H), 2.43-2.38 (m, 1H), 2.14 (br s, 1H), 1.43 (s, 9H), 1.11 (t, J=6.3 Hz, 6H), 0.97 (dd, J=16.5, 6.8 Hz, 6H) ppm;

$^{13}$C NMR (151 MHz, CDCl$_3$): δ 171.9, 168.4, 161.6, 156.1, 135.0, 129.0, 124.2, 80.2, 60.4, 55.6, 31.7, 30.6, 28.4, 19.4, 18.9, 18.2, 17.7 ppm;

HRMS (ESI-TOF, m/z): Calcd for C$_{18}$H$_{24}$N$_3$O$_5$ [M-Boc+H]$^+$ 362.1710; found 362.1705;

[α]$_D^{20}$=−31.8 (c 0.96, CHCl$_3$).

Compound S50b

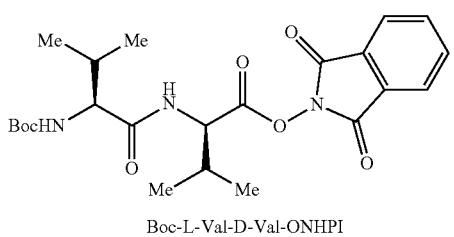

1,3-dioxoisoindolin-2-yl (tert-butoxycarbonyl)-L-valyl-L-valinate (S50b)

Physical state: white foam;

R$_f$=0.4 (silica gel, 1:2 EtOAc:hexanes);

$^1$H NMR (600 MHz, CDCl$_3$): δ 7.87-7.85 (m, 2H), 7.79-7.77 (m, 2H), 6.60 (br d, J=8.8 Hz, 1H), 5.15 (d, J=8.9 Hz, 1H), 4.96 (dd, J=8.8, 5.2 Hz, 1H), 3.92 (dd, J=8.8, 6.8 Hz, 1H), 2.41-2.36 (m, 1H), 2.10 (br s, 1H), 1.42 (s, 9H), 1.09 (dd, J=6.9, 4.6 Hz, 6H), 0.97 (d, J=6.8 Hz, 3H), 0.94 (d, J=6.8 Hz, 3H) ppm;

$^{13}$C NMR (151 MHz, CDCl$_3$): δ 172.0, 168.4, 161.6, 156.1, 134.9, 128.9, 124.1, 80.1, 60.3, 55.6, 31.6, 30.6, 28.4, 19.4, 18.9, 18.2, 17.7 ppm;

HRMS (ESI-TOF, m/z): Calcd for C$_{18}$H$_{24}$N$_3$O$_5$ [M-Boc+H]$^+$ 362.1710; found 362.1714;

[α]$_D^{20}$=−31.2 (c 1.0, CHCl$_3$).

Compound 46

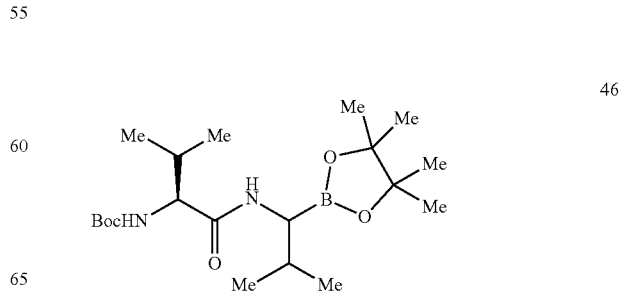

tert-butyl ((S)-3-methyl-1-(((S)-2-methyl-1-(4,4,5,5-tetramethyl-1,3,2-dioxaboro-lan-2-yl)propyl)amino)-1-oxobutan-2-yl)carbamate (46)

From S50a:

On 0.2 mmol scale, General Procedure C was followed with suspension C (NiCl$_2$.6H$_2$O/di-tBubipy in THF) from S50a (1.0 equiv. of MgBr$_2$.Et$_2$O was used in this case). Purification by flash column chromatography (silica gel, 1:3 EtOAc:hexanes) afforded 46 as a mixture of inseparable diastereomers (37.1 mg, d.r.=1.7:1, 47%)

From S50b:

On 0.2 mmol scale, General Procedure C was followed with suspension C (NiCl$_2$.6H$_2$O/di-tBubipy in THF) from S50b (1.0 equiv. of MgBr$_2$.Et$_2$O was used in this case). Purification by flash column chromatography (silica gel, 1:3 EtOAc: hexanes) afforded 46 as a mixture of inseparable diastereomers (36.5 mg, d.r.=1.7:1, 46%).

Physical state: colorless oil;

$R_f$=0.30 (silica gel, 1:2 EtOAc:hexanes);

$^1$H NMR (600 MHz, CDCl$_3$): δ 6.30 (br d, J=5.5 Hz, 0.78H), 6.22 (br s, 0.22H), 5.10 (br d, J=8.7 Hz, 1H), 3.92-3.86 (m, 1H), 3.03 (br s, 1H), 2.10 (br s, 1H), 1.96-1.90 (m, 1H), 1.42 (s, 9H), 1.28-1.16 (m, 12H), 0.95 (d, J=6.7 Hz, 3H), 0.93 (d, J=6.7 Hz, 3H), 0.92 (d, J=6.7 Hz, 6H) ppm;

$^{13}$C NMR (151 MHz, CDCl$_3$): δ 172.48 (minor), 172.46, 155.92, 83.37, 79.91, 59.57 (minor), 59.25, 44.96 (br), 31.10, 31.02 (minor), 30.01, 29.91 (minor), 28.51, 28.44, 25.18, 25.12, 25.10 (minor), 25.03 (minor), 24.97, 20.42, 20.37 (minor), 20.12, 20.03, 19.35, 19.21 (minor), 18.13 (minor), 17.90 ppm;

HRMS (ESI-TOF, m/z): Calcd for C$_{20}$H$_{40}$BN$_2$O$_5$[M+H]$^+$ 399.3025; found 399.3028.

Compound S51

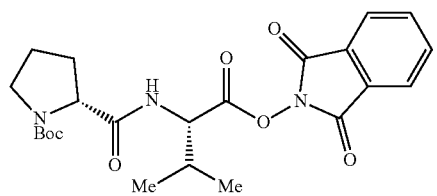

tert-butyl (R)-2-(((S)-1-((1,3-dioxoisoindolin-2-yl)oxy)-3-methyl-1-oxobutan-2-yl) carbamoyl)pyrrolidine-1-carboxylate (S51)

On 1.0 mmol scale (based on Boc-L-Pro-L-Leu-OH), the same procedure as in the synthesis of S48 was used. Purification by flash column chromatography (silica gel, 1:2 EtOAc:hexanes) afforded S51 (308 mg, 67%).

Physical state: white foam;

$R_f$=0.4 (silica gel, 1:1 EtOAc:hexanes);

$^1$H NMR (600 MHz, CDCl$_3$): δ 7.88-7.85 (m, 2H), 7.87 (br s, 0.6H), 7.79-7.77 (m, 2H), 6.63 (s, 0.4H), 4.99-4.88 (m, 1H), 4.37-4.30 (m, 1H), 3.61-3.21 (m, 2H), 2.47 (br s, 0.4H), 2.43-2.37 (m, 1H), 2.16 (br s, 0.6H), 2.03-1.76 (m, 3H), 1.51-1.39 (m, 9H), 1.12-1.03 (m, 6H); (complex spectrum was observed due to mixture of rotamers);

$^{13}$C NMR (151 MHz, CDCl$_3$): δ 172.7, 172.0, 168.4, 161.6, 156.3, 154.9, 140.9, 137.2, 134.9, 130.1, 129.0, 124.1, 115.6, 110.4, 81.4, 80.7, 61.3, 59.5, 55.7, 55.1, 47.0, 31.5, 28.5, 27.1, 24.8, 19.0, 17.5; (complex spectrum was observed due to mixture of rotamers);

HRMS (ESI-TOF, m/z): Calcd for C$_{18}$H$_{22}$N$_3$O$_5$ [M-Boc+H]$^+$ 360.1554; found 360.1554.

Compound 47

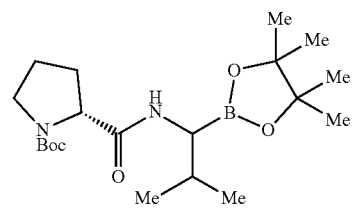

tert-butyl 2-(((S)-2-methyl-1-(4,4,5,5-tetramethyl-1,3,2-dioxaborolan-2-yl)propyl) carbamoyl)pyrrolidine-1-carboxylate (47)

On 0.28 mmol scale, General Procedure C was followed with S51 and suspension C (NiCl$_2$. 6H$_2$O/di-tBubipy in THF). Purification by flash column chromatography (silica gel, 2:1 EtOAc:hexanes) afforded 47 as a mixture of diastereomers (70.5 mg, d.r.=2.6:1, 63%). Diastereomeric ratio was determined by $^1$H NMR and NOESY in DMSO-d$_6$ at 65° C.

Physical state: colorless oil;

$R_f$=0.30 (silica gel, 2:1 EtOAc:hexanes);

$^1$H NMR (500 MHz, DMSO-d$_6$): δ 8.37 (s, 0.72H), 8.28 (s, 0.28H), 4.25 (dd, J=8.5, 2.8 Hz, 1H), 3.44-3.35 (m, 1H), 3.34-3.27 (m, 1H), 2.46 (t, J=5.3 Hz, 0.28H), 2.40 (t, J=4.7 Hz, 0.72H), 2.19-2.05 (m, 1H), 1.89-1.74 (m, 4H), 1.39 (s, 9H), 1.13 (s, 3.36H), 1.12 (s, 8.64H), 0.93-0.85 (m, 6H) ppm;

$^{13}$C NMR (126 MHz, DMSO-d$_6$): δ 174.9, 153.0, 80.6 (minor), 80.4, 78.5, 57.5 (minor), 57.3, 46.2, 28.9 (minor), 28.7, 27.8, 27.7, 24.9 (minor), 24.8, 24.7, 20.1, 20.0 (minor), 19.2 ppm;

HRMS (ESI-TOF, m/z): Calcd for C$_{20}$H$_{38}$BN$_2$O$_5$[M+H]$^+$ 397.2868; found 397.2864.

Stereoselective Synthesis of Bortezomib (Velcade)

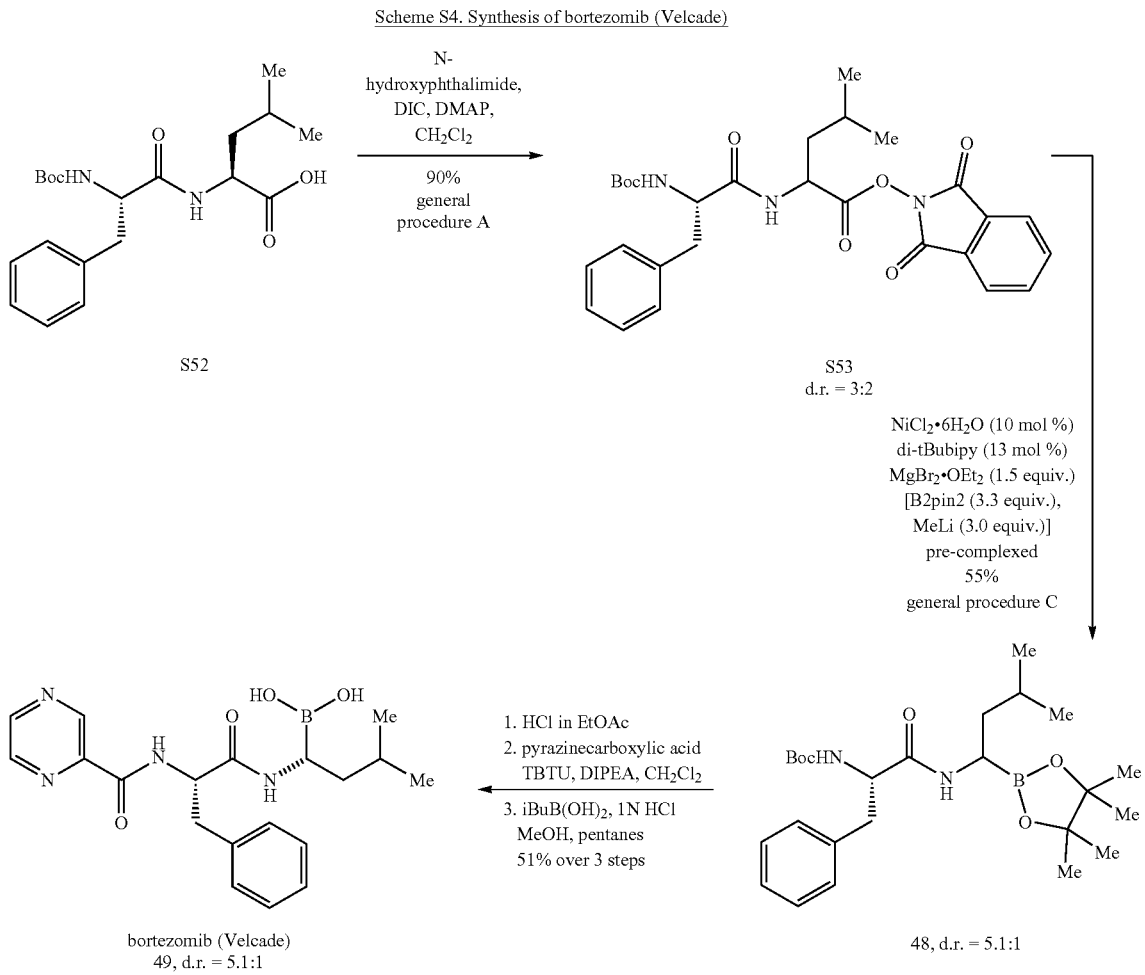

Scheme S4. Synthesis of bortezomib (Velcade)

Compound S56

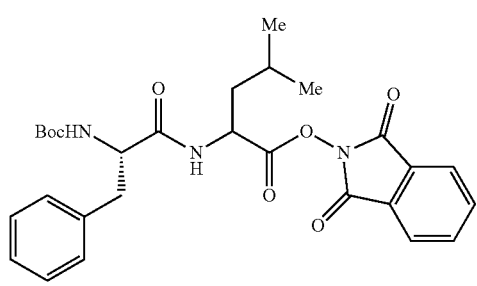

1,3-dioxoisoindolin-2-yl (tert-butoxycarbonyl)-L-phenylalanylleucinate (S53)

On 3.0 mmol scale, General Procedure A was followed with Boc-L-Phe-L-Leu-OH (64) (S62). Purification by flash column chromatography (deactivated silica gel, 1:5.6 EtOAc:hexanes) afforded S53 as a mixture of inseparable diastereomers (1.42 g, d.r.=3:2, 90%). Diastereomeric ratio was determined by $^1$H NMR and NOESY.

Physical state: White foam;

$R_f$=0.50 (silica gel, 2:3 EtOAc:hexanes);

$^1$H NMR (600 MHz, MeOH-d4): Minor isomer: δ 7.94-7.89 (m, 4H), 7.29-7.15 (m, 5H), 4.78 (dd, J=9.5 Hz, 5.8 Hz, 1H), 4.39-4.35 (m, 1H), 3.05 (dd, J=13.7 Hz, 7.2 Hz, 1H), 2.90 (dd, J=13.6 Hz, 8.1 Hz, 1H), 1.76-1.70 (m, 2H), 1.54-1.50 (m, 1H), 1.38 (s, 9H), 0.94 (d, J=6.6 Hz, 3H), 0.89 (d, J=6.6 Hz, 3H) ppm; Major isomer: δ 7.94-7.89 (m, 4H), 7.29-7.15 (m, 5H), 4.92 (dd, J=9.6 Hz, 6.0 Hz, 1H), 4.39-4.35 (m, 1H), 3.13 (dd, J=14.4 Hz, 5.4 Hz, 1H), 2.84 (dd, J=13.8 Hz, 9.0 Hz, 1H), 1.89-1.83 (m, 3H), 1.37 (s, 9H), 1.02 (d, J=6.0 Hz, 3H), 0.99 (d, J=6.0 Hz, 3H) ppm;

$^{13}$C NMR (151 MHz, MeOH-d4): Minor isomer: δ 174.4, 170.4, 163.1, 157.3, 138.3, 136.3, 135.5, 130.4, 130.1, 129.5, 127.7, 124.9, 124.0, 80.7, 57.4, 50.2, 41.2, 39.6, 28.6, 28.4, 25.7, 25.5, 23.2, 21.7 ppm; Major isomer: δ 174.6, 170.4, 163.1, 157.6, 138.4, 136.4, 135.5, 130.4, 130.1, 129.4, 127.6, 124.9, 124.0, 80.6, 57.1, 50.2, 41.5, 39.1, 28.6, 28.4, 25.7, 25.5, 23.2, 21.8 ppm;

HRMS (ESI-TOF, m/z): Calcd for $C_{23}H_{26}N_3O_5$ [M-Boc+H]$^+$ 424.1867; found 424.1871.

Compound 48

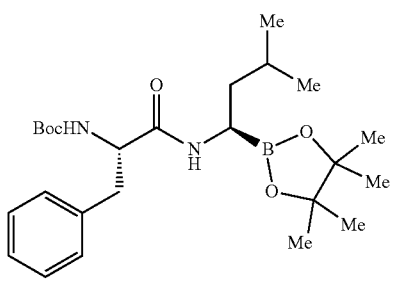

tert-butyl ((S)-1-(((R)-3-methyl-1-(4,4,5,5-tetramethyl-1,3,2-dioxaborolan-2-yl) butyl)amino)-1-oxo-3-phenylpropan-2-yl)carbamate (48)

On 0.6 mmol scale, General Procedure C was followed with suspension C (NiCl$_2$. 6H$_2$O/di-tBubipy in THF) and S53. The reaction was started from □15° C. and warmed to room temperature over 3 h. Flash column chromatography (silica gel, 1:9 EtOAc:hexanes to 1:4 EtOAc:hexanes) afforded 48, which was dissolved in hexanes and filtered through celite. The filtrate was concentrated in vacuo to afford 48 as a mixture of inseparable diastereomers (151 mg, d.r.=5.1:1, 55%).

Physical state: Pale yellow oil;

R$_f$=0.50 (silica gel, 2:3 EtOAc:hexanes);

$^1$H NMR (600 MHz, CDCl$_3$): Major isomer: δ 7.31-7.26 (m, 2H), 7.24-7.21 (m, 3H), 6.19 (br s, 1H), 5.00 (br s, 1H), 4.35 (q, J=7.3 Hz, 1H), 3.10-3.02 (m, 2H), 2.98 (ddd, J=8.8 Hz, 6.3 Hz, 4.4 Hz, 1H), 1.49-1.42 (m, 1H), 1.39 (s, 9H), 1.37-1.35 (m, 2H), 1.24 (s, 6H), 1.23 (s, 6H), 0.86 (d, J=6.6 Hz, 3H), 0.84 (d, J=6.6 Hz, 3H) ppm;

$^{13}$C NMR (151 MHz, CDCl$_3$): Major isomer: δ 172.6, 155.5, 134.4, 129.6, 128.8, 127.1, 83.0, 80.3, 54.8, 39.9, 38.3, 28.4, 25.6, 25.1, 25.0, 23.3, 22.0 ppm;

HRMS (ESI-TOF, m/z): Calcd for C$_{25}$H$_{42}$BN$_2$O$_5$[M+H]$^+$ 461.3181; found 461.3179.

Compound 49

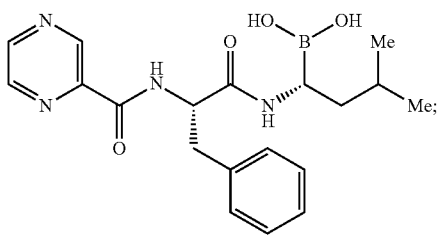

bortezomib (Velcade)

(3-methyl-1-((S)-3-phenyl-2-(pyrazine-2-carboxamido)propanamido)butyl)boronic acid (49)

Bortezomib (49) was synthesized from 48 using the literature procedure (19) with slight modifications.

Boc Deprotection:

To a screw-capped culture tube charged with 48 (151 mg, 0.33 mmol) was added HCl in EtOAc (14 wt %) at 0° C., and the reaction mixture was stirred at 0° C. for 3 h and room temperature for an additional 1 h. The reaction mixture was concentrated to dryness and the resulting solid was washed with hexanes. The desired product was afforded as a white solid and was used in next step without further purification.

Esterification:

CH$_2$Cl$_2$ (1.2 mL, 0.5 M) was added to a screw-capped culture tube containing the hydrochloride salt obtained from the previous step. The mixture was cooled to 0° C. Diisopropylethylamine (0.15 mL, 0.86 mmol) was added dropwise, and the reaction mixture was stirred for 5 min. 2-Pyrazine carboxylic acid (56 mg, 0.45 mmol) was then added to the solution in one portion. O-(Benzotriazol-1-yl)-N,N,N',N'-tetramethyluronium tetrafluoroborate (TBTU, 118 mg, 0.37 mmol) was then added to the reaction mixture which was stirred at 0° C. for 2 h and room temperature for additional 1 h. The reaction mixture was then concentrated in vacuo. The crude residue was dissolved in EtOAc (10 mL) and transferred to a separatory funnel. The organic layer was washed with deionic H$_2$O (2×10 mL), 1% phosphoric acid (2×10 mL), 2% K$_2$CO$_3$ (2×10 mL), and brine (2×10 mL) successively. Each aqueous layer was back-extracted with EtOAc (2×10 mL). The combined organic layers were dried over anhydrous Na$_2$SO$_4$, filtered and concentrated in vacuo. The resulting pale yellow foam was carried on to the next step without further purification.

Boronate Ester Exchange:

Pentane (0.8 mL) and MeOH (0.8 mL) were added to a screw-capped culture tube containing the pinacol boronate obtained from the previous step. 2-Methylpropaneboronic acid (125 mg, 1.2 mmol) was then added to the solution. 1 N aq. HCl (0.6 mL) was added to the reaction mixture, and the resulting biphasic solution was stirred vigorously for 16 h. Stirring was then stopped and the biphasic mixture was allowed to separate. The aqueous layer was washed with pentane (2×10 mL) and was then concentrated in vacuo. The resulting film was partitioned between CH$_2$Cl$_2$ and 1 N aq. NaOH (10 mL). The aqueous layer was washed with CH$_2$Cl$_2$ (3×10 mL) and the organic phase was back-extracted with 1 N aq. NaOH (2×10 mL). 1 N aq. HCl was added to the combined aqueous layers until the pH=6 when the desired product was extracted into the organic layer with CH$_2$Cl$_2$ (3×10 mL). The combined organic phase was dried over anhydrous Na$_2$SO$_4$, filtered, and concentrated in vacuo. The resulting residue was dissolved in EtOAc (2 mL), and the solution was subsequently concentrated in vacuo. To the residue was then added hexanes (2 mL), and the suspension was concentrated in vacuo to afford the product 49 (64 mg, d.r.=5.1:1, 51% over 3 steps).

Physical state: white solid;

$^1$H NMR (600 MHz, CD$_3$CN:D$_2$O=4:1): Major isomer: δ 9.10 (d, J=1.8 Hz, 1H), 8.74 (d, J=2.4 Hz, 1H)), 8.61 (dd, J=2.4 Hz, 1.8 Hz, 1H), 7.26-7.22 (m, 4H), 7.20-7.17 (m, 1H), 4.78 (dd, J=8.4 Hz, 6.0 Hz, 1H), 3.19 (dd, J=13.8 Hz, 6.0 Hz, 1H), 3.07 (dd, J=13.8 Hz, 8.2 Hz, 1H), 2.93 (dd, J=10.2 Hz, 5.4 Hz, 1H), 1.44-1.33 (m, 2H), 1.26-1.21 (m, 1H), 0.80 (d, J=6.6 Hz, 3H), 0.78 (d, J=6.6 Hz, 3H) ppm;

$^{13}$C NMR (151 MHz, CD$_3$CN:D$_2$O=4:1): Major isomer: 172.4, 164.5, 148.7, 145.0, 144.7, 144.4, 137.7, 130.4, 129.5, 127.8, 54.9, 40.2, 40.2 (br s), 38.5, 25.9, 23.6, 22.0 ppm;

HRMS (ESI-TOF, m/z): Calcd for C$_{19}$H$_{24}$BN$_4$O$_3$[M−H$_2$O+H]$^+$ 367.1936; found 367.1950.

Synthesis of Elastase Inhibitor 50

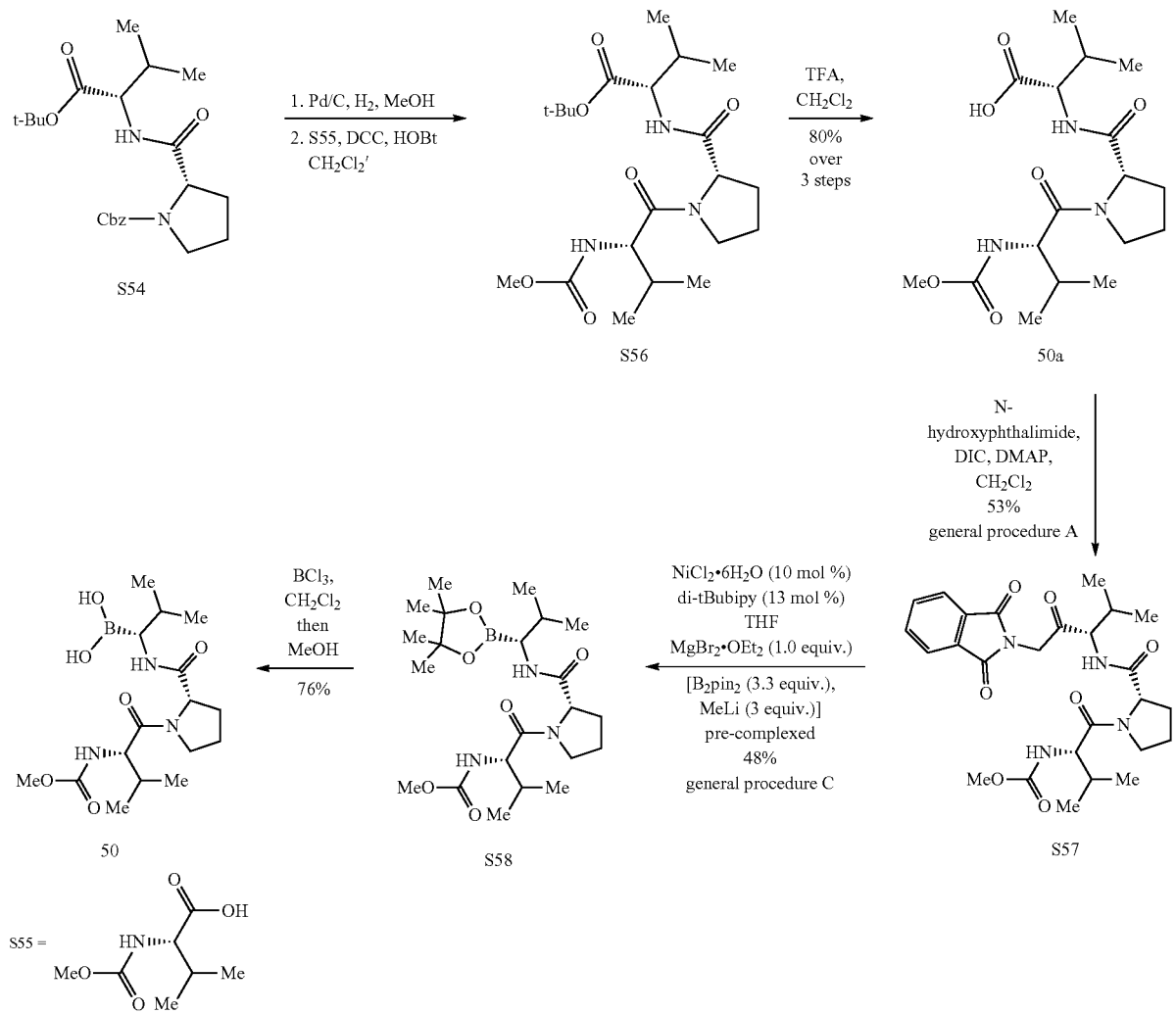

Scheme S5. Synthesis of 50 and 50a

Compound 50a

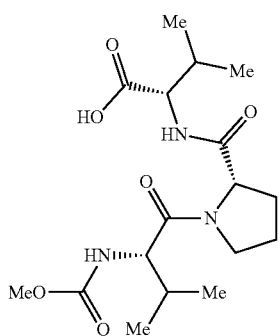

(methoxycarbonyl)-L-valyl-L-prolyl-L-valine (50a)

Cbz deprotection: A 100 mL flask equipped with a stirrer bar was charged with Z-L-Pro-L-Val-OtBu (65) (S54, 2.55 g, 6.3 mmol), 10% Pd/C (128 mg, 5 wt %), and MeOH (30 mL). The flask was then evacuated and backfilled with H$_2$ from a balloon for three times. The mixture was stirred at room temperature for 6 h and was filtered through a short pad of celite which was then rinsed with MeOH (10 mL). The filtrate was concentrated in vacuo to give the corresponding amine as colorless oil.

Amide Bond Formation:

The aforementioned amine was treated successively with S55 (1.1 g, 6.3 mmol, 1.0 equiv.), HOBt H$_2$O (96 mg, 0.07 mmol, 0.11 equiv.), and CH$_2$Cl$_2$ (25 mL). The resulting solution was cooled to 0° C. before DCC (1.43 g, 6.9 mmol, 1.1 equiv.) was added. The reaction mixture was allowed to stir at 0° C. for 30 min and then at room temperature overnight. The reaction mixture was filtered through a pad a celite; the filtrate was redissolved in EtOAc and washed with 0.1 N aq. HCl, 0.1 M aq.NH$_4$OH, and brine successively. The organic layer was dried over anhydrous Na$_2$SO$_4$ and concentrated in vacuo to give S56 (2.2 g) as colorless oil, which was used in the next step without further purification.

tBu Deprotection:

In a 25 mL flask equipped with a stirrer bar, S56 (428 mg, 1.0 mmol) was dissolved in CH$_2$Cl$_2$ (3 mL). TFA (3 mL) was added and the resulting solution was allowed to stir at room temperature for 5 h. After the volatiles were removed in vacuo, the crude mixture was purified by flash column chromatography (silica gel, 2:1 EtOAc:hexanes) furnished 50a (359 mg, 80% over 3 steps).

Physical state: white foam;

$R_f$=0.35 (silica gel, 1:2 hexanes: EtOAc);

$^1$H NMR (600 MHz, CDCl$_3$): δ 7.43 (br d, J=8.4 Hz, 2H), 6.17 (d, J=9.0 Hz, 1H), 4.64 (dd, J=7.8 Hz, 3.0 Hz, 1H), 4.48 (dd, J=8.4 Hz, 4.0 Hz, 1H), 4.29 (t, J=8.4 Hz, 1H), 3.84 (dd, J=16.8 Hz, 8.4 Hz, 1H), 3.69-3.63 (m, 4H), 2.33-2.29 (m, 1H), 2.20-2.10 (m, 2H), 2.03-1.92 (m, 3H), 0.97 (d, J=6.6 Hz, 3H), 0.95 (d, J=6.6 Hz, 3H), 0.91 (d, J=7.2 Hz, 3H), 0.89 (d, J=7.2 Hz, 3H) ppm;

$^{13}$C NMR (151 MHz, CDCl$_3$): δ 174.5, 173.5, 171.1, 157.8, 60.6, 58.1, 57.8, 52.5, 48.3, 31.4, 31.2, 27.7, 25.2, 19.4, 19.0, 18.1, 17.8 ppm;

HRMS (ESI-TOF, m/z): Calcd for C$_{17}$H$_{30}$N$_3$O$_6$ [M+H]$^+$ 372.2129; found 372.2126;

[α]$_D^{20}$=−62.9 (c 0.79, CHCl$_3$)

Compound S57

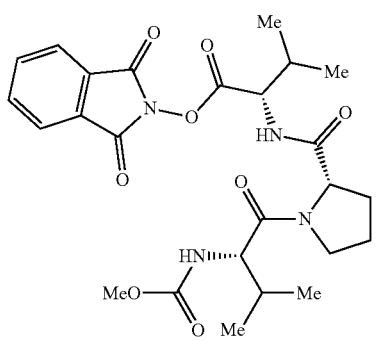

1,3-dioxoisoindolin-2-yl (methoxycarbonyl)-L-valyl-L-prolylvalinate (S57)

On 2.34 mmol scale, General Procedure A was followed with (methoxycarbonyl)-L-valyl-L-prolyl-L-valine. Purification by flash column chromatography (silica gel, 1:1 EtOAc:hexanes) furnished S57 (640 mg, 53%).

Physical state: white foam;

$R_f$=0.40 (silica gel, 1:2 hexanes: EtOAc);

$^1$H NMR (600 MHz, CDCl$_3$) δ 7.88-7.84 (m, 2H), 7.78-7.75 (m, 2H), 7.50 (d, J=8.4 Hz, 1H), 5.61 (d, J=9.2 Hz, 1H), 4.84 (dd, J=8.5, 5.0 Hz, 1H), 4.61 (dd, J=8.1, 3.0 Hz, 1H), 4.29 (dd, J=9.3, 6.9 Hz, 1H), 3.79-3.72 (m, 1H), 3.63 (s, 3H), 3.64-3.61 (m, 1H), 2.41-2.30 (m, 2H), 2.17 (dt, J=12.3, 9.1 Hz, 1H), 2.01-1.96 (m, 2H), 1.95-1.89 (m, 1H), 1.07 (d, J=7.2 Hz, 3H), 1.06 (d, J=6.6 Hz, 3H), 0.97 (d, J=6.7 Hz, 3H), 0.93 (d, J=6.7 Hz, 3H) ppm;

$^{13}$C NMR (151 MHz, CDCl$_3$) δ 172.5, 171.2, 168.4, 161.7, 157.3, 134.9, 129.0, 124.1, 60.0, 57.7, 56.0, 52.4, 48.0, 31.6, 31.4, 27.4, 25.3, 19.5, 18.8, 17.8, 17.7 ppm;

HRMS (ESI-TOF, m/z): Calcd for C$_{25}$H$_{33}$N$_4$O$_8$ [M+H]$^+$ 517.2293; found 517.2289;

[α]$_D^{20}$=−61.0 (c 1.0, CHCl$_3$).

Compound S58

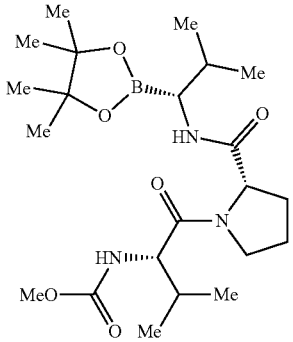

methyl ((S)-3-methyl-1-((S)-2-(((R)-2-methyl-1-(4,4,5,5-tetramethyl-1,3,2-dioxab-orolan-2-yl)propyl)carbamoyl)pyrrolidin-1-yl)-1-oxobutan-2yl)-carbamate (S58)

On 0.33 mmol scale, General Procedure C was followed with suspension C (NiCl$_2$.6H$_2$O/di-tBubipy in THF). MgBr$_2$.Et$_2$O (1.0 equiv.) was used in this case. Purification by flash column chromatography (silica gel, 2:3 EtOAc:hexanes to 20:1 CH$_2$Cl$_2$:MeOH) furnished S58 (72 mg, 48%) as slightly yellow oil.

Compound 50

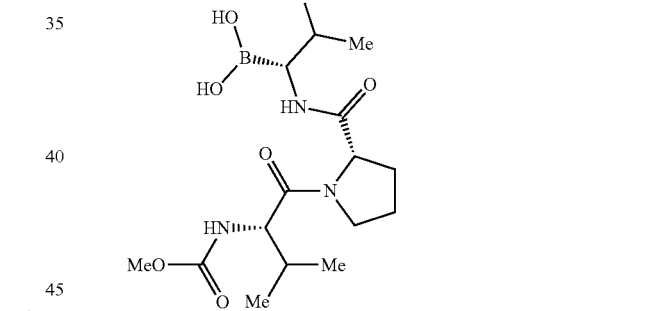

((R)-1-((S)-1-((methoxycarbonyl)-L-valyl)pyrrolidine-2-carboxamido)-2-methylpropyl)boronic Acid (50)

Aminoboronate ester S58 (24 mg, 0.053 mmol) was dissolved in CH$_2$Cl$_2$ (2 mL) under argon; the solution was cooled to −78° C. with a dry ice/acetone bath when BCl$_3$ (0.16 mL, 1.0 M in CH$_2$Cl$_2$, 3.0 equiv.) was added dropwise, after which the mixture was stirred for 1 h at −78° C. The reaction was then allowed to warm up to room temperature, and the volatiles were removed in vacuo. Anhydrous methanol (4 mL) was added and the resulting mixture was stirred for 10 minutes prior to concentration in vacuo. The resulting residue was treated with methanol (4 mL) for 10 minutes and was concentrated in vacuo. This process was repeated for three times. The resulting crude product was then purified by preparative reverse-phase HPLC (10-40% CH$_3$CN/H$_2$O over 25 min, both CH$_3$CN and H$_2$O containing 0.1% TFA) and lyophilized to afford 50 as a white floppy powder (15.0 mg, 76%).

Physical state: white powder;
$^1$H NMR (600 MHz, MeOH-d$_4$): δ 4.61 (dd, J=8.4 Hz, 6.0 Hz, 1H), 4.17 (d, J=7.8 Hz, 1H), 3.97-3.93 (m, 1H), 3.75-3.71 (m, 1H), 3.64 (s, 3H), 2.33-2.24 (m, 2H), 2.19-2.13 (m, 1H), 2.08-1.98 (m, 3H), 1.80-1.74 (m, 1H), 1.05 (d, J=6.6 Hz, 3H), 1.00 (d, J=6.6 Hz, 3H), 0.96 (d, J=6.6 Hz, 3H), 0.92 (d, J=6.6 Hz, 3H) ppm;
$^{13}$C NMR (151 MHz, MeOH-d$_4$): δ 179.3, 173.5, 159.4, 59.7, 57.9, 52.7, 31.7, 31.0, 29.8, 26.2, 21.4, 21.2, 19.6, 18.8 ppm;
HRMS (ESI-TOF, m/z): Calcd for C$_{16}$H$_{29}$BN$_3$O$_5$[M−H$_2$O+H]$^+$ 354.2195; found 354.2189;
[α]$_D^{20}$=−81.1 (c 0.44, MeOH).
Synthesis of Elastase Inhibitors mCBK320 (51) and mCBK323 (52)
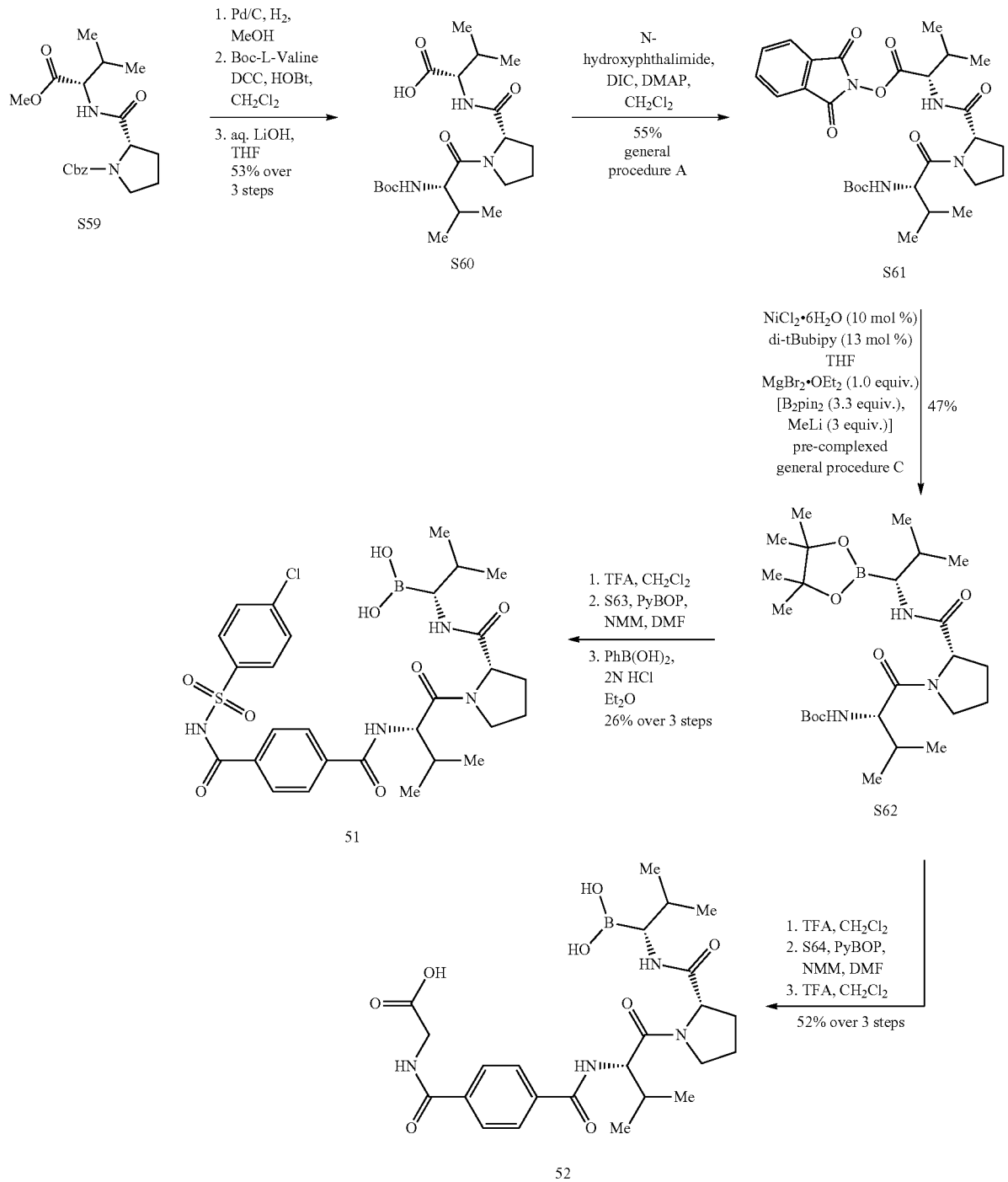
Scheme S6. Synthesis of 51 and 52

-continued

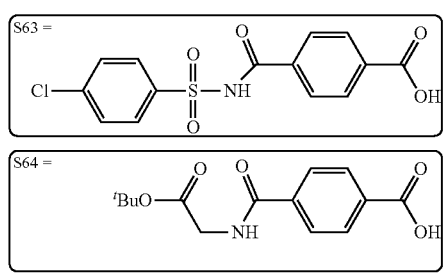

Compound S60

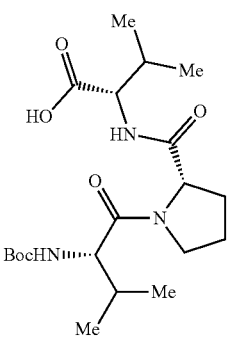

(tert-butoxycarbonyl)-L-valyl-L-prolyl-L-valine (S60)

Cbz Deprotection:
A 100 mL flask equipped with a stirrer bar was charged with Z-L-Pro-L-Val-OMe (66) (S59, 1.95 g, 5.4 mmol), 10% Pd/C (98 mg, 5 wt %), and MeOH (25 mL). This flask was then evacuated and backfilled with $H_2$ from a balloon for three times. The reaction mixture was stirred at room temperature for 6 h and was filtered through a thin pad of celite which was then rinsed with MeOH (10 mL). The filtrate was concentrated in vacuo to give the corresponding amine as colorless oil.

Amide Bond Formation:
The aforementioned amine was treated sequentially with Boc-L-Valine (1.17 g, 5.4 mmol, 1.0 equiv.), HOBt.$H_2O$ (83 mg, 0.61 mmol, 0.11 equiv.), and $CH_2Cl_2$ (25 mL). The resulting solution was cooled to 0° C. before DCC (1.23 g, 6.0 mmol, 1.1 equiv.) was added. The reaction mixture was allowed to stir at 0° C. for 30 min and then at room temperature overnight. The resulting mixture was filtered through a pad of celite; the filtrate was concentrated in vacuo, redissolved in EtOAc, and washed with 0.1N aq. HCl, 0.1 M aq. $NH_4OH$, and brine successively. The organic layer was dried over anhydrous $Na_2SO_4$, concentrated in vacuo, and purified by flash column chromatography (silica gel, 2:1 EtOAc:hexanes) to give Boc-L-Val-L-Pro-L-Val-OMe (1.32 g) as a colorless oil.

Hydrolysis of Ester:
A 25 mL flask equipped with a stirrer bar was charged with Boc-L-Val-L-Pro-L-Val-OMe (1.32 g) and THF (3 mL). LiOH (4 mL, 1 M aqueous solution) was added and the resulting solution was allowed to stir vigorously at room temperature for 12 h. 1 N HCl was added to the reaction mixture until pH=2-3 and the mixture was extracted with EtOAc. The combined organic layers were dried over anhydrous $Na_2SO_4$ and concentrated in vacuo to give S60 (1.24 g, 53% over 3 steps) as a white foam, which was used in the next step without further purification.

Compound S61

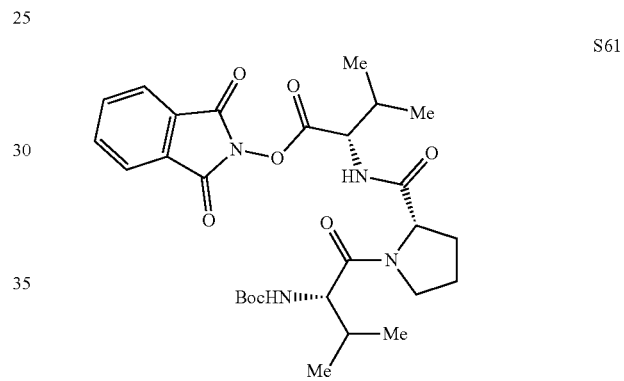

1,3-dioxoisoindolin-2-yl (tert-butoxycarbonyl)-L-valyl-L-prolylvalinate (S61)

On 3.0 mmol scale, General Procedure A was followed with Boc-L-valyl-L-prolyl-L-valine (S60). Purification by flash column chromatography (silica gel, 1:1 EtOAc: hexanes) furnished S61 (920 mg, 55%).

Physical state: white foam;

$R_f$=0.50 (silica gel, 1:2 hexane: EtOAc);

$^1$H NMR (600 MHz, CDCl$_3$): δ 7.88-7.85 (m, 2H), 7.79-7.76 (m, 2H), 7.50 (d, J=8.4 Hz, 1H), 5.28 (d, J=9.6 Hz, 1H), 4.84 (dd, J=8.4, 4.8 Hz, 1H), 4.62 (dd, J=7.8, 3.0 Hz, 1H), 4.28 (dd, J=9.6, 6.6 Hz, 1H), 3.71-3.77 (m, 1H), 3.60 (dt, J=8.4, 3.6 Hz, 1H), 2.43-2.39 (m, 1H), 2.37-2.31 (m, 1H), 2.11-2.19 (m, 1H), 1.88-2.02 (m, 3H), 1.41 (s, 9H), 1.08 (d, J=6.6 Hz, 3H), 1.07 (d, J=6.6 Hz, 3H), 0.98 (d, J=7.2 Hz, 3H), 0.92 (d, J=7.2 Hz, 3H) ppm;

$^{13}$C NMR (151 MHz, CDCl$_3$): δ 172.9, 171.1, 168.3, 161.7, 156.0, 134.9, 129.0, 124.1, 79.7, 60.0, 57.0, 56.1, 47.9, 31.6, 31.6, 28.5, 27.1, 25.4, 19.7, 18.9, 17.8, 17.6 ppm;

HRMS (ESI-TOF, m/z): Calcd for $C_{28}H_{39}N_4O_8$ [M+H]$^+$ 559.2762; found 559.2757.

$[α]_D^{20}$=−86.2 (c 1.0, CHCl$_3$).

Compound S62

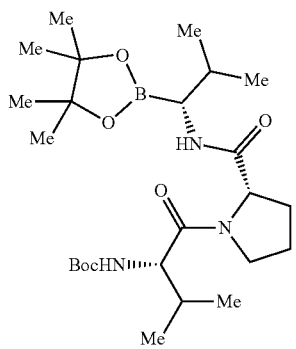

tert-butyl ((S)-3-methyl-1-((S)-2-(((R)-2-methyl-1-(4,4,5,5-tetramethyl-1,3,2-diox-aborolan-2-yl)propyl)carbamoyl)pyrrolidin-1-yl)-1-oxobutan-2-yl)carbamate (S62)

On 1.1 mmol scale, General Procedure C was followed with S61 and suspension C (NiCl$_2$.6H$_2$O/di-tBubipy in THF), 1.0 equiv. of MgBr$_2$.Et$_2$O was used in this case. Flash column chromatography (silica gel, 2:3 EtOAc:hexanes to 3:1 EtOAc:hexanes) furnished S62 (257 mg, 47%) as a slightly yellow oil.

Physical state: slight yellow oil;

R$_f$=0.65 (silica gel, 1:2 hexanes: EtOAc);

$^1$H NMR (600 MHz, CDCl$_3$): δ 7.08 (br s, 1H), 5.22 (d, J=9.3 Hz, 1H), 4.66 (dd, J=8.2, 2.6 Hz, 1H), 4.28 (dd, J=9.3, 6.0 Hz, 1H), 3.70 (q, J=8.7 Hz, 1H), 3.56 (ddd, J=9.7, 8.1, 3.7 Hz, 1H), 2.97-2.86 (m, 1H), 2.41-2.38 (m, 1H), 2.19-2.11 (m, 1H), 2.01-1.94 (m, 2H), 1.94-1.80 (m, 2H), 1.43 (s, 9H), 1.25 (d, J=5.4 Hz, 12H), 0.97 (d, J=6.8 Hz, 3H), 0.95 (d, J=6.8 Hz, 3H), 0.93 (d, J=6.8 Hz, 3H), 0.91 (d, J=6.7 Hz, 3H) ppm;

$^{13}$C NMR (151 MHz, CDCl$_3$): δ 172.8, 171.8, 156.0, 83.3, 79.8, 59.0, 56.9, 47.7, 31.6, 29.8, 28.5, 27.0, 25.3, 25.2, 25.1, 20.6, 20.3, 19.7, 17.5 ppm;

HRMS (ESI-TOF, m/z): Calcd for C$_{25}$H$_{47}$BN$_3$O$_6$[M+H]$^+$ 496.3552; found 496.3550.

$[α]_D^{20}$=−73.6 (c 1.0, CHCl$_3$).

Compound 51

(1-((S)-1-((4-(((4-chlorophenyl)sulfonyl)carbamoyl)benzoyl)-L-valyl)pyrrolidine-2-carboxamido)-2-methylpropyl)boronic Acid (51)

Boc deprotection: In a culture tube equipped with a stir bar, S62 (55 mg, 0.11 mmol) was dissolved in CH$_2$Cl$_2$ (1 mL). TFA (1 mL) was added at 0° C. and the resulting solution was allowed to stir at 0° C. for 2 h. The volatiles were removed in vacuo using a rotary evaporator (water bath temperature <25° C.), and the residue was used in next step without purification.

Esterification:

Benzoic acid S63 (45 mg, 0.13 mmol, 1.2 equiv.) and PyBOP (69 mg, 0.13 mmol, 1.2 equiv.) were then added and the mixture was dissolved in DMF (2.0 mL). N-methyl morpholine (49 µL, 0.45 mmol, 4.0 equiv.) was added and the reaction was allowed to stir at room temperature for 3 h. The mixture was then diluted with EtOAc, washed with brine, dried over anhydrous Na$_2$SO$_4$, concentrated in vacuo, and purified by flash column chromatography (silica gel, 10:1 CH$_2$Cl$_2$:MeOH) to give the pinacol boronate of 51 (69 mg) contaminated with some tripyrrolidinophosphine oxide. This mixture was used in the next step without further purification.

Boronate Ester Exchange:

In a culture tube equipped with a stir bar, the aforementioned mixture (53 mg) and PhB(OH)$_2$ (14 mg) was dissolved in Et$_2$O (3 mL). 2 N HCl (3 mL) was added and the resulting biphasic mixture was allowed to stir vigorously at room temperature for 36 h when it was extracted with EtOAc (5 mL×3). The combined organic layers were dried over anhydrous Na$_2$SO$_4$, concentrated in vacuo. The resulting residue was purified by preparative reverse-phase HPLC (20-80% CH$_3$CN/H$_2$O over 35 min, both CH$_3$CN and H$_2$O containing 0.1% TFA) and lyophilized to afford 51 (14.0 mg, 26% for 3 steps).

Physical state: white powder;

$^1$H NMR (600 MHz, MeOH-d$_4$): δ 8.10 (d, J=8.4 Hz, 2H), 7.94-7.90 (m, 4H), 7.66 (d, J=9.0 Hz, 2H), 4.64 (dd, J=8.4 Hz, 3.6 Hz, 1H), 4.61 (d, J=9.6 Hz, 1H), 4.12 (dt, J=9.6 Hz, 6.6 Hz, 1H), 3.82 (dt, J=9.6 Hz, 6.6 Hz, 1H), 2.38-2.31 (m, 2H), 2.25-2.19 (m, 2H), 2.14-2.02 (m, 2H), 1.82-1.77 (m, 1H), 1.16 (d, J=6.6 Hz, 3H), 1.10 (d, J=7.2 Hz, 3H), 0.98 (d, J=6.6 Hz, 3H), 0.94 (d, J=6.6 Hz, 3H) ppm;

$^{13}$C NMR (151 MHz, MeOH-d$_4$): δ 179.2, 173.0, 169.1, 166.9, 141.3, 139.5, 139.4, 135.9, 131.2, 130.3, 129.5, 128.9, 59.0, 57.9, 31.8, 31.1, 29.8, 26.3, 21.4, 21.2, 19.5, 19.5 ppm;

HRMS (ESI-TOF, m/z): Calcd for C$_{28}$H$_{35}$BClN$_4$O$_7$S [M−H$_2$O+H]$^+$ 617.2003; found 617.2002.

$[α]_D^{20}$=−72.2 (c 0.36, MeOH).

Compound 52

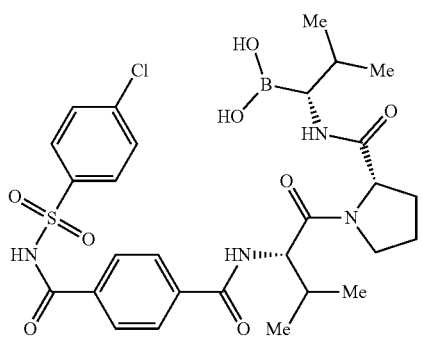

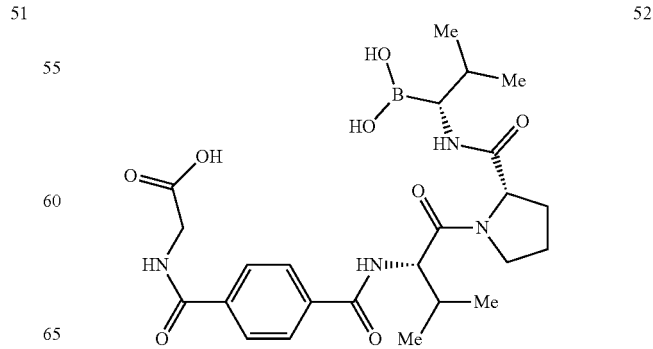

(4-(((2S)-1-((2S)-2-((1-borono-2-methylpropyl)carbamoyl)pyrrolidin-1-yl)-3-methyl-1-oxobutan-2-yl)carbamoyl)benzoyl)glycine (52)

Boc deprotection: In a culture tube equipped with a stir bar, S62 (55 mg, 0.11 mmol) was dissolved in $CH_2Cl_2$ (1 mL). TFA (1 mL) was added at 0° C. and the resulting solution was allowed to stir at 0° C. for 2 h. The volatiles were removed in vacuo using a rotary evaporator (water bath temperature <25° C.), and the residue was used in next step without purification.

Esterification:

Benzoic acid S64 (37 mg, 0.13 mmol, 1.2 equiv.) and PyBOP (69 mg, 0.13 mmol, 1.2 equiv.) were then added and the mixture was dissolved in DMF (2.0 mL). N-methyl morpholine (49 μL, 0.45 mmol, 4.0 equiv.) was added and the reaction was allowed to stir at room temperature for 3 h. The mixture was then diluted with EtOAc, washed with brine, dried over anhydrous $Na_2SO_4$, concentrated in vacuo and purified by flash column chromatography (silica gel, 10:1 $CH_2Cl_2$: MeOH) to give the pinacol boronate (63 mg, 86%) which was used in the next step without further purification.

Global Deprotection:

In a culture tube equipped with a stir bar, the aforementioned pinacol boronic ester (32 mg) was dissolved in $CH_2Cl_2$ (1 mL). TFA (1 mL) was added at 0° C. and the resulting solution was allowed to stir at room temperature overnight. The volatiles were removed in vacuo using a rotary evaporator (water bath temperature <25° C.), and the residue was purified by preparative reverse-phase HPLC (20-80% $CH_3CN/H_2O$ over 40 min, both $CH_3CN$ and $H_2O$ containing 0.1% TFA) and lyophilized to afford 52 (13.0 mg, 52% over 3 steps).

Physical state: white powder;

$^1$H NMR (600 MHz, Methanol-$d_4$): δ 7.96-7.90 (m, 4H), 4.66-4.59 (m, 2H), 4.16-4.07 (m, 3H), 3.83 (dt, J=10.1, 6.8 Hz, 1H), 2.40-2.29 (m, 2H), 2.26-2.16 (m, 2H), 2.14-2.02 (m, 2H), 1.82-1.72 (m, 1H), 1.17 (d, J=6.7 Hz, 3H), 1.12 (d, J=6.7 Hz, 3H), 0.98 (d, J=6.6 Hz, 3H), 0.95 (d, J=6.6 Hz, 3H) ppm;

$^{13}$C NMR (151 MHz, Methanol-$d_4$): δ 179.3, 173.1, 173.0, 169.50, 169.48, 138.1, 138.0, 128.8, 128.6, 59.0, 58.0, 42.3, 31.8, 31.1, 29.8, 26.3, 21.4, 21.2, 19.6, 19.5 ppm;

HRMS (ESI-TOF, m/z): Calcd for $C_{24}H_{34}BN_4O_7$[M−$H_2O$+H]$^+$ 501.2515; found 501.2516; $[\alpha]_D^{20}$=−97.3 (c 0.26, MeOH).

Stereochemistry Assignment of the Peptidic Boronic Acids 50, 51 and 52

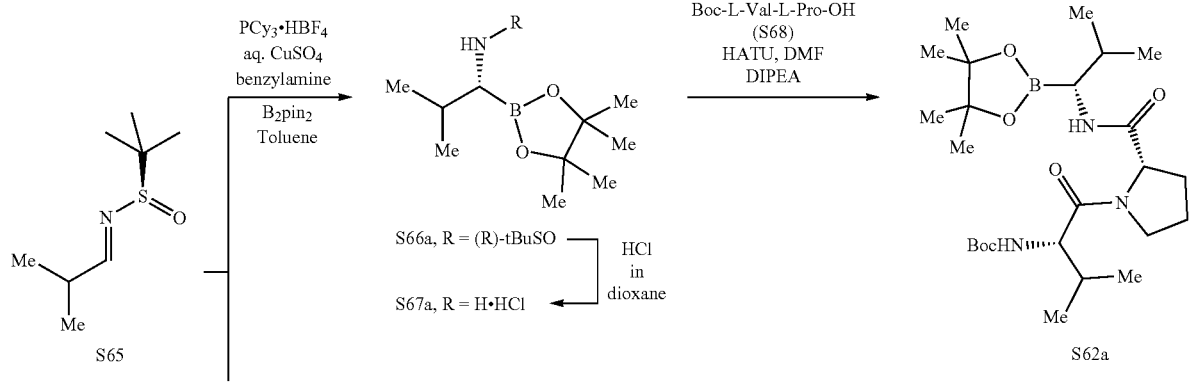

Scheme S8. Synthesis of S62a and S62b

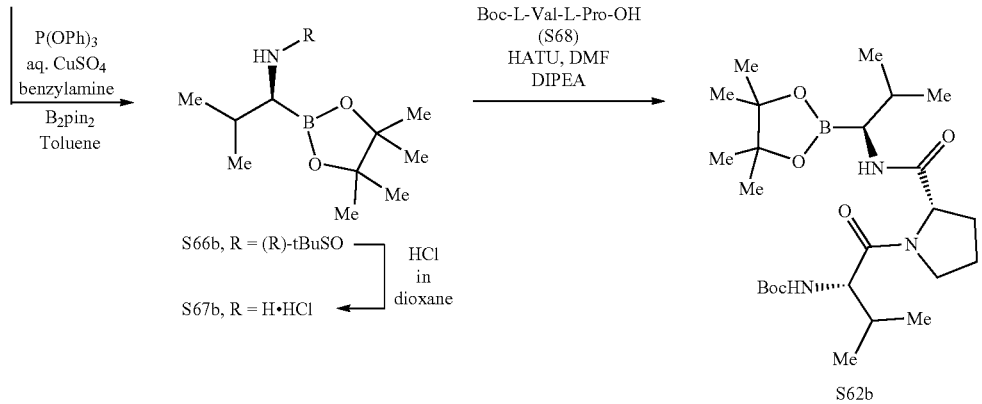

The pinacol α-amino boronate S66a/S66b was prepared using the literature procedure (67) with slight modifications.
Compound S66a

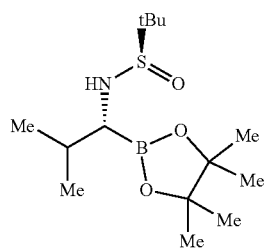

S66a (R)-2-methyl-N—((R)-2-methyl-1-(4,4,5,5-tetramethyl-1,3,2-dioxaborolan-2-yl)propyl)propane-2-sulfinamide (S66a)

A culture tube equipped with a stirrer bar was charged sequentially with PCy$_3$·HBF$_4$ (12 mg, 0.033 mmol, 1.2 mol %), toluene (0.55 mL), aqueous CuSO$_4$ (1.1 mL, 0.03 M, 1.2 mol %) and benzylamine (15.3 μL, 0.14 mmol, 5 mol %). The mixture was stirred for 10 min at the room temperature when a solution of aldimine S65 (480 mg, 2.74 mmol, 1.0 equiv.) in toluene (5.0 mL) was added, followed by B$_2$pin$_2$ (1.39 g, 5.5 mmol, 2.0 equiv.). The mixture was stirred vigorously for 14 h, diluted with EtOAc and filtered through a silica gel plug eluting with EtOAc. The filtrate was concentrated and purified by flash column chromatography (silica gel, 1:3 EtOAc:hexanes) to give S66a (1.07 g, d.r.>20:1) that was contaminated with impurities originating from B$_2$pin$_2$ which could be removed in the next step.
Compound S66b

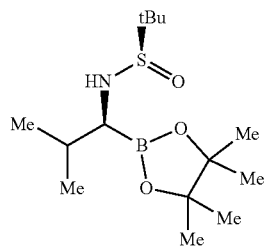

S66b (R)-2-methyl-N—((S)-2-methyl-1-(4,4,5,5-tetramethyl-1,3,2-dioxaborolan-2-yl)propyl)propane-2-sulfinamide (S66b)

To a culture tube equipped with a stirrer bar were added a solution of P(OPh)$_3$ (0.33 mL, 0.1 M in toluene, 1.2 mol %), aqueous CuSO$_4$ (1.1 mL, 0.03 M, 1.2 mol %), and benzylamine (15.3 μL, 0.14 mmol, 5 mol %) sequentially. The mixture was stirred for 10 min, after which a solution of aldimine S65 (480 mg, 2.74 mmol, 1.0 equiv.) in toluene (5.0 mL) and B$_2$pin$_2$ (1.39 g, 5.5 mmol, 2.0 equiv.) were added sequentially. The mixture was stirred vigorously for 14 h, diluted with EtOAc, and filtered through a silica gel plug eluting with EtOAc. The filtrate was concentrated in vacuo, and purified by flash column chromatography (silica gel, 1:3 EtOAc:hexanes) to give S66b (857 mg, d.r.=6.1:1) contaminated with impurities originating from B$_2$pin$_2$ which could be removed in the next step.

The α-boronic amine hydrochloride S67a/S67b was prepared using the literature procedure (19)
Compound S67a

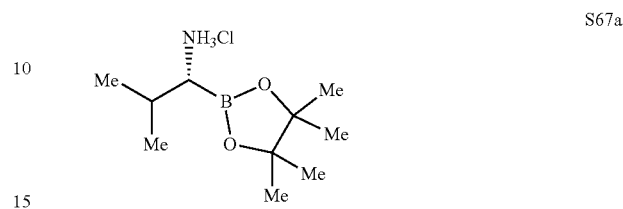

S67a (R)-2-methyl-1-(4,4,5,5-tetramethyl-1,3,2-dioxaborolan-2-yl)propan-1-amine hydrochloride (S67a)

S66a (190 mg, contaminated with B$_2$pin$_2$ impurities) was dissolved in 1,4-dioxane (1.2 mL) and methanol (0.1 mL) under argon. HCl (80 μL, 4.0 M in 1,4-dioxane) was added at room temperature and the resulting mixture was stirred at the same temperature before the volatiles were removed in vacuo. The resulting solid was triturated with a 2:1 mixture of hexanes and Et$_2$O to give S67a (48 mg, 42% over 2 steps).
Physical state: white solid;
$^1$H NMR (600 MHz, CDCl$_3$) δ 8.23 (s, 3H), 2.79 (br s, 1H), 2.26 (pd, J=6.9, 4.8 Hz, 1H), 1.28 (br s, 12H), 1.11 (d, J=7.0 Hz, 3H), 1.10 (d, J=7.0 Hz, 3H).
$^{13}$C NMR (151 MHz, CDCl$_3$) δ 85.2, 44.4 (br), 29.3, 25.2, 24.8, 20.4, 19.9.
HRMS (ESI-TOF, m/z): Calcd for C$_{10}$H$_{23}$BNO$_2$ [M+H]$^+$ 200.1816; found 200.1812.
[α]$_D^{20}$=−3.0 (c 1.0, CHCl$_3$).
Compound S67b

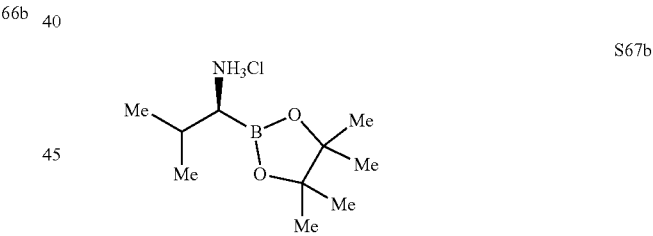

S67b (S)-2-methyl-1-(4,4,5,5-tetramethyl-1,3,2-dioxaborolan-2-yl)propan-1-amine hydrochloride (S67b)

S66b (350 mg, contaminated with Bpin impurities) was dissolved in 1,4-dioxane (2.4 mL) and methanol (0.2 mL) under argon. HCl (0.16 mL, 4.0 M in 1,4-dioxane) was added at room temperature and the resulting mixture was stirred at the same temperature before the volatiles were removed in vacuo. The resulting solid was triturated with a 2:1 mixture of hexanes and Et$_2$O to give S67b (94 mg, 37% over 2 steps).
Physical state: white solid;
$^1$H NMR (600 MHz, CDCl$_3$) δ 8.25 (s, 3H), 2.80 (q, J=5.6 Hz, 1H), 2.26 (pd, J=6.9, 4.9 Hz, 1H), 1.28 (br s, 12H), 1.12 (d, J=7.2 Hz, 3H), 1.11 (d, J=7.2 Hz, 3H);
$^{13}$C NMR (151 MHz, CDCl$_3$) δ 85.2, 44.5 (br), 29.3, 25.2, 24.8, 20.4, 19.9;

HRMS (ESI-TOF, m/z): Calcd for $C_{10}H_{23}BNO_2$ [M+H]$^+$ 200.1816; found 200.1817;
$[\alpha]_D^{20}$=+2.7 (c 1.0, CHCl$_3$).

Compound S62a

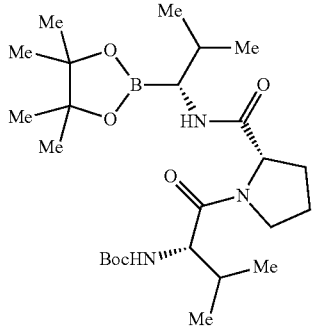

S62a

To a culture tube charged with Boc-L-Val-L-Pro-OH (S68, 34 mg, 0.11 mmol, 1.2 equiv.) and 1-[Bis(dimethylamino)methylene]-1H-1,2,3-triazolo[4,5-b]pyridinium 3-oxid hexafluorophosphate (HATU, 44 mg, 0.12 mmol, 1.3 equiv.) was added DMF (0.5 mL), followed by diisopropylethylamine (45 µL, 0.26 mmol, 2.9 equiv.). S67a (21 mg, 0.089 mmol) in DMF (1.0 mL) was added dropwise at 0° C. After the completion of addition, the reaction was kept stirring at room temperature for 1 h. The mixture was diluted with Et$_2$O, washed with brine, dried over anhydrous Na$_2$SO$_4$, concentrated in vacuo. The resulting residue was purified by flash column chromatography (silica gel, 1:1 EtOAc:hexanes to 3:1 EtOAc:hexanes) to give S62a (32.3 mg, 73%) as a colorless oil.

The NMR spectra of S62a are in agreements with those of S62 prepared via decarboxylative borylation. This confirms the configuration of the stereocenter α to boron in S62 to be R.

Compound S62b

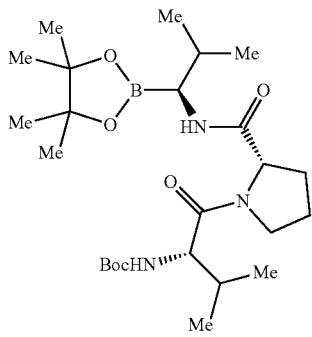

S62b

To a culture tube charged with Boc-L-Val-L-Pro-OH (S68, 26 mg, 0.083 mmol, 1.2 equiv.) and 1-[Bis(dimethylamino)methylene]-1H-1,2,3-triazolo[4,5-b]pyridinium 3-oxid hexafluorophosphate (HATU, 34 mg, 0.089 mmol, 1.3 equiv.) was added DMF (0.5 mL), followed by diisopropylethylamine (35 µL, 0.2 mmol, 2.9 equiv.). S67b (16 mg, 0.068 mmol, 1.0 equiv.) in DMF (1.0 mL) was added dropwise at 0° C. After the completion of addition, the reaction was kept stirring at room temperature for 1 h. The mixture was diluted with Et$_2$O, washed with brine, dried over anhydrous Na$_2$SO$_4$, concentrated in vacuo, and purified by flash column chromatography (silica gel, 1:1 EtOAc:hexanes to EtOAc) to give S62b (22 mg, 65%) as a colorless oil.

Physical state: colorless oil;
R$_f$=0.60 (silica gel, 1:2 EtOAc:hexanes);
$^1$H NMR (600 MHz, CDCl$_3$) δ 7.08 (br s, 1H), 5.21 (d, J=9.3 Hz, 1H), 4.65 (dd, J=8.2 Hz, 2.3 Hz, 1H), 4.28 (dd, J=9.4 Hz, 6.1 Hz, 1H), 3.70 (td, J=9.4 Hz, 7.1 Hz, 1H), 3.56 (ddd, J=9.6 Hz, 8.1 Hz, 3.4 Hz, 1H), 2.94 (td, J=5.7 Hz, 2.6 Hz, 1H), 2.39 (ddd, J=12.8 Hz, 6.1 Hz, 2.6 Hz, 1H), 2.14-2.05 (m, 1H), 1.98 (dtd, J=12.3 Hz, 6.8 Hz, 3.5 Hz, 2H), 1.88 (tdd, J=11.3 Hz, 9.0 Hz, 5.8 Hz, 2H), 1.42 (s, 9H), 1.21 (d, J=6.3 Hz, 12H), 1.00 (d, J=6.8 Hz, 3H), 0.94 (d, J=6.8 Hz, 3H), 0.91 (d, J=6.8 Hz, 6H) ppm;
$^{13}$C NMR (151 MHz, CDCl$_3$) δ 172.9, 171.8, 156.0, 83.1, 79.8, 59.0, 56.9, 47.7, 45.5, 31.6, 29.8, 28.5, 27.2, 25.2, 25.12, 25.10, 20.4, 20.3, 19.9, 17.7 ppm.

The NMR spectra of S62b differ from those of S62.

Elastase Inhibition Assay

Figure 4B:
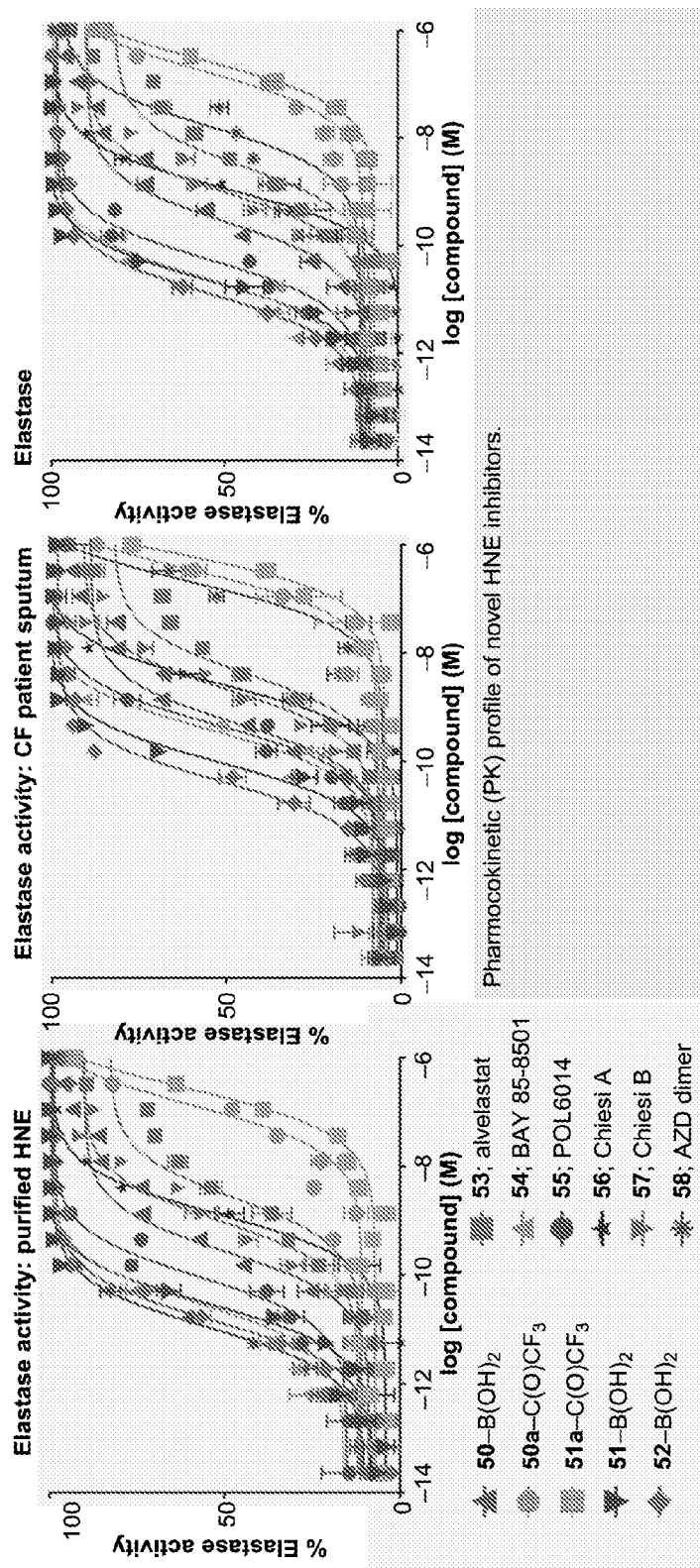

Compounds Tested:

For chemical structures, see FIG. 4A. For pharmokinetic profiles, see FIG. 4B.

Materials and Methods:

Compounds 50-58, 50a, 50b, and 51a were subjected to this assay.

Serially diluted compounds in DMSO were dispensed into a 384-well black opaque plate by Echo dispenser. 0.1 µg/mL human neutrophil elastase (EPC, Catalog #SE563, Owensville, Miss.) or human sputum diluted with assay buffer (100 mM HEPES, 500 mM NaCl, 0.02% Tween 20) was added into the 384-well plate, and was incubated with different compounds at different concentrations for 30 minutes at room temperature. The final concentration of DMSO in the reaction was 0.1%. Elastase substrate MeOSuc-AAPV-AMC (Bachem, Catalog #I-1270, Torrance, Calif.) of 100 µM final concentration was then added into the reaction system just before enzyme kinetics were read on PheraSTAR plate reader at excitation of 380 nm and emission of 460 nm with a 3-minutes interval for 30 minutes in total. Slope of fluorescence intensity vs. time representing the V$_{max}$ of enzyme activity was calculated with MARS software. % relative inhibition was calculated as:

$$\frac{Slope_{DMSO} = Slope_{inhibitor}}{Slope_{DMSO}} \times 100\%$$

IC$_{50}$ was calculated based on the % relative inhibition curve using log(agonist) vs. response (three parameters) method with Prism software. All experiments were performed in triplicate for at least three independent times. The IC$_{50}$ results of all experiments are shown as the average of triplicates with error bar indicating standard deviation as indicated in individual figures. For compounds 51, 52, and 58, the assay above was repeated with 2.5, 25, 50 and 100 µM of elastase substrate (MeOSuc-AAPV-AMC) and Ki/nM values were calculated based on these results using the mixed model (68).

Quantification of Elastase Concentration in Human Sputum:

Human sputum was purchased from Discovery Life Sciences (Los Osos, Calif.). Human sputum was diluted 1:10 in volume with assay buffer (100 mM HEPES, 500 mM NaCl, 0.02% Tween 20) followed by vigorous vortexing. The 1:10 diluted human sputum was further diluted into 1:30, 1:90, 1:270, 1:810, and 1:2430. The elastase concentration was determined by elastase inhibition assay as described above.

Specifically, a series of standards of human neutrophil elastase (starting at 2 µg/mL and further diluted 1:2 in volume) were prepared in the assay buffer. The samples and standards were plated in a 384-well black solid bottom plate; the substrate MeOSuc-AAPV-AMC of 100 µM final concentration was then added into the reaction system just before enzyme kinetics were read on PheraSTAR plate reader as mentioned above. The slope of enzymatic kinetic reading was calculated by MARS software. The elastase levels of the human sputum were calculated based on the standard curve.

Results:

| Compound | Purified NHE IC$_{50}$/nM | LipE | CF sputum IC$_{50}$/nM | LipE | COPD sputum IC$_{50}$/nM | LipE |
|---|---|---|---|---|---|---|
| 50-B(OH)$_2$ | 0.27 ± 0.02 | 8.37 | 0.51 ± 0.04 | 8.09 | 0.274 ± 0.004 | 8.36 |
| 50a-C(O)CF$_3$ | 134.9 ± 12.2 | 4.57 | 358.3 ± 54.5 | 4.15 | 178.9 ± 15.0 | 4.45 |
| 50b-CO$_2$H | Not Active | N.A. | N.A. | N.A | N.A. | N.A. |
| 51-B(OH)$_2$ | 0.030 ± 0.002 | 7.33 | 0.096 ± 0.002 | 6.83 | 0.0223 ± 0.0006 | 7.46 |
| 51a-C(O)CF$_3$ | 289.8 ± 32.1 | 1.95 | 833.4 ± 220.5 | 1.49 | 282.2 ± 23.1 | 1.96 |
| 52-B(OH)$_2$ | 0.015 ± 0.001 | 10.1 | 0.043 ± 0.002 | 9.62 | 0.0127 ± 0.0008 | 10.2 |
| 53 | 2.62 ± 0.39 | 7.32 | 4.08 ± 0.39 | 7.11 | 2.98 ± 0.82 | 7.22 |
| 54 | 0.031 ± 0.002 | 6.76 | 0.40 ± 0.04 | 5.87 | 0.024 ± 0.003 | 6.85 |
| 55 | 0.093 ± 0.008 | 18.6 | 0.48 ± 0.03 | 17.8 | 0.051 ± 0.004 | 18.8 |
| 56 | 1.34 ± 0.13 | 4.59 | 2.68 ± 0.04 | 4.29 | 1.12 ± 0.04 | 4.67 |
| 57 | 0.99 ± 0.13 | 9.46 | 2.04 ± 0.08 | 9.16 | 0.97 ± 0.14 | 9.45 |
| 58 | 0.0111 ± 0.0002 | 5.04 | 202.8 ± 31.2 | 0.77 | 16.23 ± 2.13 | 1.87 |

Note:
Average ± SD, n = 3 plotted, representative of 3 independent, triplicate experiments. A non-linear, 3-parameter log inhibitor curve was used to calculate the IC$_{50}$ values. Curve fit statistics: purified HNE, $R^2 \geq 0.95$, CF patient sputum, $R^2 \geq 0.93$, COPD patient sputum, $R^2 \geq 0.93$.

Ki Values:

| | Compound | | |
|---|---|---|---|
| | 51 | 52 | 58 |
| Ki/nM | 0.034 | 0.0037 | 0.0027 |
| Standard deviation | 0.002 | 0.0005 | 0.0029 |

Note:
Measurements were performed in 3 replicates and average values were reported.

Time Dependence of Elastase Inhibition

Method:
The procedure for the elastase inhibition assay was followed with slight modifications. 0.1 µg/mL human neutrophil elastase was incubated with a range of concentrations of inhibitors for 5, 15, 30 and 60 minutes before substrate MeOSuc-AAPV-AMC of 100 µM final concentration was added. Enzyme kinetics were read on PheraSTAR plate reader and IC$_{50}$ was calculated with the method described above.

Results:

Plasma Stability Assay

Materials:
1) Compounds 50, 50a, 51, 51a and 52 were tested. Propantheline was used as the reference compound in this assay; all stock solutions were stored at −40° C. before use.
2) Test system: CD-1 Mouse Plasma from a minimum of 20 male individuals were obtained from BioreclamationIVT (Catalog #: MSEPLEDTA2-M; Batch #: MSE244515). EDTA-K2 was used as the anticoagulant.

Procedure:
The frozen plasma was thawed in a water bath at 37° C. prior to the experiments. The plasma was centrifuged at 4000 rpm for 5 min and the clots were removed if necessary. The pH was adjusted to 7.4±0.1 as necessary. An intermediate solution (1 mM) was prepared and a 100 µM dosing solution was prepared by diluting 10 µL of the intermediate solution with 90 µL 45% MeOH/H$_2$O. Duplicate of test samples were made by mixing 98 µL of blank plasma with 2 µL of dosing solution (100 µM) to achieve the final concentration of 2 µM. Samples were incubated at 37° C. At each time point (0, 10, 30, 60, and 120 min), 400 µL of stop solution (consisting of 200 ng/mL tolbutamide and 20 ng/mL buspirone in 50% MeOH/CH$_3$CN) was added to precipitate protein under thorough mixing. The sample plates were then centrifuged at 4,000 rpm for 10 min. An aliquot of supernatant (100 µL) was transferred from each well and mixed with 200 of µL ultrapure water. The samples were shaken at 800 rpm for about 10 min before LC-MS/MS analysis.

| | 51 | | 52 | | 58 | |
|---|---|---|---|---|---|---|
| Compound | IC$_{50}$/nM | Standard deviation | IC$_{50}$/nM | Standard deviation | IC$_{50}$/nM | Standard deviation |
| 5 min | 0.027 | 0.002 | 0.0040 | 0.0015 | 0.011 | 0.002 |
| 15 min | 0.030 | 0.007 | 0.0047 | 0.0009 | 0.0040 | 0.0011 |
| 30 min | 0.037 | 0.005 | 0.0042 | 0.0015 | 0.0026 | 0.0003 |
| 60 min | 0.026 | 0.010 | 0.0042 | 0.00076 | 0.00029 | 0.00021 |

Note:
Measurements were performed in 3 replicates and average values were reported.

Data Analysis:

The % remaining of test compound after incubation in plasma was calculated using following equation:

% Remaining=100×($P_{AR}$ at $T_n$/$P_{AR}$ at $T_0$)

where $P_{AR}$ is the peak area ratio of analyte versus internal standard (IS) and The appointed incubation time points are $T_0$ (0 min), $T_n$ (n=0, 10, 30, 60, 120 min).

LC-MS/MS Condition:

Each compound was analyzed by LC/MS using an ACE 5-phenyl 50×2.1 mm column (Part No. ACE-125-0502) with 0.1% formic acid in water and 0.1% formic acid in acetonitrile as the mobile phases. Tobultamide was used as the internal standard. Data collected were processed by Analyst 1.6.2 software and MultiQuant 3.0.2 software.

Results:

| Compound | Species/Matrix | Time Point (min) | % Remaining (mean) |
|---|---|---|---|
| 50 | CD-1 Mouse Plasma | 0 | 100.0 |
|  |  | 10 | 100.5 |
|  |  | 30 | 105.2 |
|  |  | 60 | 88.0 |
|  |  | 120 | 76.7 |
| 50a | CD-1 Mouse Plasma | 0 | 100.0 |
|  |  | 10 | 101.7 |
|  |  | 30 | 98.8 |
|  |  | 60 | 100.0 |
|  |  | 120 | 92.5 |
| 51 | CD-1 Mouse Plasma | 0 | 100.0 |
|  |  | 10 | 90.0 |
|  |  | 30 | 79.4 |
|  |  | 60 | 84.1 |
|  |  | 120 | 90.3 |
| 51a | CD-1 Mouse Plasma | 0 | 100.0 |
|  |  | 10 | 99.0 |
|  |  | 30 | 109.1 |
|  |  | 60 | 99.5 |
|  |  | 120 | 106.6 |
| 52 | CD-1 Mouse Plasma | 0 | 100.0 |
|  |  | 10 | 116.1 |
|  |  | 30 | 104.8 |
|  |  | 60 | 96.4 |
|  |  | 120 | 79.2 |
| Propantheline | CD-1 Mouse Plasma | 0 | 100.0 |
|  |  | 10 | 76.8 |
|  |  | 30 | 39.1 |
|  |  | 60 | 21.7 |
|  |  | 120 | 7.7 |

Mouse Liver Microsomal Metabolic Stability Assay

Materials:

1) Compounds 50, 50a, 51, 51a, and 52 were tested in this assay. Testosterone, Dichlofenac, and Propafenone were used as control.
2) Buffers:
   1. 100 mM potassium phosphate buffer, pH 7.4.
   2. 10 mM $MgCl_2$
3) Compound Dilution:

Intermediate solution was prepared by diluting 5 µL of compound or control stock solution (10 mM in DMSO) with DMSO (45 µL) and 1:1 Methanol/Water (450 µL) (concentration=100 µM, 45% MeOH). Working solution was prepared by diluting 50 µL of the intermediate solution with 450 µL of 100 mM potassium phosphate buffer, pH=7.4 (centration=10 µM, 4.5% MeOH).

4) NADPH regenerating system (final Isocitric dehydrogenase concentration=1 unit/mL at incubation) comprised:

β-Nicotinamide adenine dinucleotide phosphate acquired from Sigma (Catalog #N0505), isocitric acid from Sigma (Cat. No. 11252) and isocitric dehydrogenase from Sigma (Catalog #12002).

5) Liver microsome solution (final concentration of 0.5 mg protein/mL) was prepared using Mouse liver microsomes from Xenotech (Catalog #M1000, Lot #1310028).

6) Stop solution: Cold acetonitrile containing 100 ng/mL Tolbutamide and 100 ng/mL Labetalol as internal standards (IS)

Procedure:

10 µL/well of compound working solution or control working solution was added to all plates (T0, T5, T10, T20, T30, T60, NCF60) except the matrix blank. 80 µL/well of microsome solution was added to every plate. The mixtures of microsome solution and compound were incubated at 37° C. for about 10 min. 10 µL/well of NADPH regenerating system (pre-warmed to 37° C.) was then added to every plate to start the reaction. The plates were incubated for the durations indicated (matrix blank: 1 h; T60: 1 h; T30: 31 min; T20: 40 min; T1050 min; T5: 55 min). For NCF60 (abbreviation of no co-factor) no NADPH regenerating system was added, but was replaced by 10 µL/well of potassium phosphate buffer (100 mM, pH 7.4); the resulting mixture was incubated at 37° C. for 1 h.

The reactions were then terminated with the stop solution (cold at 4° C.) containing 100 ng/mL Tolbutamide and 100 ng/mL Labetalol (300 µL/well). The sampling plates were shaken for approximately 10 minutes, then were centrifuged at 4000 rpm for 20 min at 4° C. While centrifuging, 8 new 96 well plates were loaded with 300 µL of HPLC grade water. 100 µL of supernatant was finally added to 300 µL of HPLC grade water and mixed for LC/MS/MS analysis.

Apricot pipetting robot was used for all additions, mixing, and transformations described above in 96-well plate format.

Data Analysis

The equation of first order kinetics was used to calculate $T_{1/2}$ and $Cl_{int(mic)}$:

$$C_t = C_o \cdot e^{-k_e \cdot t}$$

when $C_t = \frac{1}{2}C_o$, $T_{1/2} = \frac{\ln 2}{k_e} = 0.693/k_e$ $$CL_{int(mic)} = \frac{0.693}{\text{in vitro } T_{1/2}} \cdot \left( \frac{1}{\frac{mg}{mL} \text{microsomal protein in reaction system}} \right)$$

$$CL_{int(liver)} = CL_{int(mic)} \cdot \left( \frac{mg \text{ microsomes}}{g \text{ liver}} \right) \cdot \left( \frac{g \text{ liver}}{Kg \text{ body weight}} \right)$$

Results:

| Compounds | $R^2$ | $T_{1/2}$(min) | $CL_{int(mic)}$ (µL/min/mg) | $CL_{int(liver)}$ (mL/min/kg) | Extraction ratio | Remaining (T = 60 min) | Remaining (*NCF = 60 min) |
|---|---|---|---|---|---|---|---|
| 50 | 0.8919 | >145 | <9.6 | <38.0 | <0.3 | 78.5% | 99.0% |
| 50a | 0.6722 | >145 | <9.6 | <38.0 | <0.3 | 92.9% | 82.3% |

-continued

| | | | MLM 0.5 | | | | |
|---|---|---|---|---|---|---|---|
| Compounds | $R^2$ | $T_{1/2}$(min) | $CL_{int(mic)}$ (µL/min/mg) | $CL_{int(liver)}$ (mL/min/kg) | Extraction ratio | Remaining (T = 60 min) | Remaining (*NCF = 60 min) |
| 51 | 0.2713 | >145 | <9.6 | <38.0 | <0.3 | 85.8% | 95.0% |
| 51a | 0.9190 | 71.6 | 19.4 | 76.6 | 0.5 | 52.2% | 91.7% |
| 52 | 0.4436 | >145 | <9.6 | <38.0 | <0.3 | 78.9% | 103.6% |
| Testosterone | 0.9992 | 2.3 | 597.4 | 2365.5 | 1.0 | 0.0% | 70.3% |
| Diclofenac | 0.9820 | 51.0 | 27.2 | 107.6 | 0.5 | 43.0% | 88.0% |
| Propafenone | 0.9858 | 1.3 | 1.3 | 4188.4 | 1.0 | 0.2% | 84.3% |

Notes:
1)* NCF: the abbreviation of no co-factor. No NADPH regenerating system was added into NCF samples (replaced by buffer) during the 60 min-incubation, if the NCF remaining is less than 60%, then Non-NADPH dependent occurs.
1) $R^2$ is the correlation coefficient of the linear regression for the determination of kinetic constant.
2) $T_{1/2}$ is half-life and $CL_{int(mic)}$ is the intrinsic clearance.

3) $\frac{\text{mg microsomes}}{\text{g liver}} = 45$ mg/g for five species.

4) $\frac{\text{g liver weight}}{\text{Kg body weight}} = 88$ g/Kg for mouse.

5) Hepatic blood clearance (CLH) = $\frac{CLint(liver) \times Qh}{CLint(liver) + Qh}$ Hepatic extraction ratio (EH) = $\frac{CLH}{QH} = \frac{Clint(liver)}{Clint(liver) + Qh}$ Whereby Qh(mL/min/Kg liver) = 90.0 mL/min/Kg for mouse liver Kinetic Solubility Test
Materials:
Compounds 50, 50a, 51, 51a, and 52 were tested.
Procedure:
The stock solution of each compound (10 µL; 10 mM in DMSO) was diluted with phosphate buffer solution (490 µL; 50 mM, pH 6.8). The resulting mixture was shaken for 24 h. Samples were then filtered. Kinetic solubility was then determined by UV spectroscopy [calibrated by a standard curve (1, 20, and 200 µM)].
Results:

| Compound | Kinetic Solubility pH = 6.8 (µg/mL) | Kinetic Solubility pH = 6.8 (µM) |
|---|---|---|
| 50 | >74.25 | >200.00 |
| 50a | >84.69 | >200.00 |
| 51 | >126.99 | >200.00 |
| 51a | 119.75 | 174.28 |
| 52 | >103.67 | >200.00 |

Caco-2 Permeability Assay
Materials:
1) Caco-2 culture: Caco-2 cells purchased from ATCC were seeded onto polyethylene membranes (PET) in 96-well BD Insert plates at 1×105 cells/cm2, and refreshed medium every 4-5 days until to the 21st to 28th day for confluent cell monolayer formation.
2) Compound information: compounds 51 and 51a were subjected to the assay. Digoxin, fenoterol, and propranol were used as standards respectively.
Transport Method:
The transport buffer used in the study was HBSS with 10 mM HEPES at pH 7.40±0.05. Compounds were tested at 2 µM bi-directionally in duplicates. Digoxin was tested at 10 µM bi-directionally in a duplicate, while fenoterol and propranolol were tested at 2 µM in A (apical) to B (basolateral) direction in duplicates. The final DMSO concentration was adjusted to less than 1%. The plate was incubated for 2 hours in a $CO_2$ incubator at 37±1° C., with 5% $CO_2$ at saturated humidity without shaking. All samples, after mixing with acetonitrile containing internal standard, were centrifuged at 4000 rpm for 20 min. Subsequently, 100 µL supernatant solution was diluted with 100 µL distilled water for LC/MS/MS analysis. Concentrations of test and control compounds in starting solution, donor solution, and receiver solution were quantified by LC/MS/MS methodologies, using peak area ratio of analyte/internal standard. After transport assay, lucifer yellow rejection assay was applied to determine the Caco-2 cell monolayer integrity. All data presented herein have passed this test.
Data Analysis:
The apparent permeability coefficient Papp (cm/s) was calculated using the equation:

$$P_{app} = \left(\frac{dC_r}{dt}\right) \cdot V_r / (A \cdot C_0)$$

Where $$\frac{dC_r}{dt}$$

is the cumulative concentration of compound in the receiver chamber as a function of time (µM/s); $V_r$ is the solution volume in the receiver chamber (0.075 mL on the apical side, 0.25 mL on the basolateral side); A is the surface area for the transport, i.e. 0.0804 cm$^2$ for the area of the monolayer; $C_0$ is the initial concentration in the donor chamber (µM).
The efflux ratio was calculated using the equation:

$$\text{Efflux ratio} = P_{app}(BA)/P_{app}(AB)$$

Percent recovery was calculated using the equation:

$$\% \text{ Recovery} = 100 \times [(V_r \cdot C_r) + (V_d \cdot C_d)]/(V_d \cdot C_0)$$

Where $V_d$ is the volume in the donor chambers (0.075 mL on the apical side, 0.25 mL on the basolateral side); $C_d$ and $C_r$ are the final concentrations of transport compound in donor and receiver chambers, respectively.

LC/MS Conditions:

Each compound was analyzed by LC/MS using an ACE 5-phenyl 50×2.1 mm column (Part No. ACE-125-0502) with 0.1% formic acid in water and 0.1% formic acid in acetonitrile as the mobile phases. Tobultamide was used as the internal standard. Data collected were processed by Analyst 1.6.2 software and MultiQuant 3.0.2 software.

Results:

| Compound ID | Mean $P_{app}$ ($10^{-6}$ cm/s) | | Efflux Ratio | Mean Recovery % | |
|---|---|---|---|---|---|
| | A to B | B to A | | A to B | B to A |
| Fenoterol | 0.24 | ND | — | 93.38 | ND |
| Propranolol | 19.76 | ND | — | 69.25 | ND |
| Digoxin | <0.02 | 8.50 | >364.02 | <91.21 | 100.33 |
| 51 | <0.16 | 0.61 | >3.91 | <88.25 | 99.12 |
| 51a | <0.08 | <0.12 | NA | <74.15 | <90.87 |

Note:
1) For digoxin and test compound, the signal responses in receiver samples were lower than the limit of quantification. For the convenience of calculating $P_{app}$ values, 50 was used as the peak area of analyte in receiver samples instead.
2) The permeation was assessed over a 120-minute incubation at 37 ± 1° C. and 5% $CO_2$ with saturated humidity.

Summary of ADME Data for Boronates 51 and 52 Compared to Trifluoromethylketone 51a

| Compound | Kinetic solubility (pH 6.8) [µM] | CD-1 Mouse Plasma % Remaining @ 2 hr [%] | Microsomal stability (Mouse ER) | Caco-2 ($P_{app}$ A-B) [$10^{-6}$ cm/s] | Caco-2 ($P_{app}$ B-A) [$10^{-6}$ cm/s] |
|---|---|---|---|---|---|
| 51 - B(OH)$_2$ | >200 | 90.3% | <0.3 | <0.080 | <0.12 |
| 51a - C(O)CF$_3$ | 174.28 | 106.6% | <0.3 | <0.16 | 0.61 |
| 52 - B(OH)$_2$ | >200 | 79.2% | <0.3 | | |

DOCUMENTS CITED IN EXAMPLES SECTION

69. A. Suzuki, *Angew. Chem. Int. Ed.* 50, 6722 (2011).
70. W. L. A. Brooks, B. S. Sumerlin, *Chem. Rev.* 116, 1375 (2016).
71. S. D. Bull, et al. *Acc. Chem. Res.* 46, 312 (2013).
72. P. C. Trippier, C. McGuigan Med. *Chem. Commun.* 1, 183 (2010).
73. A. Draganov, D. Wang, B. Wang, *Top. Med. Chem.* 17, 1 (2016).
74. C. Ballatore, D. M. Huryn, A. B. Smith, *ChemMedChem* 8, 385 (2013).
75. R. Smoum, A. Rubinstein, V. M. Dembitsky, M. Srebnik, *Chem. Rev.* 112, 4156 (2012).
76. H. C. Brown, *Hydroboration* (Benjamin/Cummings, 1980).
77. C. M. Vogels, S. A. Westcott, *Curr. Org. Chem.* 9, 687 (2005).
78. A. S. Dudnik, G. C. Fu, *J. Am. Chem. Soc.* 134, 10693 (2012).
79. T. C. Atack, R. M. Lecker, S. P. Cook, *J. Am. Chem. Soc.* 136, 9521 (2014).
80. R. B. Bedford et al., *Organometallics* 33, 5940 (2014).
81. C.-T. Yang et al., *Angew. Chem. Int. Ed.* 51, 528 (2012).
82. H. Ito, K. Kubota, *Org. Lett.* 14, 890 (2012).
83. H. C. Brown, T. E. Cole, *Organometallics* 2, 1316 (1983).
84. K.-s. Lee, A. R. Zhugralin, A. H. Hoveyda, *J. Am. Chem. Soc.* 131, 7253 (2009).
85. J. A. Schniffner, K. Mither, M. Oestreich, *Angew. Chem. Int. Ed.* 49, 1194 (2010).
86. P. Andres, G. Ballano, M. Isabel Calaza, C. Cativiela, *Chem. Soc. Rev.* 45, 2291 (2016).
87. M. A. Beenen, C. An, J. A. Ellman, *J. Am. Chem. Soc.* 130, 6910 (2008).
88. I. A. Mkhalid, J. H. Barnard, T. B. Marder, J. M. Murphy, J. F. Hartwig, *Chem. Rev.* 110, 890 (2010). E. J. Olhava, M. D. Danca, U.S. Pat. No. 7,442,830B1 (2008).
89. T. Qin et al., *Science* 352, 801 (2016).
90. J. Cornella et al., *J. Am. Chem. Soc.* 138, 2174 (2016).
91. J. Wang et al., *Angew. Chem. Int. Ed.* 55, 9676 (2016).
92. F. Toriyama et al., *J. Am. Chem. Soc.* 138, 11132 (2016).
93. T. Qin et al., *Angew. Chem. Int. Ed.* 55, 266 (2016).
94. T. Hatakeyama et al., *J. Am. Chem. Soc.* 132, 10674 (2010).
95. R. B. Bedford et al., *Chem. Eur. J.* 20, 7935 (2014).
96. R. A. Hussainy et al., *J. Med. Chem.* 54, 3480 (2011).
97. P. Lassalas et al., *ACS Med. Chem. Lett.* 59, 3183 (2016).
98. J. Schmidt, J. Choi, A. Liu, M. Slusarczyk, G. C. Fu, *Science* 354, 1265 (2016).
99. Y. Xi, J. Hartwig, *J. Am. Chem. Soc.* 138, 6703 (2016).
100. G. A. Molander, N. Ellis, *Acc. Chem. Res.* 40, 275 (2007).
101. S. N. Mlyanrski, A. S. Karns, J. P. Morken, *J. Am. Chem. Soc.* 134, 16449 (2012).
102. A. Bonet, M. Odachowski, D. Leonori, S. Essafi. V. K. Aggarwal, *Nat. Chem.* 6, 584 (2014).
103. S. Laulhé, J. M. Blackburn, J. L. Roizen, *Org. Lett.* 18, 4440 (2016). V. M. Dembitsky, M. Srebnik, *Tetrahedron* 59, 579 (2003). J. J. McAtee, S. L. Castle, Q. Jin, D. L. Boger, *Bioorg. Med. Chem. Lett.* 12, 1319 (2002).
104. P. R. Bernstein et al., *J. Med. Chem.* 37, 1259 (1994).
105. C. A. Veale et al., *J. Med. Chem.* 40, 3173 (1997).
106. P. R. Bernstein et al., *J. Med. Chem.* 38, 212 (1995).
107. J. P. Burkhart et al., *J. Med. Chem.* 37, 223 (1995).
108. P. D. Edwards et al., *J. Med. Chem.* 40, 1876 (1997).
109. K. Hemmi, I. Shima, K. Imai, H. Tanaka, EP0494071A2 (1992).
110. T. Kinoshita, I. Nakanishi, A. Sato, T. Tada, *Bioorg. Med. Chem. Lett.* 13, 21 (2003).
111. F. von Nussbaum, V. M.-J. Li, *Bioorg. Med. Chem. Lett.* 25, 4370 (2015).
112. F. von Nussbaum, et al., *ChemMedChem* 10, 1163 (2015).
113. F. Otto, et al., WO 2015096873 (2015).
114. T. J. Blench, et al., WO2013037809A1 (2013).
115. L. Bergstrom, M. Lundkvist, H. Lönn, P. Sjö, WO2008030158 A1 (2008).
116. M. D. Schultz, *Bioorg. Med. Chem. Lett.* 23, 5992 (2013).
117. A. Zervosen, et al., *J. Am. Chem. Soc.* 133, 10839 (2011).
118. M. Groll, C. R. Berkers, H. L. Ploegh, H. Ovaa, *Structure* 14, 451 (2006).
119. M. D. Schultz, *Bioorg. Med. Chem. Lett.* 23, 5992 (2013).
120. A. Zervosen, et al., *J. Am. Chem. Soc.* 133, 10839 (2011).
121. M. Groll, C. R. Berkers, H. L. Ploegh, H. Ovaa, *Structure* 14, 451 (2006).

What is claimed is:
1. A compound selected from the group consisting of:
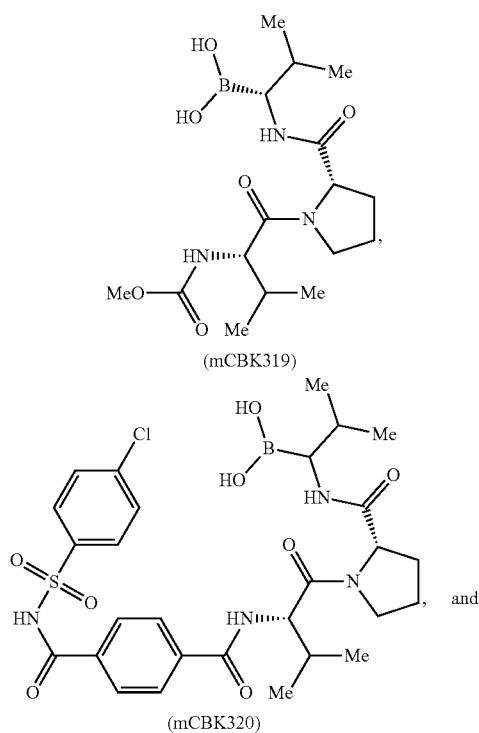
(mCBK319)
(mCBK320)
(mCBK323)
2. The compound according to claim 1, wherein the compound is:
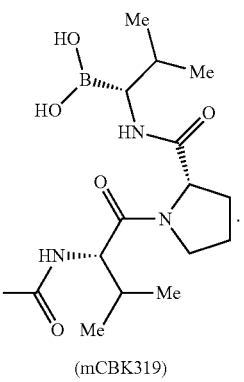
(mCBK319)
3. The compound according to claim 1, wherein the compound is:
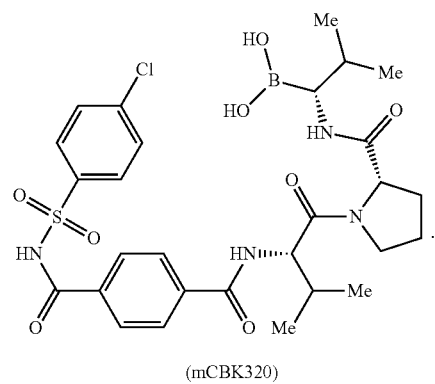 [SMILES: CC(C)[C@H](NC(=O)[C@@H]1CCCN1C(=O)[C@@H](NC(=O)c1ccc(C(=O)NS(=O)(=O)c2ccc(Cl)cc2)cc1)C(C)C)B(O)O]
(mCBK320)
4. The compound according to claim 1, wherein the compound is:
(mCBK323)
* * * * *